US008716281B2

(12) United States Patent
Bryan et al.

(10) Patent No.: US 8,716,281 B2
(45) Date of Patent: May 6, 2014

(54) PYRIMIDINE COMPOUNDS THAT INHIBIT ANAPLASTIC LYMPHOMA KINASE

(75) Inventors: Marian C. Bryan, West Hills, CA (US); Alan C. Cheng, San Francisco, CA (US); Elizabeth M. Doherty, Thousand Oaks, CA (US); James R. Falsey, Moorpark, CA (US); Ingrid M. Fellows, Clovis, CA (US); Joseph L. Kim, Wayland, MA (US); Richard T. Lewis, Framingham, MA (US); Michele H. Potashman, Cambridge, MA (US); Douglas A. Whittington, Waltham, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/697,730

(22) PCT Filed: May 4, 2011

(86) PCT No.: PCT/US2011/035186
§ 371 (c)(1),
(2), (4) Date: Nov. 13, 2012

(87) PCT Pub. No.: WO2011/143033
PCT Pub. Date: Nov. 17, 2011

(65) Prior Publication Data
US 2013/0158019 A1   Jun. 20, 2013

Related U.S. Application Data

(60) Provisional application No. 61/333,623, filed on May 11, 2010.

(51) Int. Cl.
*A61K 31/18* (2006.01)
(52) U.S. Cl.
USPC ................. 514/227.8; 514/235.8; 514/252.18
(58) Field of Classification Search
USPC ................. 514/227.8, 235.8, 252.18
See application file for complete search history.

(56) References Cited

U.S. PATENT DOCUMENTS

| | | | |
|---|---|---|---|
| 5,739,127 A | 4/1998 | Schohe-Loop et al. | |
| 2003/0171359 A1 | 9/2003 | Dahmann et al. | |
| 2005/0277642 A1 | 12/2005 | Erickson et al. | |
| 2007/0191370 A1 | 8/2007 | Devasagayaraj et al. | |
| 2007/0213319 A1 | 9/2007 | Zembower et al. | |
| 2008/0004285 A1 | 1/2008 | De Jonghe et al. | |
| 2008/0081818 A1 | 4/2008 | Abe et al. | |
| 2008/0234303 A1 | 9/2008 | Bhattacharya et al. | |
| 2008/0249102 A1* | 10/2008 | Ekegren et al. ............. | 514/252.1 |
| 2009/0005381 A1 | 1/2009 | Brown et al. | |
| 2009/0005382 A1 | 1/2009 | Brown et al. | |
| 2009/0036430 A1 | 2/2009 | De Jonghe et al. | |
| 2009/0054308 A1 | 2/2009 | Sands | |

FOREIGN PATENT DOCUMENTS

| | | | | |
|---|---|---|---|---|
| WO | WO-02102313 A2 | 12/2002 | | |
| WO | WO-2005068468 A2 | 7/2005 | | |
| WO | WO-2006069805 A2 | 7/2006 | | |
| WO | WO-2006135993 A1 | 12/2006 | | |
| WO | WO 2007/048557 A1 * | 5/2007 | ............. | A61K 31/18 |
| WO | WO-2007072158 A2 | 6/2007 | | |
| WO | WO-2009014972 A1 | 1/2009 | | |

OTHER PUBLICATIONS

Mahaligam, A.K. et la, HIV-1 Protease Inhibitors with a Transition state Mimic Comprising a Tertiary Alcohol: Improved Antiviral Activity in Cells:.Mahalingam AK, Axelsson L, Ekegren JK, Wannberg J, Kihlström J, Unge T, Wallberg H, Samuelsson B, Larhed M, Hallberg A. J Med Chem. Jan. 28, 2010;53(2):607-15. doi: 10.1021/jm901165g.*
Bischof, D. et al., Role of the Nucleophosmin (NPM) Portion of the Non-Hodgkin's Lymphoma-Associated NPM-Anaplastic Lymphoma Kinase Fusion Protein in Oncogenesis, Molecular and Cellular Biology, 17(4):2312-2325 (1997).
Gunby, R.H. et al., Structural Insights into the ATP Binding Pocket of the Anaplastic Lymphoma Kinase by Site-Directed Mutagenesis, Inhibitor Binding Analysis, and Homology Modeling, Journal of Medicinal Chemistry, 49:5759-5768 (2006).
International Preliminary Report on Patentability for PCT/US2011/035186, 6 pages (Nov. 13, 2012).
International Search Report for PCT/US2011/035186, 3 pages (Oct. 4, 2011).
Ladanyi, M. et al., Reverse Transcriptase Polymerase Chain Reaction for the Ki-1 Anaplastic Large Cell Lymphoma-Associated t(2;5) Translocation in Hodgkin's Disease, The American Journal of Pathology, 145(6):1296-1300 (1994).
Lawrence, B. et al., TPM3-Alk and TPM4-ALK Oncogenes in Inflammatory Myofibroblastic Tumors, The American Journal of Pathology, 157(2):377-384 (2000).
Lin, E. et al., Exon Array Profiling Detects EML4-ALK Fusion in Breast, Colorectal, and Non-Small Cell Lung Cancers, Molecular Cancer Research 7:1466-1476 (2009).
Morris, S.W. et al., Fusion of a Kinase Gene, ALK, to a Nucleolar Protein Gene, NPM, in Non-Hodgkin's Lymphoma, Science, 263:1281-1284 (1994).
Mosse, Y.P. et al., Identification of ALK as a Major Familial Neuroblastoma Predisposition Gene, Nature, 455(7215):930-935 (2008).
Pulford, K. et al., The Emerging Normal and Disease-Related Roles of Anaplastic Lymphoma Kinase, Cellular and Molecular Life Sciences, 61:2939-2953 (2004).
Soda, M. et al., Identification of the Transforming EML4-ALK Fusion Gene in Non-Small-Cell Lung Cancer, Nature, 448:561-566 (2007).
Touriol, C. et al., Further Demonstration of the Diversity of Chromosomal Changes Involving 2p23 in ALK-Positive Lymphoma: 2 Cases Expressing ALK Kinase Fused to CLTCL (Clathrin Chain Polypeptide-Like), Blood, 95(10):3204-3207 (2000).
Written Opinion for PCT/US2011/035186, 7 pages (Oct. 4, 2011).

* cited by examiner

*Primary Examiner* — San-Ming Hui
*Assistant Examiner* — Jeanmarie Calvillo
(74) *Attorney, Agent, or Firm* — Choate, Hall and Stewart LLP; Brenda Herschbach Jarrell; Kristen C. Buteau

(57) ABSTRACT

The present invention describes pyrimidine compounds of Formula I that are useful as anaplastic lymphoma kinase inhibitors, pharmaceutically acceptable compositions thereof, and methods of using the same.

41 Claims, No Drawings

PYRIMIDINE COMPOUNDS THAT INHIBIT ANAPLASTIC LYMPHOMA KINASE

CROSS REFERENCES TO RELATED APPLICATIONS

This application is a National Stage Entry of International Patent Application No. PCT/US11/35186, filed May 4, 2011, which claims the benefit of, and priority to, U.S. Provisional Application No. 61/333,623, filed on May 11, 2010, each of which is hereby incorporated by reference in its entirety for all purposes as if fully set forth herein.

FIELD OF THE INVENTION

The present invention relates to compounds capable of inhibiting the kinase activity of anaplastic lymphoma kinase (ALK), and compositions that include compounds that inhibit ALK. The compounds and compositions may be used to treat diseases or conditions modulated by ALK such as cancer and may be used to treat neurological disorders such as depression and are especially useful in treating patients with cancers expressing modified ALK or cancers related to ALK expression. For example, the compounds and compositions are especially useful in treating cancers that are positive for ALK fusion proteins EML4-ALK and/or NPM-ALK or have kinase activating point mutations in the ALK protein as well as amplifications of the ALK locus on chromosome 2p23.

BACKGROUND OF THE INVENTION

ALK is a receptor tyrosine kinase conserved across species and plays a key role in the growth and differentiation of neural tissues in the developing embryo. The receptor belongs in the insulin receptor superfamily and was initially identified as a member of a novel intracellular fusion protein with constitutive kinase activity in anaplastic large-cell lymphoma (ALCL). Bischof, D. et al., "Role of the Nucleophosmin (NPM) Portion of the Non-Hodgkin's Lymphoma-Associated NPM-Anaplastic Lymphoma Kinase Fusion Protein in Oncogenesis," Molecular and Cellular Biology. 17, 2312-2325 (1997); Pulford, K. et al., "The Emerging Normal and Disease-Related Roles of Anaplastic Lymphoma Kinase," Cell Mol Life Sci. 61, 2939-2953 (2004). Subsequent studies have identified ALK fusion proteins in diffuse large B-cell lymphomas, systemic histiocytosis, inflammatory myofibroblastic tumors, breast cancers, colorectal carcinomas, and non-small cell lung cancers. Morris, S. W. et al., "Fusion of a Kinase Gene, ALK, to a Nucleolar Protein Gene, NPM, in Non-Hodgkin's Lymphoma", Science (New York, N.Y. 263, 1281-1284 (1994)); Lawrence, B. et al., "TPM3-ALK and TPM4-ALK Oncogenes in Inflammatory Myofibroblastic Tumors," The American Journal of Pathology. 157, 377-384 (2000); Touriol, C. et al., "Further Demonstration of the Diversity of Chromosomal Changes Involving 2p23 in ALK-Positive Lymphoma: 2 Cases Expressing ALK Kinase Fused to CLTCL (Clathrin Chain Polypeptide-Like)," Blood. 95, 3204-3207 (2000); Soda, M. et al., "Identification of the Transforming EML4-ALK Fusion Gene in Non-Small-Cell Lung Cancer," Nature. 448, 561-566 (2007); Lin, E. et al., "Exon Array Profiling Detects EML4-ALK Fusion in Breast, Colorectal, and Non-Small Cell Lung Cancers," Mol Cancer Res. 7, 1466-1476 (2009). In addition, activating point mutations, as well as genomic DNA amplification and overexpression of ALK have recently been described in neuroblastomas. Mosse, Y. P. et al., "Identification of ALK as a Major Familial Neuroblastoma Predisposition Gene," Nature. 455, 930-935 (2008).

Using immunostaining and other methods, 60-80% of ALCLs have been found to be ALK fusion-positive. Morris, S. W. et al., "Fusion of a Kinase Gene, ALK, to a Nucleolar Protein Gene, NPM, in Non-Hodgkin's Lymphoma", Science (New York, N.Y. 263, 1281-1284 (1994)); Ladanyi, M. et al., "Reverse Transcriptase Polymerase Chain Reaction for the Ki-1 Anaplastic Large Cell Lymphoma-Associated t(2; 5) Translocation in Hodgkin's Disease," The American Journal of Pathology. 145, 1296-1300 (1994). ALK-positive ALCL cells express the cell surface protein CD30 and exhibit a cytotoxic T-cell or null phenotype. This lymphoma entity is now officially classified as 'ALK-positive ALCL' in the WHO classification of NHL.

More recently, ALK has been identified in a subset of non small cell lung carcinoma patients (NSCLC). In 2006, genetic analysis of a patient with NSCLC led to the discovery of a novel fusion gene between the echinoderm microtubule-associated protein-like 4 (EML4) and the anaplastic lymphoma kinase (ALK) genes. Oncogenic activity of EML4-ALK requires the N-terminal coiled-coil domain within EML4 that leads to the constitutive dimerization and, thereby, activation of the fusion protein. Soda, M. et al., "Identification of the Transforming EML4-ALK Fusion Gene in Non-Small-Cell Lung Cancer," Nature. 448, 561-566 (2007). Since both of the EML4 and ALK genes are closely mapped in an opposite direction to the same short arm of human chromosome 2, a small chromosome inversion involving the two genes is likely to be the underlining mechanism for the generation of the gene fusion, which was indeed evidenced by both Fluorescence In Situ Hybridization (FISH) and genomic PCR analyses.

SUMMARY OF THE INVENTION

In one aspect, the invention provides a compound of Formula I:

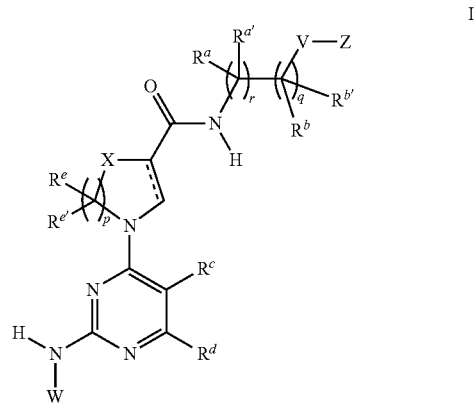

or a pharmaceutically acceptable salt thereof, a stereoisomer thereof, a pharmaceutically acceptable salt of the stereoisomer, or a mixture thereof,
wherein:
X is selected from —$CH_2$—, —N(H)—, —O—, or —S—;
V is absent or is selected from —$CH_2$—, —O—, —S—, or —NH—; wherein if V is —O—, —S—, or —NH—, then r is 1 and q is 1;

the subscript p is selected from 0, 1, 2, or 3, wherein X is $CH_2$ if p is 0;

the subscript q is selected from 0 or 1;

the subscript r is selected from 0 or 1:

the ----- symbol indicates that the bond can be a single or double bond;

Z is a $C_6$-$C_{10}$ aryl or a 5-10 membered heteroaryl comprising 1, 2, 3, or 4 heteroatoms independently selected from O, S, or N, wherein the $C_6$-$C_{10}$ aryl or the 5-10 membered heteroaryl are unsubstituted or are optionally substituted with 1, 2, 3, or 4 substituents independently selected from —Z', —O—Z', —S—Z', —NH—Z', —$CH_2$Z', —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —C(=O)NH—Z', —$SO_2NH_2$, —$SO_2$NH(($C_1$-$C_4$)alkyl), —$SO_2$N(($C_1$-$C_4$)alkyl)$_2$, —$SO_2$NH—Z', —$NHSO_2$—($C_1$-$C_4$)alkyl, —$NHSO_2$—Z', —NHC(=O)—($C_1$-$C_4$)alkyl, —NHC(=O)—Z', —$SO_2$—($C_1$-$C_4$)alkyl, —$SO_2$—Z', —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—Z', —C(=O)—O—($C_1$-$C_4$)alkyl, —C(=O)NH—($C_1$-$C_4$)alkylene-$NH_2$, —C(=O)$NH_4C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered heteroaryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to V, if present, or to the C atom bearing $R^b$ and $R^{b'}$ if V is not present, or to the C atom bearing $R^a$ and $R^{a'}$ if V is not present and q is 0, or to the N atom bonded to the C(=O) if V is not present, q is 0, and r is 0; and further wherein, the partially saturated ring of a bicyclic $C_6$-$C_{10}$ aryl or a bicyclic 5-10 membered heteroaryl may include a —C(=O)— ring member;

Z' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

$R^a$ and $R^{a'}$ are absent if r is 0 or are independently selected from —H, —($C_1$-$C_6$)alkyl, —C≡N, —OH, or —$CF_3$; or $R^a$ and $R^{a'}$ may together represent a =O; or $R^a$ and $R^{a'}$ may join together with the carbon atom to which they are attached to form a cycloalkyl ring having from 3 to 6 members;

$R^b$ and $R^{b'}$ are absent if q is 0 or are independently selected from —H, —($C_1$-$C_6$)alkyl, —C≡N, —OH, or —$CF_3$; or $R^b$ and $R^{b'}$ may together represent a =O; or $R^b$ and $R^{b'}$ may join together with the carbon atom to which they are attached to form a cycloalkyl ring having from 3 to 6 members;

$R^c$ is selected from —H, —($C_1$-$C_6$)alkyl, —$CF_3$, —F, —Cl, —Br, or —I;

$R^d$ is selected from —H, —($C_1$-$C_6$)alkyl, —$CF_3$, —F, —Cl, —Br, or —I;

$R^e$ and $R^{e'}$ are independently selected from —H or —($C_1$-$C_6$)alkyl;

W is a $C_6$-$C_{10}$ aryl, a 5-10 membered heteroaryl comprising 1, 2, 3 or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1, 2, 3, or 4 substituents independently selected from —W', —O—W', —S—W', —N(H)—W', —O—CH2-W', —C(=O)—W', —C(=O)NH—W', —$SO_2$NH—W', —$NHSO_2$—W', —NHC(=O)—W', —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered heteroaryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to the N atom to which W is attached; and further wherein, the partially saturated ring of a bicyclic $C_6$-$C_{10}$ aryl or a bicyclic 5-10 membered heteroaryl may include a —C(=O)— ring member and the 5-7 membered heterocyclyl group may include a —C(=O)— ring member; and W' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —NH$_2$, —NH((C$_1$-C$_4$)alkyl), —N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$.

In some embodiments of the compound of Formula I or the pharmaceutically acceptable salt thereof, stereoisomer thereof, pharmaceutically acceptable salt of the stereoisomer, or the mixture thereof, X is selected from —CH$_2$—, —N(H)—, —O—, or —S—;

V is absent or is selected from —CH$_2$—, —O— or —S—; wherein if V is —O—, —S—, then r is 1 and q is 1 the subscript p is selected from 0, 1, 2, or 3, wherein X is CH$_2$ if p is 0;

the subscript q is selected from 0 or 1;

the subscript r is selected from 0 or 1:

the ----- symbol indicates that the bond can be a single or double bond;

Z is a C$_6$-C$_{10}$ aryl or a 5-10 membered heteroaryl comprising 1, 2, 3 or 4 heteroatoms independently selected from O, S, or N, wherein the C$_6$-C$_{10}$ aryl or the 5-10 membered heteroaryl are unsubstituted or are optionally substituted with 1, 2, 3, or 4 substituents independently selected from —Z', —OZ', —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$; and two adjacent substituents on the C$_6$-C$_{10}$ aryl or the 5-10 membered heteroaryl may join to form a 5 or 6 membered ring comprising 0, 1, or 2 heteroatoms selected from O, N, or S; and further wherein the C$_6$-C$_{10}$ aryl and the 5-10 membered hetero aryl may be monocyclic or bicyclic and further wherein both rings of a bicyclic C$_6$-C$_{10}$ aryl or a bicyclic 5-10 membered heteroaryl may be aromatic or one of the rings may be partially saturated and the other ring may be aromatic and either the partially saturated ring or the aromatic ring may be bonded to V, if present, or to the C atom bearing R$^b$ and R$^{b'}$ if V is not present, or to the C atom bearing R$^a$ and R$^{a'}$ if V is not present and q is 0, or to the N atom bonded to the C(=O) if V is not present, q is 0, and r is 0; and further wherein, the partially saturated ring of a bicyclic C$_6$-C$_{10}$ aryl or a bicyclic 5-10 membered heteroaryl may include a —C(=O)— ring member;

Z' is a C$_6$-C$_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the C$_6$-C$_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$;

R$^a$ and R$^{a'}$ are absent if r is 0 or are independently selected from —H, —(C$_1$-C$_6$)alkyl, —C≡N, —OH, or —CF$_3$; or R$^a$ and R$^{a'}$ may together represent a =O;

R$^b$ and R$^{b'}$ are absent if q is 0 or are independently selected from —H, —(C$_1$-C$_6$)alkyl, —C≡N, —OH, or —CF$_3$; or R$^b$ and R$^{b'}$ may together represent a =O;

R$^c$ is selected from —H, —(C$_1$-C$_6$)alkyl, —CF$_3$, —F, —Cl, —Br, or —I;

R$^d$ is selected from —H, —(C$_1$-C$_6$)alkyl, —CF$_3$, —F, —Cl, —Br, or —I;

R$^e$ and R$^{e'}$ are independently selected from —H or —(C$_1$-C$_6$)alkyl;

W is a C$_6$-C$_{10}$ aryl, a 5-10 membered heteroaryl comprising 1, 2, 3 or 4 heteroatoms independently selected from O, S, or N, or a 5-7 membered heterocyclyl comprising 1, 2, or 3 heteroatoms selected from O, S, or N, wherein the C$_6$-C$_{10}$ aryl, the 5-10 membered heteroaryl, or the 5-7 membered heterocyclyl are unsubstituted or are optionally substituted with 1, 2, 3, or 4 substituents independently selected from —W', —O—W', —CH$_2$—W', N(H)—W', —O—CH2-W', —C(=O)—W', —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$; and two adjacent substituents on the C$_6$-C$_{10}$ aryl or the 5-10 membered heteroaryl may join to form a 5 or 6 membered ring comprising 0, 1, or 2 heteroatoms selected from O, N, or S; and further wherein the C$_6$-C$_{10}$ aryl and the 5-10 membered hetero aryl may be monocyclic or bicyclic and further wherein both rings of a bicyclic C$_6$-C$_{10}$ aryl or a bicyclic 5-10 membered heteroaryl may be aromatic or one of the rings may be partially saturated and the other ring may be aromatic and either the partially saturated ring or the aromatic ring may be bonded to the N atom to which W is attached; and further wherein, the partially saturated ring of a bicyclic C$_6$-C$_{10}$ aryl or a bicyclic 5-10 membered heteroaryl may include a —C(=O)— ring member and the 5-7 membered heterocyclyl group may include a —C(=O)— ring member; and W' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$.

In some embodiments, p is 2. In other embodiments, p is 1. In still further embodiments, p is 3.

In some embodiments, r is 1. In some such embodiments, r is 1 and q is 1. In other such embodiments, r is 1 and q is 0. In other embodiments, r is 0.

In some embodiments, V is absent. In other embodiments, V is —$CH_2$—. In still other embodiments, V is —O—.

In some embodiments, X is —$CH_2$—. In still other embodiments, X is —O—. In still other embodiments, X is —S—. In still further embodiments, X is —N(H)—.

In some embodiments, q is 0. In still other embodiments, q is 1. In some embodiments where q is 1, $R^b$ and $R^{b'}$ are independently selected from —H, —$CH_3$, or $R^b$ and $R^{b'}$, when taken together, represent a =O. In some such embodiments, $R^b$ and $R^{b'}$ are both —H. In other embodiments where q is 1, $R^b$ and $R^{b'}$ join together with the carbon atom to which they are attached to form a cyclopropyl, cyclobutyl, cyclopentyl, or cyclohexyl ring. In some such embodiments, $R^b$ and $R^{b'}$ join together with the carbon atom to which they are attached to form a cyclopropyl ring.

In some embodiments, the compound of Formula I is a compound of Formula IA:

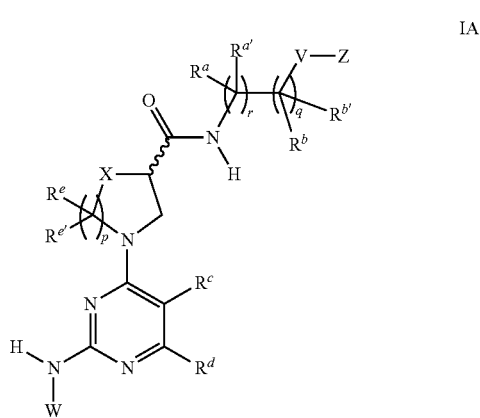

IA or a pharmaceutically acceptable salt thereof, a stereoisomer thereof, a pharmaceutically acceptable salt of the stereoisomer, or a mixture thereof, wherein the symbol ⌇ indicates that the chiral carbon atom to which the ⌇ is attached may have the R stereochemistry, the S stereochemistry, or may be a mixture of compounds with the R and S stereochemistry wherein the mixture may be racemic, or the mixture may include a greater amount of compounds with the R stereochemistry compared to the amount of compounds with the S stereochemistry, or the mixture may include a greater amount of compounds with the S stereochemistry compared to the amount of compounds with the R stereochemistry. In such embodiments, the variables have the same meaning as in any of the embodiments of the compounds of formula I.

In some embodiments, the compound of Formula I is a compound of Formula II:

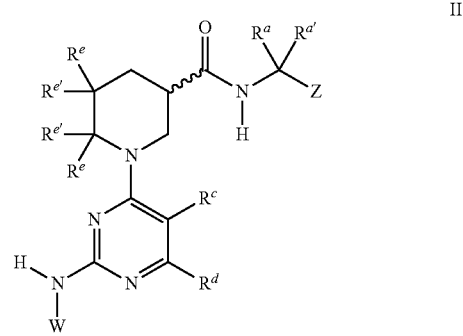

II or a pharmaceutically acceptable salt thereof, a stereoisomer thereof, a pharmaceutically acceptable salt of the stereoisomer, or a mixture thereof, wherein the symbol ⌇ indicates that the chiral carbon atom to which the ⌇ is attached may have the R stereochemistry, the S stereochemistry, or may be a mixture of compounds with the R and S stereochemistry wherein the mixture may be racemic, or the mixture may include a greater amount of compounds with the R stereochemistry compared to the amount of compounds with the S stereochemistry, or the mixture may include a greater amount of compounds with the S stereochemistry compared to the amount of compounds with the R stereochemistry.

In some embodiments, the compound of Formula II is a compound of Formula IIA:

IIA or a pharmaceutically acceptable salt thereof.

In some embodiments, the compound of Formula II is a compound of Formula IIB:

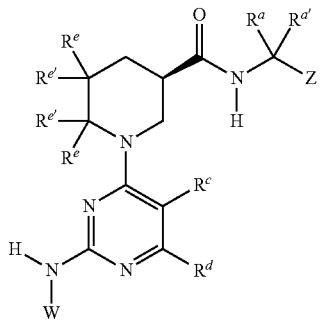

IIB or a pharmaceutically acceptable salt thereof.

In some embodiments, $R^e$ and $R^{e'}$ are independently selected from —H or —CH$_3$. In some such embodiments, $R^e$ and $R^{e'}$ are both —H.

In some embodiments, $R^a$ and $R^{a'}$ are independently selected from —H or —CH$_3$. In some such embodiments, $R^a$ and $R^{a'}$ are both —H.

In some embodiments, $R^a$ and $R^{a'}$ join together with the carbon atom to which they are attached to form a cyclopropyl, butyl, cyclopentyl, or cyclohexyl ring. In some such embodiments, $R^a$ and $R^{a'}$ join together with the carbon atom to which they are attached to a cyclopropyl ring.

In some embodiments, $R^c$ is selected from —H or —CH$_3$. In some such embodiments, $R^c$ is —H.

In some embodiments, $R^d$ is selected from —H or —CH$_3$. In some such embodiments, $R^d$ is —H.

In some embodiments, Z is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, quinolinyl, isoquinolinyl, 1,2,3,4,4a,8a-hexahydroquinolinyl, 2,3-dihydrobenzo[b][1,4]dioxinyl, pyridazinyl, pyrazinyl, indazolyl, isothiazolyl, or oxazolyl.

In some embodiments, Z is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, quinolinyl, isoquinolinyl, 1,2,3,4,4a,8a-hexahydroquinolinyl, or 2,3-dihydrobenzo[b][1,4]dioxinyl. In some such embodiments, Z is an unsubstituted or substituted phenyl. In still other such embodiments, Z is selected from

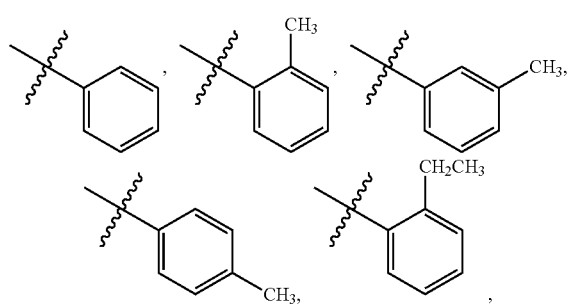

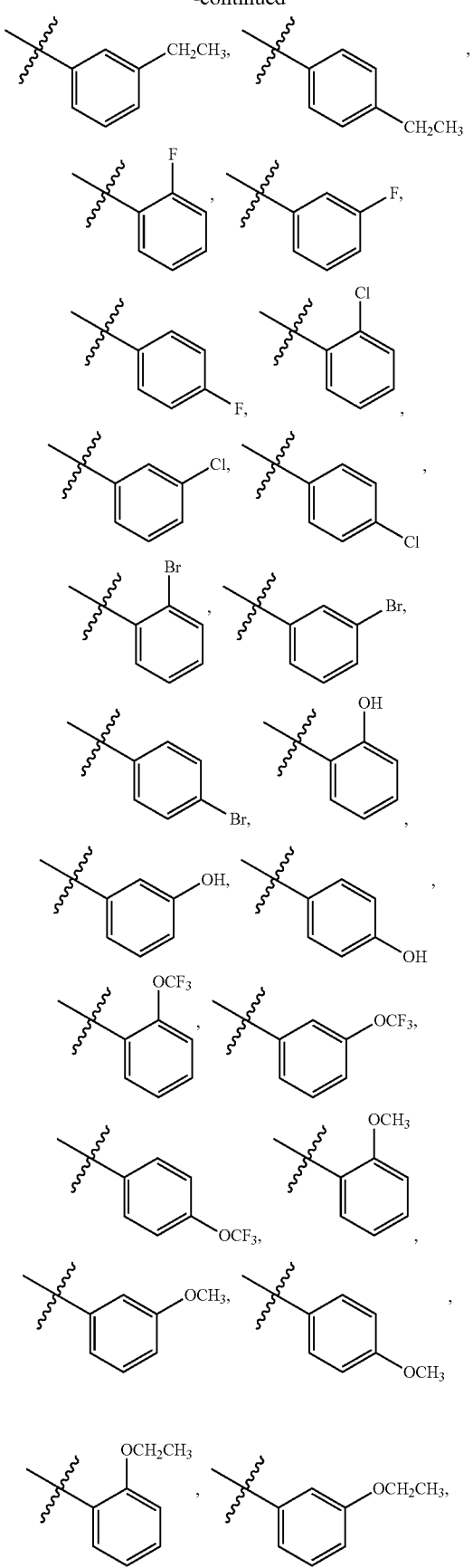

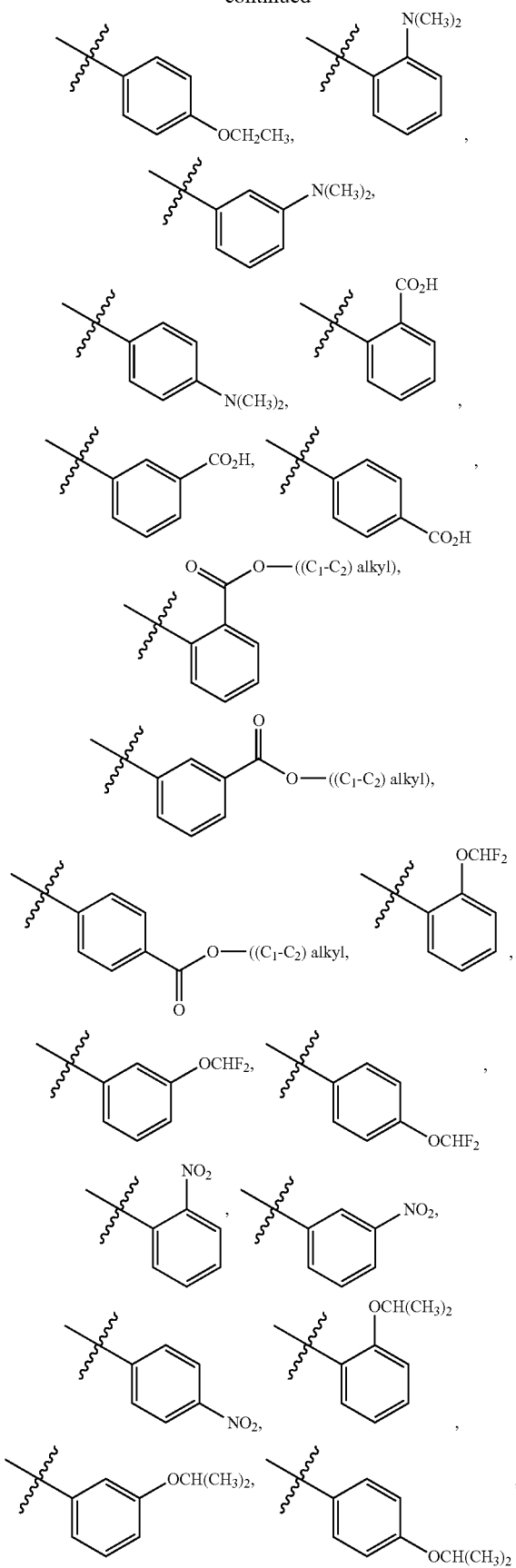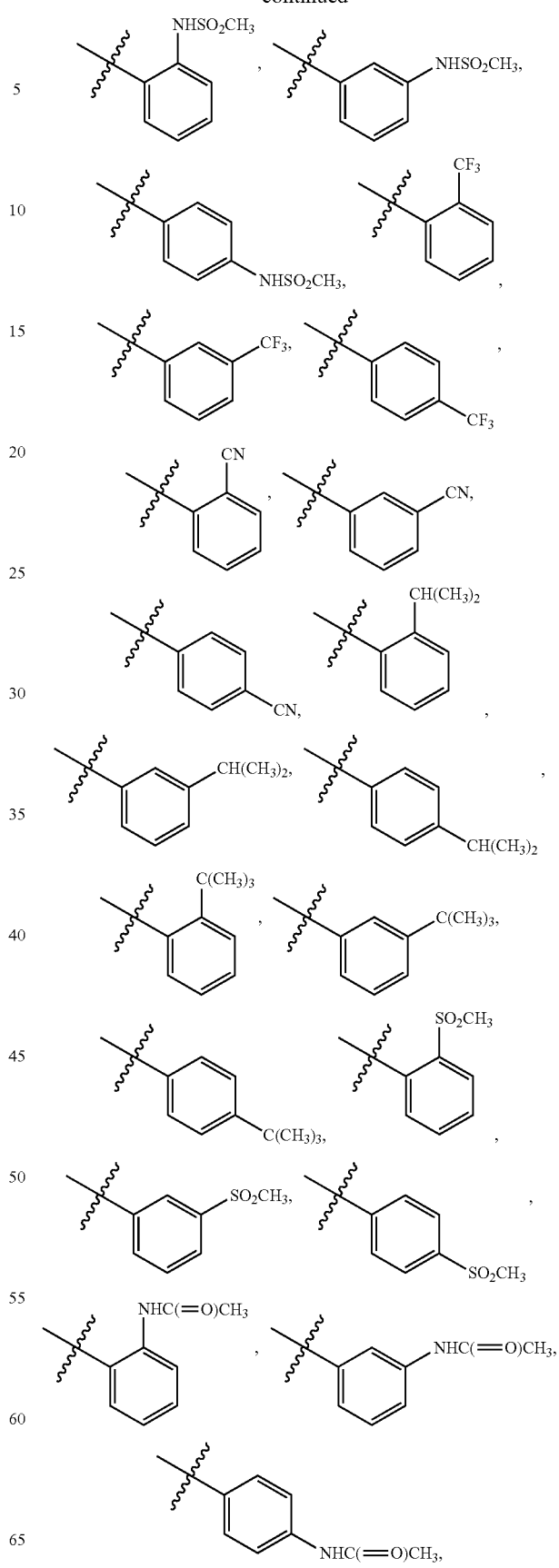

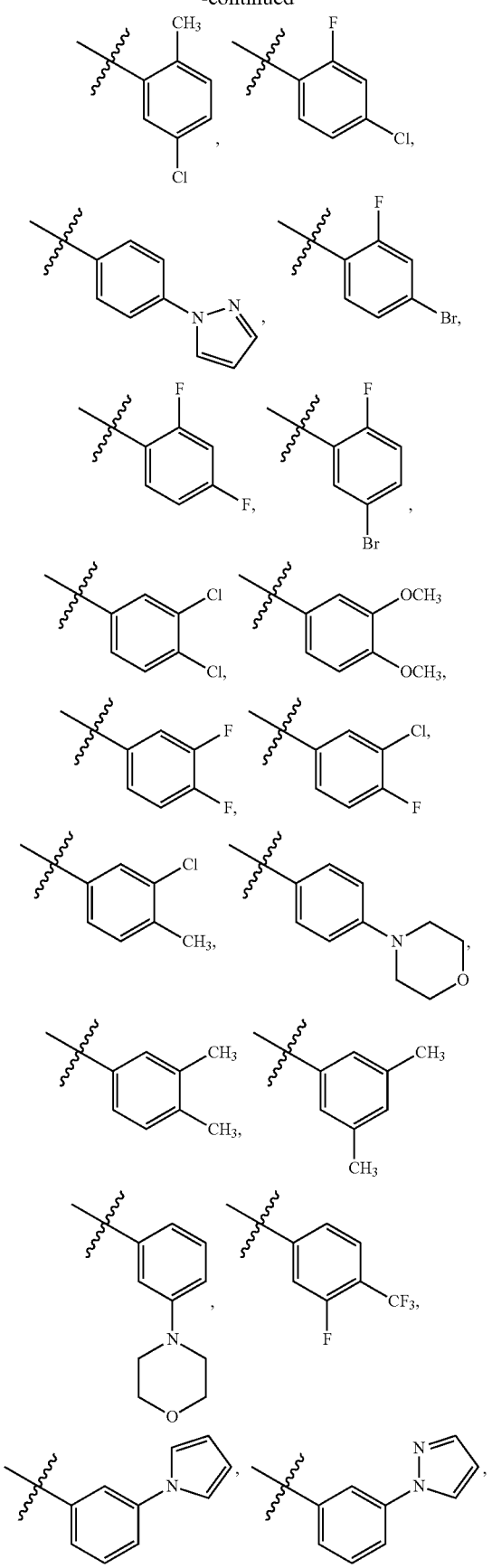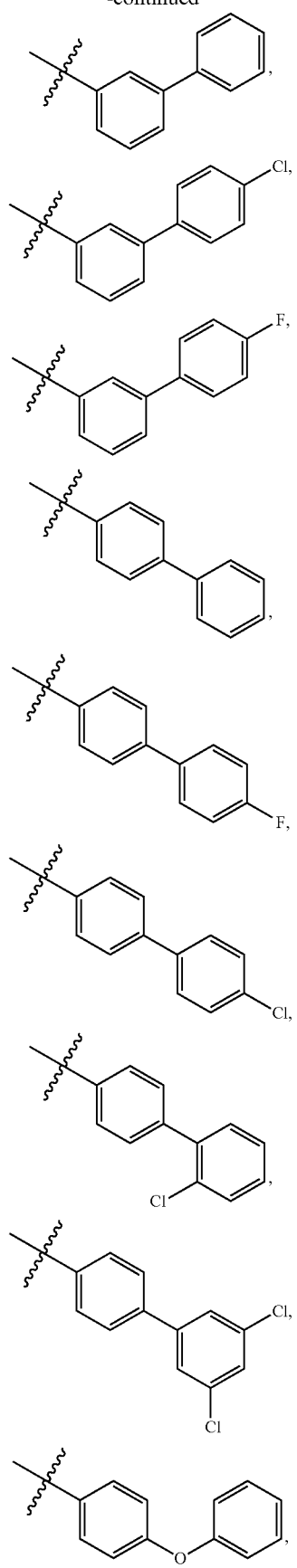

-continued

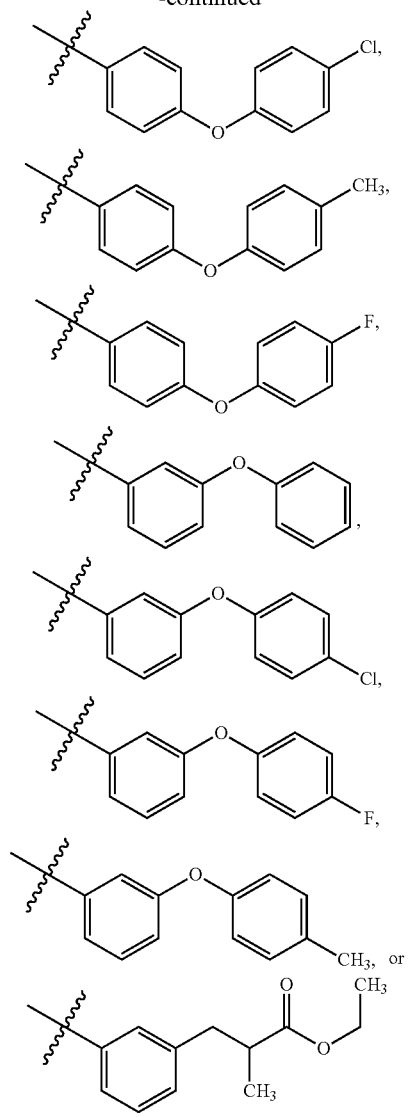

wherein the symbol ⁓ when drawn through a bond indicates the point of attachment to the rest of the molecule.

In some embodiments, Z is selected from

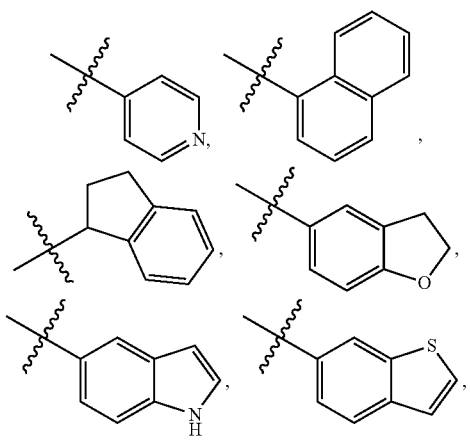

-continued

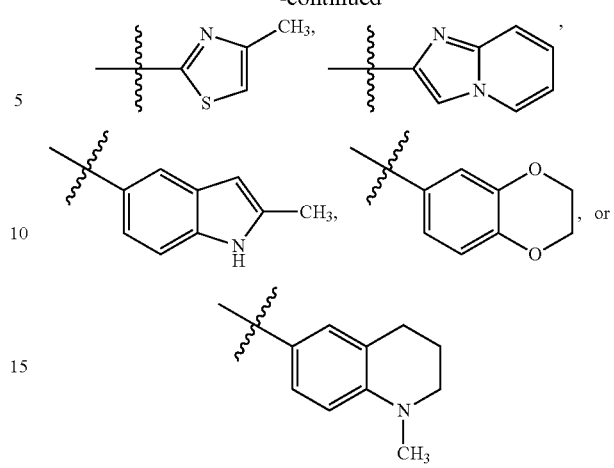

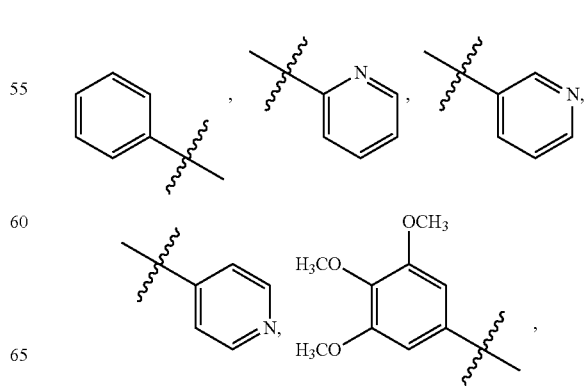

wherein the symbol ⁓ when drawn through a bond indicates the point of attachment to the rest of the molecule.

In some embodiments, Z is substituted with at least one substituent selected from —Z' or —OZ'. In some such embodiments, Z is phenyl and Z' is an optionally substituted phenyl.

In some embodiments, W is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, isoindolin-1-onyl, indolinyl, pyrazolyl, pyridinonyl, quinolinyl, isoquinolinyl, 1,2,3,4,4a,8a-hexahydroquinolinyl, 2,3-dihydrobenzo[b][1,4]dioxinyl, pyridazinyl, pyrazinyl, indazolyl, isothiazolyl, or oxazolyl In some embodiments, W is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, isoindolin-1-onyl, indolinyl, pyrazolyl, pyridinonyl, quinolinyl, isoquinolinyl, 1,2,3,4,4a,8a-hexahydroquinolinyl, or 2,3-dihydrobenzo[b][1,4]dioxinyl.

In some embodiments, W is an unsubstituted or substituted phenyl, pyridyl, indolyl, isoindolin-1-onyl, indolinyl, pyrazolyl, pyridinonyl, quinolinyl, isoquinolinyl, or 2,3-dihydrobenzo[b][1,4]dioxinyl. In some such embodiments, W is an unsubstituted or substituted phenyl.

In some embodiments, W is selected from

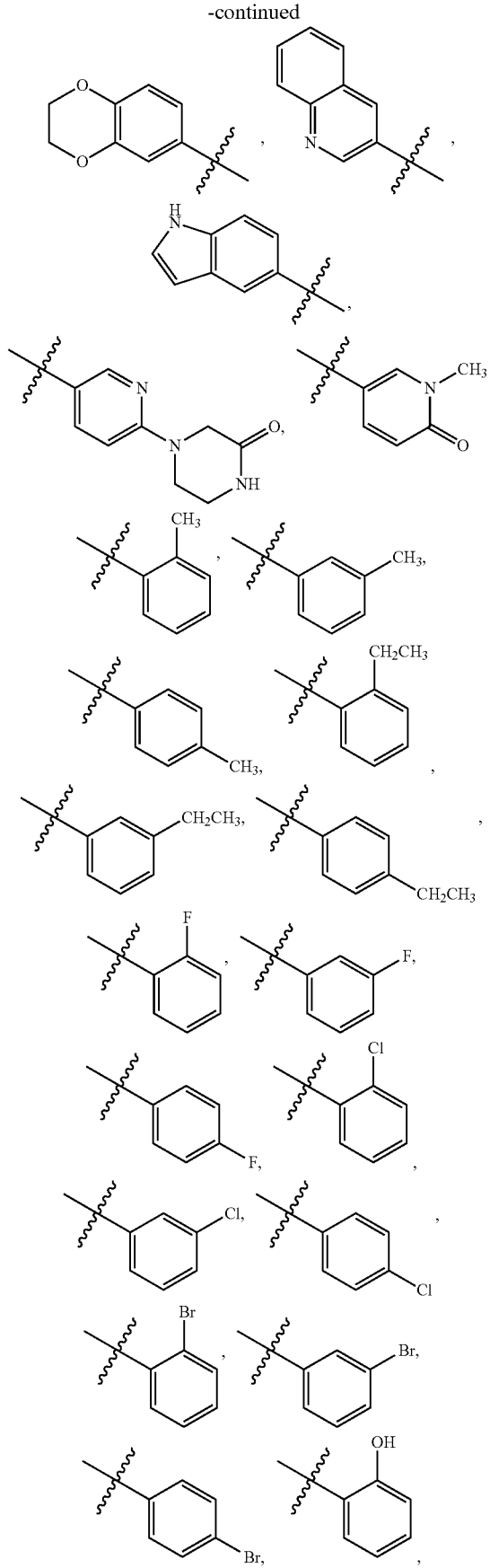
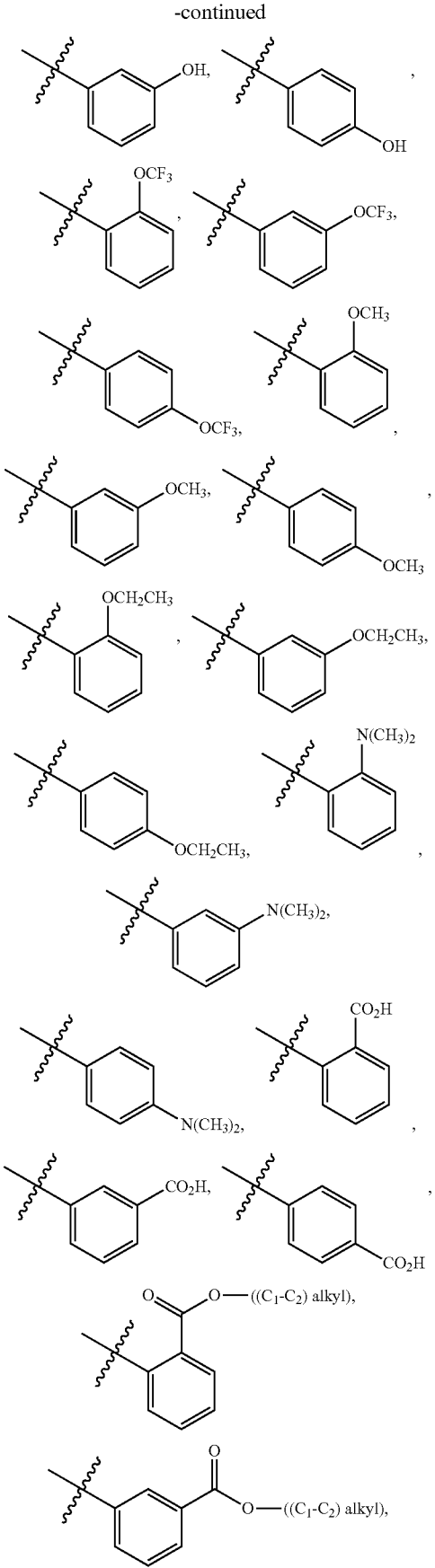

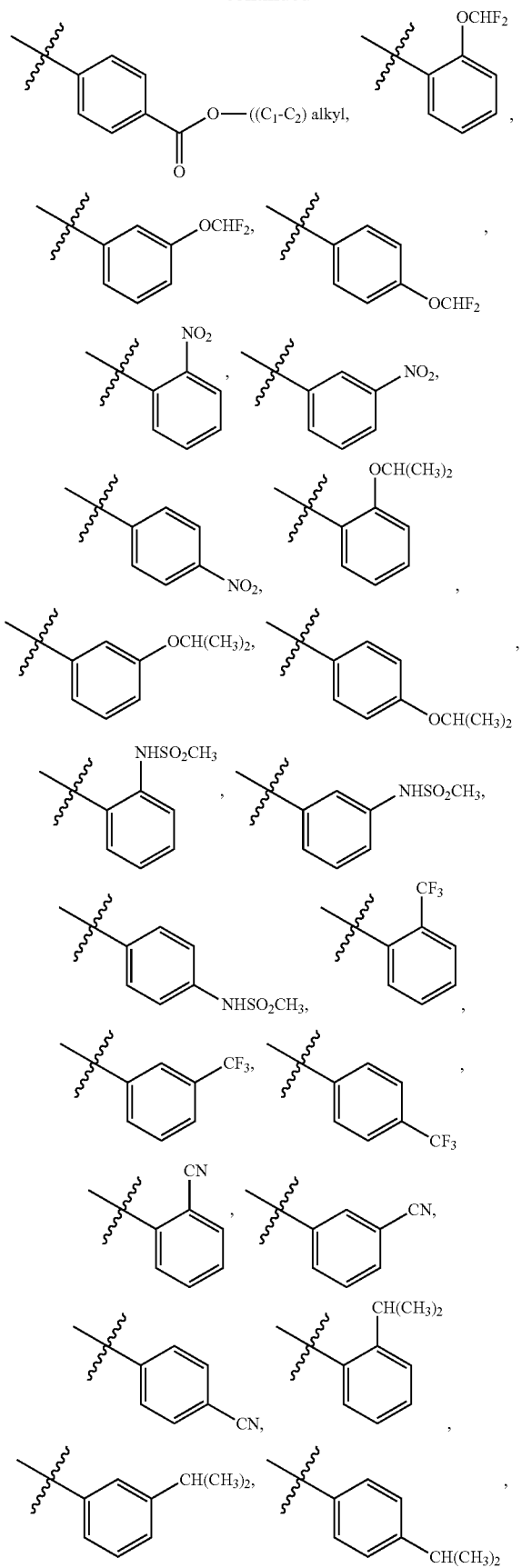
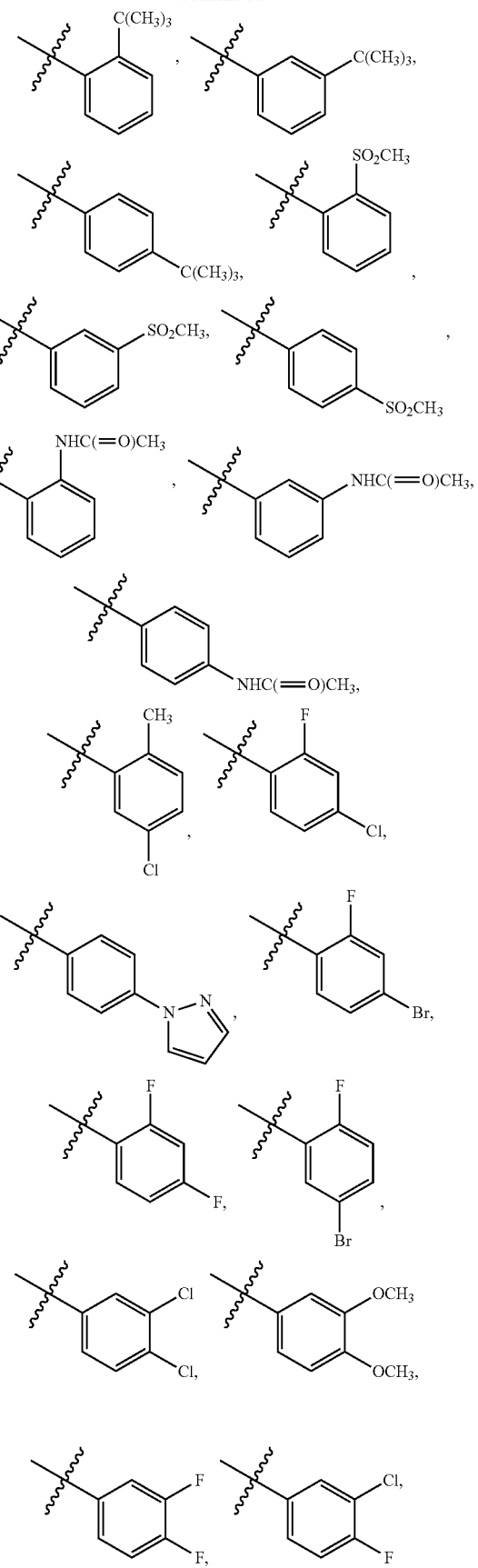

-continued
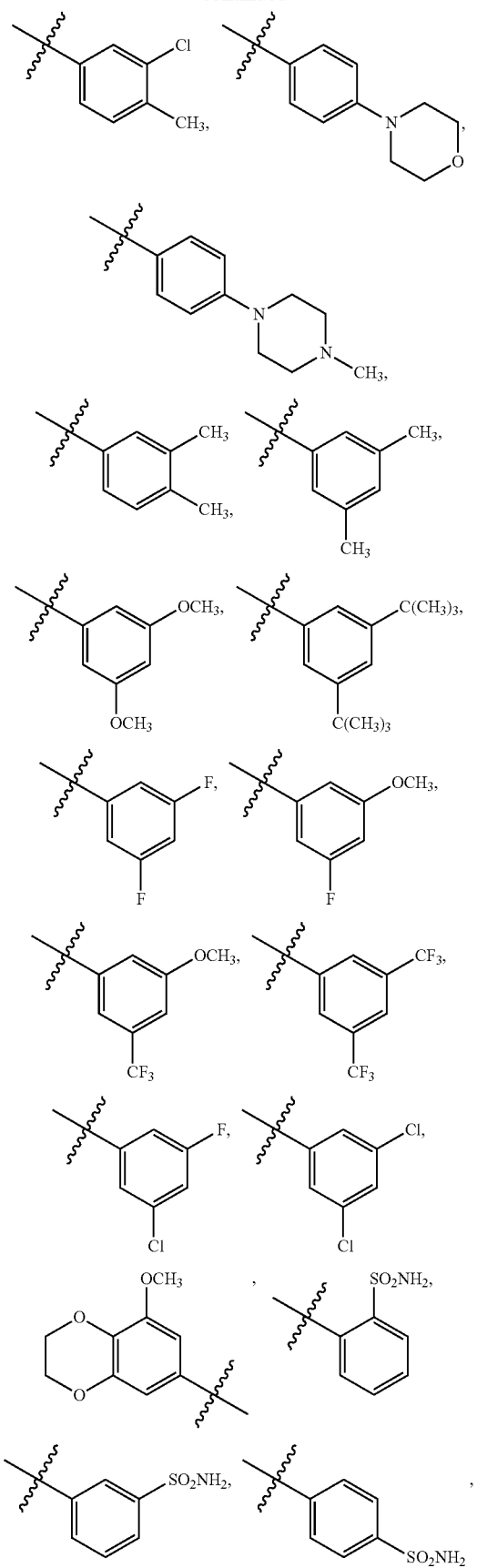
-continued
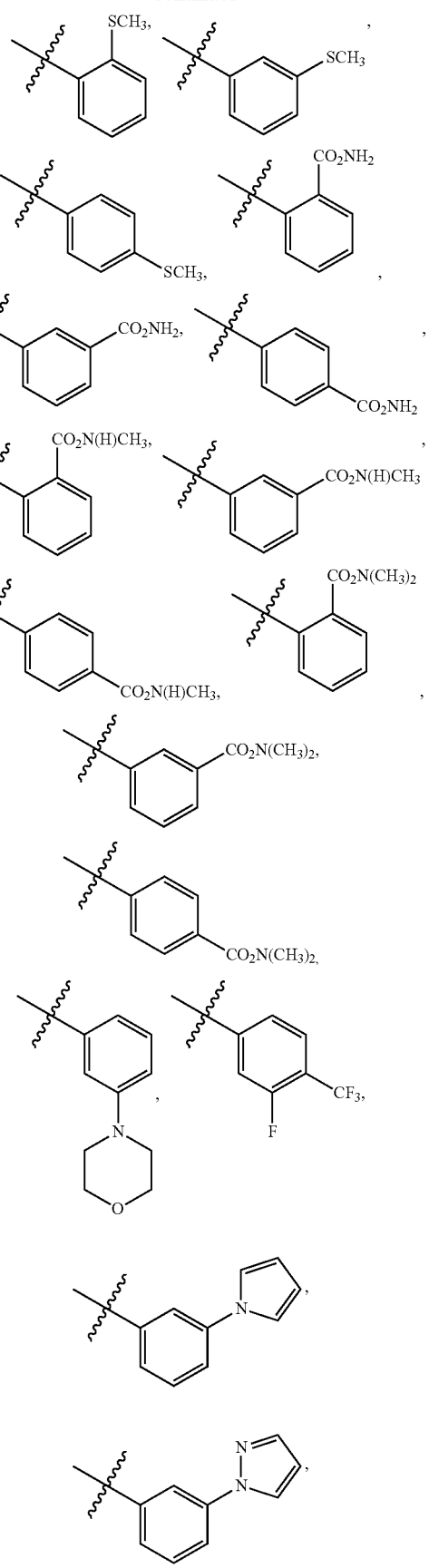

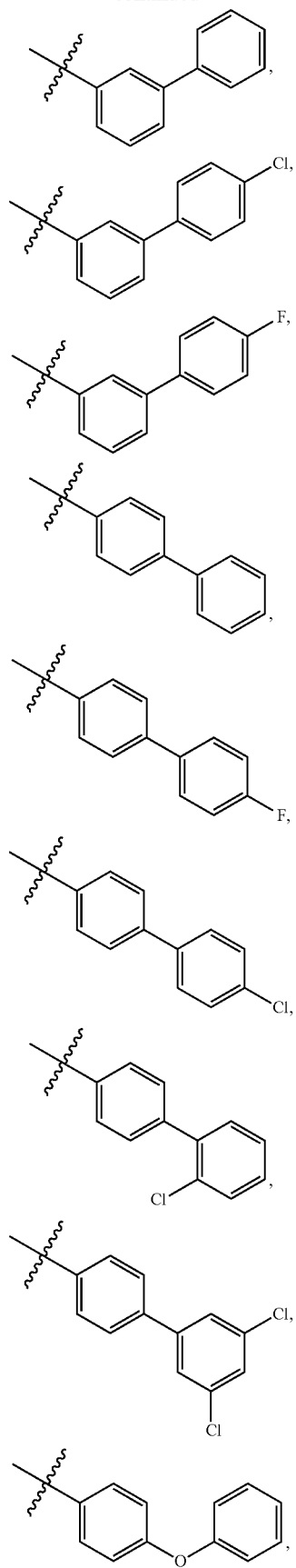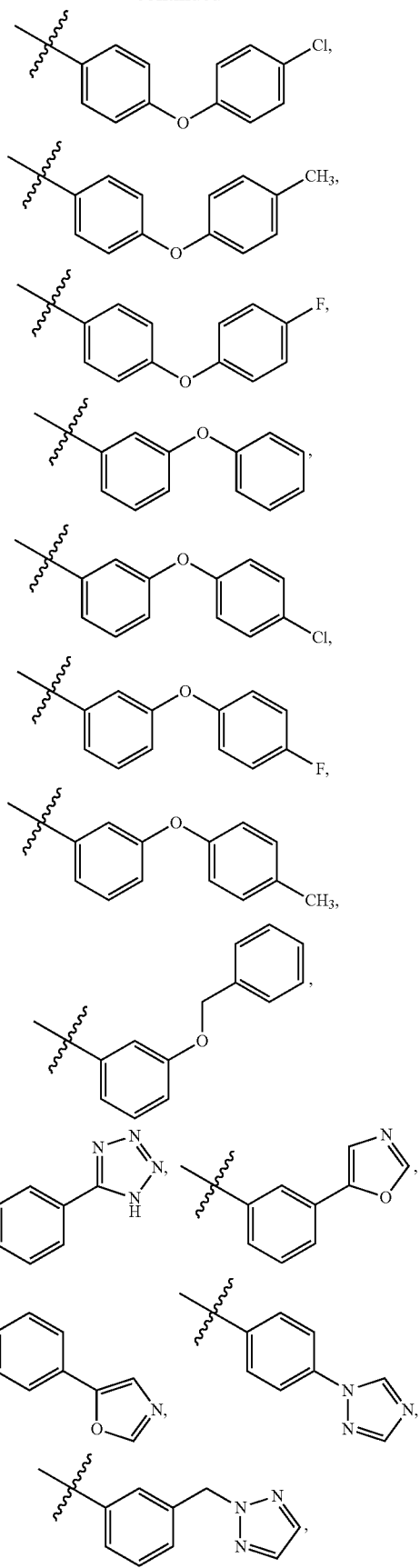

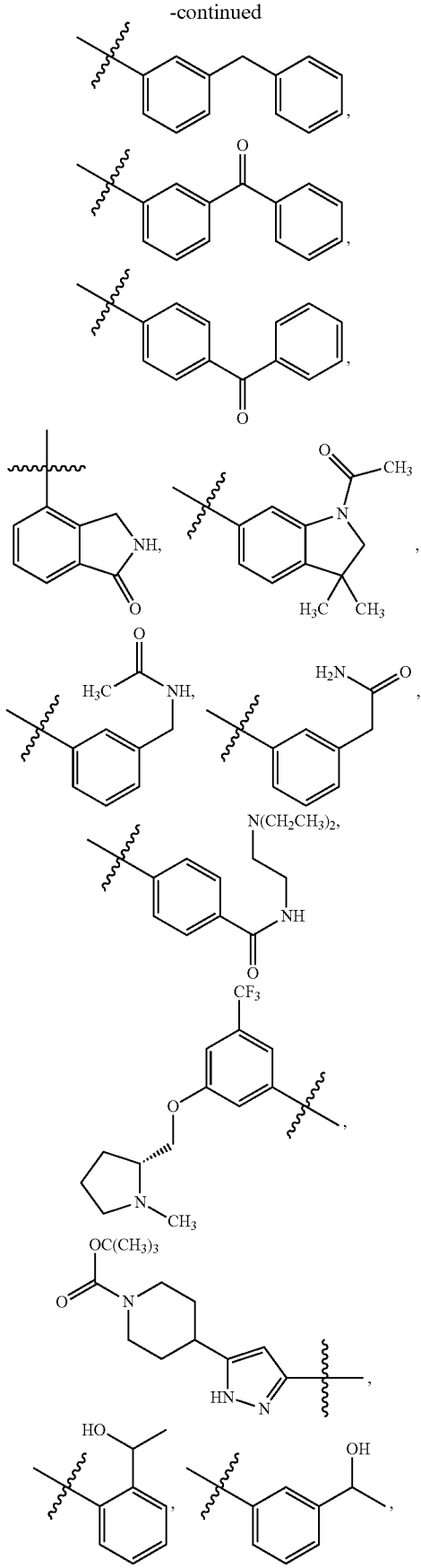

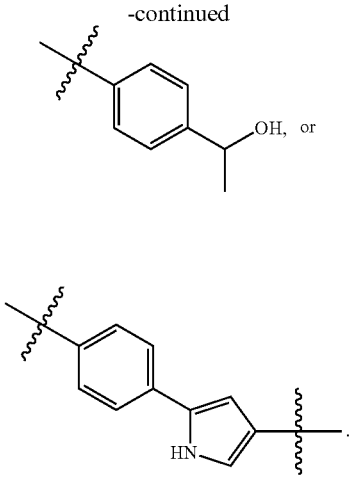

wherein the symbol ∼ when drawn through a bond indicates the point of attachment to the rest of the molecule.

In some embodiments, W is substituted with at least one substituent selected from —W', —O—W', N(H)—W', —O—CH2-W', or —C(=O)—W'.

In some embodiments, W is a phenyl substituted with at least one —O—($C_1$-$C_6$)alkyl group such as a —$OCH_3$, —$OCH_2CH_3$, —$OCH_2CH_2CH_3$, —$OCH_2CH_2CH_2CH_3$, —$OCH(CH_3)_2$, or —$OC(CH_3)_3$ group. In some such embodiments, W is a phenyl substituted with at least two —O—($C_1$-$C_6$)alkyl group which may be the same or different. In still further embodiments, W is a phenyl substituted with at least three —O—($C_1$-$C_6$)alkyl groups which may be the same or different.

In some embodiments, the compound is selected from

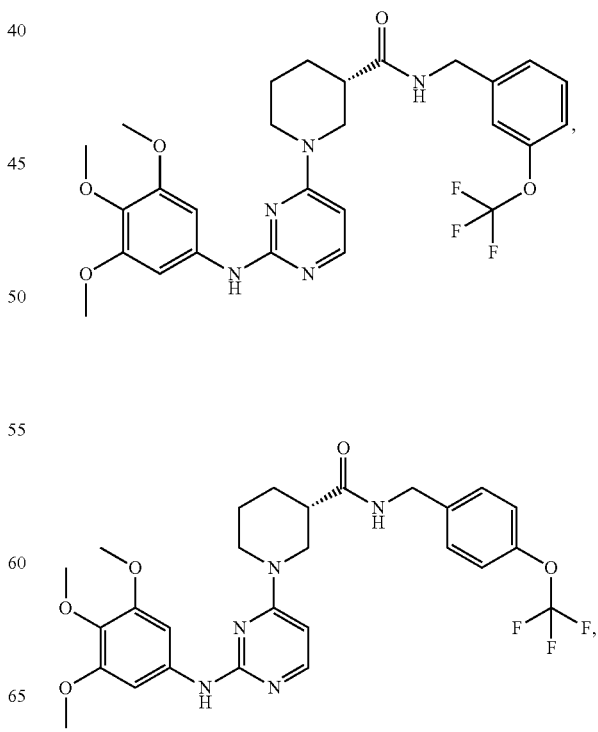

-continued

-continued

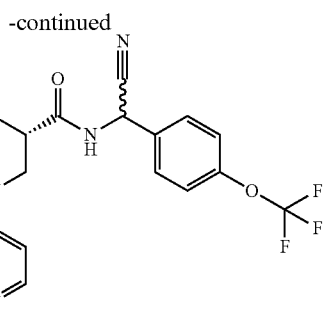

or a pharmaceutically acceptable salt thereof.

In some embodiments, the compound is a salt. Such salts may be anhydrous or associated with water as a hydrate.

In some embodiments, the compound is a prodrug.

Also provided are pharmaceutical formulations that include at least one pharmaceutically acceptable carrier, excipient or diluent and a therapeutically effective amount of the compound of any of the embodiments described herein. In some such embodiments, the compound is present in an amount effective for the treatment of cancer.

Further provided are pharmaceutical formulations that include at least one pharmaceutically acceptable carrier, and a therapeutically effective amount of the composition of matter of any of the embodiments described herein in combination with at least one additional compound such as a cytotoxic agent or a compound that inhibits another kinase.

In other embodiments, the invention provides a method of treating cancer. Such methods typically include administering to a subject an effective amount of a compound of any one of the embodiments or a pharmaceutical composition that includes any of the compounds of any of the embodiments. In some such embodiments, the subject has a cancer that expresses an ALK fusion protein, point mutation, or overexpression. In other such embodiments, the ALK fusion protein is EML4-ALK fusion protein or NPM-ALK fusion protein. In some embodiments, the subject is a human cancer patient, and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors. In some such embodiments, the cancer is non-small cell lung carcinoma (NSCLC). In some embodiments, the cancer is an EML4-ALK positive cancer or is a NPM-ALK positive cancer.

In still other embodiments, the invention provides a method of treating a condition where it is desired to inhibit ALK activity. Such methods typically include administering to a subject an effective amount of a compound of any of the embodiments or a pharmaceutical composition that includes a compound of any of the embodiments.

In some embodiments, the compound of any of the embodiments is used in the preparation of a medicament. In some such embodiments, the medicament is for use in treating cancer. In some such embodiments, a medicament is for use in inhibiting ALK. In still other such embodiments, the medicament is for use in treating a cancer that expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein.

In some such embodiments, a compound or pharmaceutical formulation of any of the embodiments is provided for use in treating cancer. In some such embodiments, the cancer expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein. In some embodiments, a compound or pharmaceutical formulation of any of the embodiments is provided for use in treating cancer and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors. In some such embodiments, the cancer is non-small cell lung carcinoma (NSCLC). In still other embodiments, a compound or pharmaceutical formulation of any of the embodiments is provided for use in inhibiting ALK or for use in treating a disease or condition wherein inhibition of ALK is desired.

Other objects, features and advantages of the invention will become apparent to those skilled in the art from the following description and claims.

DETAILED DESCRIPTION OF THE INVENTION

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or hetero aromatic rings bonded to one another are intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N.Y., 1962); and Wilen, S. H., Tables of Resolving Agents and Optical Resolutions p. 268 (E.L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula:

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as $(C_1$-$C_4)$alkyl esters. In other embodiments, the term "compound" encompasses the compound itself, pharmaceutically acceptable salts thereof, tautomers of the compound, pharmaceutically acceptable salts of the tautomers.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

"ALK" refers to anaplastic lymphoma kinase, tyrosine kinase. ALK was originally identified as part of the chimeric nucleophosmin-ALK protein in the t(2; 5) chromosomal rearrangement associated with anaplastic large cell lymphoma.

"EML4-ALK fusion protein" refers to a protein that results from a fusion of echinoderm microtubule-associated protein-like 4 (EML4) and ALK.

"NPM-ALK fusion protein" refers to a protein that results from a fusion of nucleophosmin (NPM) with ALK.

"Alkyl" refers to a saturated, branched, straight-chain, or cyclic monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises 1 to 20 carbon atoms. In some embodiments, alkyl groups include 1 to 6 carbon atoms whereas in other embodiments, alkyl groups include 1 to 4 carbon atoms. In still other embodiments, an alkyl group includes 1 or 2 carbon atoms. Cyclic and branched chain alkyl groups include at least 3 carbon atoms and typically include 3 to 7, or in some embodiments, 3 to 6 carbon atoms. An alkyl group having 1 to 6 carbon atoms may be referred to as a —$(C_1$-$C_6)$alkyl group and an alkyl group having 1 to 4 carbon atoms may be referred to as a —$(C_1$-$C_4)$alkyl.

"Alkenyl" refers to an unsaturated branched, straight-chain, or cyclic hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has 2 to 20 carbon atoms and in other embodiments, has 2 to 6 carbon atoms. An alkenyl group having 2 to 6 carbon atoms may be referred to as a —($C_2$-$C_6$) alkenyl group "Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group "Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O($C_{1-6}$) alkyl or as —O—($C_{1-6}$) alkyl groups. In some embodiments, an alkoxy group may include 1 to 4 carbon atoms and may be designated as an —O($C_{1-4}$) alkyl or as an —O—($C_{1-4}$) alkyl group.

"Alkylene" refers to a divalent saturated hydrocarbon group derived from a parent alkane by removal of two hydrogen atoms. Examples of alkylene group include, but are not limited to, —$CH_2$—, —$CH_2CH_2$—, —CH($CH_3$)—, —$CH_2CH_2CH_2$—, —$CH_2C(CH_3)(H)$—, and the like. In some embodiments an alkylene may include 1 to 6 carbon atoms and in other embodiments may include 1 to 4 carbon atoms. Such groups may be designated as —($C_1$-$C_6$)alkylene- and —($C_1$-$C_4$)alkylene- groups.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl groups may include fused ring systems where one ring is a carbocyclic aromatic ring and the other ring(s) are not aromatic and may be heterocyclic or carcocyclic. For example, aryl groups include systems where a carbocyclic aromatic ring is fused to a 5- to 7-membered heterocyclic ring containing 1 or more hetero atoms chosen from N, O, and S. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with a heterocyclic aromatic ring, the resulting ring system is heteroaryl, not aryl, as defined herein. Bicyclic and tricyclic aryl groups include at least one ring that is aromatic. The other rings in such systems may be partially unsaturated. For example, tetralin (1,2,3,4-tetrahydronaphthalene) includes a benzene ring fused to a ring that includes saturation and is therefore, partially saturated. Examples of other aryl groups with a partially saturated ring include, but are not limited to, indane, 1,4-dihydronaphthalene, chroman, 2,3-dihydrobenzo[b][1,4]dioxine, 1,2,3,4-tetrahydroquinoline, and indoline. The nonaromatic rings of such systems may also include a carbon that is double-bonded to an O. Examples of such aryl groups include, but are not limited to, 2-indanone, 1-indanone, 3,4-dihydronaphthalen-2(1H)-one, chroman-3-one, indolin-2-one, and 1,2-dihydroquinolin-3(4H)-one.

"Carbonyl" refers to the radical —C(O) or —C(=O) group.

"Carboxy" refers to the radical —C(O)OH.

"Cyano" refers to the radical —CN.

"Cycloalkyl" refers to a saturated or unsaturated, but non-aromatic, cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocyclic", "heterocyclo" or "heterocyclyl" refer to a saturated or unsaturated, but non-aromatic, cyclic hydrocarbon group in which one or more carbon atoms (and any associated hydrogen atoms) are independently replaced with the same or a different heteroatom and its associated hydrogen atoms, where appropriate. Typical heteroatoms to replace the carbon atom(s) include, but are not limited to, N, O, and S. In some embodiments, a heterocyclyl group includes 3 to 10 ring members of which 1, 2, or 3 ring members are independently selected from N, O, or S. In other embodiments, a heterocyclyl group includes 5 to 7 ring members of which 1, 2, or 3 are heteroatoms independently selected from N, O, or S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 10-membered aromatic, monocyclic and bicyclic rings containing one or more, for example, 1, 2, 3, or 4, or in certain embodiments, 1, 2, or 3, heteroatoms chosen from N, O, and S, with the remaining ring atoms being carbon. The term heteroaryl may also encompass tricyclic ring systems containing one or more, for example, 1, 2, 3, or 4, or in certain embodiments, 1, 2, or 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or to a carbocyclic aromatic ring or to a 5-7 membered heteroaromatic ring, and heteroaryl includes a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, carbazole, β-carboline, cinnoline, furan, imidazole, indazole, indole, indolizine, isobenzofuran, isochromene, isoindole, isoquinoline, isothiazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, benzimidazole, oxazole, tetrazole, and pyrazine.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides a compound of Formula I:

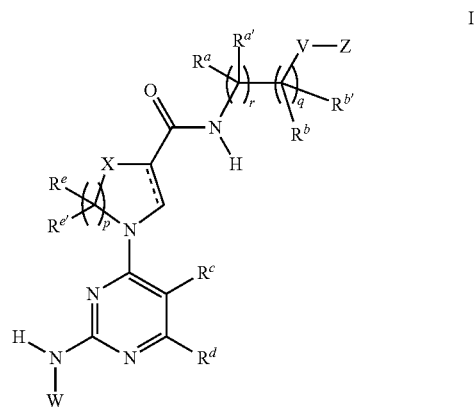

or a pharmaceutically acceptable salt thereof, a stereoisomer thereof, a pharmaceutically acceptable salt of the stereoisomer, or a mixture thereof, wherein:

X is selected from —$CH_2$—, —N(H)—, —O—, or —S—;

V is absent or is selected from —$CH_2$—, —O—, —S—, or —NH—; wherein if V is —O—, —S—, or —NH—, then r is 1 and q is 1;

the subscript p is selected from 0, 1, 2, or 3, wherein X is $CH_2$ if p is 0;

the subscript q is selected from 0 or 1;

the subscript r is selected from 0 or 1:

the ----- symbol indicates that the bond can be a single or double bond;

Z is a $C_6$-$C_{10}$ aryl or a 5-10 membered heteroaryl comprising 1, 2, 3, or 4 heteroatoms independently selected from O, S, or N, wherein the $C_6$-$C_{10}$ aryl or the 5-10 membered heteroaryl are unsubstituted or are optionally substituted with 1, 2, 3, or 4 substituents independently selected from —Z', —O—Z', —S—Z', —NH—Z', —$CH_2$Z'—F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —C(=O)NH—Z', —$SO_2NH_2$, —$SO_2$NH(($C_1$-$C_4$)alkyl), —$SO_2$N(($C_1$-$C_4$)alkyl)$_2$, —$SO_2$NH—Z', —$NHSO_2$—($C_1$-$C_4$)alkyl, —$NHSO_2$—Z', —NHC(=O)—($C_1$-$C_4$)alkyl, —NHC(=O)—Z', —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—Z', —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered heteroaryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to V, if present, or to the C atom bearing $R^b$ and $R^{b'}$ if V is not present, or to the C atom bearing $R^a$ and $R^{a'}$ if V is not present and q is 0, or to the N atom bonded to the C(=O) if V is not present, q is 0, and r is 0; and further wherein, the partially saturated ring of a bicyclic $C_6$-$C_{10}$ aryl or a bicyclic 5-10 membered heteroaryl may include a —C(=O)— ring member;

Z' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

$R^a$ and $R^{a'}$ are absent if r is 0 or are independently selected from —H, —($C_1$-$C_6$)alkyl, —C≡N, —OH, or —$CF_3$; or $R^a$ and $R^{a'}$ may together represent a =O; or $R^a$ and $R^{a'}$ may join together with the carbon atom to which they are attached to form a cycloalkyl ring having from 3 to 6 members;

$R^b$ and $R^{b'}$ are absent if q is 0 or are independently selected from —H, —($C_1$-$C_6$)alkyl, —C≡N, —OH, or —$CF_3$; or $R^b$ and $R^{b'}$ may together represent a =O; or $R^b$ and $R^{b'}$ may join together with the carbon atom to which they are attached to form a cycloalkyl ring having from 3 to 6 members;

$R^c$ is selected from —H, —($C_1$-$C_6$)alkyl, —$CF_3$, —F, —Cl, —Br, or —I;

$R^d$ is selected from —H, —($C_1$-$C_6$)alkyl, —$CF_3$, —F, —Cl, —Br, or —I;

$R^e$ and $R^{e'}$ are independently selected from —H or —($C_1$-$C_6$)alkyl;

W is a $C_6$-$C_{10}$ aryl, a 5-10 membered heteroaryl comprising 1, 2, 3 or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1, 2, 3, or 4 substituents independently selected from —W', —O—W', —S—W', —N(H)—W', —O—CH2-W', —C(=O)—W', —C(=O)NH—W', —$SO_2$NH—W', —$NHSO_2$—W', —NHC(=O)—W', —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered heteroaryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to the N atom to which W is attached; and further wherein, the partially saturated ring of a bicyclic $C_6$-$C_{10}$ aryl or a bicyclic 5-10 membered heteroaryl may include a —C(=O)— ring member and the 5-7 membered heterocyclyl group may include a —C(=O)— ring member; and W' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC (=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2H$, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$.

In some embodiments of the compound of Formula I or the pharmaceutically acceptable salt thereof, stereoisomer thereof, pharmaceutically acceptable salt of the stereoisomer, or the mixture thereof, X is selected from —$CH_2$—, —N(H)—, —O—, or —S—;

V is absent or is selected from —$CH_2$—, —O— or —S—; wherein if V is —O—, —S—, then r is 1 and q is 1 the subscript p is selected from 0, 1, 2, or 3, wherein X is $CH_2$ if p is 0;

the subscript q is selected from 0 or 1;

the subscript r is selected from 0 or 1:

the ----- symbol indicates that the bond can be a single or double bond;

Z is a $C_6$-$C_{10}$ aryl or a 5-10 membered heteroaryl comprising 1, 2, 3 or 4 heteroatoms independently selected from O, S, or N, wherein the $C_6$-$C_{10}$ aryl or the 5-10 membered heteroaryl are unsubstituted or are optionally substituted with 1, 2, 3, or 4 substituents independently selected from —Z', —OZ', —$CH_2$Z', —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2H$, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, ($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered hetero aryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to V, if present, or to the C atom bearing $R^b$ and $R^{b'}$ if V is not present, or to the C atom bearing $R^a$ and $R^{a'}$ if V is not present and q is 0, or to the N atom bonded to the C(=O) if V is not present, q is 0, and r is 0; and further wherein, the partially saturated ring of a bicyclic $C_6$-$C_{10}$ aryl or a bicyclic 5-10 membered heteroaryl may include a —C(=O)— ring member;

Z' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2H$, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$;

$R^a$ and $R^{a'}$ are absent if r is 0 or are independently selected from —H, —($C_1$-$C_6$)alkyl, —C≡N, —OH, or —$CF_3$; or $R^a$ and $R^{a'}$ may together represent a =O;

$R^b$ and $R^{b'}$ are absent if q is 0 or are independently selected from —H, —($C_1$-$C_6$)alkyl, —C≡N, —OH, or —$CF_3$; or $R^b$ and $R^{b'}$ may together represent a =O;

$R^c$ is selected from —H, —($C_1$-$C_6$)alkyl, —$CF_3$, —F, —Cl, —Br, or —I;

$R^d$ is selected from —H, —($C_1$-$C_6$)alkyl, —$CF_3$, —F, —Cl, —Br, or —I;

$R^e$ and $R^{e'}$ are independently selected from —H or —($C_1$-$C_6$)alkyl;

W is a $C_6$-$C_{10}$ aryl, a 5-10 membered heteroaryl comprising 1, 2, 3 or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1, 2, 3, or 4 substituents independently selected from —W', —O—W', —$CH_2$—W', N(H)—W', —O—CH2-W', —C(=O)—W', —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2H$, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered hetero aryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to the N atom to which W is attached; and further wherein, the partially saturated ring of a bicyclic $C_6$-$C_{10}$ aryl or a bicyclic 5-10 membered heteroaryl may include a —C(=O)— ring member and the 5-7 membered heterocyclyl group may include a —C(=O)— ring member; and W' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)NH$_2$, —C(=O)NH((C$_1$-C$_4$)alkyl), —C(=O)N ((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$.

In some embodiments, p is 2. In other embodiments, p is 1. In still further embodiments, p is 3.

In some embodiments, r is 1. In some such embodiments, r is 1 and q is 1. In other such embodiments, r is 1 and q is 0. In other embodiments, r is 0.

In some embodiments, V is absent. In other embodiments, V is —CH$_2$—. In still other embodiments, V is —O—.

In some embodiments, X is —CH$_2$—. In still other embodiments, X is —O—. In still other embodiments, X is —S—. In still further embodiments, X is —N(H)—.

In some embodiments, q is 0. In still other embodiments, q is 1. In some embodiments where q is 1, R$^b$ and R$^{b'}$ are independently selected from —H, —CH$_3$, or R$^b$ and R$^{b'}$, when taken together, represent a =O. In some such embodiments, R$^b$ and R$^{b'}$ are both —H. In other embodiments where q is 1, R$^b$ and R$^{b'}$ join together with the carbon atom to which they are attached to form a cyclopropyl, cyclobutyl, cyclopentyl, or cyclohexyl ring. In some such embodiments, R$^b$ and R$^{b'}$ join together with the carbon atom to which they are attached to form a cyclopropyl ring.

In some embodiments, the compound of Formula I is a compound of Formula IA:

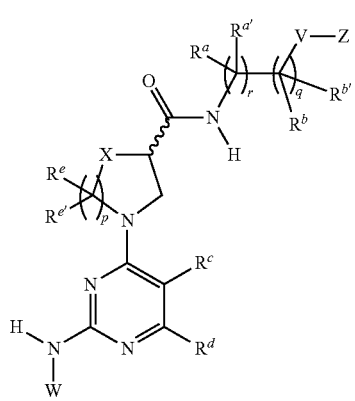

IA or a pharmaceutically acceptable salt thereof, a stereoisomer thereof, a pharmaceutically acceptable salt of the stereoisomer, or a mixture thereof, wherein the symbol ∿ indicates that the chiral carbon atom to which the ∿ is attached may have the R stereochemistry, the S stereochemistry, or may be a mixture of compounds with the R and S stereochemistry wherein the mixture may be racemic, or the mixture may include a greater amount of compounds with the R stereochemistry compared to the amount of compounds with the S stereochemistry, or the mixture may include a greater amount of compounds with the S stereochemistry compared to the amount of compounds with the R stereochemistry. In such embodiments, the variables have the same meaning as in any of the embodiments of the compounds of formula I.

In some embodiments, the compound of Formula I is a compound of Formula IB:

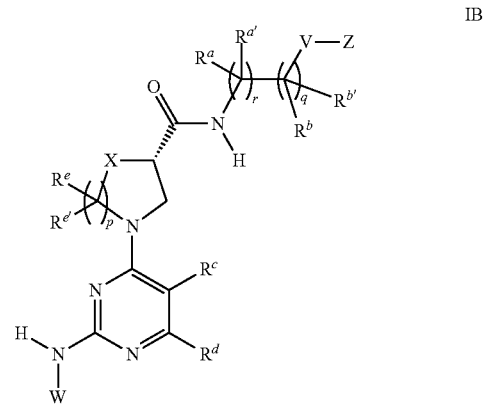

IB or a pharmaceutically acceptable salt thereof.

In some embodiments, the compound of Formula I is a compound of Formula IC:

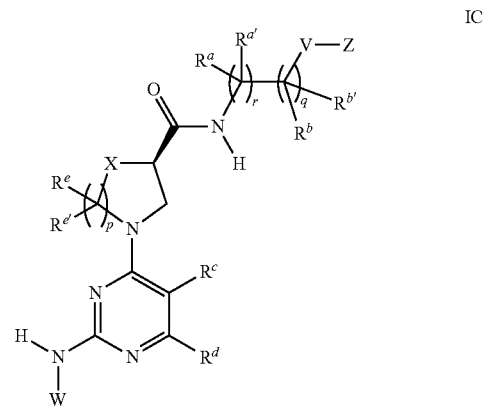

IC or a pharmaceutically acceptable salt thereof.

In some embodiments, the compound of Formula I is a compound of Formula II:

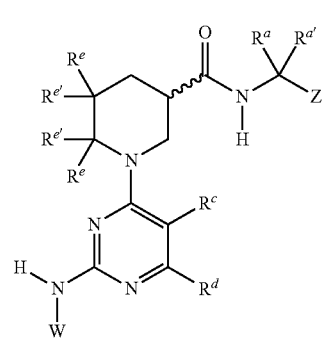

II or a pharmaceutically acceptable salt thereof, a stereoisomer thereof, a pharmaceutically acceptable salt of the stereoisomer, or a mixture thereof, wherein the symbol ∿ indicates that the chiral carbon atom to which the ~~~ is attached may have the R stereochemistry, the S stereochemistry, or may be a mixture of compounds with the R and S stereochemistry wherein the mixture may be racemic, or the mixture may include a greater amount of compounds with the R stereochemistry compared to the amount of compounds with the S stereochemistry, or the mixture may include a greater amount of compounds with the S stereochemistry compared to the amount of compounds with the R stereochemistry.

In some embodiments, the compound of Formula II is a compound of Formula IIA:

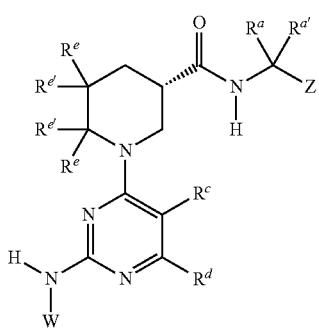

or a pharmaceutically acceptable salt thereof.

In some embodiments, the compound of Formula II is a compound of Formula IIB:

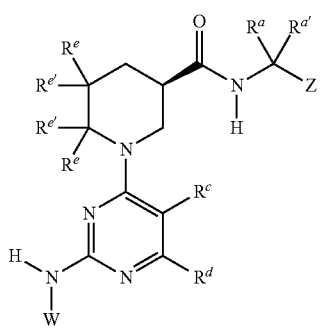

or a pharmaceutically acceptable salt thereof.

In some embodiments, $R^e$ and $R^{e'}$ are independently selected from —H or —CH$_3$. In some such embodiments, $R^e$ and $R^{e'}$ are both —H.

In some embodiments, $R^a$ and $R^{a'}$ are independently selected from —H or —CH$_3$. In some such embodiments, $R^a$ and $R^{a'}$ are both —H.

In some embodiments, $R^a$ and $R^{a'}$ join together with the carbon atom to which they are attached to form a cyclopropyl, butyl, cyclopentyl, or cyclohexyl ring. In some such embodiments, $R^a$ and $R^{a'}$ join together with the carbon atom to which they are attached to a cyclopropyl ring.

In some embodiments, $R^c$ is selected from —H or —CH$_3$. In some such embodiments, $R^c$ is —H.

In some embodiments, $R^d$ is selected from —H or —CH$_3$. In some such embodiments, $R^d$ is —H.

In some embodiments, Z is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, quinolinyl, isoquinolinyl, 1,2,3,4,4a,8a-hexahydroquinolinyl, 2,3-dihydrobenzo[b][1,4]dioxinyl, pyridazinyl, pyrazinyl, indazolyl, isothiazolyl, or oxazolyl.

In some embodiments, Z is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, quinolinyl, isoquinolinyl, 1,2,3,4,4a,8a-hexahydroquinolinyl, or 2,3-dihydrobenzo[b][1,4]dioxinyl. In some such embodiments, Z is an unsubstituted or substituted phenyl. In still other such embodiments, Z is selected from

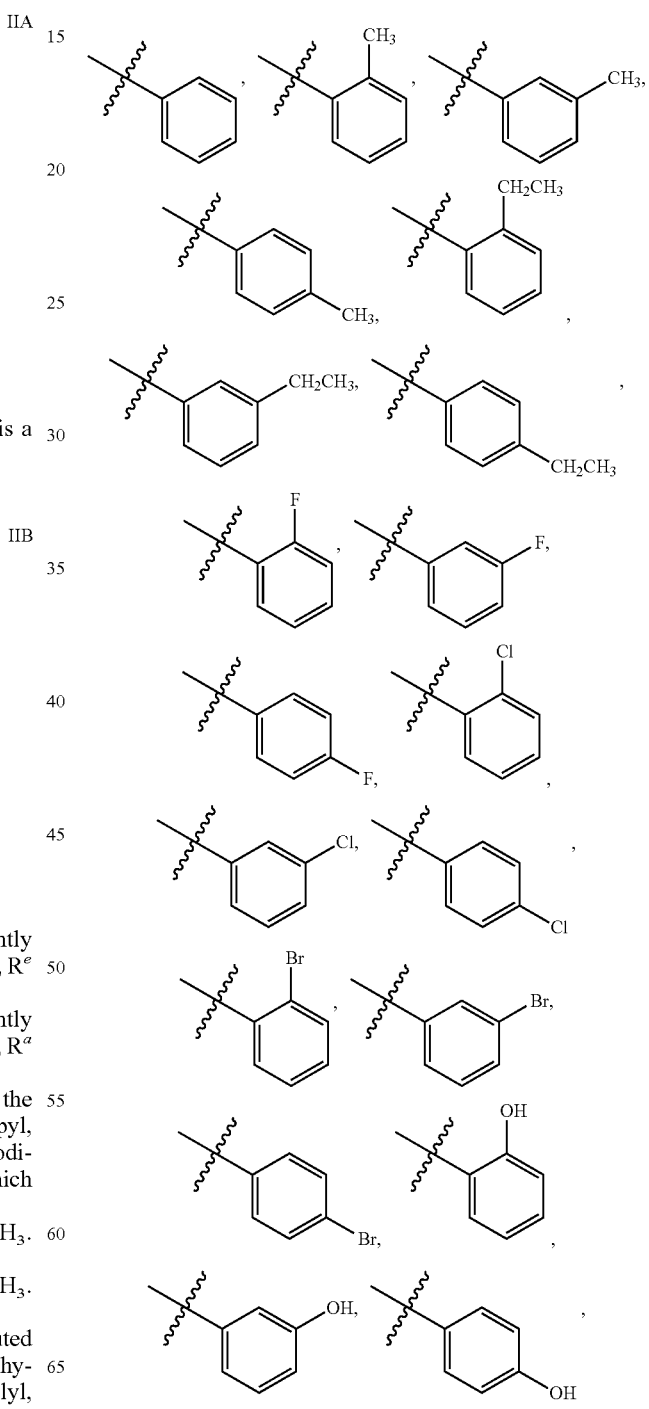

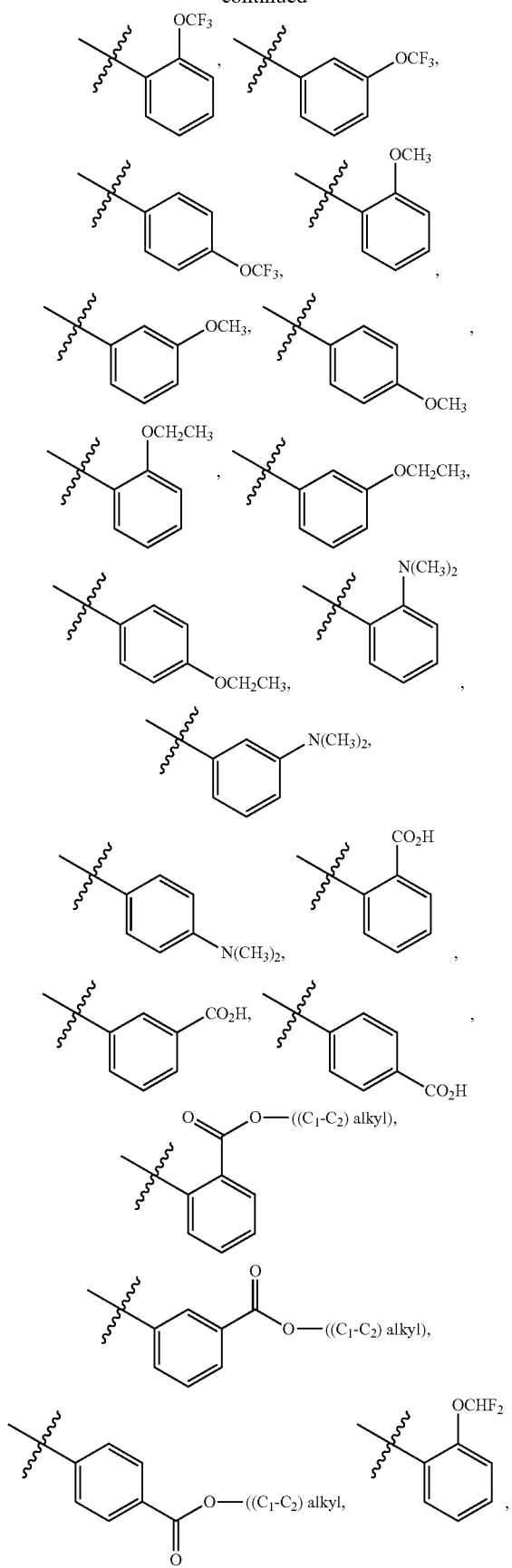
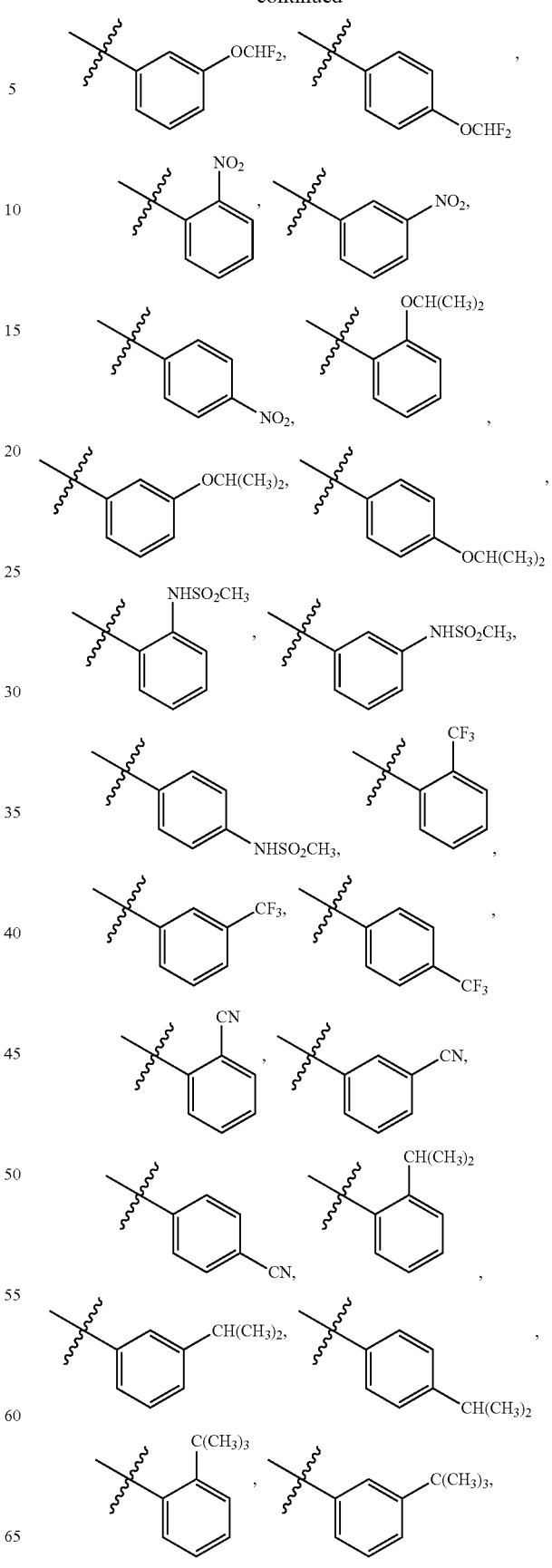

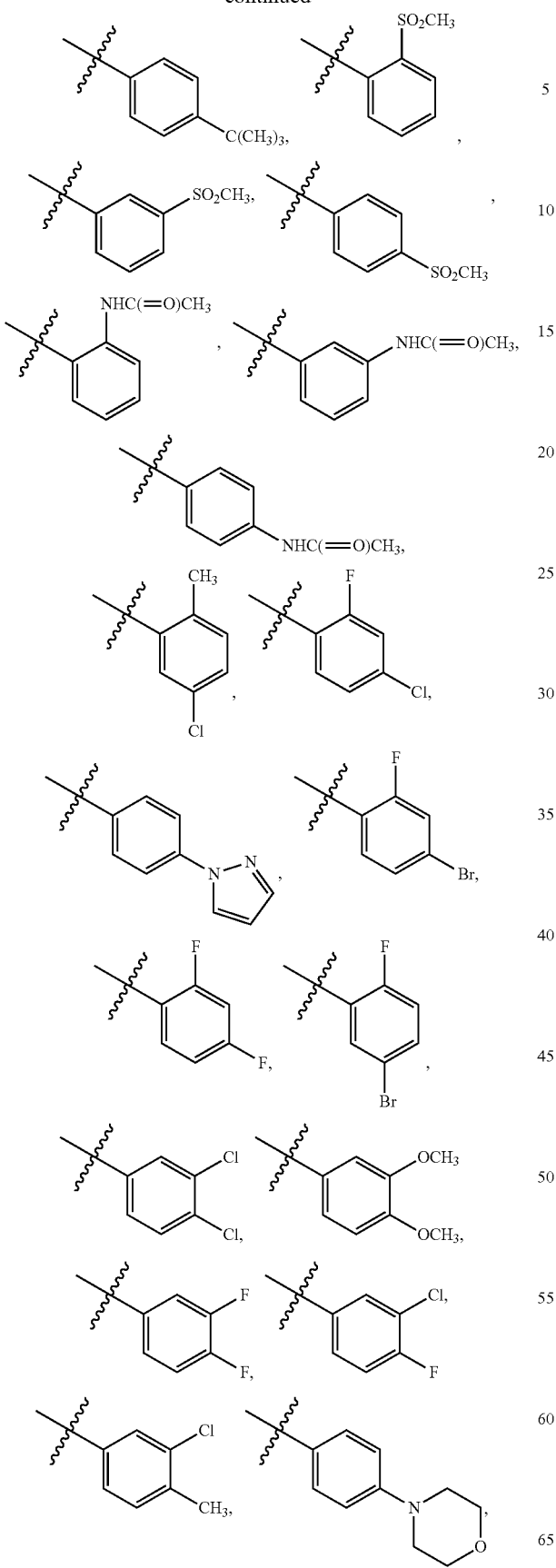
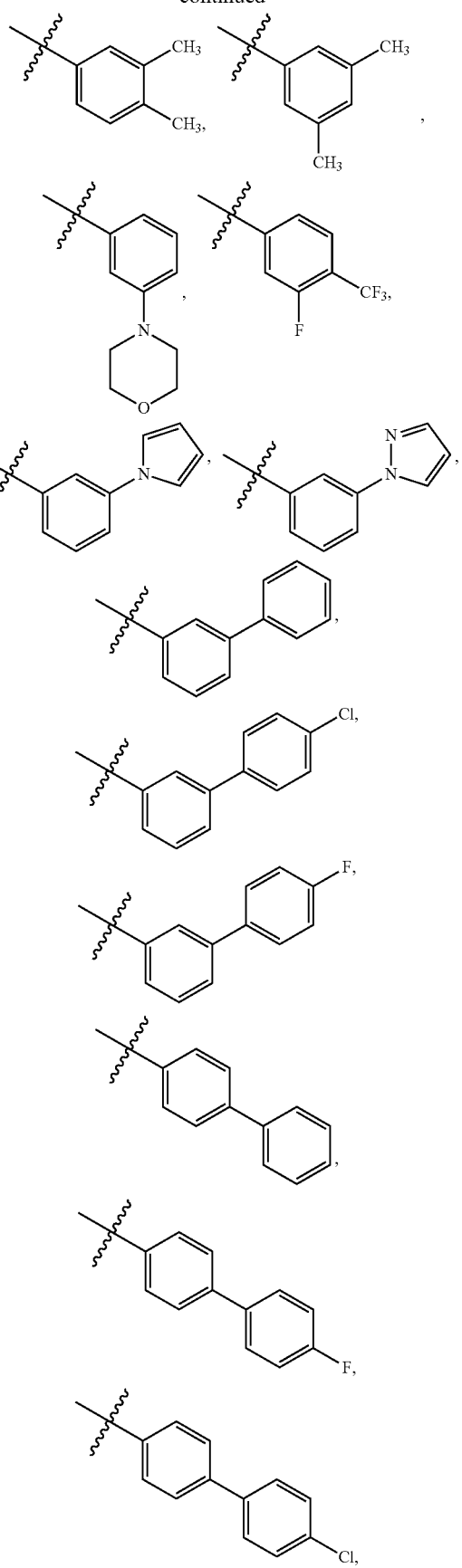

-continued

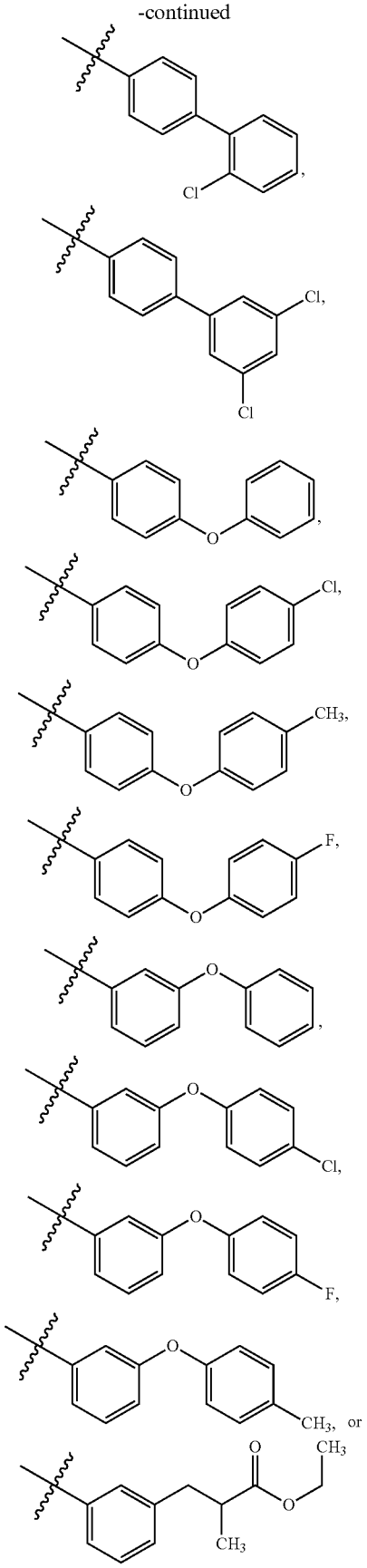

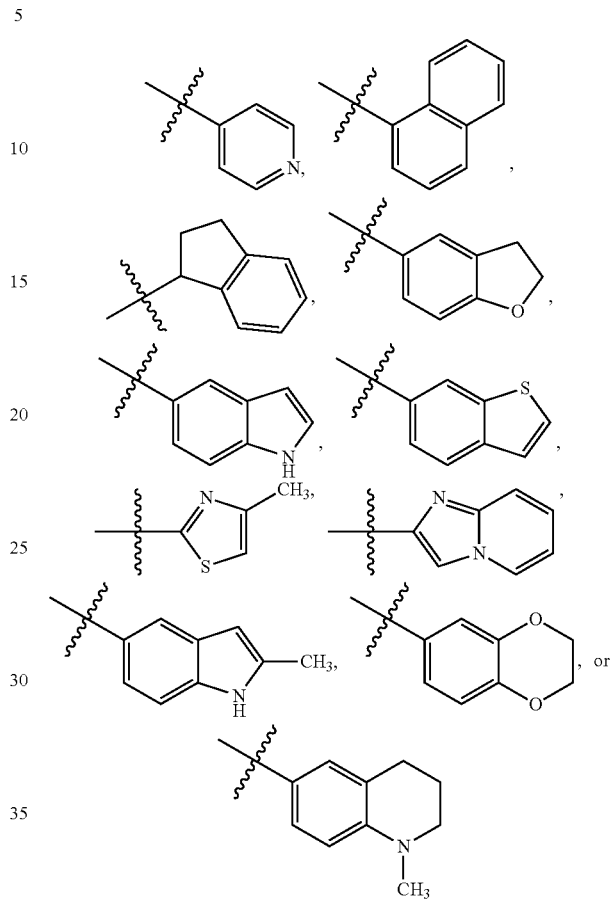

wherein the symbol ∿ when drawn through a bond indicates the point of attachment to the rest of the molecule.

In some embodiments, Z is selected from wherein the symbol ∿ when drawn through a bond indicates the point of attachment to the rest of the molecule.

In some embodiments, Z is substituted with at least one substituent selected from —Z' or —OZ'. In some such embodiments, Z is phenyl and Z' is an optionally substituted phenyl.

In some embodiments, W is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, isoindolin-1-onyl, indolinyl, pyrazolyl, pyridinonyl, quinolinyl, isoquinolinyl, 1,2,3,4,4a,8a-hexahydroquinolinyl, 2,3-dihydrobenzo[b][1,4]dioxinyl, pyridazinyl, pyrazinyl, indazolyl, isothiazolyl, or oxazolyl In some embodiments, W is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, isoindolin-1-onyl, indolinyl, pyrazolyl, pyridinonyl, quinolinyl, isoquinolinyl, 1,2,3,4,4a,8a-hexahydroquinolinyl, or 2,3-dihydrobenzo[b][1,4]dioxinyl.

In some embodiments, W is an unsubstituted or substituted phenyl, pyridyl, indolyl, isoindolin-1-onyl, indolinyl, pyrazolyl, pyridinonyl, quinolinyl, isoquinolinyl, or 2,3-dihydrobenzo[b][1,4]dioxinyl. In some such embodiments, W is an unsubstituted or substituted phenyl.

In some embodiments, W is selected from
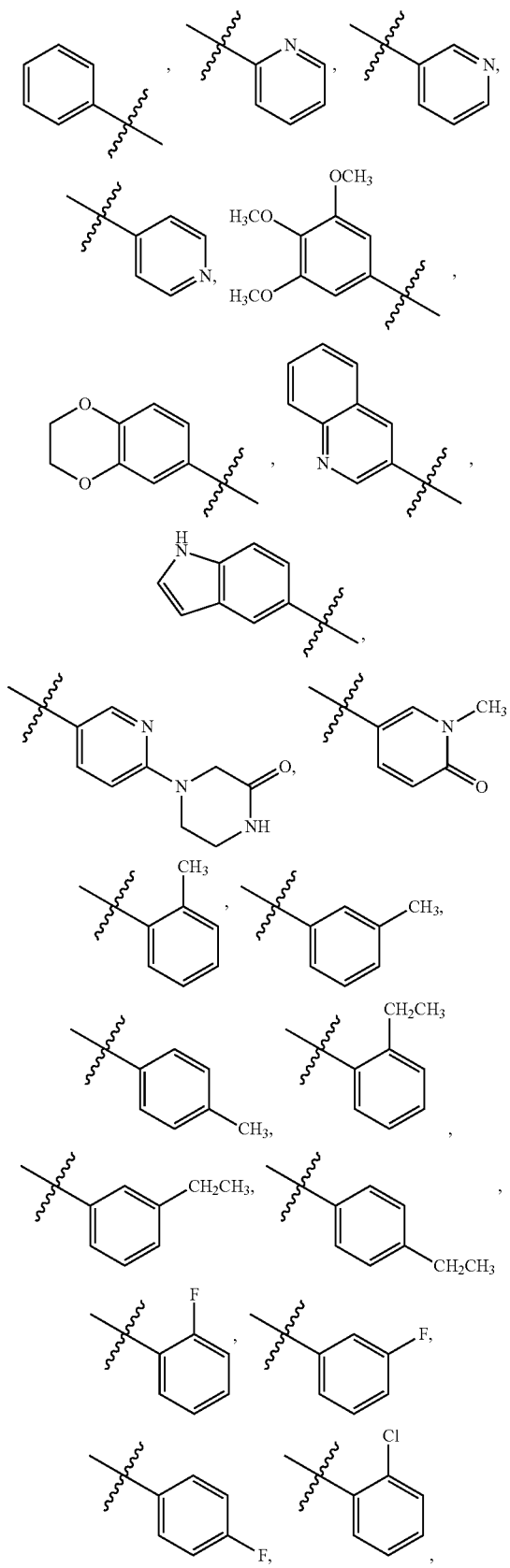
-continued
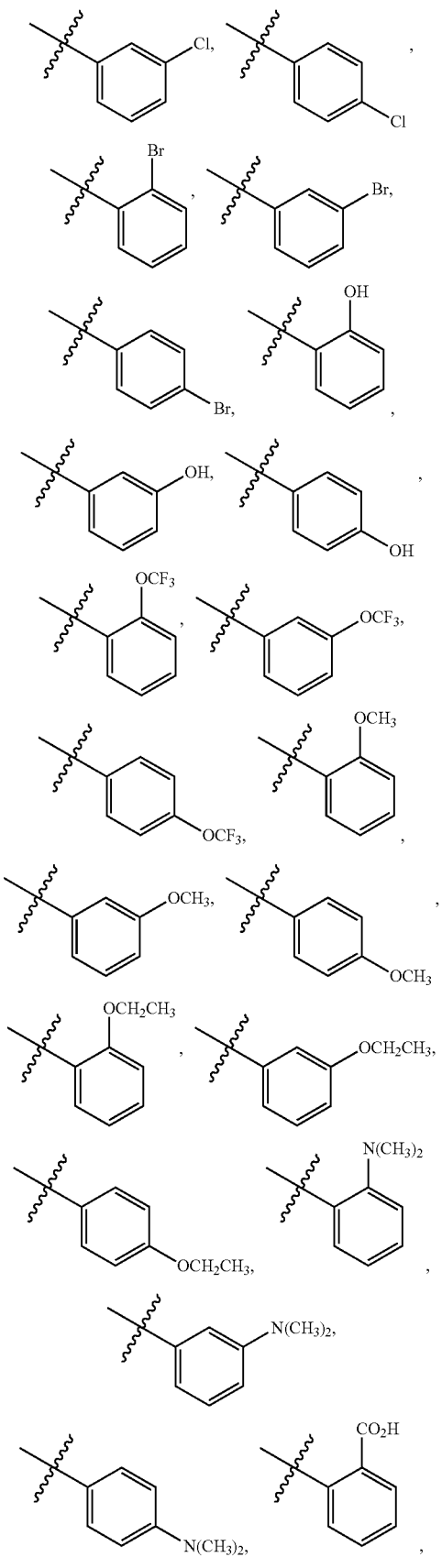

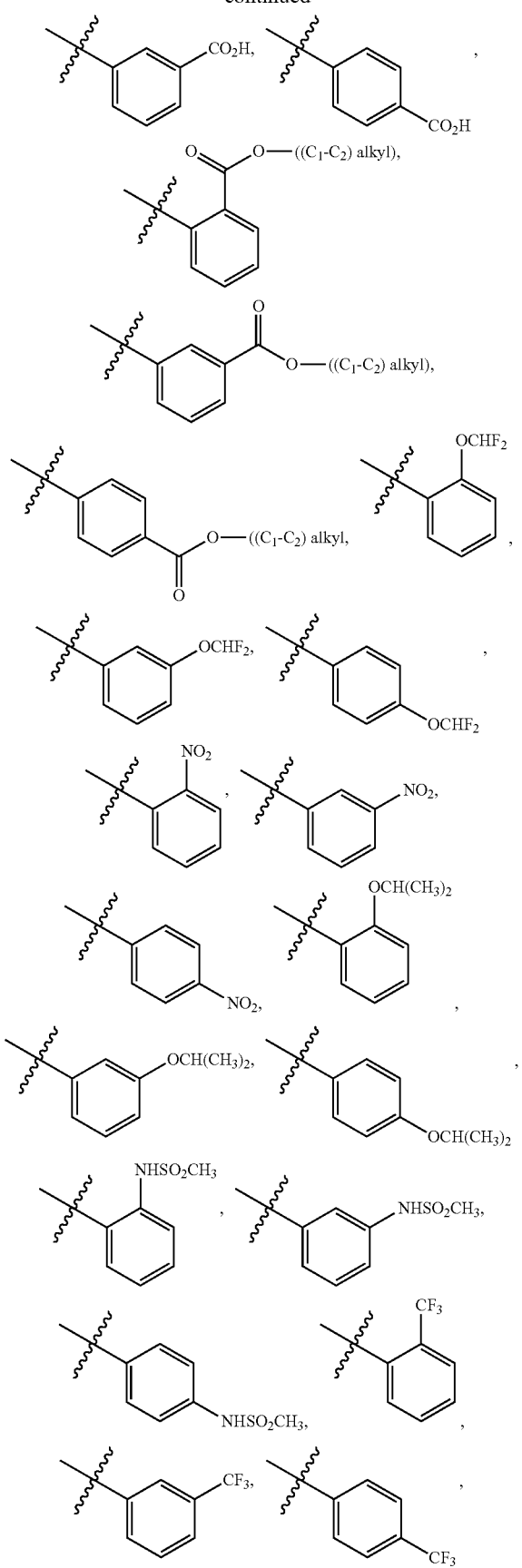
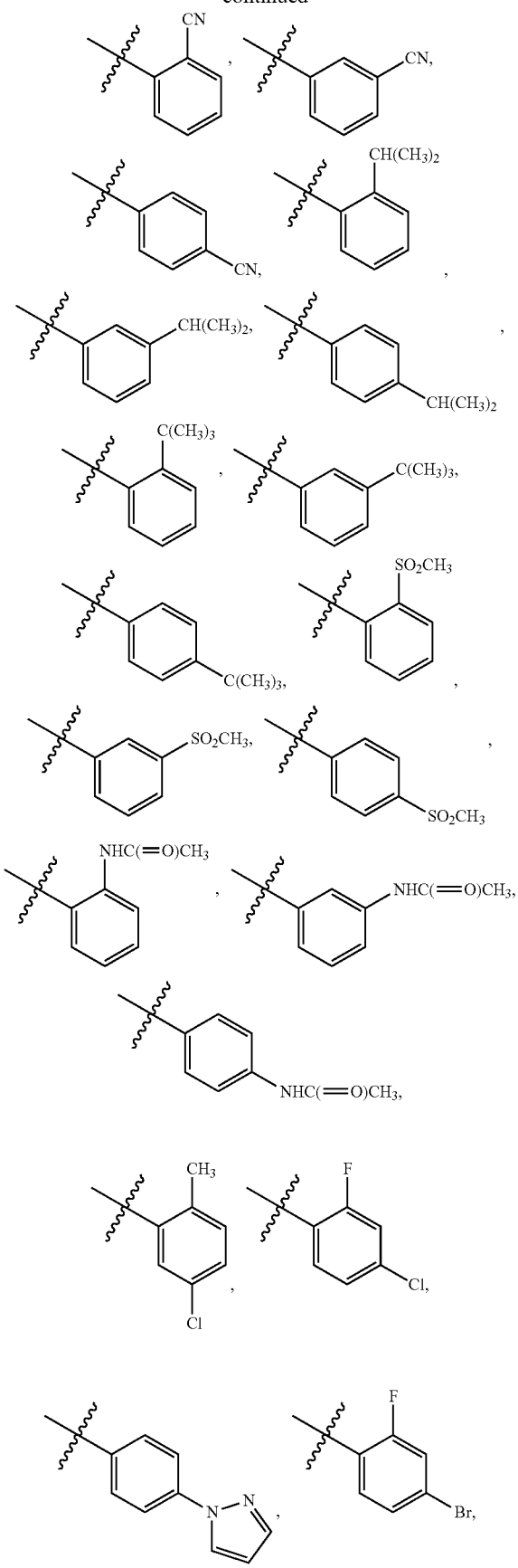

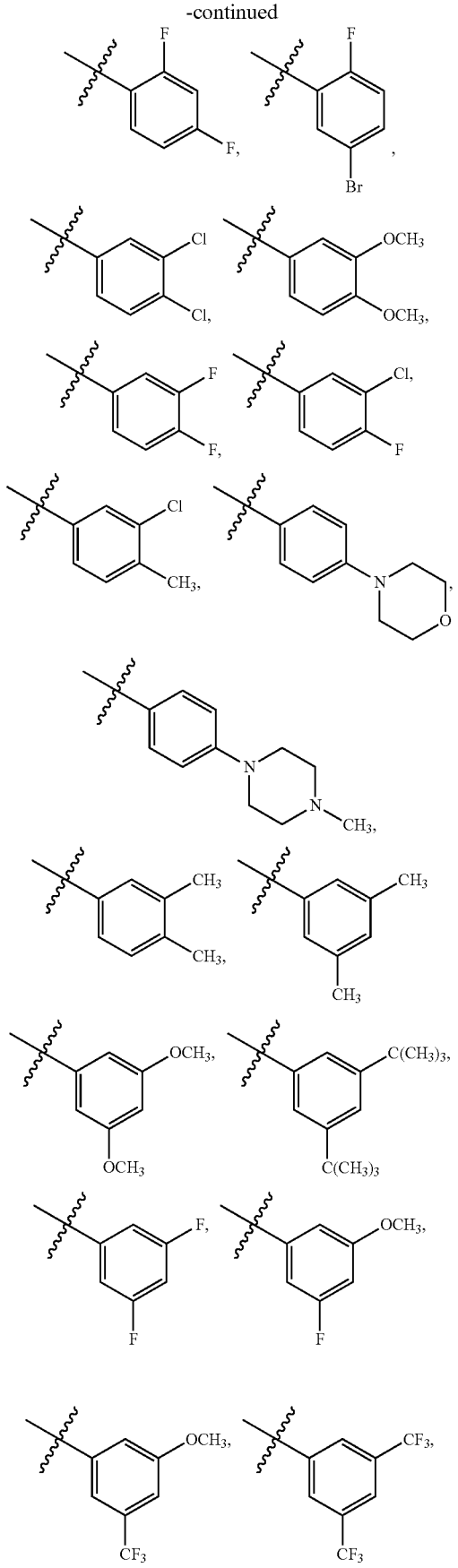
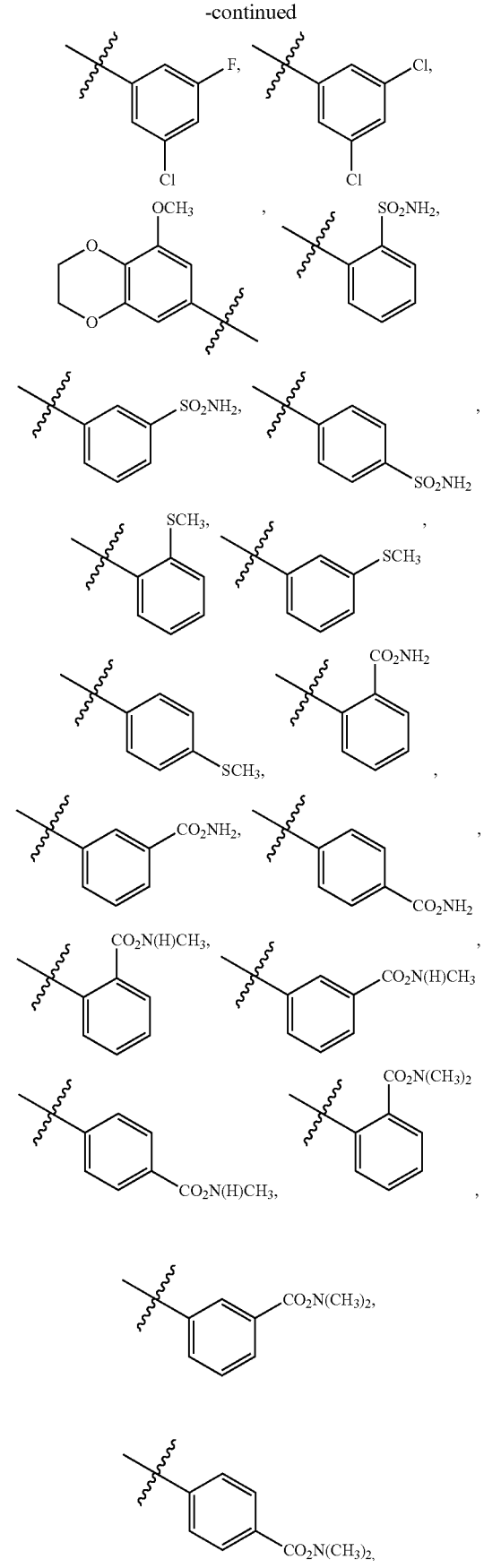

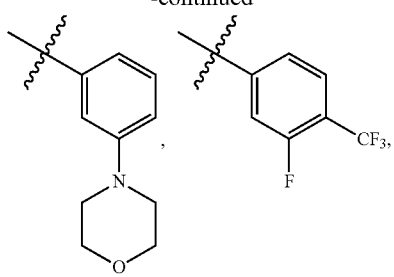
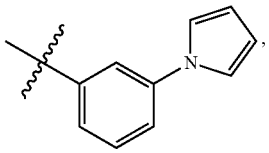
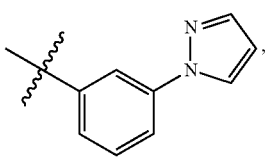
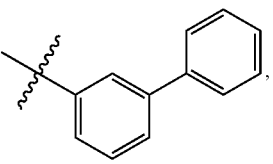
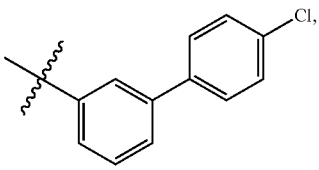
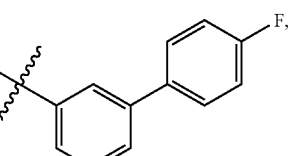
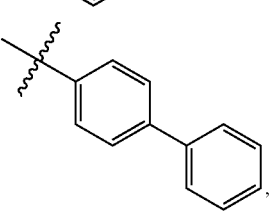
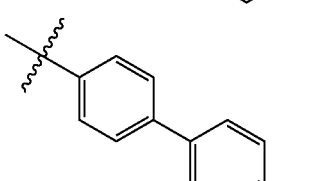
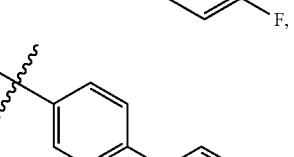
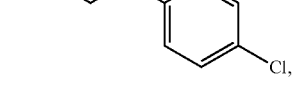
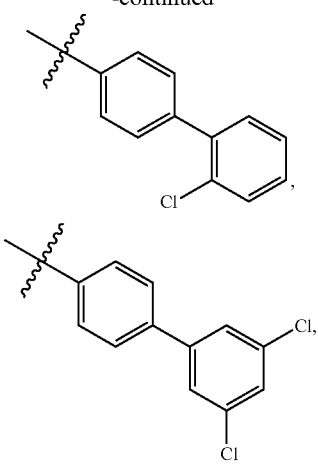
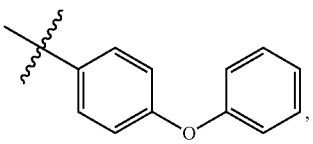
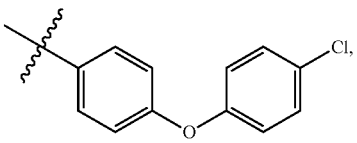
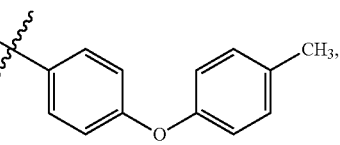
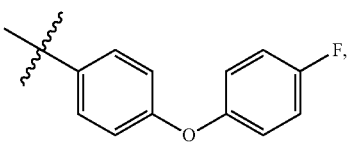
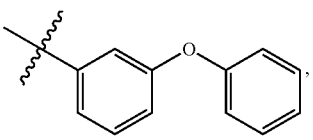
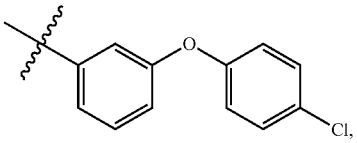
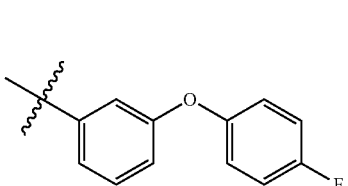
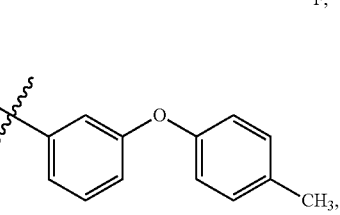

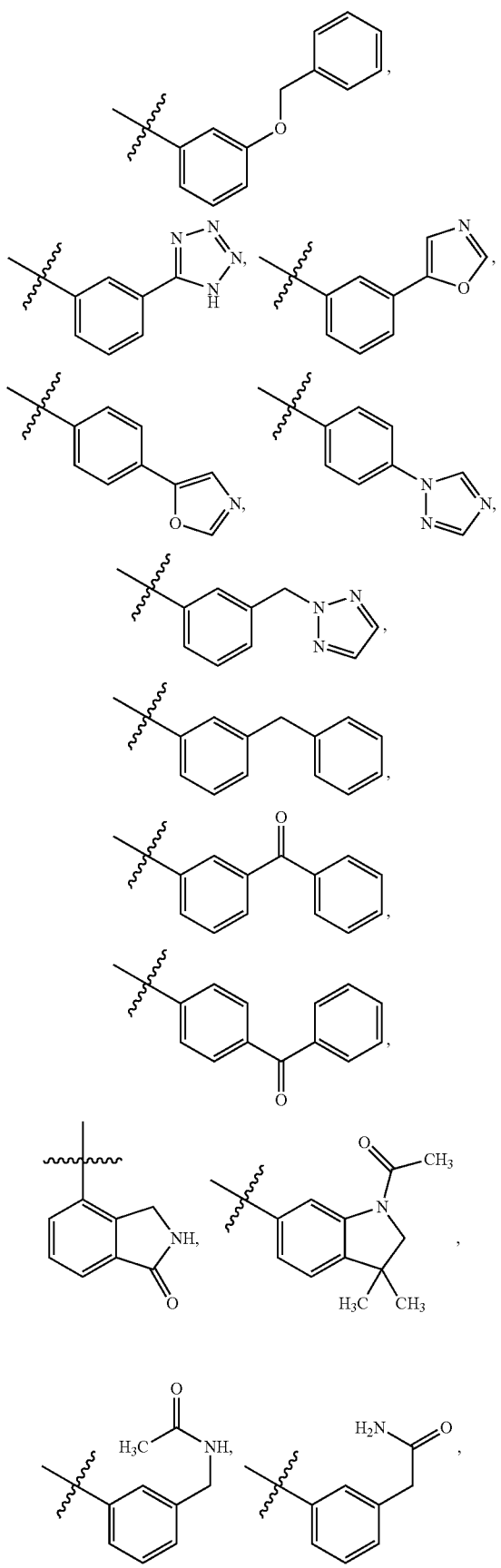

wherein the symbol ∿∿∿ when drawn through a bond indicates the point of attachment to the rest of the molecule.

In some embodiments, W is substituted with at least one substituent selected from —W', —O—W', N(H)—W', —O—CH2-W', or —C(=O)—W'.

In some embodiments, W is a phenyl substituted with at least one —O—($C_1$-$C_6$)alkyl group such as a —$OCH_3$, —$OCH_2CH_3$, —$OCH_2CH_2CH_3$, —$OCH_2CH_2CH_2CH_3$, —$OCH(CH_3)_2$, or —$OC(CH_3)_3$ group. In some such embodiments, W is a phenyl substituted with at least two —O—($C_1$-$C_6$)alkyl group which may be the same or different. In still further embodiments, W is a phenyl substituted with at least three —O—($C_1$-$C_6$)alkyl groups which may be the same or different.

In some embodiments, the compound is selected from
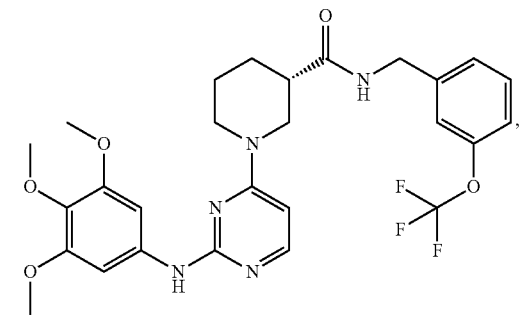
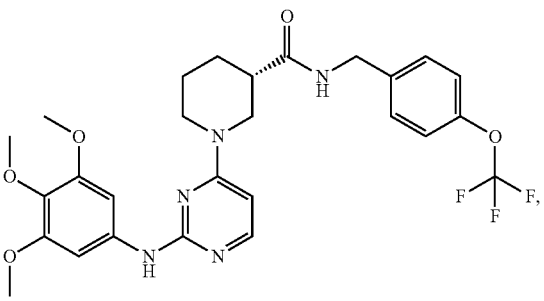
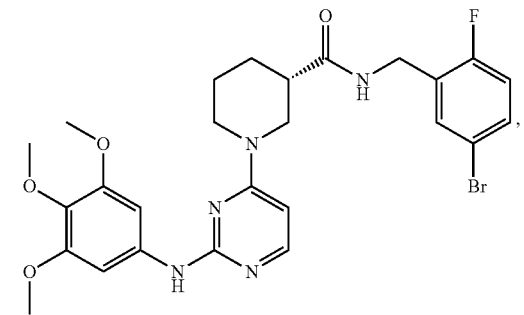
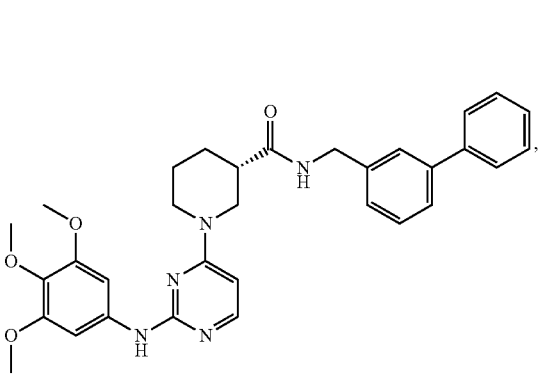
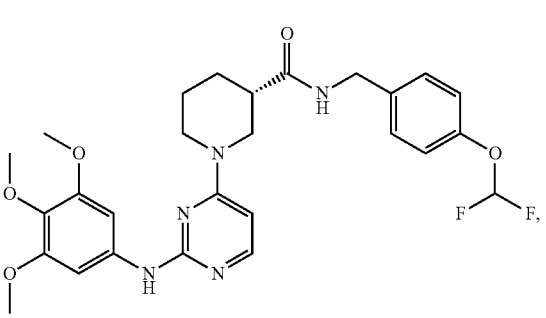
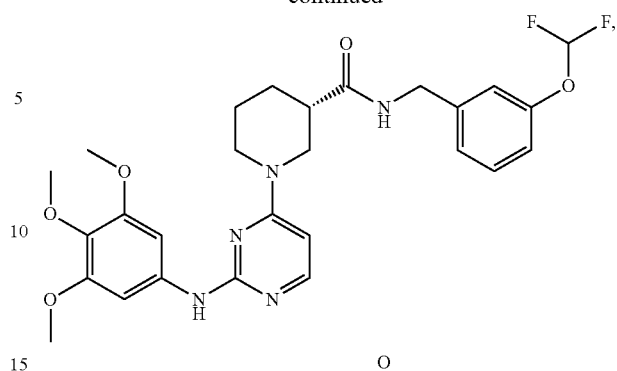
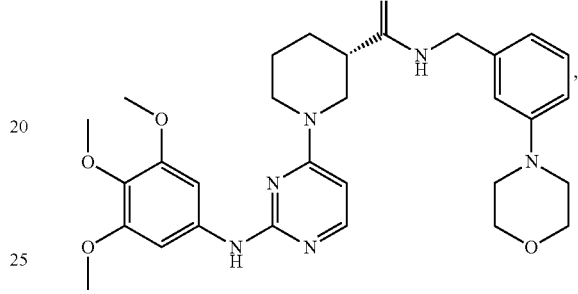
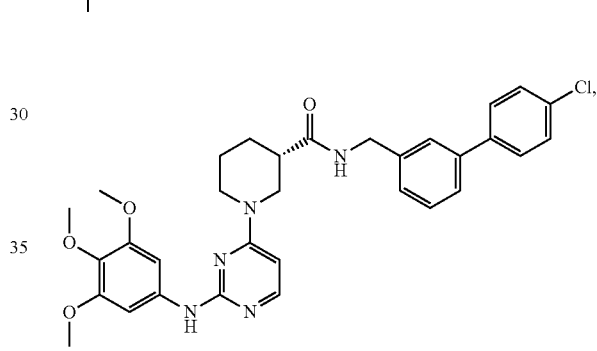
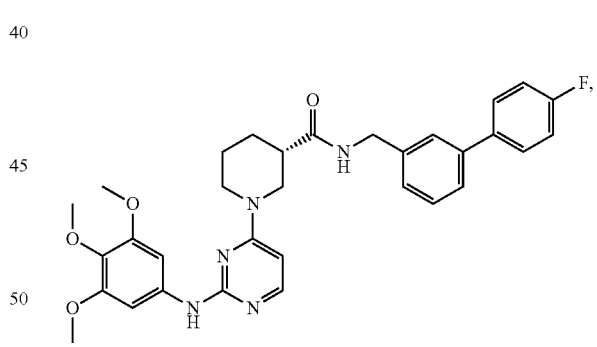
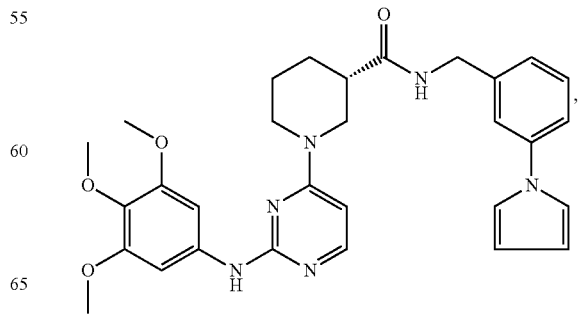

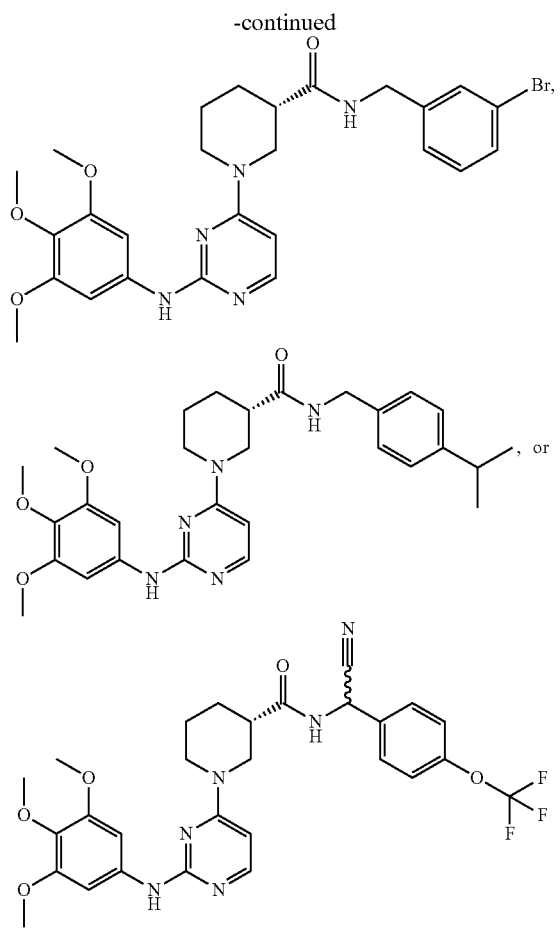

or a pharmaceutically acceptable salt thereof.

In some embodiments, the compound is a salt. Such salts may be anhydrous or associated with water as a hydrate.

In some embodiments, the compound is a prodrug.

Also provided are pharmaceutical formulations that include at least one pharmaceutically acceptable carrier, excipient or diluent and a therapeutically effective amount of the compound of any of the embodiments described herein. In some such embodiments, the compound is present in an amount effective for the treatment of cancer.

Further provided are pharmaceutical formulations that include at least one pharmaceutically acceptable carrier, and a therapeutically effective amount of the composition of matter of any of the embodiments described herein in combination with at least one additional compound such as a cytotoxic agent or a compound that inhibits another kinase.

In other embodiments, the invention provides a method of treating cancer. Such methods typically include administering to a subject an effective amount of a compound of any one of the embodiments or a pharmaceutical composition that includes any of the compounds of any of the embodiments. In some such embodiments, the subject has a cancer that expresses an ALK fusion protein, point mutation, or overexpression. In other such embodiments, the ALK fusion protein is EML4-ALK fusion protein or NPM-ALK fusion protein. In some embodiments, the subject is a human cancer patient, and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors. In some such embodiments, the cancer is non-small cell lung carcinoma (NSCLC).

In still other embodiments, the invention provides a method of treating a condition where it is desired to inhibit ALK activity. Such methods typically include administering to a subject an effective amount of a compound of any of the embodiments or a pharmaceutical composition that includes a compound of any of the embodiments.

In some embodiments, the compound of any of the embodiments is used in the preparation of a medicament. In some such embodiments, the medicament is for use in treating cancer. In some such embodiments, a medicament is for use in inhibiting ALK. In still other such embodiments, the medicament is for use in treating a cancer that expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein.

In some such embodiments, a compound or pharmaceutical formulation of any of the embodiments is provided for use in treating cancer. In some such embodiments, the cancer expresses an ALK fusion protein. In some such embodiments, the ALK fusion protein is EML4-ALK fusion protein or NPM-ALK fusion protein. In some such embodiments, the ALK fusion protein is EML4-ALK fusion protein. In other such embodiments, the ALK fusion protein is NPM-ALK fusion protein. In some embodiments, a compound or pharmaceutical formulation of any of the embodiments is provided for use in treating cancer and the cancer is selected from adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors. In some such embodiments, the cancer is non-small cell lung carcinoma (NSCLC). In still other embodiments, a compound or pharmaceutical formulation of any of the embodiments is provided for use in inhibiting ALK or for use in treating a disease or condition wherein inhibition of ALK is desired.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of any of the embodiments or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, ALK KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some such embodiments, the disorder is mediated by ALK. In some such embodiments, the administration of the compound or pharmaceutical composition produces selective inhibition of ALK. In some embodiments, the disorder is cancer. The present invention thus provides methods for treating or preventing ALK-mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a compound of any of the embodiments or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of any of the embodiments described herein may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AL esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RH retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC: antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, c-met inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

The compounds of the invention can be prepared using the general synthetic route shown below in Scheme 1 and described more fully in the Examples. In this method, the fragment including the piperidine ring is attached to the pyrimidine and is then attached to the fragment including the Z group.

Scheme 1

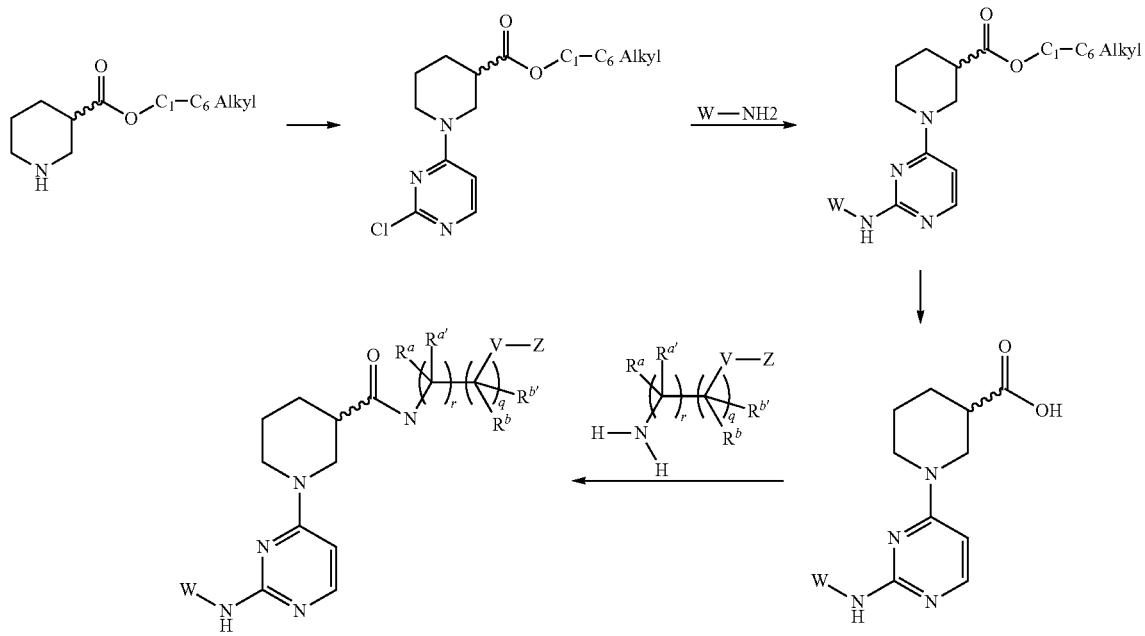

The compounds of the invention can also be prepared using the alternative general synthetic route shown below in Scheme 2 and also described more fully in the Examples. In this method, the fragment with the Z group is attached to the piperidine fragment which is followed by attachment of the pyrimidine group.

Scheme 2

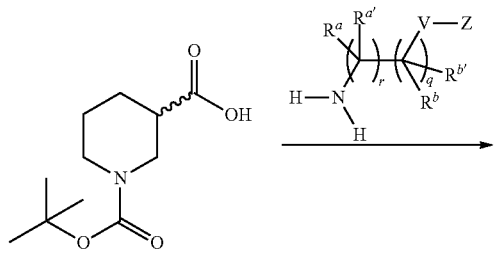

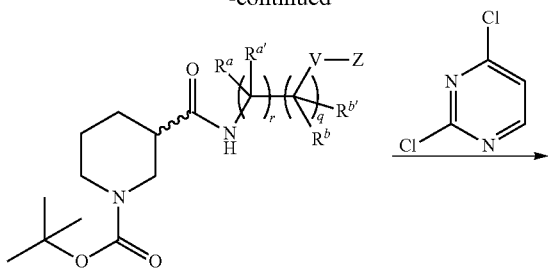

Modification of the above Schemes can be used to synthesize compounds where the piperidine is replaced with a piperazine (see Example 2), a thiomorpholine (see Example 4), or a morpholine (see Example 5) as will be apparent to those skilled in the art. Furthermore, these schemes may be modified to prepare compounds of the invention where the piperidine ring is replaced by 4, 5, or 7 membered rings.

The invention is further described by reference to the following examples, which are intended to exemplify the claimed invention but not to limit it in any way.

EXAMPLES

Unless otherwise stated, all compounds were obtained from commercial sources or were prepared using the methods and experimental procedures described herein. The following Abbreviations are used to refer to various reagents and solvents:

ACN Acetonitrile
AcOH Acetic Acid
DCE Dichloroethane
DCM Dichloromethane
DMF N,N-Dimethylformamide
DMSO Dimethylsulfoxide
EtOAc Ethyl Acetate
EtOH Ethanol
HATU O-(7-Azabenzotriazol-1-yl)-N,N,N',N'-tetramethyluronium hexafluorophosphate
iPrOH Isopropanol
MeOH Methanol
PS Polystyrene
TEA Triethylamine
TFA Trifluoroacetic acid

PREPARATION OF THE COMPOUNDS: METHODS

Method 1

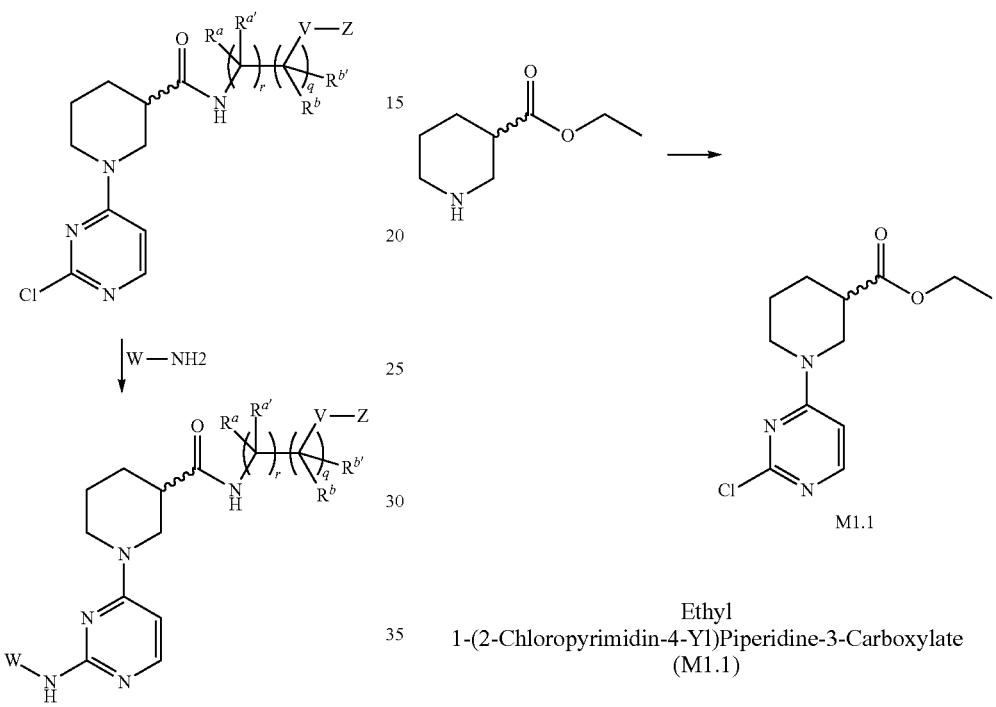

Ethyl 1-(2-Chloropyrimidin-4-Yl)Piperidine-3-Carboxylate (M1.1)

To a solution of 2,4-dichloropyrimidine (Alfa Aesar, 10 g, 65.8 mmol) and TEA (Sigma-Aldrich, 9.15 mL, 65.8 mmol) in EtOH (68.5 mL) at 0° C. was added ethyl piperidine-3-carboxylate (Sigma-Aldrich, 10.64 mL, 65.8 mmol) in EtOH (13.70 mL). The reaction was then allowed to warm to room temperature while stirring. After 1 hour, the reaction was concentrated and the residue was purified by chromatography through a 340 g silica gel column, eluting with 10% to 80% EtOAc/hexanes, to provide ethyl 1-(2-chloropyrimidin-4-yl) piperidine-3-carboxylate as a colorless oil in 80% yield. $^1$H NMR (300 MHz, CDCl$_3$) δ ppm 0.94 (t, J=6.94 Hz, 3H) 1.26 (d, J=9.35 Hz, 1H) 1.38-1.62 (m, 2H) 1.66-1.85 (m, 1H) 2.26 (m, 1H) 2.90-3.20 (m, 2H) 3.64 (m, 1H) 3.69-4.09 (m, 3H) 6.23 (d, J=5.85 Hz, 1H) 7.68 (d, J=5.99 Hz, 1H); ESI-MS M+H 270.0.

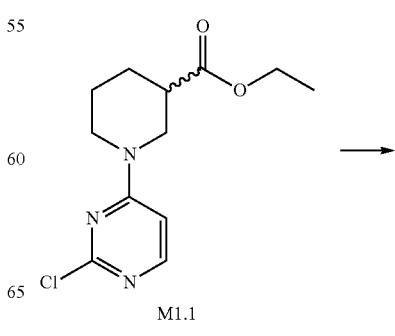

M1.1

79
-continued

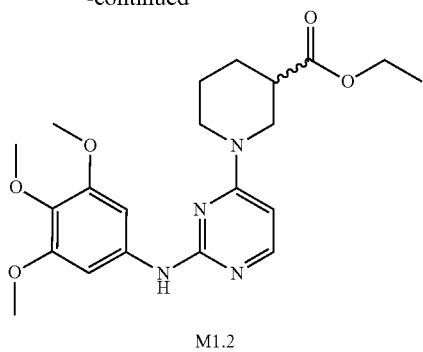

M1.2

Trimethoxyphenylamino)Pyrimidin-2-Yl)Piperidine-3-Carboxylate (M1.2)

To a solution of M1.1 (1422 mg, 5.27 mmol) in DMF (52.7 mL) was added and 3,4,5-trimethoxyaniline (Acros Organics, 966 mg, 5.27 mmol). The resulting solution was heated to 90° C. while stirring. After 20 hours, the reaction was cooled to room temperature and diluted with DCM. The organic phase was washed with water and brine, dried over sodium sulfate, filtered and concentrated to give a residue. The residue was adsorbed onto a plug of silica gel and purified by chromatography through a 100 g silica gel column, eluting with 10% to 100% EtOAc/hexanes to provide M1.2 as an off-white foam in 55% yield. $^1$H NMR (300 MHz, CDCl$_3$) δ ppm 1.26 (t, J=7.09 Hz, 3H) 1.47-1.66 (m, 2H) 1.66-1.84 (m, 2H) 2.05-2.17 (m, 1H) 2.45-2.58 (m, 1H) 2.89-3.02 (m, 1H) 3.08-3.19 (m, 1H) 3.79-3.89 (m, 8H) 4.15 (q, J=7.02 Hz, 2H) 4.55-4.65 (m, 1H) 4.77-4.88 (m, 1H) 5.93 (d, J=5.70 Hz, 1H) 6.36 (s, 1H) 6.67 (s, 2H) 7.99 (d, J=5.70 Hz, 1H); ESI-MS M+H 417.1.

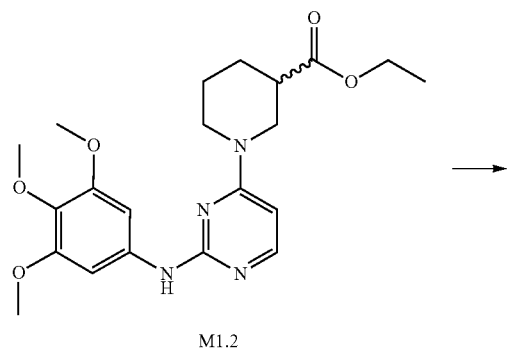

M1.2 →

80

1-(2-(3,4,5-Trimethoxyphenylamino)Pyrimidin-4-Yl)Piperidine-3-Carboxylic Acid (M1)

To a solution of M1.2 (1073.4 mg, 3.18 mmol) in dioxane (8.59 mL) was added lithium hydroxide monohydrate (Sigma-Aldrich, 162 mg, 3.87 mmol) in water (8.59 mL). The resulting reaction was stirred at room temperature. After 1 hour, the reaction was diluted with DCM and washed with 1N hydrochloric acid. The organic layer was extracted with aqueous sodium hydroxide. The aqueous layer was then acidified with 5N hydrochloric acid to give a precipitate. The desired product was then filtered off to give M1 as a white solid in 86% yield. $^1$H NMR (300 MHz, CD$_3$OD) δ ppm 1.67 (br. s., 1H) 1.89 (br. s., 2H) 2.12 (br. s., 1H) 2.66 (br. s., 1H) 3.49-3.92 (m, 12H) 4.03 (br. s., 1H) 6.63 (s, 1H) 6.80 (s, 2H) 7.72 (s, 1H); ESI-MS M+H 389.0.

Method 2

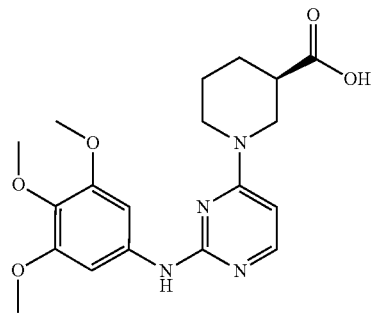

M2

(R)-1-(2-(3,4,5-Trimethoxyphenylamino)-Pyrimidin-4-Yl)Piperidine-3-Carboxylic Acid (M2)

M2 was prepared in a method analogous to M1 using (R)-(−)-nipecotic acid ethyl ester (TCI Tokyo Kasei Kogyo Co., Ltd.) in place of ethyl piperidine-3-carboxylate to provide the desired product as a light purple solid. $^1$H NMR (300 MHz, CD$_3$OD) δ ppm 1.67 (m, 1H); 1.80-1.96 (m, 2H); 2.10 (m, 1H); 2.66 (m, 1H); 3.77-3.84 (m, 12H); 4.00-4.09 (m, 1H); 6.61 (d, J=7.45 Hz, 1H); 6.79 (s, 2H); 7.69 (d, J=7.16 Hz, 1H); ESI-MS M+H 389.1.

Method 3

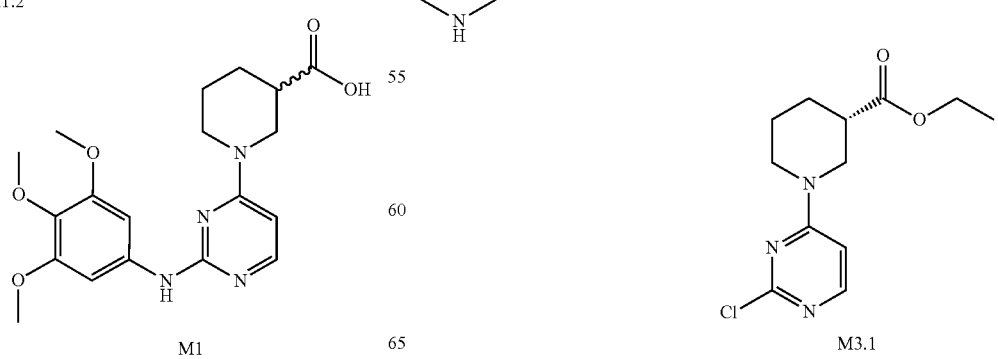

(S)-Ethyl 1-(2-Chloropyrimidin-4-Yl)Piperidine-3-Carboxylate (M3.1)

M3.1 was prepared in a method analogous to M1.1 using (s)-(+)-nipecotic acid ethyl ester (TCI America) in place of ethyl piperidine-3-carboxylate to provide the desired product as a clear oil in 88% yield. ESI-MS M+H 270.0.

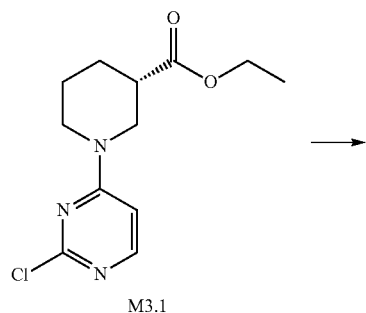

M3.1

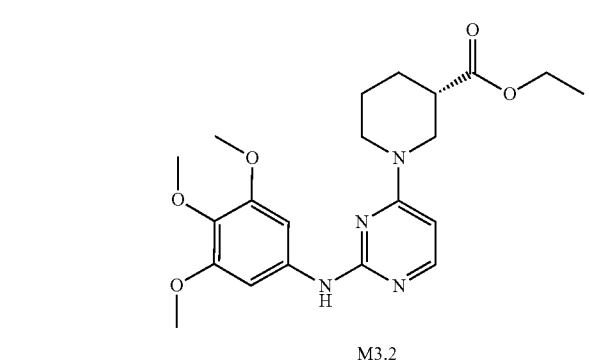

M3.2

(S)-Ethyl 1-(2-(3,4,5-Trimethoxyphenylamino)-Pyrimidin-4-Yl)Piperidine-3-Carboxylate (M3.2)

M3.2 was prepared in a method analogous to M1.2 using M3.1 in place of M1.1 to provide the desired product as a clear oil in 88% yield. ESI-MS M+H 417.1.

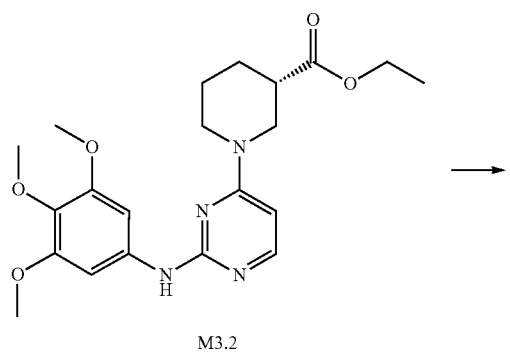

M3.2

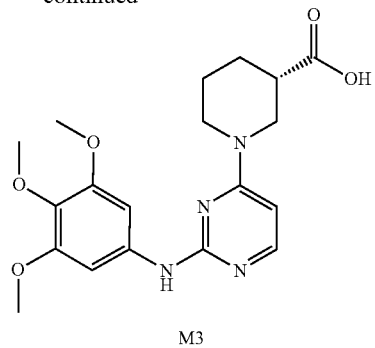

M3

(S)-1-(2-(3,4,5-Trimethoxyphenylamino)-Pyrimidin-4-Yl)Piperidine-3-Carboxylic Acid (M3)

M3 was prepared in a method analogous to M1 using M3.2 in place of M1.2 to provide (S)-1-(2-(3,4,5-trimethoxyphenylamino)pyrimidin-4-yl)piperidine-3-carboxylic acid as a light purple solid. $^1$H NMR (300 MHz, DMSO-$d_6$) δ ppm 1.47-1.65 (m, 1H); 1.65-1.86 (m, 2H); 1.93-2.07 (m, 1H); 2.53-2.64 (m, 1H); 3.57-3.77 (m, 12H); 3.98-4.21 (m, 1H); 6.69 (d, J=7.60 Hz, 1H); 6.86 (s, 2H); 7.95 (d, J=7.60 Hz, 1H); 10.49 (s, 1H); ESI-MS M+H 389.1.

Method 4

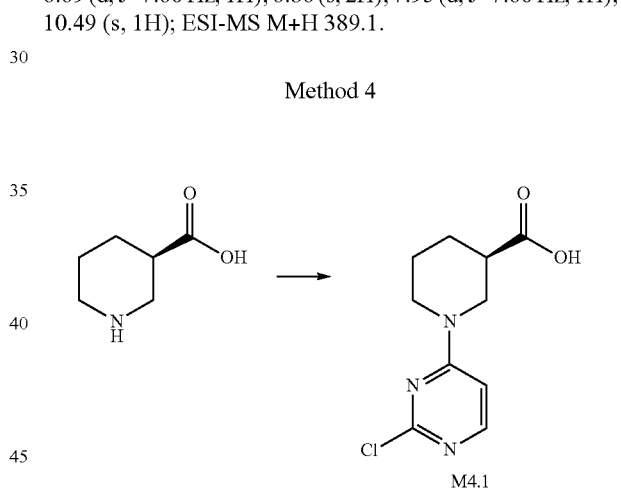

M4.1

(R)-1-(2-Chloropyrimidin-4-Yl)Piperidine-3-Carboxylic Acid (M4.1)

To a solution of 2,4-dichloropyrimidine (2.307, 15.49 mmol) and TEA (2.15 mL, 15.49 mmol) in EtOH (19.36 mL) at −10° C. was added (R)-piperidine-3-carboxylic acid (Sigma Aldrich, 2 g, 15.49 mmol). The reaction was allowed to slowly warm to room temperature while stirring. After 20 hours, the reaction was concentrated. The residue was adsorbed onto a plug of silica gel and purified by chromatography through a 100 g silica gel column, eluting with 2% to 10% MeOH in DCM followed by 20% to 50% 5:45:50 folic acid:EtOH:DCM, to provide M4.1 as a white solid in 21% yield. $^1$H NMR (400 MHz, CD$_3$OD) δ ppm 1.51-1.63 (m, 1H) 1.76-1.91 (m, 2H) 2.09 (dd, J=8.71, 4.40 Hz, 1H) 2.51-2.60 (m, 1H) 3.33-3.51 (m, 3H) 4.01 (br. s., 1H) 6.74 (d, J=6.46 Hz, 1H) 7.96 (d, J=6.26 Hz, 1H); ESI-MS M+H 241.9.

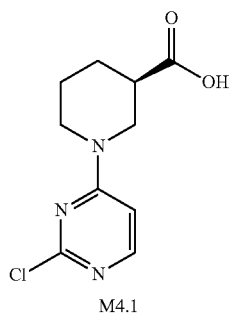

M4.1

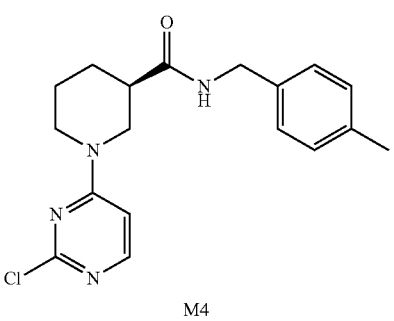

M4

(R)-1-(2-Chloropyrimidin-4-Yl)-N-(4-Methylbenzyl) Piperidine-3-Carboxamide (M4)

To a solution of 4-methylbenzylamine (Acros Organics, 7.61 mL, 59.8 mmol) and M4.1 (15.38 g, 29.9 mmol) in DCM (350 mL) was added PS-Carbodiimide (Argonaut Technologies Inc., 53.4 g, 59.8 mmol). The reaction was stirred at room temperature for 1 hour. The reaction was then filtered, and the filtrate was concentrated. The residue was adsorbed onto a plug of silica gel and purified by chromatography through a 340 g silica gel column, eluting with 1% MeOH/DCM followed by a 340 g silica gel column eluting with 30-100% to EtOAc/hexanes, to provide M4 as a white solid in 13% yield. $^1$H NMR (300 MHz, CDCl$_3$) δ ppm 1.60 (s, 1H) 1.79 (d, J=13.30 Hz, 1H) 1.91-2.13 (m, 2H) 2.27-2.45 (m, 4H) 3.16 (br. s., 1H) 3.55 (d, J=4.24 Hz, 1H) 4.02 (br. s., 1H) 4.18 (br. s., 1H) 4.26-4.48 (m, 2H) 6.11 (br. s., 1H) 6.40 (d, J=6.14 Hz, 1H) 7.13 (s, 4H) 8.00 (d, J=6.28 Hz, 1H); ESI-MS M+H 345.0.

Method 5

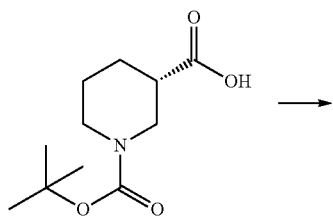

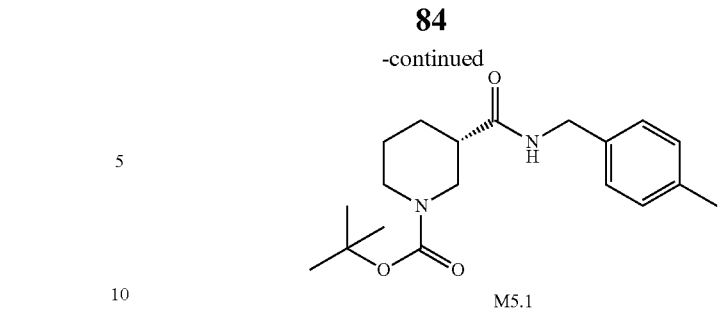

M5.1

(S)-Tert-Butyl 3-(4-Methylbenzylcarbamoyl)-Piperidine-1-Carboxylate (M5.1)

To a solution of (S)-1-(tert-butoxycarbonyl)piperidine-3-carboxylic acid (Beta Pharma Inc., 500 mg, 2.181 mmol) and TEA (0.912 mL, 6.54 mmol) in DCM (11 mL) was added HATU (912 mg, 2.399 mmol) followed by 4-methylbenzylamine (0.305 mL, 2.399 mmol). The resulting solution was stirred at room temperature for 48 hours. The reaction was concentrated, and the residue was adsorbed onto a plug of silica gel and purified by chromatography through a 50 g silica gel column, eluting with 0.5% to 5% MeOH in DCM, to provide M5.1 in 70% yield as a white foam. $^1$H NMR (300 MHz, CDCl$_3$) δ ppm 7.08-7.20 (m, 4H), 6.13 (br. s., 1H), 4.38 (d, J=5.26 Hz, 2H), 3.92 (d, J=13.30 Hz, 1H), 3.62-3.83 (m, 1H), 3.21 (dd, J=13.01, 9.65 Hz, 1H), 3.00 (dd, J=10.40 Hz, 1H), 2.33 (s, 3H), 2.20-2.30 (m, 1H), 1.80-1.95 (m, 2H), 1.58-1.71 (m, 1H), 1.43-1.52 (m, 1H), 1.42 (s, 9H); ESI-MS M+Na 355.2.

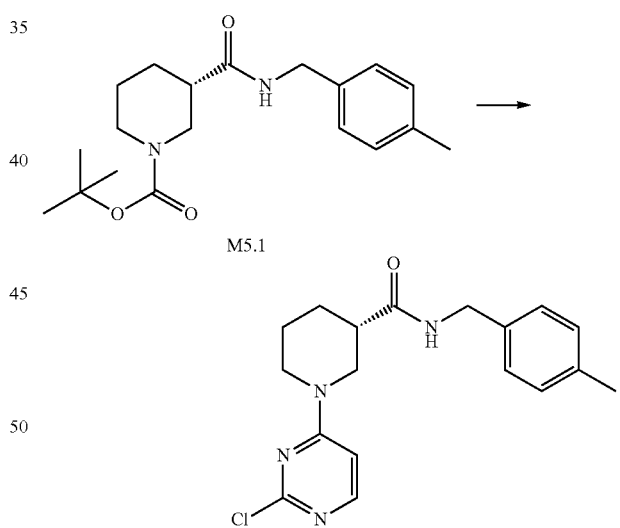

(S)-1-(2-Chloropyrimidin-4-Yl)-N-(4-Methylbenzyl) Piperidine-3-Carboxamide (M5)

To a solution of M5.1 (506.1 mg, 1.522 mmol) in DCM (15.200 mL) was added 1M HCl in diethyl ether (7.61 mL, 7.61 mmol). The reaction was maintained at room temperature for 20 hours while stirring. The reaction was concentrated to dryness and taken on to the next step without further purification. To a solution of the intermediate (409 mg, 1.522 mmol) in EtOH (3043 μL) was added 2,4-dichloropyrimidine (227 mg, 1.522 mmol), and TEA (423 μL, 3.04 mmol). The resulting solution was stirred at room temperature for 20 hours. The reaction was then concentrated and the residue was adsorbed onto a plug of silica gel and purified by chromatography through a 50 g silica gel column, eluting with 0.5% to 5% MeOH in DCM, to provide (S)-1-(2-chloropyrimidin-4-yl)-N-(4-methylbenzylipiperidine-3-carboxamide (32% yield) as a white solid. $^1$H NMR (300 MHz, CDCl$_3$) δ ppm 1.49-1.63 (m, 1H) 1.74-1.85 (m, 1H) 1.93-2.09 (m, 2H) 2.29-2.43 (m, 4H) 3.11-3.22 (m, 1H) 3.57 (m, 1H) 4.03 (m, 1H) 4.18 (m, 1H) 4.40 (m, 2H) 6.40 (d, J=6.28 Hz, 1H) 7.14 (s, 4H) 8.00 (d, J=6.14 Hz, 1H); ESI-MS M+H 345.0.

EXAMPLES

Example 1

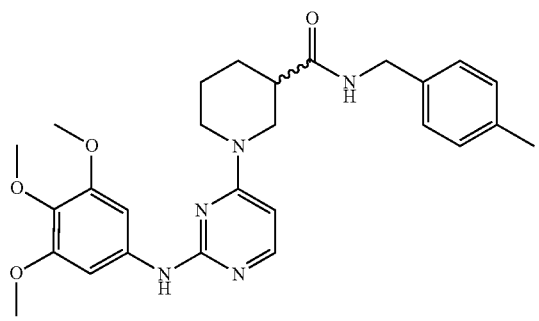

N-(4-Methylbenzyl)-1-(2-(3,4,5-Trimethoxyphenylamino)Pyrimidin-4-Yl)Piperidine-3-Carboxamide (1)

Example 1 was synthesized in a method analogous to M5.1 using M1 in place of (S)-1-(tert-butoxycarbonyl)piperidine-3-carboxylic acid to provide 1 as a white solid. $^1$H NMR (300 MHz, CDCl$_3$) δ ppm 1.55 (br. s., 1H), 1.69 (br. s., 1H), 1.97 (br. s., 2H), 2.24-2.43 (m, 4H), 3.04-3.23 (m, 1H), 3.48-3.62 (m, 1H), 3.74-3.89 (m, 9H), 3.99 (br. s., 1H), 4.19-4.43 (m, 3H), 6.02 (d, J=5.85 Hz, 1H), 6.33 (br. s., 1H), 6.82 (s, 2H), 7.02-7.17 (m, 5H), 7.95 (d, J=5.85 Hz, 1H); M+H 492.26019.

Example 2

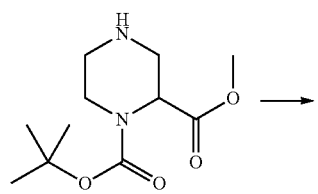

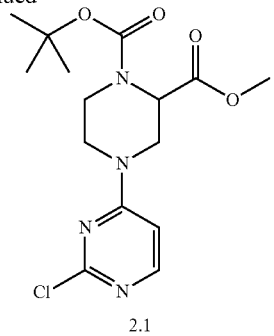

1-Tert-Butyl 2-Methyl 4-(2-Chloropyrimidin-4-Yl) Piperazine-1,2-Dicarboxylate (2.1)

2.1 was prepared in a method analogous to M1.1 using 1-tert-butyl 2-methyl piperazine-1,2-dicarboxylate (AstaTech) in place of ethyl piperidine-3-carboxylate to provide 1-tert-butyl 2-methyl 4-(2-chloropyrimidin-4-yl)piperazine-1,2-dicarboxylate in 69% yield. ESI-MS M+H 357.2.

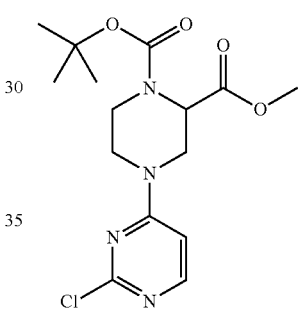

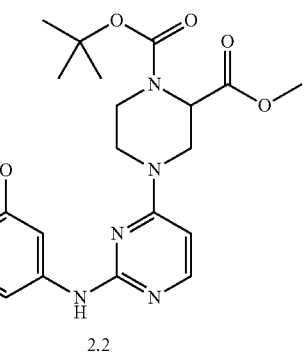

1-Tert-Butyl 2-Methyl 4-(2-(3,4,5-Trimethoxy-Phenylamino)Pyrimidin-4-Yl)Piperazine-1,2-Dicarboxylate (2.2)

2.2 was prepared in a method analogous to M1.2 using 2.1 in place of M1.1 to provide 1-tert-butyl 2-methyl 4-(2-(3,4,5-trimethoxyphenylamino)pyrimidin-4-yl)piperazine-1,2-dicarboxylate in 41% yield. ESI-MS M+H 504.2.

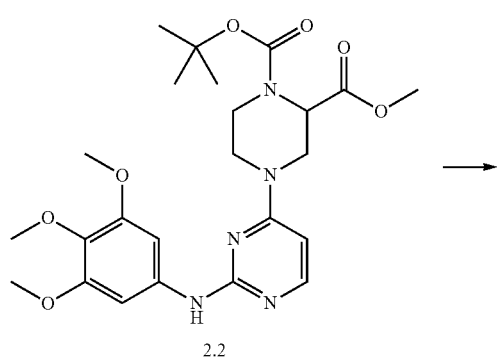

2.2

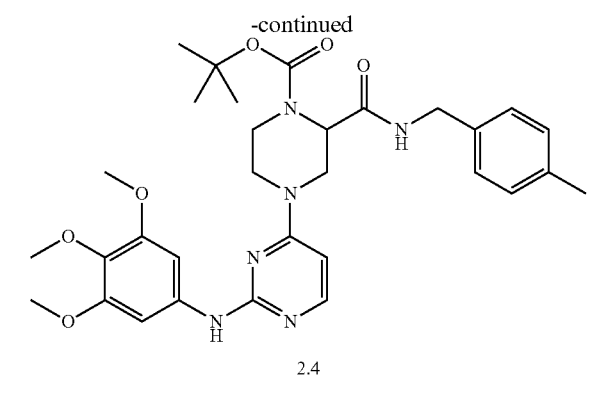

2.4

Tert-Butyl 2-(4-Methylbenzylcarbamoyl)-4-(2-(3,4,5-Trimethoxyphenylamino)Pyrimidin-4-Yl)Piperazine-1-Carboxylate (2.4)

2.4 was prepared in a method analogous to M5.1 using 2.3 in place of 1.1 to provide tert-butyl 2-(4-methylbenzylcarbamoyl)-4-(2-(3,4,5-trimethoxyphenylamino)pyrimidin-4-yl)piperazine-1-carboxylate as a white solid. ESI-MS M+H 593.2.

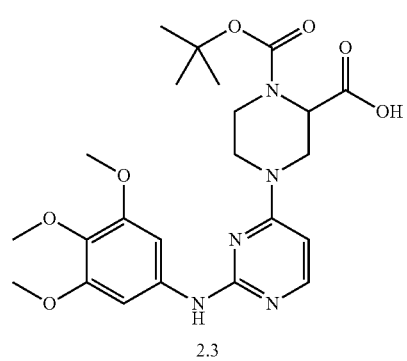

2.3

1-(Tert-Butoxycarbonyl)-4-(2-(3,4,5-Trimethoxyphenylamino)Pyrimidin-4-Yl)Piperazine-2-Carboxylic Acid (2.3)

To 2.2 (0.05 g, 0.099 mmol) in dioxane (0.331 mL) was added lithium hydroxide monohydrate (6.25 mg, 0.149 mmol) in water (0.331 mL). The reaction was stirred at room temperature for 1 hour. The reaction was then acidified with 1N HCl and diluted with DCM. The organic layer was extracted, dried over Na$_2$SO$_4$, filtered and concentrated to provide 2.3 as a light yellow solid. ESI-MS M+H 490.0.

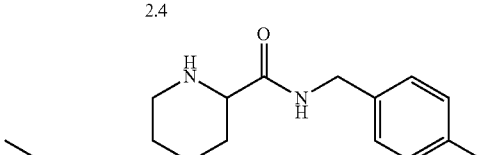

2.4

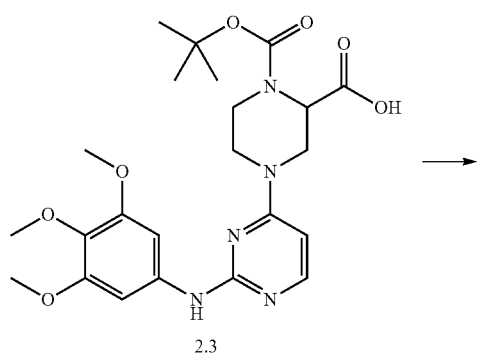

2.3

2

N-(4-Methylbenzyl)-4-(2-(3,4,5-Trimethoxyphenylamino)Pyrimidin-4-Yl)Piperazine-2-Carboxamide (2)

To a solution of 2.4 (43 mg, 0.073 mmol) in DCM was added TFA (10.8 µL, 0.145 mmol). The resulting solution was stirred at room temperature. After 18 hours, additional TFA (0.145 mmol) was introduced. After 30 hours, the reaction was concentrated. The material was brought up in MeOH (2 mL) and filtered through a Si-carbonate cartridge to give 2 in 89% yield. $^1$H NMR (300 MHz, CDCl$_3$) δ ppm 1.86 (br. s., 1H) 2.31 (s, 3H) 2.79-3.07 (m, 2H) 3.25-3.37 (m, 1H) 3.40-3.54 (m, 2H) 3.75-3.97 (m, 10H) 4.09-4.22 (m, 1H) 4.39 (d, J=5.41 Hz, 2H) 6.10 (d, J=6.14 Hz, 1H) 6.87 (s, 2H) 7.11 (s, 4H) 7.26-7.34 (m, 1H) 8.00 (d, J=5.99 Hz, 1H); M+H 493.25580.

Example 3

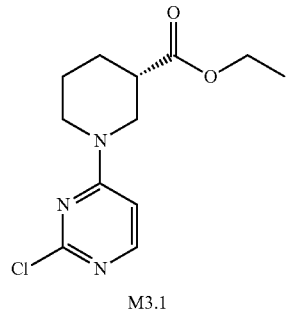

M3.1

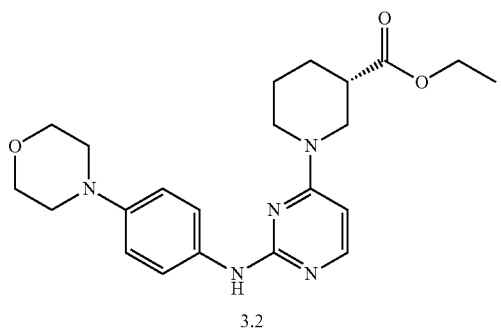

3.2

(S)-Ethyl 1-(2-(4-Morpholinophenylamino)-Pyrimidin-4-Yl)Piperidine-3-Carboxylate (3.2)

A solution of M3.1 (345.2 mg, 1.280 mmol) and 4-morpholinoaniline (Maybridge, 228 mg, 1.280 mmol) were combined in DMSO (5119 μL) and heated to 90° C. After 18 hours, the reaction was cooled to room temperature, diluted with water and extracted with DCM containing 10% iPrOH (5×). The combined organic layers were dried over Na$_2$SO$_4$, filtered and concentrated to give (S)-ethyl 1-(2-(4-morpholinophenylamino)pyrimidin-4-yl)piperidine-3-carboxylate as a purple solid. ESI-MS M+H 412.0.

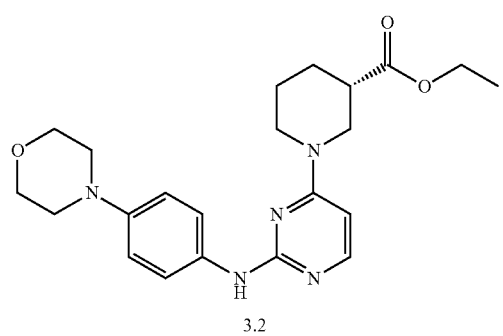

3.2

-continued

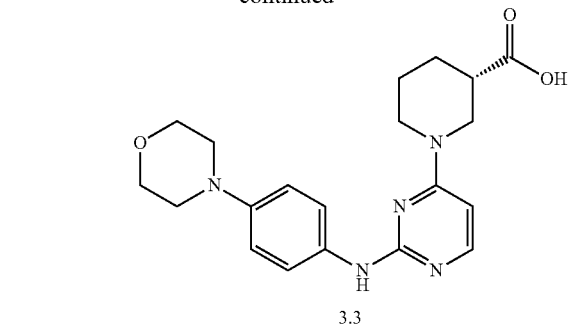

3.3

(S)-1-(2-(4-Morpholinophenylamino)Pyrimidin-4-Yl)Piperidine-3-Carboxylic Acid (3.3)

3.3 was prepared in a method analogous to M1 using 3.2 in place of M1.2 to provide (S)-1-(2-(4-morpholinophenylamino)pyrimidin-4-yl)piperidine-3-carboxylic acid as a light purple solid. ESI-MS M+H 384.0.

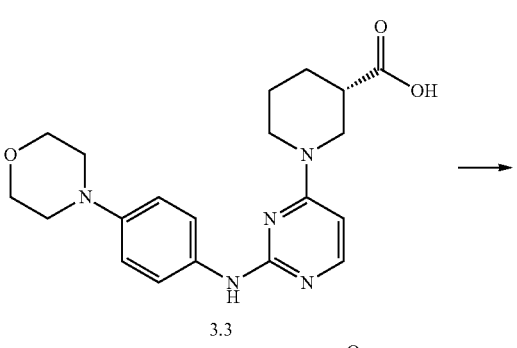

3.3

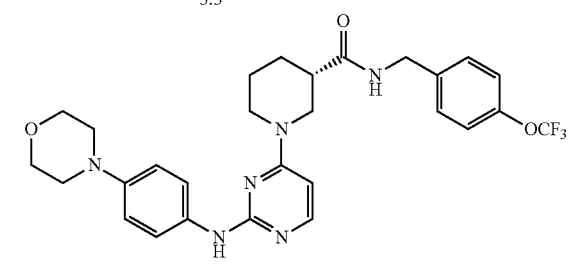

3

(S)-1-(2-(4-Morpholinophenylamino)Pyrimidin-4-Yl)-N-(4-(Trifluoromethoxy)Benzyl)Piperidine-3-Carboxamide (3)

To a solution of 3.3 (491 mg, 1.280 mmol) and TEA (535 μL, 3.84 mmol) in DCM (6402 μL) was added HATU (536 mg, 1.409 mmol) followed by 4-(trifluoromethoxy)benzylamine (Apollo Scientific Ltd., 215 μL 1.409 mmol) The reaction was stirred at room temperature for 40 hours. The reaction then was concentrated and the residue was adsorbed onto a plug of silica gel and purified by chromatography through a 50 g silica gel column, eluting with 0.5 to 5% MeOH in DCM, to provide 3 as a light purple solid in 23% yield. $^1$H NMR (300 MHz, CD$_3$OD) δ ppm 1.62 (br. s., 1H) 1.79-1.93 (m, 2H) 1.93-2.10 (m, 1H) 2.54 (br. s., 1H) 3.12 (br. s., 4H) 3.35-3.52 (m, 2H) 3.81 (br. s., 4H) 4.22-4.37 (m, 4H)

6.45 (d, J=7.31 Hz, 1H) 6.99 (d, J=8.62 Hz, 2H) 7.21 (d, J=8.04 Hz, 2H) 7.33 (t, J=8.40 Hz, 4H) 7.65 (d, J=7.31 Hz, 1H); M+H 557.24764.

Example 4

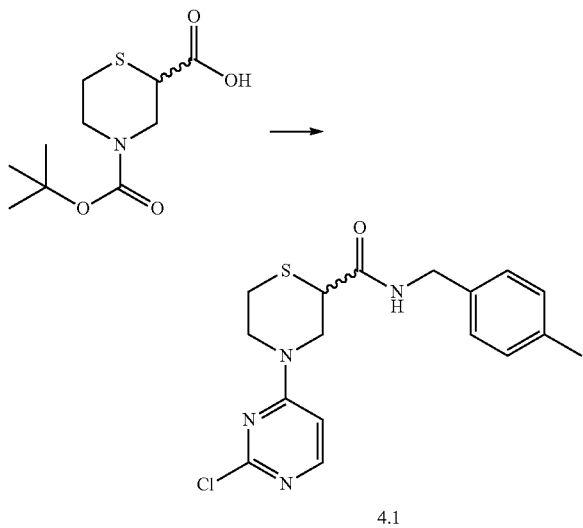

4.1

4-Methylbenzyl 4-(2-Chloropyrimidin-4-Yl)Thiomorpholine-2-Carboxylate (4.1)

4.1 was prepared in a method analogous to M5 using 4-(tert-butoxycarbonyl)thiomorpholine-2-carboxylic acid (Oakwood) in place of (S)-1-(tert-butoxycarbonyl)piperidine-3-carboxylic acid to provide 4-methylbenzyl 4-(2-chloropyrimidin-4-yl)thiomorpholine-2-carboxylate as a white solid. ESI-MS M+Na 373.2.

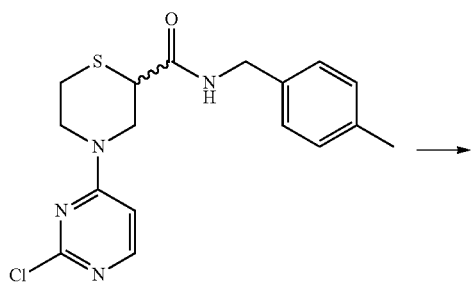

4.1

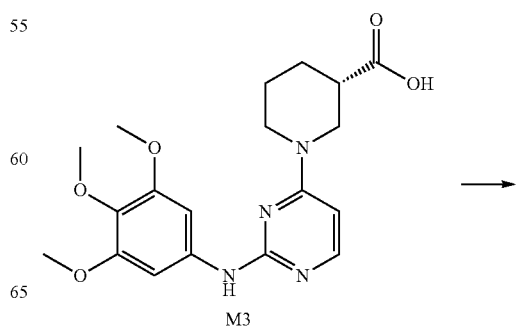

4

N-(4-Methylbenzyl)-4-(2-(3,4,5-Trimethoxy-Phenylamino)Pyrimidin-4-Yl)Thiomorpholine-2-Carboxamide (4)

To a solution of 4.1 (21.5 mg, 0.059 mmol) in DMSO (237 μL) was added 3,4,5-trimethoxyaniline (10.85 mg, 0.059 mmol). The resulting mixture was heated to 50° C. After 20 hours, the reaction was warmed to 90° C. After 36 hours, the reaction was cooled to room temperature, diluted with DCM and extracted with water (2×). The organic layer was dried over Na$_2$SO$_4$, filtered and concentrated. The residue was adsorbed onto a plug of silica gel and purified by chromatography through a 10 g silica gel column, eluting with 0.5% to % 3% MeOH to provide 4 in 49% yield. $^1$H NMR (300 MHz, CDCl$_3$) δ ppm 2.26 (s, 3H) 2.47-2.59 (m, 1H) 2.66-2.79 (m, 1H) 3.41-3.61 (m, 2H) 3.74-3.90 (m, 10H) 4.21-4.34 (m, 1H) 4.41-4.54 (m, 1H) 4.64-4.69 (m, 2H) 6.27 (d, J=6.14 Hz, 1H) 6.85 (s, 2H) 6.96 (s, 1H) 7.00-7.11 (m, 4H) 7.22-7.31 (br. s., 1H) 8.01 (d, J=6.14 Hz, 1H); ESI-MS M+Na 510.21582.

Example 5

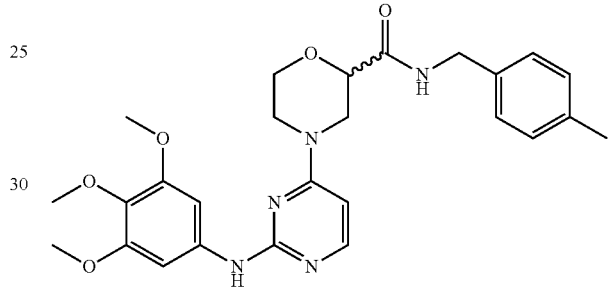

5

N-(4-Methylbenzyl)-4-(2-(3,4,5-Trimethoxy-Phenylamino)Pyrimidin-4-Yl)Morpholine-2-Carboxamide (5)

5 was prepared in a method analogous to example 4 using 4-(tert-butoxycarbonyl)morpholine-2-carboxylic acid (Chem Impex International) in place of 4-(tert-butoxycarbonyl)thiomorpholine-2-carboxylic acid to provide N-(4-methylbenzyl)-4-(2-(3,4,5-trimethoxyphenylamino)-pyrimidin-4-yl)morpholine-2-carboxamide as a white solid. $^1$H NMR (300 MHz, CDCl$_3$) δ ppm 2.34 (s, 3H) 2.88-3.09 (m, 2H) 3.66 (t, J=11.18 Hz, 1H) 3.79-3.89 (m, 9H) 3.96-4.10 (m, 2H) 4.28 (d, J=12.72 Hz, 1H) 4.44 (d, J=5.70 Hz, 2H) 4.55 (d, J=13.01 Hz, 1H) 6.11 (d, J=6.14 Hz, 1H) 6.87 (s, 3H) 7.08 (s, 1H) 7.12-7.22 (m, 4H) 8.04 (d, J=5.85 Hz, 1H); M+H 494.24052.

Example 6

M3

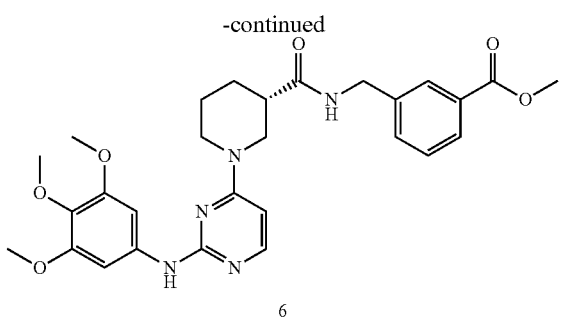

6

(S)-Methyl 3-((1-(2-(3,4,5-Trimethoxy-Phenylamino)Pyrimidin-4-Yl)Piperidine-3-Carboxamido)Methyl)Benzoate (6)

6 was prepared in a method analogous to Example 3 using M3 in place of M2 and methyl 3-(aminomethyl)benzoate (Maybridge) in place of 4-fluorobenzylamine to provide (S)-methyl 3-((1-(2-(3,4,5-trimethoxyphenylamino)pyrimidin-4-yl)piperidine-3-carboxamido)methyl)benzoate as a light purple foam. $^1$H NMR (300 MHz, CDCl$_3$) δ ppm 1.49-1.65 (m, 1H) 1.65-1.80 (m, 1H) 1.89-2.03 (m, 1H) 2.03-2.15 (m, 1H) 2.39-2.52 (m, 1H) 3.68-3.96 (m, 15H) 4.13 (dd, J=13.59, 2.48 Hz, 1H) 4.29-4.51 (m, 2H) 6.06 (d, J=6.28 Hz, 1H) 6.69-6.84 (m, 3H) 6.92-7.19 (m, 1H) 7.29-7.40 (m, 2H) 7.81-7.92 (m, 3H); M+H 536.24978.

Example 7

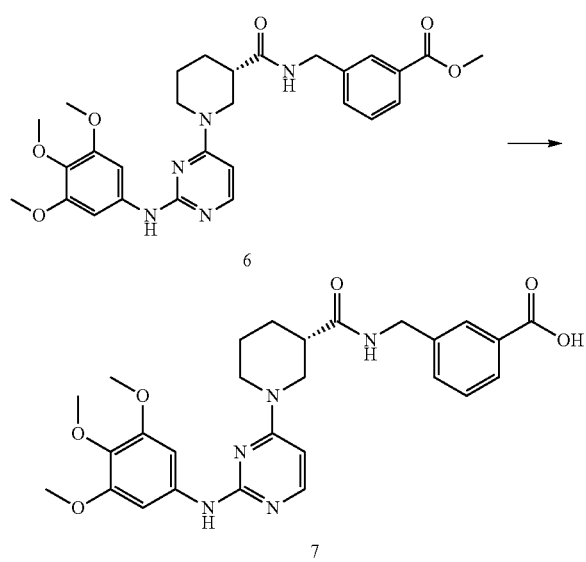

(S)-3-((1-(2-(3,4,5-Trimethoxyphenylamino)-Pyrimidin-4-Yl)Piperidine-3-Carboxamido)Methyl)-Benzoic Acid (7)

To a solution of 6 (353.7 mg, 0.660 mmol) in a mixture of dioxane (3302 μL) and water (3302 μL) was added lithium hydroxide monohydrate (27.7 mg, 0.660 mmol). The reaction was stirred at room temperature for 72 hours. The reaction mixture was then extracted with DCM. The aqueous layer was diluted with 1N HCl. A precipitate was formed and separated by filtration to give 7 as a light purple solid. $^1$H NMR (400 MHz, CDCl$_3$ with 1% TFA) δ ppm 1.50-1.70 (m, 1H) 1.83-2.00 (m, 2H) 2.00-2.13 (m, 1H) 2.43-2.56 (m, 1H) 3.23-3.30 (m, 1H) 3.50-3.61 (m, 1H) 3.78-3.92 (m, 10H) 4.01 (d, J=14.08 Hz, 1H) 4.45 (d, J=10.76 Hz, 2H) 6.25-6.37 (m, 1H) 6.86 (s, 2H) 7.38-7.51 (m, 2H) 7.69 (d, J=7.43 Hz, 1H) 7.89-7.99 (m, 2H); M+H 522.23432.

Example 8

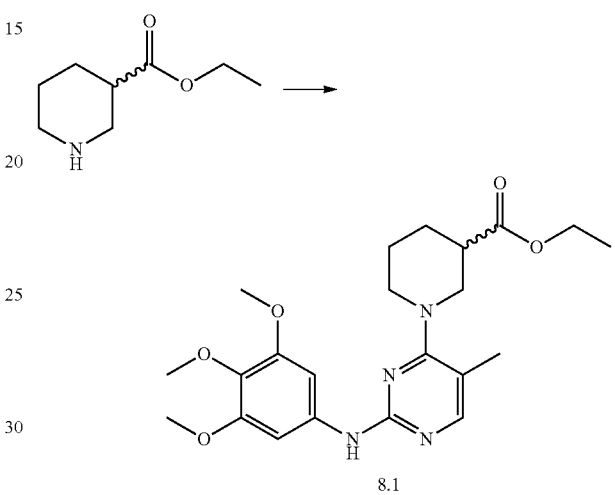

Ethyl 1-(5-Methyl-2-(3,4,5-Trimethoxy-Phenylamino)Pyrimidin-4-Yl)Piperidine-3-Carboxylate (8.1)

To a solution of 2,4-dichloro-5-methylpyrimidine (Sigma-Aldrich, 1 g, 6.13 mmol) and TEA (0.855 mL, 6.13 mmol) in EtOH (6.39 mL) was added ethyl piperidine-3-carboxylate (0.993 mL, 6.13 mmol) in EtOH (1.278 mL). The reaction was then allowed to stir at room temperature. After 4 hours, 3,4,5-trimethoxyaniline (1.124 g, 6.13 mmol) was added and the reaction was heated in the microwave to 150° C. for 30 minutes. The reaction was then cooled to room temperature and concentrated to dryness. The residue was adsorbed onto a plug of silica gel and purified by chromatography through a 100 g silica gel column, eluting with 10% to 100% EtOAc in hexanes to provide 8.1. ESI-MS M+H 430.8.

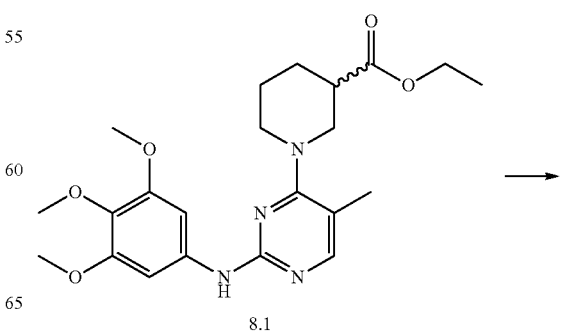

8.1

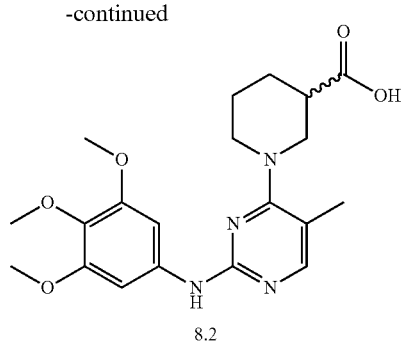

1-(5-Methyl-2-(3,4,5-Trimethoxyphenylamino)-Pyrimidin-4-Yl)Piperidine-3-Carboxylic Acid (8.2)

8.2 was prepared in a method analogous to M1 using 8.1 in place of M1.2 to provide 1-(5-methyl-2-(3,4,5-trimethoxyphenylamino)pyrimidin-4-yl)piperidine-3-carboxylic acid as a light tan solid. ESI-MS M+H 403.0.

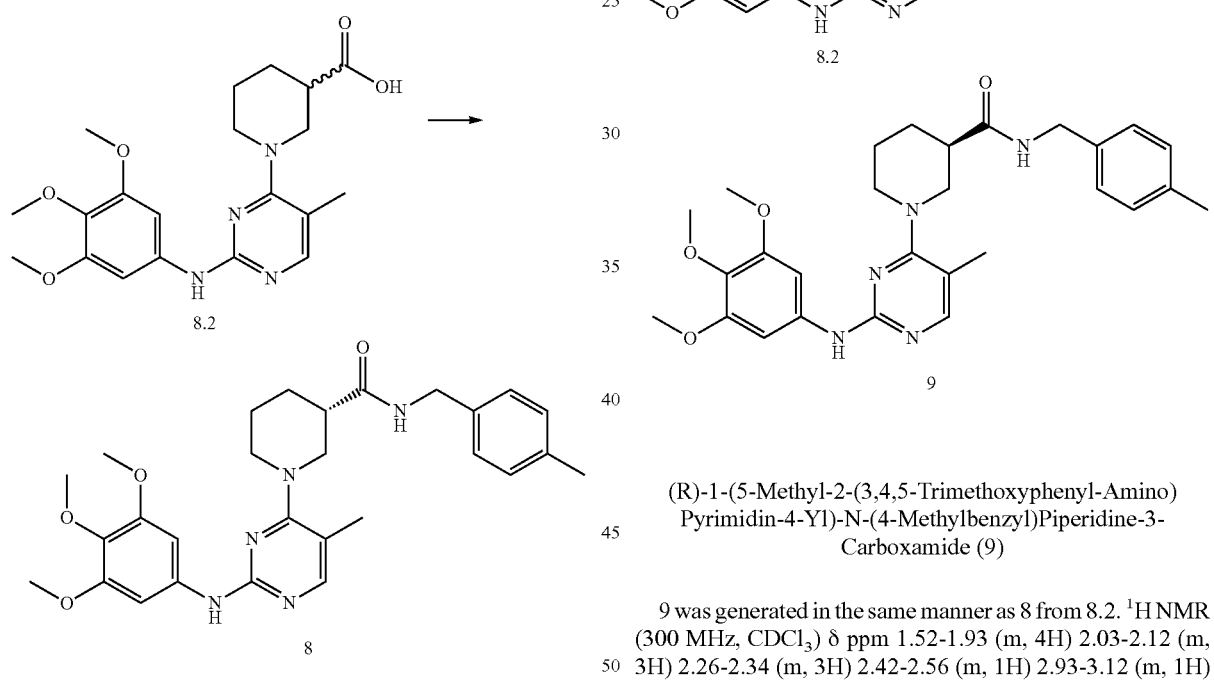

(S)-1-(5-Methyl-2-(3,4,5-Trimethoxyphenyl-Amino)Pyrimidin-4-Yl)-N-(4-Methylbenzyl)Piperidine-3-Carboxamide (8)

To a solution of 8.2 (380 mg, 0.866 mmol), TEA (0.362 mL, 2.60 mmol) and 4-methylbenzylamine (0.331 mL, 2.60 mmol) in DCM (21.7 mL) was added HATU (494 mg, 1.299 mmol). The reaction was stirred at room temperature for 2 hours. The reaction was then concentrated and the residue was adsorbed onto a plug of silica gel and purified by chromatography through a 50 g silica gel column, eluting with 0.5 to 10% MeOH in DCM to give 8 as a stereomeric mixture. This mixture was brought up in a mixture of MeOH and DCM and purified by supercritical fluid chromatography using an ODH (21×250 mm, 5 um) column. The stereoisomer was then resolved with a mixture of 35% MeOH with 0.2% diethylamine going to 40% MeOH with 0.2% diethylamine at 4 minutes with a flow rate of 65 mL per minute to provide 8. $^1$H NMR (300 MHz, CDCl$_3$) δ ppm 1.61 (br. s., 1H) 1.66-1.81 (m, 1H) 1.81-2.00 (m, 2H) 2.07 (s, 3H) 2.30 (s, 3H) 2.37-2.72 (m, 1H) 2.76-3.12 (m, 1H) 3.16-3.55 (m, 1H) 3.55-3.88 (m, 10H) 3.99 (d, J=11.98 Hz, 1H) 4.13-4.50 (m, 2H) 6.51 (br. s., 1H) 6.84 (s, 2H) 6.95-7.26 (m, 4H) 7.34 (br. s., 1H) 7.85 (s, 1H); M+H 506.27637.

Example 9

(R)-1-(5-Methyl-2-(3,4,5-Trimethoxyphenyl-Amino)Pyrimidin-4-Yl)-N-(4-Methylbenzyl)Piperidine-3-Carboxamide (9)

9 was generated in the same manner as 8 from 8.2. $^1$H NMR (300 MHz, CDCl$_3$) δ ppm 1.52-1.93 (m, 4H) 2.03-2.12 (m, 3H) 2.26-2.34 (m, 3H) 2.42-2.56 (m, 1H) 2.93-3.12 (m, 1H) 3.34 (dd, J=13.15, 9.35 Hz, 1H) 3.68-3.88 (m, 10H) 3.99 (d, J=13.01 Hz, 1H) 4.24-4.47 (m, J=14.40, 14.18, 14.18, 5.77 Hz, 2H) 6.79-6.88 (m, 2H) 7.11 (br. s., 4H) 7.81-7.90 (m, 1H) HR-MS 506.27620.

Example 10

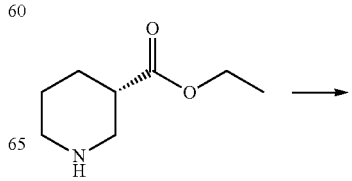

J=13.01, 10.38 Hz, 1H) 3.78-3.92 (m, 9H) 4.07-4.28 (m, 3H) 4.43 (dt, J=13.04, 1.66 Hz, 1H) 6.85 (s, 2H) 8.02 (s, 1H) ESI-MS M+H 451.0.

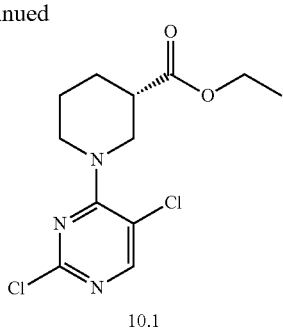

10.1

(S)-Ethyl 1-(2,5-Dichloropyrimidin-4-Yl)-Piperidine-3-Carboxylate (10.1)

10.1 was prepared in a method analogous to M3.1 using 2,4,5-trichloropyrimidine (Sigma-Aldrich) in place of 2,4-dichloropyrimidine to provide the desired product as a clear oil in 90% yield. $^1$H NMR (400 MHz, CDCl$_3$) δ ppm 1.25 (t, J=7.04 Hz, 3H) 1.59-1.72 (m, 1H) 1.73-1.91 (m, 2H) 2.08-2.18 (m, 1H) 2.60-2.71 (m, 1H) 3.16-3.26 (m, 1H) 3.39 (dd, J=13.40, 9.88 Hz, 1H) 4.15 (q, J=7.04 Hz, 2H) 4.23 (d, J=13.69 Hz, 1H) 4.46 (dd, J=13.50, 2.15 Hz, 1H) 8.09 (s, 1H); ESI-MS M+H 304.0.

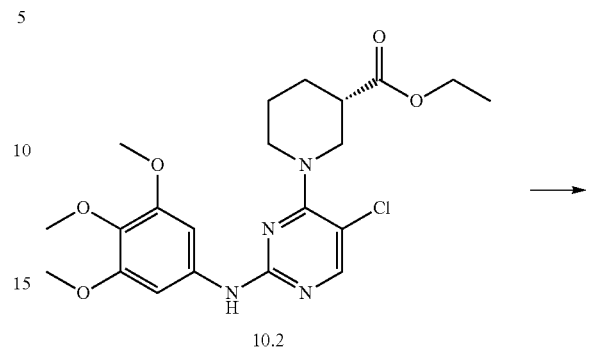

10.2

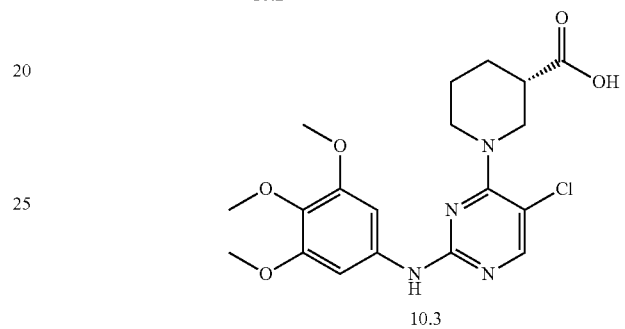

10.3

(S)-1-(5-Chloro-2-(3,4,5-Trimethoxyphenylamino)Pyrimidin-4-Yl)Piperidine-3-Carboxylic Acid (10.3)

10.3 was prepared in a method analogous to M1 using 1021 in place of M1.2 to provide (S)-1-(5-chloro-2-(3,4,5-trimethoxyphenylamino)pyrimidin-4-yl)piperidine carboxylic acid as an off-white solid. ESI-MS M+H 423.0.

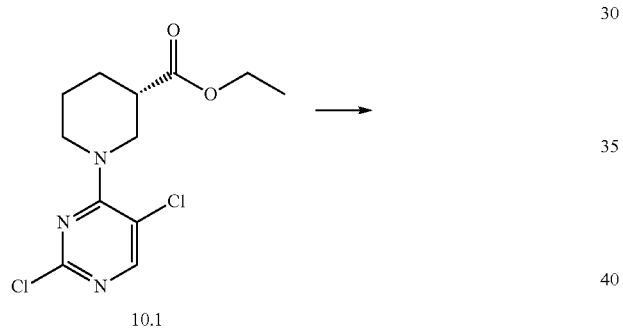

10.1

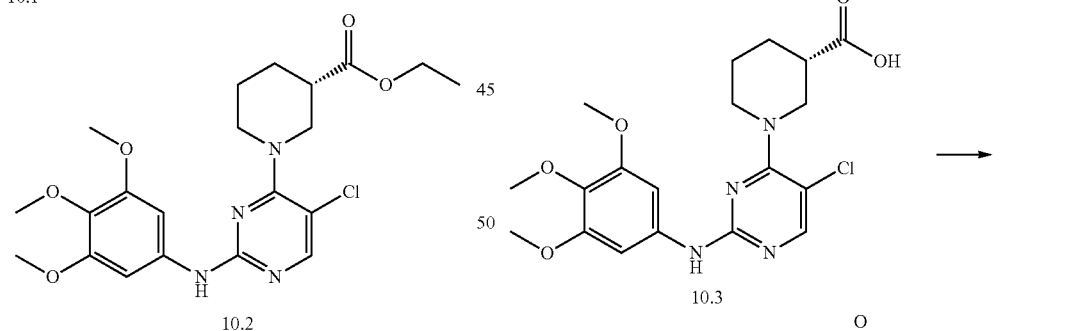

(S)-Ethyl 1-(5-Chloro-2-(3,4,5-Trimethoxy-Phenylamino)Pyrimidin-4-Yl)Piperidine-3-Carboxylate (10.2)

10.2 was prepared in a method analogous to M1.2 using 10.1 in place of M1.1 to provide (S)-ethyl 1-(5-chloro-2-(3,4,5-trimethoxyphenylamino)-pyrimidin-4-yl)piperidine-3-carboxylate as an off-white foam. $^1$H NMR (300 MHz, CDCl$_3$) δ ppm 1.19-1.30 (m, 3H) 1.63-1.90 (m, 3H) 2.08-2.20 (m, 1H) 2.60-2.73 (m, 1H) 2.97-3.10 (m, 1H) 3.22 (dd,

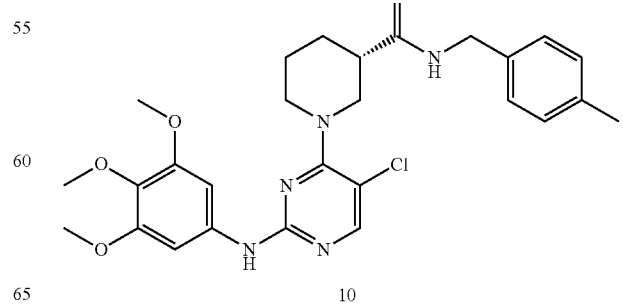

10

(S)-1-(5-Chloro-2-(3,4,5-Trimethoxyphenyl-Amino) Pyrimidin-4-Yl)-N-(4-Methylbenzyl)Piperidine-3-Carboxamide (10)

10 was prepared in a method analogous to M5.1 using 10.3 in place of (S)-1-(tert-butoxycarbonyl)piperidine-3-carboxylic acid to provide (S)-1-(5-chloro-2-(3,4,5-trimethoxyphenylamino)pyrimidin-4-yl)-N-(4-methylbenzyl)piperidine-3-carboxamide as a white solid. $^1$H NMR (400 MHz, CDCl$_3$) δ ppm 1.60-1.72 (m, 1H) 1.75-1.84 (m, 1H) 1.86-2.01 (m, 2H) 2.32 (s, 3H) 2.45-2.54 (m, 1H) 3.11 (ddd, J=13.16, 10.81, 2.84 Hz, 1H) 3.33 (dd, J=13.11, 9.78 Hz, 1H) 3.81 (s, 3H) 3.85 (s, 6H) 4.16-4.24 (m, 1H) 4.26-4.38 (m, 2H) 4.38-4.47 (m, 1H) 6.06 (br. s., 1H) 6.81 (s, 3H) 7.13 (m, 4H) 7.99 (s, 1H); M+H 526.22074.

Example 11

11

(S)-1-(6-Methyl-2-(3,4,5-Trimethoxyphenyl-Amino) Pyrimidin-4-Yl)-N-(4-Methylbenzyl)Piperidine-3-Carboxamide (11)

11 was prepared in a method analogous to Example 10 using 2,4-dichloro-6-methylpyrimidine (Sigma-Aldrich) in place of 2,4,5-trichloropyrimidine to provide the desired product as light purple foam. $^1$H NMR (400 MHz, CDCl$_3$) δ ppm 1.39-1.52 (m, 1H) 1.62-1.72 (m, 1H) 1.79-1.98 (m, 2H) 2.22 (d, J=18.98 Hz, 6H) 2.38 (td, J=8.90, 4.30 Hz, 1H) 3.04 (t, J=10.76 Hz, 1H) 3.40 (dd, J=12.91, 9.98 Hz, 1H) 3.75 (d, J=4.30 Hz, 9H) 3.96-4.09 (m, 1H) 4.17-4.36 (m, 3H) 5.94 (s, 1H) 6.80 (s, 2H) 6.96-7.07 (m, 5H) 7.58 (br. s., 1H); M+H 506.27554.

Example 12

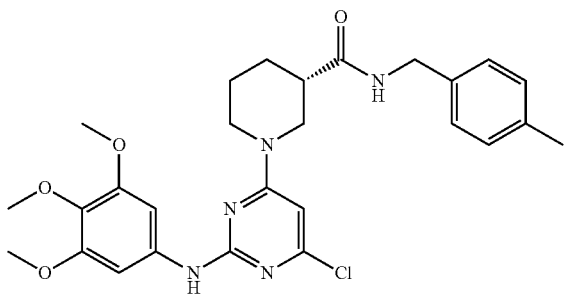

12

(S)-1-(6-Chloro-2-(3,4,5-Trimethoxyphenyl-Amino) Pyrimidin-4-Yl)-N-(4-Methylbenzyl)Piperidine-3-Carboxamide (12)

12 was prepared in a method analogous to Example 10 using 2,4,6-trichloro-6-methylpyrimidine (Sigma-Aldrich) in place of 2,4,5-trichloropyrimidine to provide the desired product as a white solid. $^1$H NMR (400 MHz, CDCl$_3$) δ ppm 1.38-1.51 (m, 1H) 1.63-1.73 (m, 1H) 1.85-1.97 (m, 2H) 2.24-2.36 (m, 4H) 3.00 (t, J=11.05 Hz, 1H) 3.37 (dd, J=13.01, 10.27 Hz, 1H) 3.72-3.81 (m, 9H) 3.95-4.17 (m, 2H) 4.29 (qd, J=14.51, 5.58 Hz, 2H) 5.99 (s, 1H) 6.66 (t, J=5.48 Hz, 1H) 6.77-6.81 (m, 2H) 7.06 (s, 4H); M+H 526.22066.

Example 13

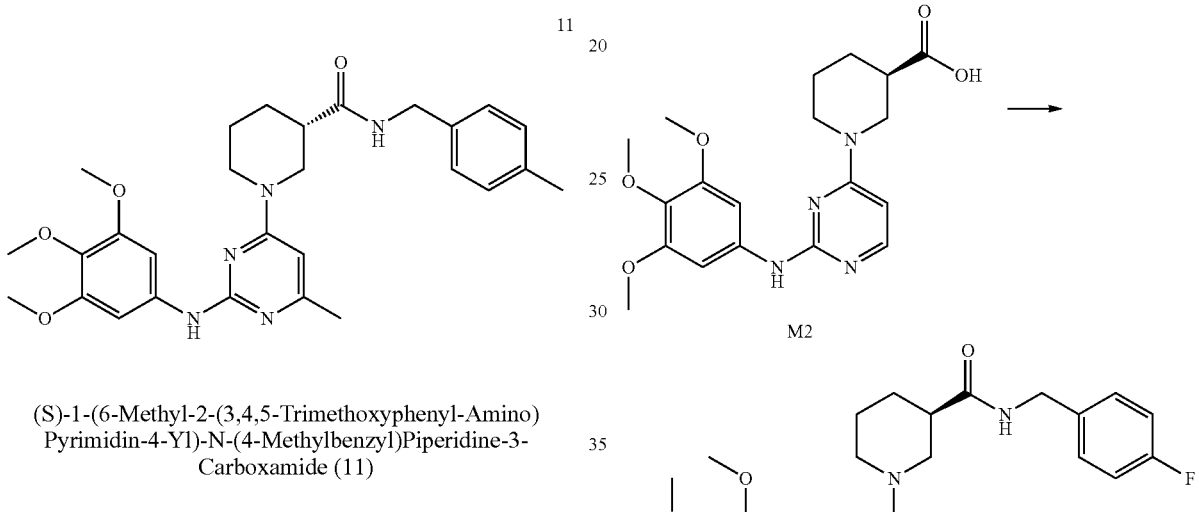

13

(R)—N-(4-Fluorobenzyl)-1-(2-(3,4,5-Trimethoxy-Phenylamino)Pyrimidin-4-Yl)Piperidine-3-Carboxamide (13)

To a solution of M2 (50 mg, 0.118 mmol) in DCE (1.5 mL) in a 24 well plate (Thomson Instrument Company) was added TEA (16.40 μL, 0.118 mmol). To this mixture was added HATU (67.1 mg, 0.177 mmol) in DCE (1 mL) followed by 4-fluorobenzylamine (Acros, 353 μL, 0.353 mmol). The reaction plate was then shaken at 256 rpm for 24 hours. The reaction was then diluted with MeOH (2 mL) and filtered. The filtrate was concentrated and the reaction mixture was purified by preparative HPLC through a C18 Sum 19×100 column (Sunfire Prep) eluting between water containing 0.1% TFA and MeOH containing 0.1% TFA over 2.50 minutes to give 13 as a light purple solid. $^1$H NMR (400 MHz, CDCl$_3$ with 1% TFA) δ ppm 1.47 (br. s., 1H) 1.66-1.84 (m, 2H) 1.84-2.01 (m, 1H) 2.34 (br. s., 1H) 3.07-3.18 (m, 1H) 3.23-3.39 (m, 1H) 3.65-3.75 (m, 9H) 4.07-4.19 (m, 2H) 4.19-4.31 (m, 1H) 4.59-4.85 (m, 1H) 6.17-6.27 (m, 1H) 6.67-6.74 (m, 2H) 6.81-6.92 (m, 2H) 7.09 (br. s., 2H) 7.50-7.60 (m, 1H); M+H 496.23510.

TABLE 1

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 14 | 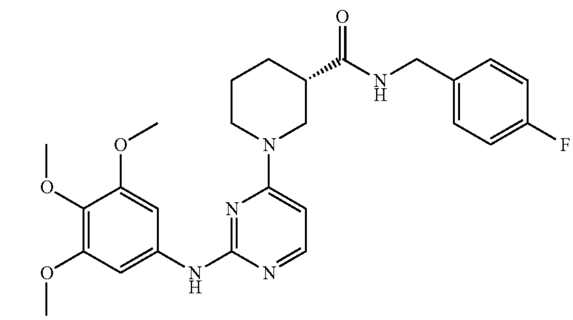 [SMILES: COc1cc(Nc2nccc(N3CCC[C@H](C(=O)NCc4ccc(F)cc4)C3)n2)cc(OC)c1OC] | (S)-N-((4-fluorophenyl)methyl)-1-(2-((3,4,5-tris(methyloxy)phenyl)amino)-4-pyrimidinyl)-3-piperidinecarboxamide | 495.55 | 496.23574 |
| 15 | 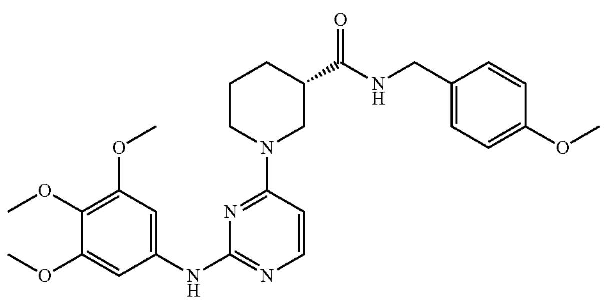 | (S)-N-((4-(methyloxy)phenyl)methyl)-1-(2-((3,4,5-tris(methyloxy)phenyl)amino)-4-pyrimidinyl)-3-piperidinecarboxamide | 507.59 | 508.25490 |
| 16 | 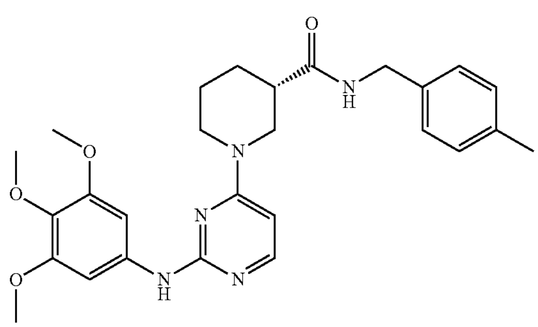 [SMILES: COc1cc(Nc2nccc(N3CCC[C@H](C(=O)NCc4ccc(C)cc4)C3)n2)cc(OC)c1OC] | (S)-N-(4-methylbenzyl)-1-(2-((3,4,5-trimethoxyphenyl)amino)-4-pyrimidinyl)-3-piperidinecarboxamide | 491.59 | 492.26004 |
| 17 | 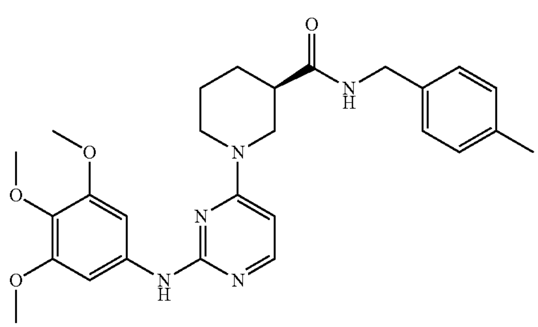 [SMILES: COc1cc(Nc2nccc(N3CCC[C@@H](C(=O)NCc4ccc(C)cc4)C3)n2)cc(OC)c1OC] | (R)-N-(4-methylbenzyl)-1-(2-((3,4,5-trimethoxyphenyl)amino)-4-pyrimidinyl)-3-piperidinecarboxamide | 491.59 | 492.26048 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 18 | 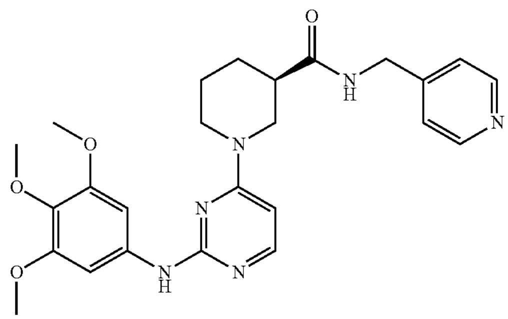 [SMILES: COc1cc(Nc2nccc(N3CCC[C@@H](C(=O)NCc4ccncc4)C3)n2)cc(OC)c1OC] | (R)-N-(4-pyridinylmethyl)-1-(2-((3,4,5-trimethoxyphenyl)amino)-4-pyrimidinyl)-3-piperidinecarboxamide | 478.55 | 479.23994 |
| 19 | 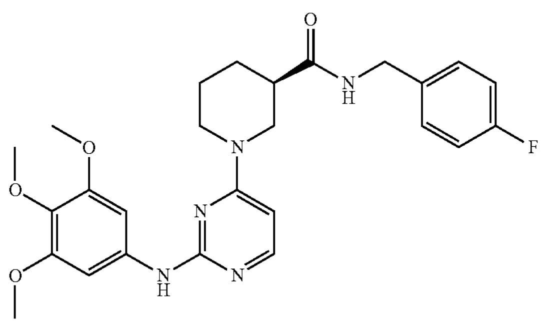 [SMILES: COc1cc(Nc2nccc(N3CCC[C@@H](C(=O)NCc4ccc(F)cc4)C3)n2)cc(OC)c1OC] | (R)-N-(4-fluorobenzyl)-1-(2-((3,4,5-trimethoxyphenyl)amino)-4-pyrimidinyl)-3-piperidinecarboxamide | 495.55 | 496.23574 |
| 20 | 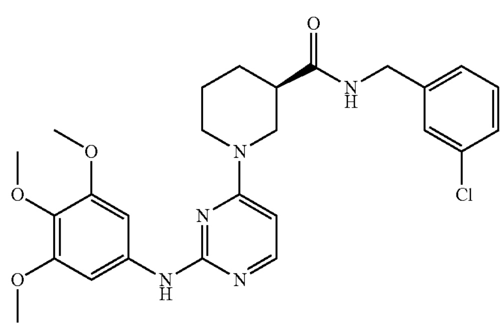 [SMILES: COc1cc(Nc2nccc(N3CCC[C@@H](C(=O)NCc4cccc(Cl)c4)C3)n2)cc(OC)c1OC] | (R)-N-(3-chlorobenzyl)-1-(2-((3,4,5-trimethoxyphenyl)amino)-4-pyrimidinyl)-3-piperidinecarboxamide | 511.20 | 512.20583 |
| 21 | 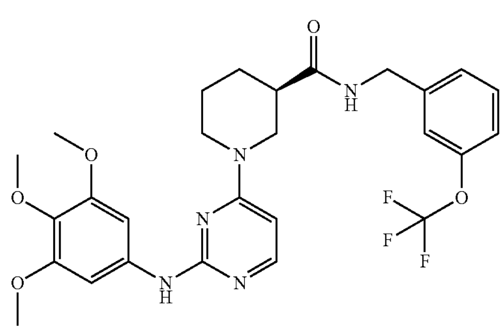 [SMILES: COc1cc(Nc2nccc(N3CCC[C@@H](C(=O)NCc4cccc(OC(F)(F)F)c4)C3)n2)cc(OC)c1OC] | (R)-N-(3-(trifluoromethoxy)benzyl)-1-(2-((3,4,5-trimethoxyphenyl)amino)-4-pyrimidinyl)-3-piperidinecarboxamide | 561.56 | 562.22712 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 22 | 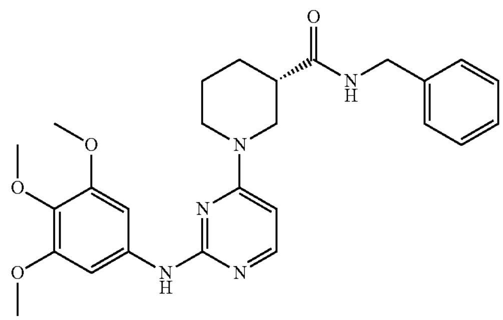 [SMILES: COc1cc(Nc2nccc(N3CCC[C@H](C(=O)NCc4ccccc4)C3)n2)cc(OC)c1OC] | (S)-N-benzyl-1-(2-((3,4,5-trimethoxyphenyl)amino)-4-pyrimidinyl)-3-piperidinecarboxamide | 477.56 | 478.24470 |
| 23 | 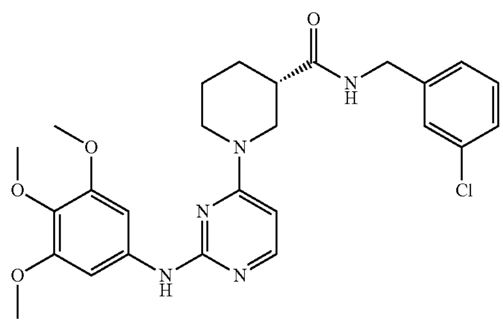 [SMILES: COc1cc(Nc2nccc(N3CCC[C@H](C(=O)NCc4cccc(Cl)c4)C3)n2)cc(OC)c1OC] | (S)-N-(3-chlorobenzyl)-1-(2-((3,4,5-trimethoxyphenyl)amino)-4-pyrimidinyl)-3-piperidinecarboxamide | 511.20 | 512.20556 |
| 24 | 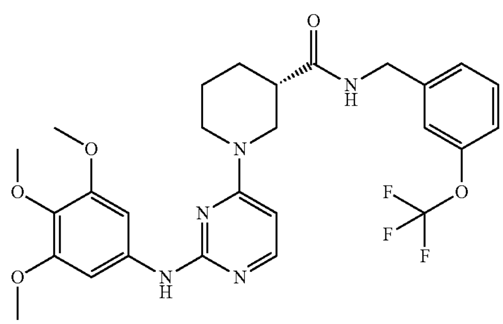 [SMILES: COc1cc(Nc2nccc(N3CCC[C@H](C(=O)NCc4cccc(OC(F)(F)F)c4)C3)n2)cc(OC)c1OC] | (S)-N-(3-(trifluoromethoxy)benzyl)-1-(2-((3,4,5-trimethoxyphenyl)amino)-4-pyrimidinyl)-3-piperidinecarboxamide | 561.56 | 562.2267 |
| 25 | 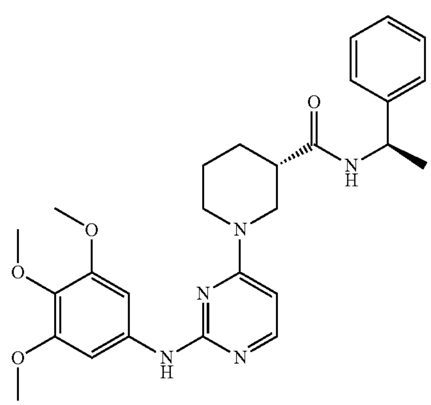 [SMILES: COc1cc(Nc2nccc(N3CCC[C@H](C(=O)N[C@H](C)c4ccccc4)C3)n2)cc(OC)c1OC] | (S)-N-((R)-1-phenylethyl)-1-(2-((3,4,5-trimethoxyphenyl)amino)-4-pyrimidinyl)-3-piperidinecarboxamide | 491.59 | 492.26028 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 26 | 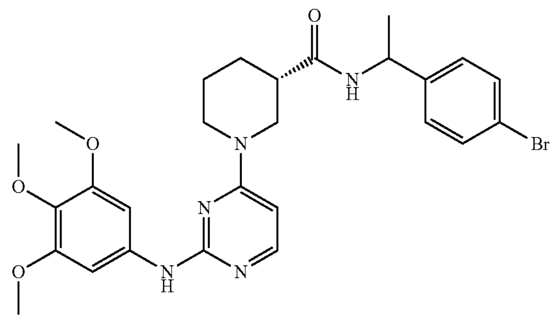 [SMILES: COc1cc(Nc2nccc(N3CCC[C@H](C(=O)NC(C)c4ccc(Br)cc4)C3)n2)cc(OC)c1OC] | (S)-N-(1-(4-bromophenyl)ethyl)-1-(2-((3,4,5-trimethoxyphenyl)amino)-4-pyrimidinyl)-3-piperidinecarboxamide | 569.16 | 570.17072 |
| 27 | 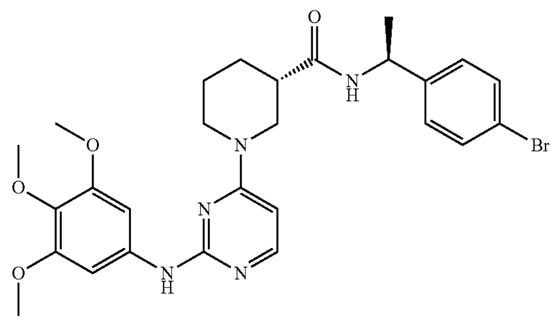 [SMILES: COc1cc(Nc2nccc(N3CCC[C@H](C(=O)N[C@@H](C)c4ccc(Br)cc4)C3)n2)cc(OC)c1OC] | (S)-N-((S)-1-(4-bromophenyl)ethyl)-1-(2-((3,4,5-trimethoxyphenyl)amino)-4-pyrimidinyl)-3-piperidinecarboxamide | 570.48 | 570.17099 |
| 28 | 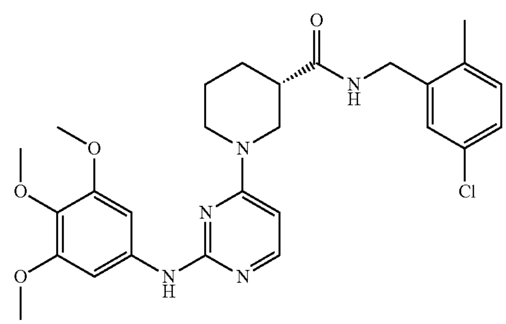 [SMILES: COc1cc(Nc2nccc(N3CCC[C@H](C(=O)NCc4cc(Cl)ccc4C)C3)n2)cc(OC)c1OC] | (S)-N-(5-chloro-2-methylbenzyl)-1-(2-((3,4,5-trimethoxyphenyl)amino)-4-pyrimidinyl)-3-piperidinecarboxamide | 522.21 | 526.22136 |
| 29 | 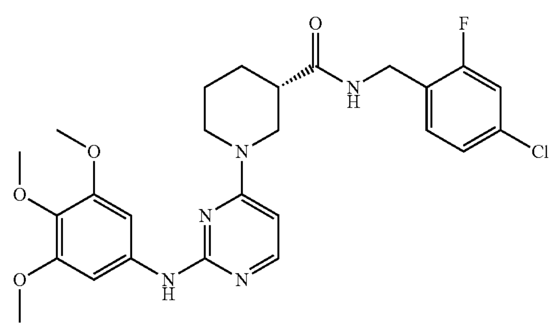 [SMILES: COc1cc(Nc2nccc(N3CCC[C@H](C(=O)NCc4ccc(Cl)cc4F)C3)n2)cc(OC)c1OC] | (S)-N-(4-chloro-2-fluorobenzyl)-1-(2-((3,4,5-trimethoxyphenyl)amino)-4-pyrimidinyl)-3-piperidinecarboxamide | 530.00 | 530.19596 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 30 | 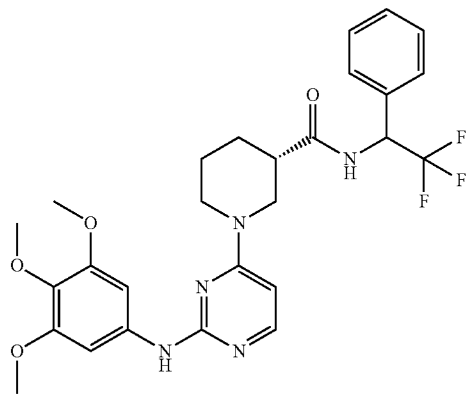 [SMILES: COc1cc(Nc2nccc(N3CCC[C@H](C(=O)NC(c4ccccc4)C(F)(F)F)C3)n2)cc(OC)c1OC] | (S)-N-(2,2,2-trifluoro-1-phenylethyl)-1-(2-((3,4,5-trimethoxyphenyl)amino)-4-pyrimidinyl)-3-piperidinecarboxamide | 545.56 | 546.23180 |
| 31 | 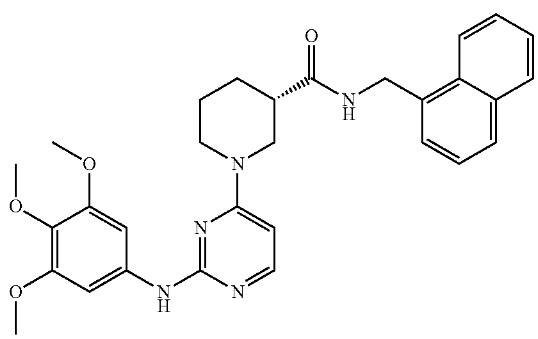 [SMILES: COc1cc(Nc2nccc(N3CCC[C@H](C(=O)NCc4cccc5ccccc45)C3)n2)cc(OC)c1OC] | (S)-N-(1-naphthalenylmethyl)-1-(2-((3,4,5-trimethoxyphenyl)amino)-4-pyrimidinyl)-3-piperidinecarboxamide | 527.62 | 528.25990 |
| 32 | 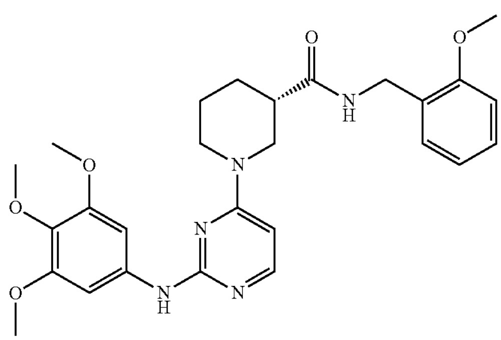 [SMILES: COc1ccccc1CNC(=O)[C@H]1CCCN(c2ccnc(Nc3cc(OC)c(OC)c(OC)c3)n2)C1] | (S)-N-(2-methoxybenzyl)-1-(2-((3,4,5-trimethoxyphenyl)amino)-4-pyrimidinyl)-3-piperidinecarboxamide | 507.59 | 508.25521 |
| 33 | 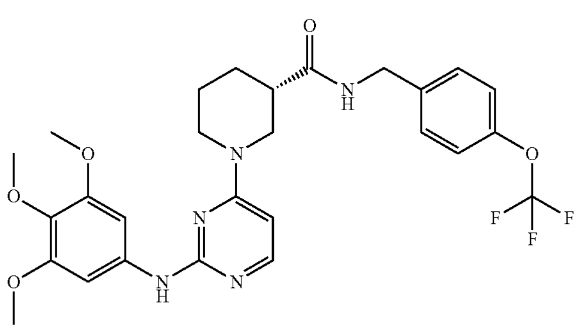 [SMILES: COc1cc(Nc2nccc(N3CCC[C@H](C(=O)NCc4ccc(OC(F)(F)F)cc4)C3)n2)cc(OC)c1OC] | (S)-N-(4-(trifluoromethoxy)benzyl)-1-(2-((3,4,5-trimethoxyphenyl)amino)-4-pyrimidinyl)-3-piperidinecarboxamide | 561.56 | 562.2261 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 34 | 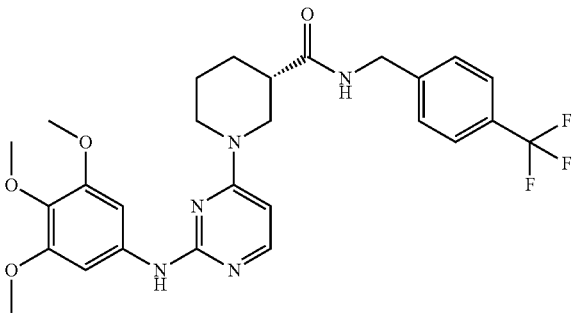 [SMILES: COc1cc(Nc2nccc(N3CCC[C@H](C(=O)NCc4ccc(C(F)(F)F)cc4)C3)n2)cc(OC)c1OC] | (S)-N-(4-(trifluoromethyl)benzyl)-1-(2-((3,4,5-trimethoxyphenyl)amino)-4-pyrimidinyl)-3-piperidinecarboxamide | 545.56 | 546.23177 |
| 35 | 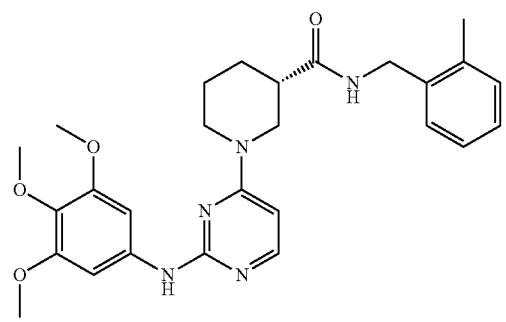 [SMILES: COc1cc(Nc2nccc(N3CCC[C@H](C(=O)NCc4ccccc4C)C3)n2)cc(OC)c1OC] | (S)-N-(2-methylbenzyl)-1-(2-((3,4,5-trimethoxyphenyl)amino)-4-pyrimidinyl)-3-piperidinecarboxamide | 491.59 | 492.26019 |
| 36 | 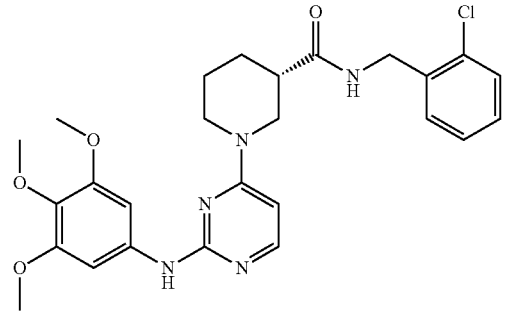 | (S)-N-(2-chlorobenzyl)-1-(2-((3,4,5-trimethoxyphenyl)amino)-4-pyrimidinyl)-3-piperidinecarboxamide | 511.20 | 512.20556 |
| 37 | 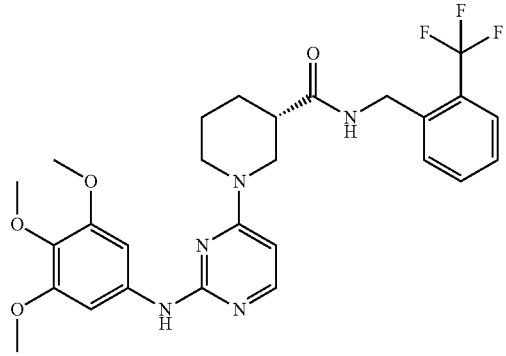 [SMILES: COc1cc(Nc2nccc(N3CCC[C@H](C(=O)NCc4ccccc4C(F)(F)F)C3)n2)cc(OC)c1OC] | (S)-N-(2-(trifluoromethyl)benzyl)-1-(2-((3,4,5-trimethoxyphenyl)amino)-4-pyrimidinyl)-3-piperidinecarboxamide | 545.56 | 546.23179 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 38 | 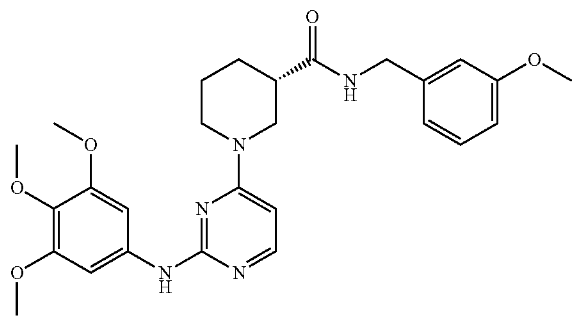 [SMILES: COc1cccc(CNC(=O)[C@H]2CCCN(c3ccnc(Nc4cc(OC)c(OC)c(OC)c4)n3)C2)c1] | (S)-N-(3-methoxybenzyl)-1-(2-((3,4,5-trimethoxyphenyl)amino)-4-pyrimidinyl)-3-piperidinecarboxamide | 507.59 | 508.25469 |
| 39 | 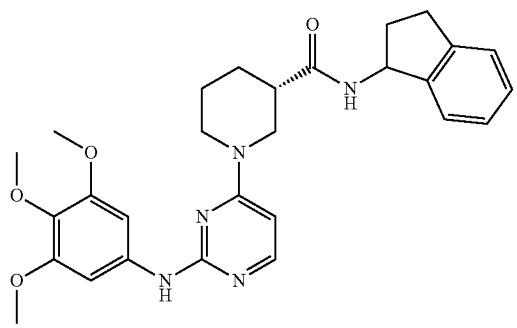 [SMILES: COc1cc(Nc2nccc(N3CCC[C@H](C(=O)NC4CCc5ccccc54)C3)n2)cc(OC)c1OC] | (S)-N-(2,3-dihydro-1H-inden-1-yl)-1-(2-((3,4,5-trimethoxyphenyl)amino)-4-pyrimidinyl)-3-piperidinecarboxamide | 503.60 | 504.25983 |
| 40 | 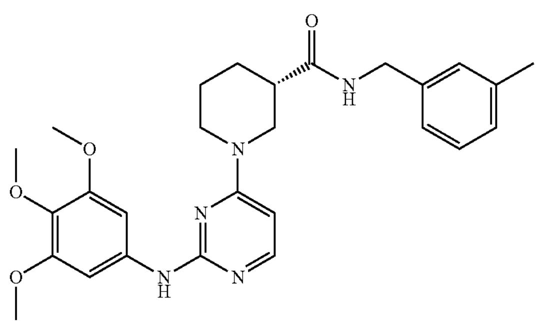 [SMILES: COc1cc(Nc2nccc(N3CCC[C@H](C(=O)NCc4cccc(C)c4)C3)n2)cc(OC)c1OC] | (S)-N-(3-methylbenzyl)-1-(2-((3,4,5-trimethoxyphenyl)amino)-4-pyrimidinyl)-3-piperidinecarboxamide | 491.59 | 492.26017 |
| 41 | 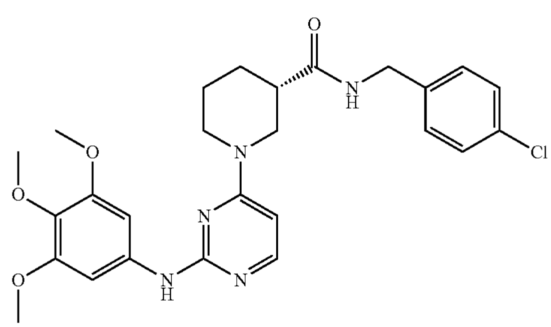 [SMILES: COc1cc(Nc2nccc(N3CCC[C@H](C(=O)NCc4ccc(Cl)cc4)C3)n2)cc(OC)c1OC] | (S)-N-(4-chlorobenzyl)-1-(2-((3,4,5-trimethoxyphenyl)amino)-4-pyrimidinyl)-3-piperidinecarboxamide | 511.20 | 512.20560 |

TABLE 1-continued

Examples 14-124.
All the example compounds in the following Table were synthesized using either intermediate M2 or M3 following the method exemplified in 13.

| Example | Structure | Final Compound Name | MS (calc'd) | M + H (observed) |
|---|---|---|---|---|
| 42 | 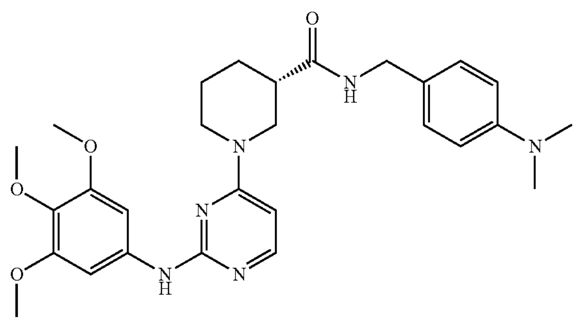 [SMILES: COc1cc(Nc2nccc(N3CCC[C@H](C(=O)NCc4ccc(N(C)C)cc4)C3)n2)cc(OC)c1OC] | (S)-N-(4-(dimethylamino)benzyl)-1-(2-((3,4,5-trimethoxyphenyl)amino)-4-pyrimidinyl)-3-piperidinecarboxamide | 520.63 | 521.28648 |
| 43 | 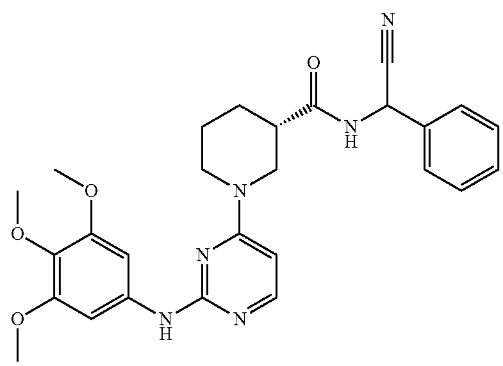 [SMILES: COc1cc(Nc2nccc(N3CCC[C@H](C(=O)NC(C#N)c4ccccc4)C3)n2)cc(OC)c1OC] | (S)-N-(cyano(phenyl)methyl)-1-(2-((3,4,5-trimethoxyphenyl)amino)-4-pyrimidinyl)-3-piperidinecarboxamide | 502.57 | 503.23967 |
| 44 | 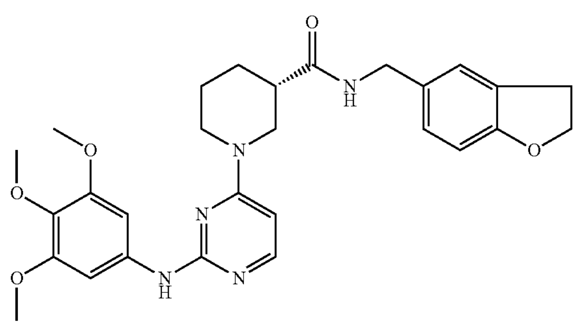 [SMILES: COc1cc(Nc2nccc(N3CCC[C@H](C(=O)NCc4ccc5c(c4)CCO5)C3)n2)cc(OC)c1OC] | (S)-N-(2,3-dihydro-1-benzofuran-5-ylmethyl)-1-(2-((3,4,5-trimethoxyphenyl)amino)-4-pyrimidinyl)-3-piperidinecarboxamide | 519.60 | 520.25507 |
| 45 | 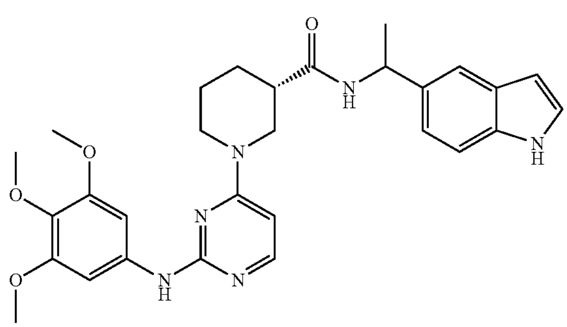 [SMILES: COc1cc(Nc2nccc(N3CCC[C@H](C(=O)NC(C)c4ccc5[nH]ccc5c4)C3)n2)cc(OC)c1OC] | (S)-N-(1-(1H-indol-5-yl)ethyl)-1-(2-((3,4,5-trimethoxyphenyl)amino)-4-pyrimidinyl)-3-piperidinecarboxamide | 530.63 | 531.27140 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 46 | 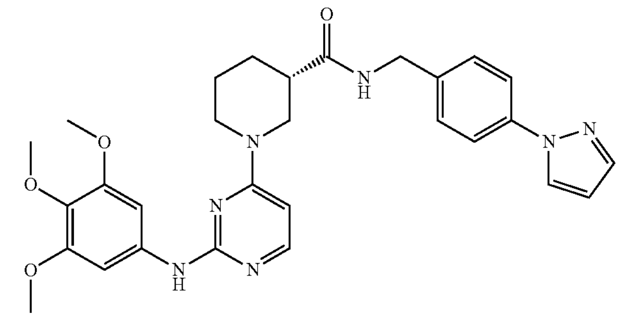 [SMILES: COc1cc(Nc2nccc(N3CCC[C@H](C(=O)NCc4ccc(-n5cccn5)cc4)C3)n2)cc(OC)c1OC] | (S)-N-(4-(1H-pyrazol-1-yl)benzyl)-1-(2-((3,4,5-trimethoxyphenyl)amino)-4-pyrimidinyl)-3-piperidinecarboxamide | 543.62 | 544.26635 |
| 47 | 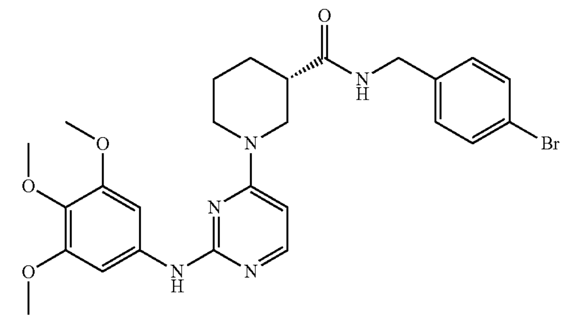 [SMILES: COc1cc(Nc2nccc(N3CCC[C@H](C(=O)NCc4ccc(Br)cc4)C3)n2)cc(OC)c1OC] | (S)-N-(4-bromobenzyl)-1-(2-((3,4,5-trimethoxyphenyl)amino)-4-pyrimidinyl)-3-piperidinecarboxamide | 555.15 | 556.15594 |
| 48 | 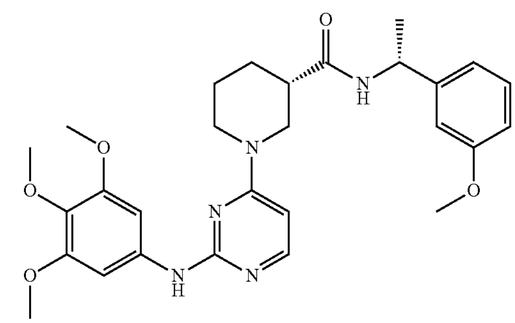 [SMILES: COc1cccc([C@@H](C)NC(=O)[C@H]2CCCN(c3ccnc(Nc4cc(OC)c(OC)c(OC)c4)n3)C2)c1] | (S)-N-((R)-1-(3-methoxyphenyl)ethyl)-1-(2-((3,4,5-trimethoxyphenyl)amino)-4-pyrimidinyl)-3-piperidinecarboxamide | 521.61 | 522.27053 |
| 49 | 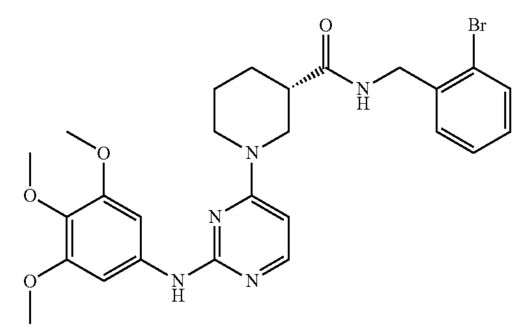 | (S)-N-(2-bromobenzyl)-1-(2-((3,4,5-trimethoxyphenyl)amino)-4-pyrimidinyl)-3-piperidinecarboxamide | 555.15 | 556.15499 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 50 | 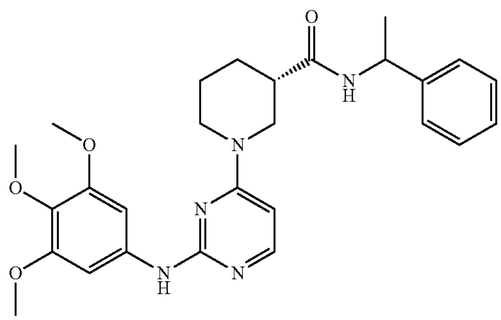 [SMILES: COc1cc(Nc2nccc(N3CCC[C@H](C(=O)NC(C)c4ccccc4)C3)n2)cc(OC)c1OC] | (S)-N-(1-phenylethyl)-1-(2-((3,4,5-trimethoxyphenyl)amino)-4-pyrimidinyl)-3-piperidinecarboxamide | 491.59 | 492.26019 |
| 51 | 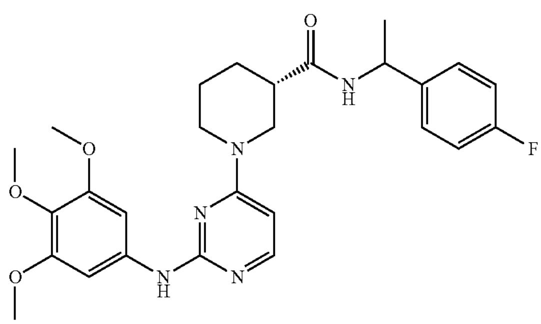 [SMILES: COc1cc(Nc2nccc(N3CCC[C@H](C(=O)NC(C)c4ccc(F)cc4)C3)n2)cc(OC)c1OC] | (S)-N-(1-(4-fluorophenyl)ethyl)-1-(2-((3,4,5-trimethoxyphenyl)amino)-4-pyrimidinyl)-3-piperidinecarboxamide | 509.58 | 510.25075 |
| 52 | 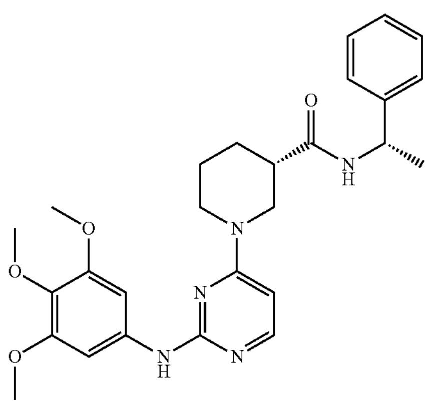 [SMILES: COc1cc(Nc2nccc(N3CCC[C@H](C(=O)N[C@@H](C)c4ccccc4)C3)n2)cc(OC)c1OC] | (S)-N-((S)-1-phenylethyl)-1-(2-((3,4,5-trimethoxyphenyl)amino)-4-pyrimidinyl)-3-piperidinecarboxamide | 491.59 | 492.25997 |
| 53 | 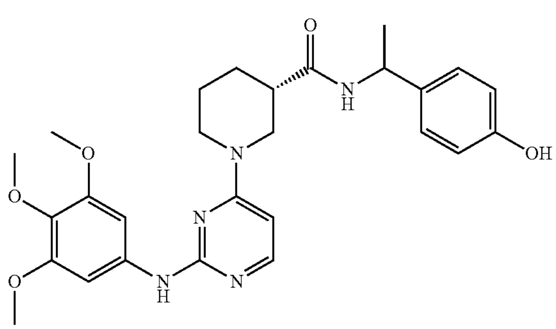 [SMILES: COc1cc(Nc2nccc(N3CCC[C@H](C(=O)NC(C)c4ccc(O)cc4)C3)n2)cc(OC)c1OC] | (S)-N-(1-(4-hydroxyphenyl)ethyl)-1-(2-((3,4,5-trimethoxyphenyl)amino)-4-pyrimidinyl)-3-piperidinecarboxamide | 507.59 | 508.25494 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 54 | 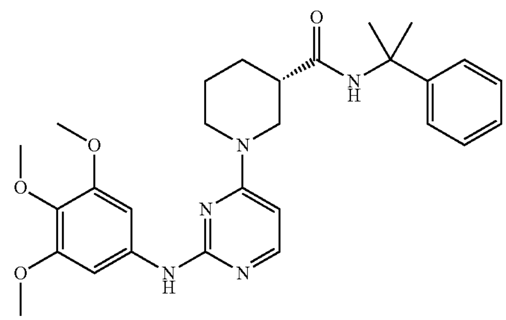 [SMILES: COc1cc(Nc2nccc(N3CCC[C@H](C(=O)NC(C)(C)c4ccccc4)C3)n2)cc(OC)c1OC] | (S)-N-(1-methyl-1-phenylethyl)-1-(2-((3,4,5-trimethoxyphenyl)amino)-4-pyrimidinyl)-3-piperidinecarboxamide | 505.62 | 506.27592 |
| 55 | 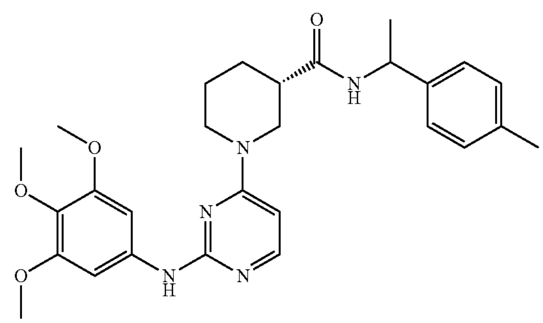 [SMILES: COc1cc(Nc2nccc(N3CCC[C@H](C(=O)NC(C)c4ccc(C)cc4)C3)n2)cc(OC)c1OC] | (S)-N-(1-(4-methylphenyl)ethyl)-1-(2-((3,4,5-trimethoxyphenyl)amino)-4-pyrimidinyl)-3-piperidinecarboxamide | 505.62 | 506.27598 |
| 56 | 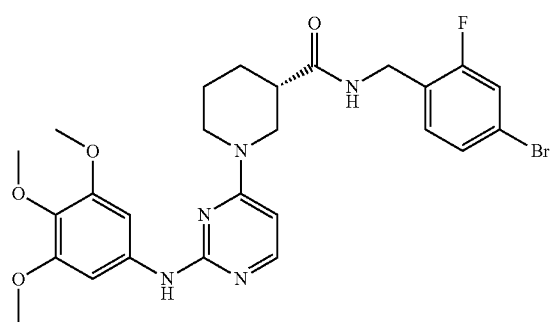 [SMILES: COc1cc(Nc2nccc(N3CCC[C@H](C(=O)NCc4ccc(Br)cc4F)C3)n2)cc(OC)c1OC] | (S)-N-(4-bromo-2-fluorobenzyl)-1-(2-((3,4,5-trimethoxyphenyl)amino)-4-pyrimidinyl)-3-piperidinecarboxamide | 574.45 | 574.14618 |
| 57 | 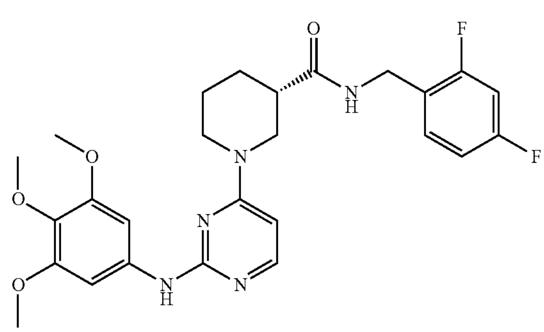 [SMILES: COc1cc(Nc2nccc(N3CCC[C@H](C(=O)NCc4ccc(F)cc4F)C3)n2)cc(OC)c1OC] | (S)-N-(2,4-difluorobenzyl)-1-(2-((3,4,5-trimethoxyphenyl)amino)-4-pyrimidinyl)-3-piperidinecarboxamide | 513.54 | 514.22624 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 58 | 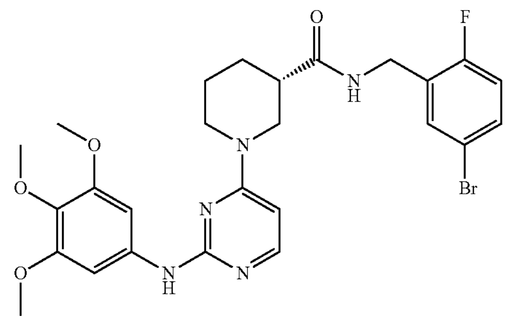 [SMILES: COc1cc(Nc2nccc(N3CCC[C@H](C(=O)NCc4cc(Br)ccc4F)C3)n2)cc(OC)c1OC] | (S)-N-(5-bromo-2-fluorobenzyl)-1-(2-((3,4,5-trimethoxyphenyl)amino)-4-pyrimidinyl)-3-piperidinecarboxamide | 573.14 | 574.14608 |
| 59 | 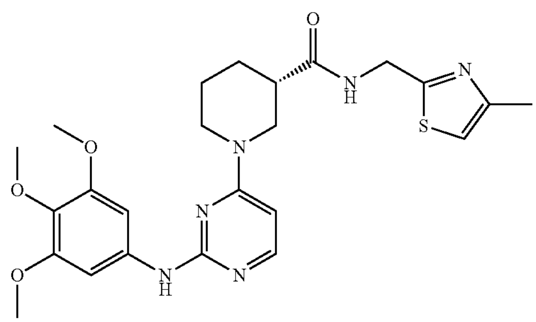 [SMILES: COc1cc(Nc2nccc(N3CCC[C@H](C(=O)NCc4nc(C)cs4)C3)n2)cc(OC)c1OC] | (S)-N-((4-methyl-1,3-thiazol-2-yl)methyl)-1-(2-((3,4,5-trimethoxyphenyl)amino)-4-pyrimidinyl)-3-piperidinecarboxamide | 498.61 | 499.21218 |
| 60 | 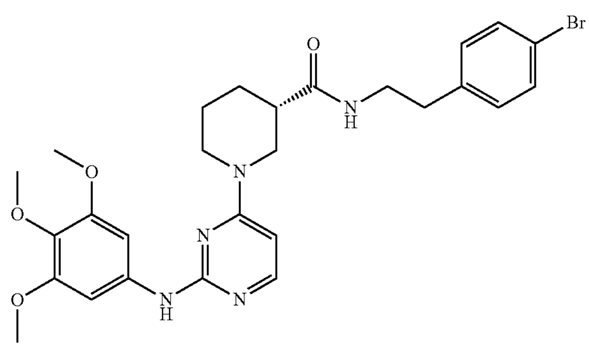 [SMILES: COc1cc(Nc2nccc(N3CCC[C@H](C(=O)NCCc4ccc(Br)cc4)C3)n2)cc(OC)c1OC] | (S)-N-(2-(4-bromophenyl)ethyl)-1-(2-((3,4,5-trimethoxyphenyl)amino)-4-pyrimidinyl)-3-piperidinecarboxamide | 570.48 | 570.17116 |
| 61 | 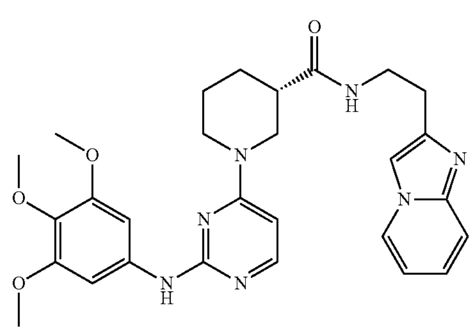 [SMILES: COc1cc(Nc2nccc(N3CCC[C@H](C(=O)NCCc4cn5ccccc5n4)C3)n2)cc(OC)c1OC] | (S)-N-(2-imidazo[1,2-a]pyridin-2-ylethyl)-1-(2-((3,4,5-trimethoxyphenyl)amino)-4-pyrimidinyl)-3-piperidinecarboxamide | 531.61 | 532.26694 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 62 | 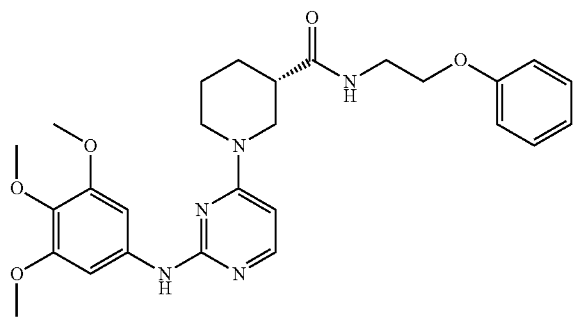 | (S)-N-(2-phenoxyethyl)-1-(2-((3,4,5-trimethoxyphenyl)amino)-4-pyrimidinyl)-3-piperidinecarboxamide | 507.59 | 508.25538 |
| 63 | 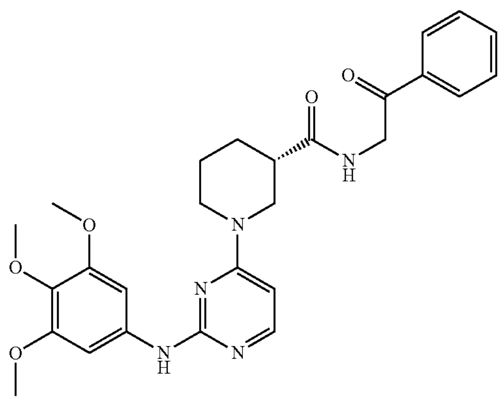 [SMILES: COc1cc(Nc2nccc(N3CCC[C@H](C(=O)NCC(=O)c4ccccc4)C3)n2)cc(OC)c1OC] | (S)-N-(2-oxo-2-phenylethyl)-1-(2-((3,4,5-trimethoxyphenyl)amino)-4-pyrimidinyl)-3-piperidinecarboxamide | 505.57 | 506.23970 |
| 64 | 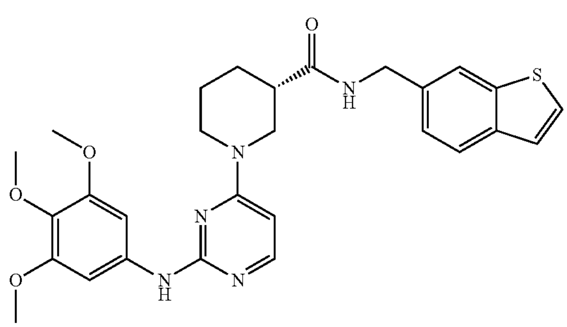 [SMILES: COc1cc(Nc2nccc(N3CCC[C@H](C(=O)NCc4ccc5ccsc5c4)C3)n2)cc(OC)c1OC] | (S)-N-(1-benzothiophen-6-ylmethyl)-1-(2-((3,4,5-trimethoxyphenyl)amino)-4-pyrimidinyl)-3-piperidinecarboxamide | 533.65 | 534.21666 |
| 65 | 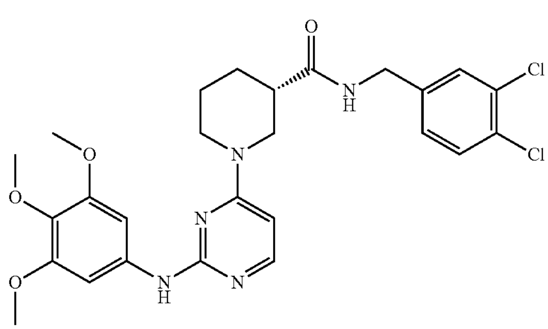 | (S)-N-(3,4-dichlorobenzyl)-1-(2-((3,4,5-trimethoxyphenyl)amino)-4-pyrimidinyl)-3-piperidinecarboxamide | 546.45 | 546.16654 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 66 | 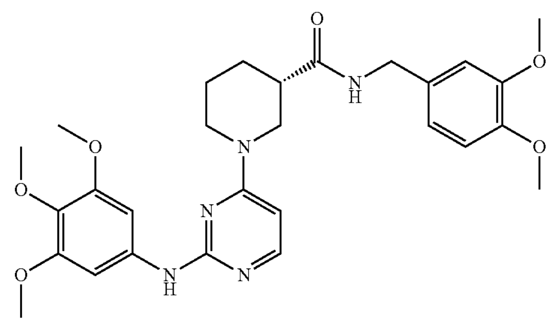 [SMILES: COc1ccc(CNC(=O)[C@H]2CCCN(c3ccnc(Nc4cc(OC)c(OC)c(OC)c4)n3)C2)cc1OC] | (S)-N-(3,4-dimethoxybenzyl)-1-(2-((3,4,5-trimethoxyphenyl)amino)-4-pyrimidinyl)-3-piperidinecarboxamide | 537.61 | 538.26567 |
| 67 | 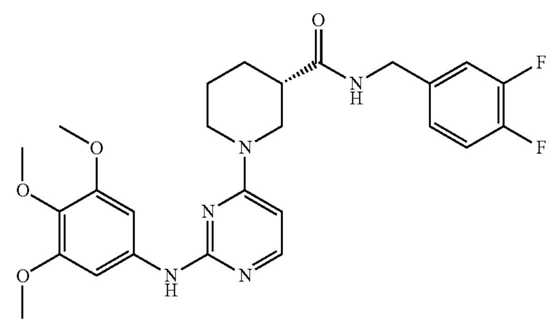 [SMILES: COc1cc(Nc2nccc(N3CCC[C@H](C(=O)NCc4ccc(F)c(F)c4)C3)n2)cc(OC)c1OC] | (S)-N-(3,4-difluorobenzyl)-1-(2-((3,4,5-trimethoxyphenyl)amino)-4-pyrimidinyl)-3-piperidinecarboxamide | 513.54 | 514.22538 |
| 68 | 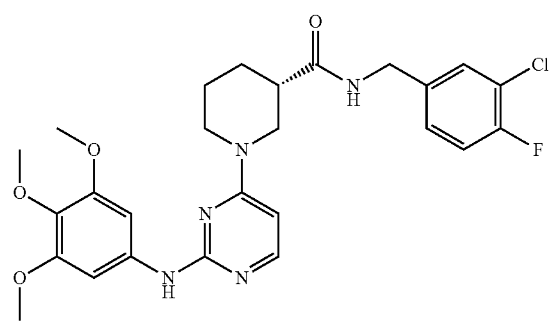 [SMILES: COc1cc(Nc2nccc(N3CCC[C@H](C(=O)NCc4ccc(F)c(Cl)c4)C3)n2)cc(OC)c1OC] | (S)-N-(3-chloro-4-fluorobenzyl)-1-(2-((3,4,5-trimethoxyphenyl)amino)-4-pyrimidinyl)-3-pipcridinecarboxamide | 530.00 | 530.19617 |
| 69 | 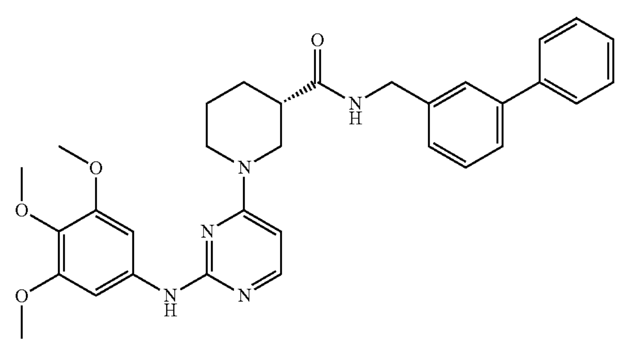 [SMILES: COc1cc(Nc2nccc(N3CCC[C@H](C(=O)NCc4cccc(-c5ccccc5)c4)C3)n2)cc(OC)c1OC] | (S)-N-(3-biphenylylmethyl)-1-(2-((3,4,5-trimethoxyphenyl)amino)-4-pyrimidinyl)-3-piperidinecarboxamide | 553.66 | 554.2758 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 70 | 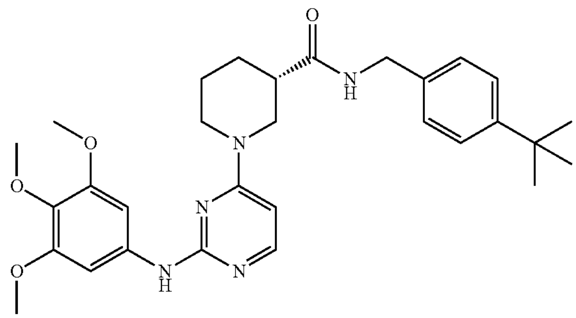 [SMILES: COc1cc(Nc2nccc(N3CCC[C@H](C(=O)NCc4ccc(C(C)(C)C)cc4)C3)n2)cc(OC)c1OC] | (S)-N-(4-tert-butylbenzyl)-1-(2-((3,4,5-trimethoxyphenyl)amino)-4-pyrimidinyl)-3-piperidinecarboxamide | 533.67 | 534.30703 |
| 71 | 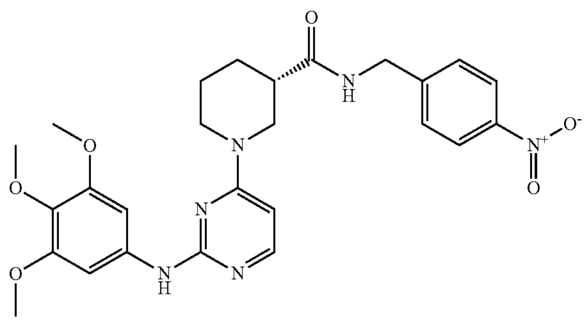 [SMILES: COc1cc(Nc2nccc(N3CCC[C@H](C(=O)NCc4ccc([N+](=O)[O-])cc4)C3)n2)cc(OC)c1OC] | (S)-N-(4-nitrobenzyl)-1-(2-((3,4,5-trimethoxyphenyl)amino)-4-pyrimidinyl)-3-piperidinecarboxamide | 522.56 | 523.22945 |
| 72 | 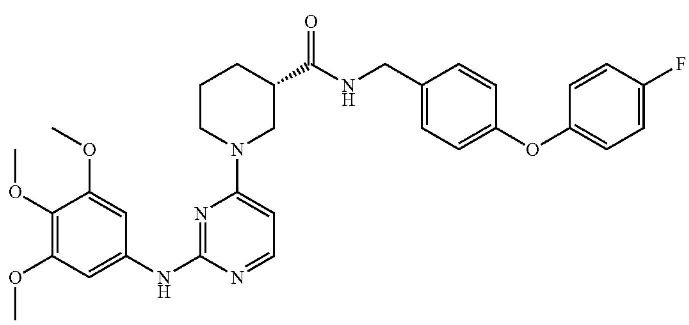 [SMILES: COc1cc(Nc2nccc(N3CCC[C@H](C(=O)NCc4ccc(Oc5ccc(F)cc5)cc4)C3)n2)cc(OC)c1OC] | (S)-N-(4-(4-fluorophenoxy)benzyl)-1-(2-((3,4,5-trimethoxyphenyl)amino)-4-pyrimidinyl)-3-piperidinecarboxamide | 587.65 | 588.26126 |
| 73 | 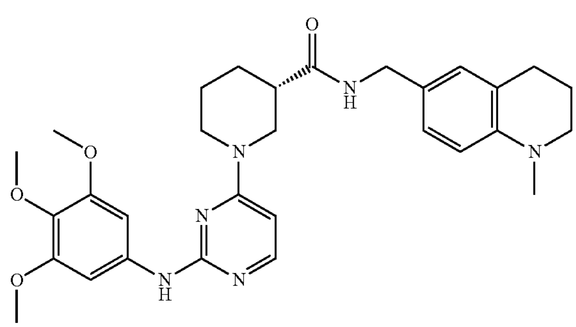 [SMILES: COc1cc(Nc2nccc(N3CCC[C@H](C(=O)NCc4ccc5c(c4)CCCN5C)C3)n2)cc(OC)c1OC] | (S)-N-((1-methyl-1,2,3,4-tetrahydro-6-quinolinyl)methyl)-1-(2-((3,4,5-trimethoxyphenyl)amino)-4-pyrimidinyl)-3-piperidinecarboxamide | 546.67 | 547.30207 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 74 | 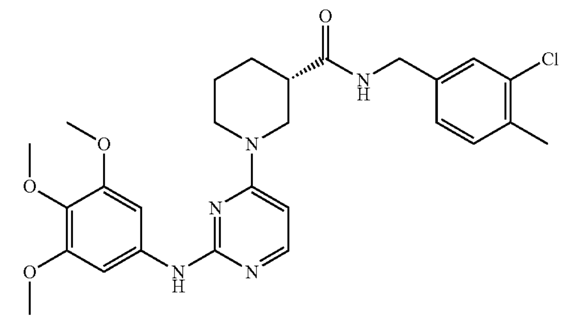 [SMILES: COc1cc(Nc2nccc(N3CCC[C@H](C(=O)NCc4ccc(C)c(Cl)c4)C3)n2)cc(OC)c1OC] | (S)-N-(3-chloro-4-methylbenzyl)-1-(2-((3,4,5-trimethoxyphenyl)amino)-4-pyrimidinyl)-3-piperidinecarboxamide | 526.03 | 526.22136 |
| 75 | 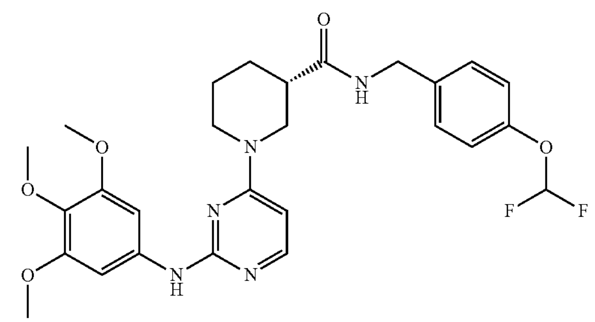 [SMILES: COc1cc(Nc2nccc(N3CCC[C@H](C(=O)NCc4ccc(OC(F)F)cc4)C3)n2)cc(OC)c1OC] | (S)-N-(4-(difluoromethoxy)benzyl)-1-(2-((3,4,5-trimethoxyphenyl)amino)-4-pyrimidinyl)-3-piperidinecarboxamide | 543.57 | 544.23563 |
| 76 | 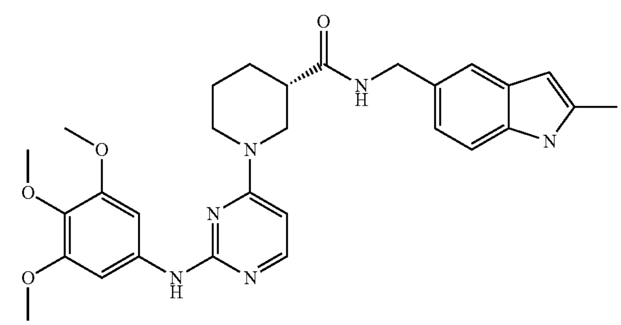 [SMILES: COc1cc(Nc2nccc(N3CCC[C@H](C(=O)NCc4ccc5[nH]c(C)cc5c4)C3)n2)cc(OC)c1OC] | (S)-N-((2-methyl-1H-indol-5-yl)methyl)-1-(2-((3,4,5-trimethoxyphenyl)amino)-4-pyrimidinyl)-3-piperidinecarboxamide | 530.63 | 531.27110 |
| 77 | 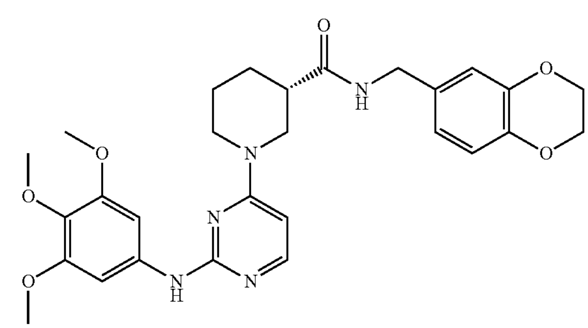 [SMILES: COc1cc(Nc2nccc(N3CCC[C@H](C(=O)NCc4ccc5c(c4)OCCO5)C3)n2)cc(OC)c1OC] | (S)-N-(2,3-dihydro-1,4-benzodioxin-6-ylmethyl)-1-(2-((3,4,5-trimethoxyphenyl)amino)-4-pyrimidinyl)-3-piperidinecarboxamide | 535.60 | 536.25020 |

TABLE 1-continued

Examples 14-124.
All the example compounds in the following Table were synthesized using either intermediate M2 or M3 following the method exemplified in 13.

| Example | Structure | Final Compound Name | MS (calc'd) | M + H (observed) |
|---|---|---|---|---|
| 78 | 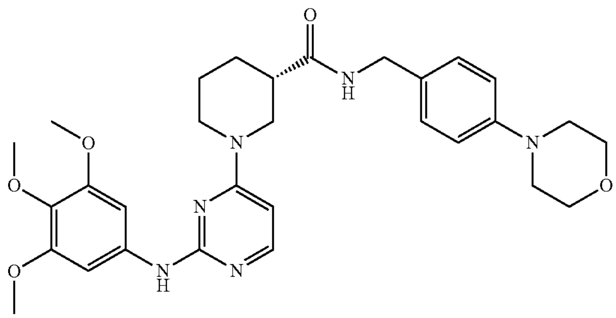 [SMILES: COc1cc(Nc2nccc(N3CCC[C@H](C(=O)NCc4ccc(N5CCOCC5)cc4)C3)n2)cc(OC)c1OC] | (S)-N-(4-(4-morpholinyl)benzyl)-1-(2-((3,4,5-trimethoxyphenyl)amino)-4-pyrimidinyl)-3-piperidinecarboxamide | 562.67 | 563.29671 |
| 79 | 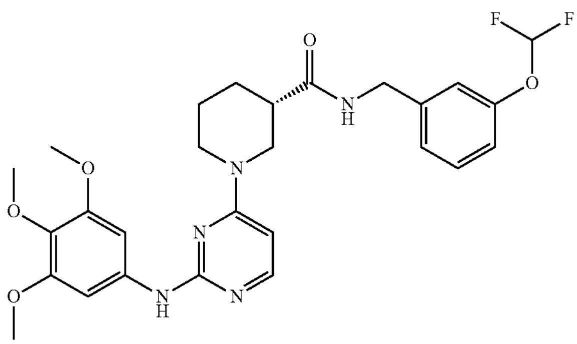 [SMILES: COc1cc(Nc2nccc(N3CCC[C@H](C(=O)NCc4cccc(OC(F)F)c4)C3)n2)cc(OC)c1OC] | (S)-N-(3-(difluoromethoxy)benzyl)-1-(2-((3,4,5-trimethoxyphenyl)amino)-4-pyrimidinyl)-3-piperidinecarboxamide | 543.57 | 544.23613 |
| 80 | 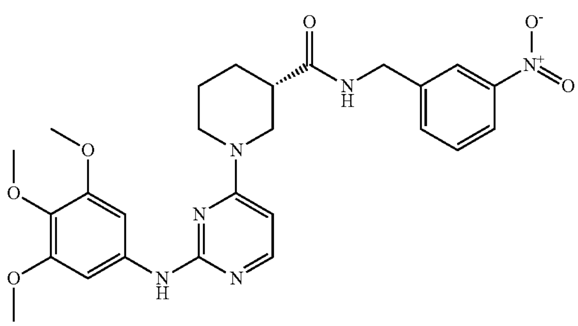 [SMILES: COc1cc(Nc2nccc(N3CCC[C@H](C(=O)NCc4cccc([N+](=O)[O-])c4)C3)n2)cc(OC)c1OC] | (S)-N-(3-nitrobenzyl)-1-(2-((3,4,5-trimethoxyphenyl)amino)-4-pyrimidinyl)-3-piperidinecarboxamide | 522.56 | 523.22929 |
| 81 | 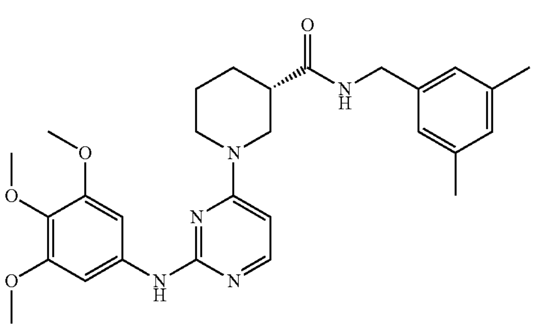 [SMILES: COc1cc(Nc2nccc(N3CCC[C@H](C(=O)NCc4cc(C)cc(C)c4)C3)n2)cc(OC)c1OC] | (S)-N-(3,5-dimethylbenzyl)-1-(2-((3,4,5-trimethoxyphenyl)amino)-4-pyrimidinyl)-3-piperidinecarboxamide | 505.62 | 506.27598 |

TABLE 1-continued

Examples 14-124.
All the example compounds in the following Table were synthesized using either intermediate M2 or M3 following the method exemplified in 13.

| Example | Structure | Final Compound Name | MS (calc'd) | M + H (observed) |
|---|---|---|---|---|
| 82 | 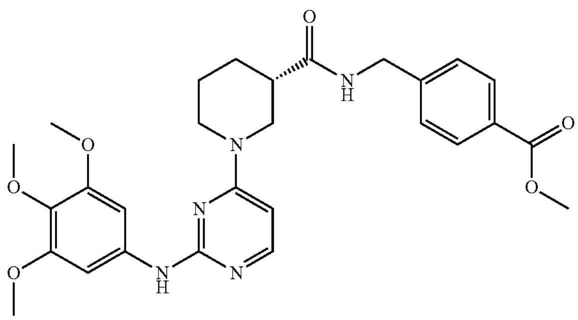 [SMILES: COC(=O)c1ccc(CNC(=O)[C@H]2CCCN(c3ccnc(Nc4cc(OC)c(OC)c(OC)c4)n3)C2)cc1] | (S)-methyl 4-((1-(2-(3,4,5-trimethoxyphenylamino)pyrimidin-4-yl)piperidine-3-carboxamido)methyl)benzoate | 535.60 | 536.25000 |
| 83 | 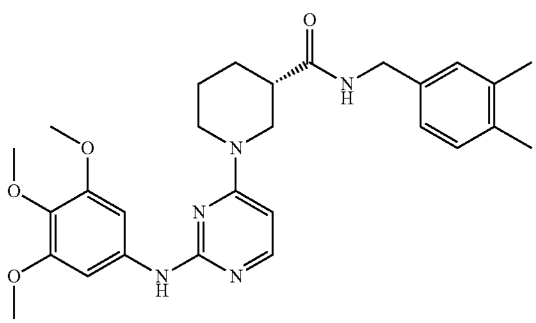 [SMILES: COc1cc(Nc2nccc(N3CCC[C@H](C(=O)NCc4ccc(C)c(C)c4)C3)n2)cc(OC)c1OC] | (S)-N-(3,4-dimethylbenzyl)-1-(2-((3,4,5-trimethoxyphenyl)amino)-4-pyrimidinyl)-3-piperidinecarboxamide | 505.62 | 506.27639 |
| 84 | 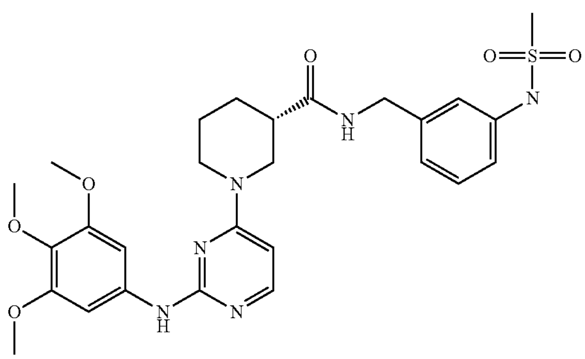 [SMILES: COc1cc(Nc2nccc(N3CCC[C@H](C(=O)NCc4cccc(NS(C)(=O)=O)c4)C3)n2)cc(OC)c1OC] | (S)-N-(3-((methylsulfonyl)amino)benzyl)-1-(2-((3,4,5-trimethoxyphenyl)amino)-4-pyrimidinyl)-3-piperidinecarboxamide | 570.67 | 571.23258 |
| 85 | 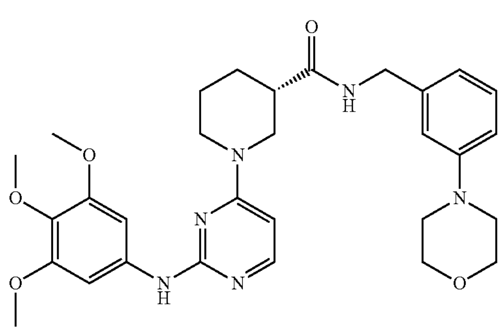 [SMILES: COc1cc(Nc2nccc(N3CCC[C@H](C(=O)NCc4cccc(N5CCOCC5)c4)C3)n2)cc(OC)c1OC] | (S)-N-(3-(4-morpholinyl)benzyl)-1-(2-((3,4,5-trimethoxyphenyl)amino)-4-pyrimidinyl)-3-piperidinecarboxamide | 562.67 | 563.29729 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 86 | 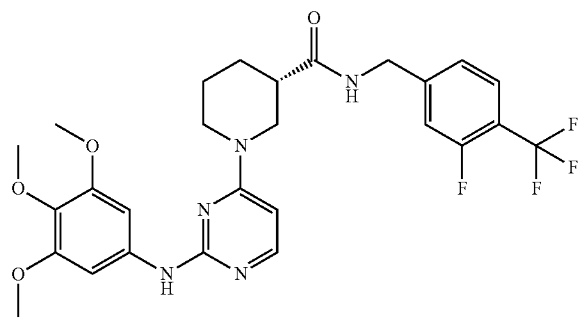 [SMILES: COc1cc(Nc2nccc(N3CCC[C@H](C(=O)NCc4ccc(C(F)(F)F)c(F)c4)C3)n2)cc(OC)c1OC] | (S)-N-(3-fluoro-4-(trifluoromethyl)benzyl)-1-(2-((3,4,5-trimethoxyphenyl)amino)-4-pyrimidinyl)-3-piperidinecarboxamide | 563.55 | 564.22255 |
| 87 | 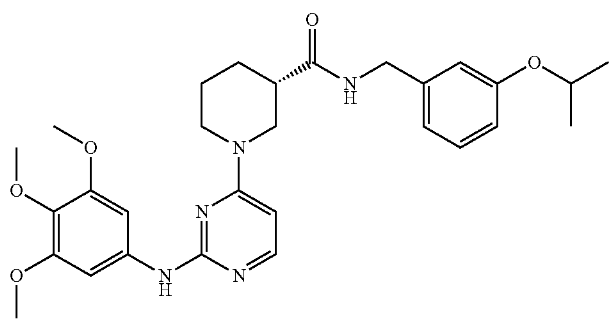 [SMILES: COc1cc(Nc2nccc(N3CCC[C@H](C(=O)NCc4cccc(OC(C)C)c4)C3)n2)cc(OC)c1OC] | (S)-N-(3-(1-methylethoxy)benzyl)-1-(2-((3,4,5-trimethoxyphenyl)amino)-4-pyrimidinyl)-3-piperidinecarboxamide | 535.64 | 536.28697 |
| 88 | 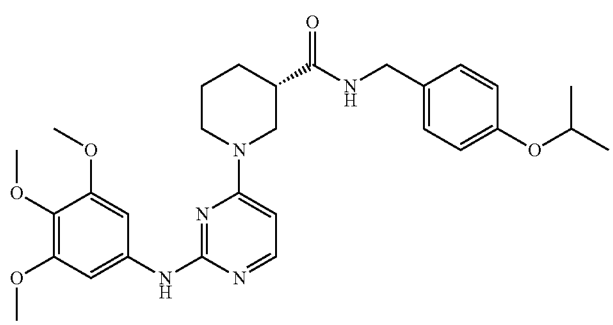 [SMILES: COc1cc(Nc2nccc(N3CCC[C@H](C(=O)NCc4ccc(OC(C)C)cc4)C3)n2)cc(OC)c1OC] | (S)-N-(4-(1-methylethoxy)benzyl)-1-(2-((3,4,5-trimethoxyphenyl)amino)-4-pyrimidinyl)-3-piperidinecarboxamide | 535.64 | 536.28687 |
| 89 | 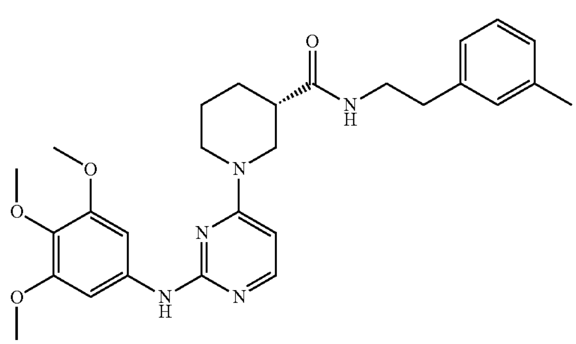 [SMILES: COc1cc(Nc2nccc(N3CCC[C@H](C(=O)NCCc4cccc(C)c4)C3)n2)cc(OC)c1OC] | (S)-N-(2-(3-methylphenyl)ethyl)-1-(2-((3,4,5-trimethoxyphenyl)amino)-4-pyrimidinyl)-3-piperidinecarboxamide | 505.62 | 506.27680 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 90 | 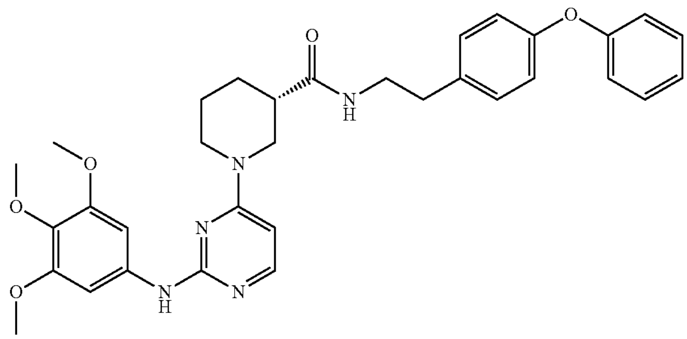 [SMILES: COc1cc(Nc2nccc(N3CCC[C@H](C(=O)NCCc4ccc(Oc5ccccc5)cc4)C3)n2)cc(OC)c1OC] | (S)-N-(2-(4-phenoxyphenyl)ethyl)-1-(2-((3,4,5-trimethoxyphenyl)amino)-4-pyrimidinyl)-3-piperidinecarboxamide | 583.69 | 584.28630 |
| 91 | 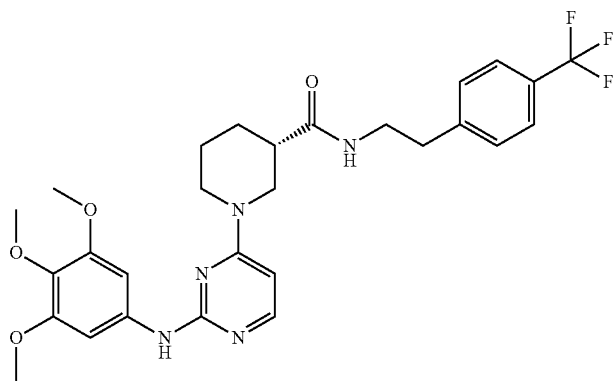 [SMILES: COc1cc(Nc2nccc(N3CCC[C@H](C(=O)NCCc4ccc(C(F)(F)F)cc4)C3)n2)cc(OC)c1OC] | (S)-N-(2-(4-(trifluoromethyl)phenyl)ethyl)-1-(2-((3,4,5-trimethoxyphenyl)amino)-4-pyrimidinyl)-3-piperidinecarboxamide | 559.59 | 560.24829 |
| 92 | 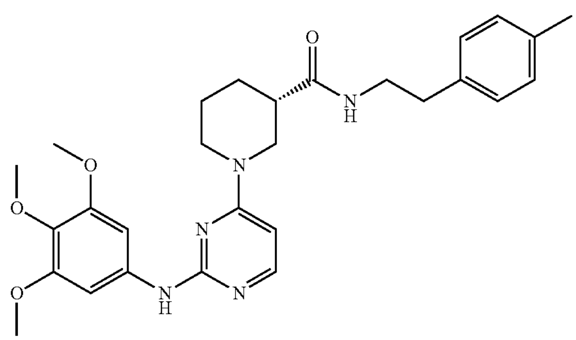 [SMILES: COc1cc(Nc2nccc(N3CCC[C@H](C(=O)NCCc4ccc(C)cc4)C3)n2)cc(OC)c1OC] | (S)-N-(2-(4-methylphenyl)ethyl)-1-(2-((3,4,5-trimethoxyphenyl)amino)-4-pyrimidinyl)-3-piperidinecarboxamide | 505.62 | 506.27674 |
| 93 | 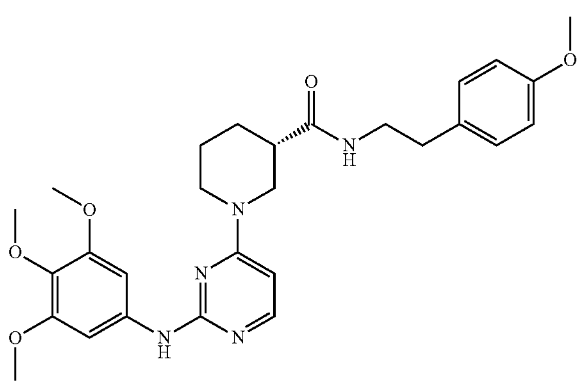 [SMILES: COc1ccc(CCNC(=O)[C@H]2CCCN(c3ccnc(Nc4cc(OC)c(OC)c(OC)c4)n3)C2)cc1] | (S)-N-(2-(4-methoxyphenyl)ethyl)-1-(2-((3,4,5-trimethoxyphenyl)amino)-4-pyrimidinyl)-3-piperidinecarboxamide | 521.61 | 522.27087 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 94 | 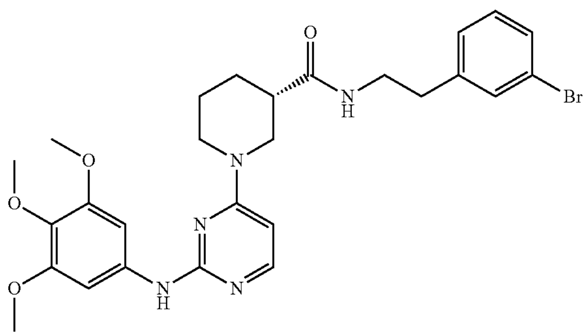 [SMILES: COc1cc(Nc2nccc(N3CCC[C@H](C(=O)NCCc4cccc(Br)c4)C3)n2)cc(OC)c1OC] | (S)-N-(2-(3-bromophenyl)ethyl)-1-(2-((3,4,5-trimethoxyphenyl)amino)-4-pyrimidinyl)-3-piperidinecarboxamide | 569.16 | 570.17103 |
| 95 | 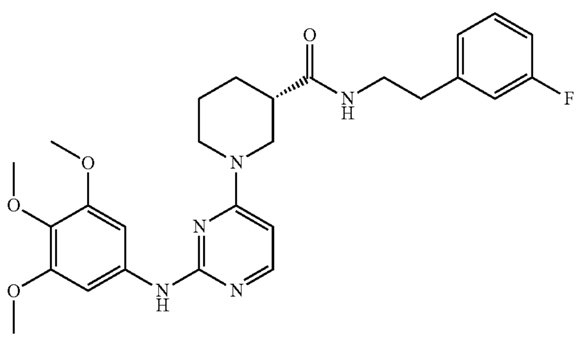 [SMILES: COc1cc(Nc2nccc(N3CCC[C@H](C(=O)NCCc4cccc(F)c4)C3)n2)cc(OC)c1OC] | (S)-N-(2-(3-fluorophenyl)ethyl)-1-(2-((3,4,5-trimethoxyphenyl)amino)-4-pyrimidinyl)-3-piperidinecarboxamide | 509.58 | 510.25112 |
| 96 | 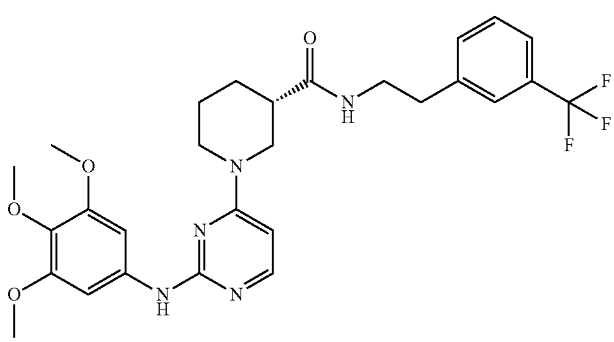 [SMILES: COc1cc(Nc2nccc(N3CCC[C@H](C(=O)NCCc4cccc(C(F)(F)F)c4)C3)n2)cc(OC)c1OC] | (S)-N-(2-(3-(trifluoromethyl)phenyl)ethyl)-1-(2-((3,4,5-trimethoxyphenyl)amino)-4-pyrimidinyl)-3-piperidinecarboxamide | 559.59 | 560.24789 |
| 97 | 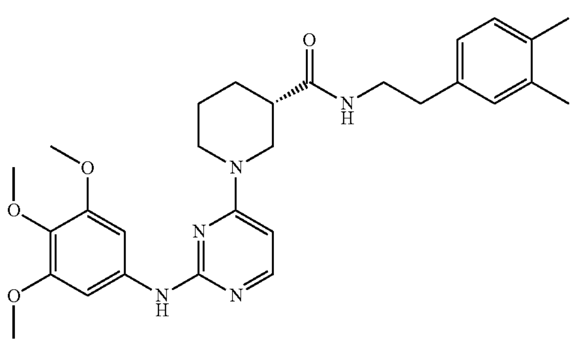 [SMILES: COc1cc(Nc2nccc(N3CCC[C@H](C(=O)NCCc4ccc(C)c(C)c4)C3)n2)cc(OC)c1OC] | (S)-N-(2-(3,4-dimethylphenyl)ethyl)-1-(2-((3,4,5-trimethoxyphenyl)amino)-4-pyrimidinyl)-3-piperidinecarboxamide | 519.64 | 520.29187 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 98 | 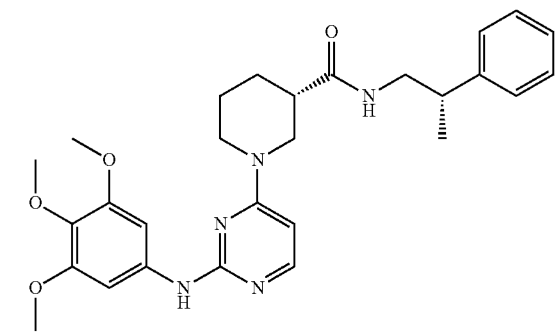 [SMILES: COc1cc(Nc2nccc(N3CCC[C@H](C(=O)NC[C@@H](C)c4ccccc4)C3)n2)cc(OC)c1OC] | (S)-N-((S)-2-phenylpropyl)-1-(2-((3,4,5-trimethoxyphenyl)amino)-4-pyrimidinyl)-3-piperidinecarboxamide | 505.62 | 506.27611 |
| 99 | 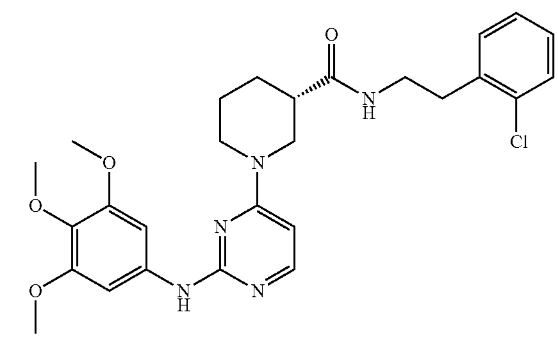 [SMILES: COc1cc(Nc2nccc(N3CCC[C@H](C(=O)NCCc4ccccc4Cl)C3)n2)cc(OC)c1OC] | (S)-N-(2-(2-chlorophenyl)ethyl)-1-(2-((3,4,5-trimethoxyphenyl)amino)-4-pyrimidinyl)-3-piperidinecarboxamide | 525.21 | 526.22155 |
| 100 | 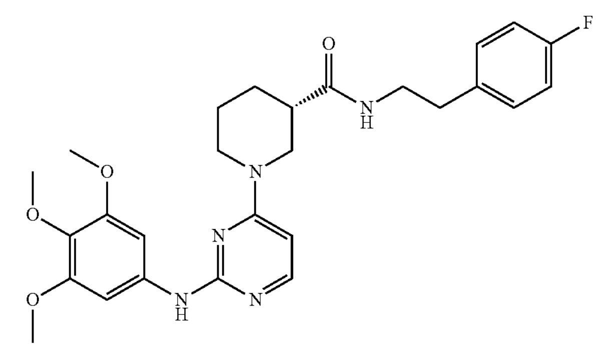 [SMILES: COc1cc(Nc2nccc(N3CCC[C@H](C(=O)NCCc4ccc(F)cc4)C3)n2)cc(OC)c1OC] | (S)-N-(2-(4-fluorophenyl)ethyl)-1-(2-((3,4,5-trimethoxyphenyl)amino)-4-pyrimidinyl)-3-piperidinecarboxamide | 509.58 | 510.25080 |
| 101 | 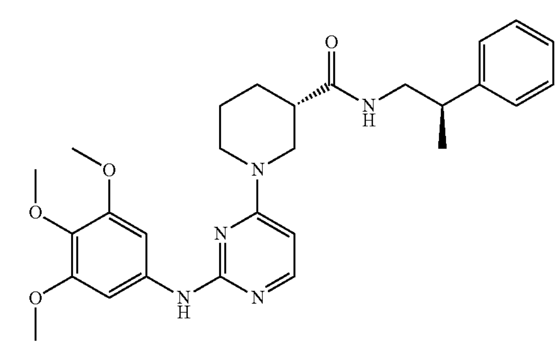 [SMILES: COc1cc(Nc2nccc(N3CCC[C@H](C(=O)NC[C@H](C)c4ccccc4)C3)n2)cc(OC)c1OC] | (S)-N-((R)-2-phenylpropyl)-1-(2-((3,4,5-trimethoxyphenyl)amino)-4-pyrimidinyl)-3-piperidinecarboxamide | 505.62 | 506.27669 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 102 | 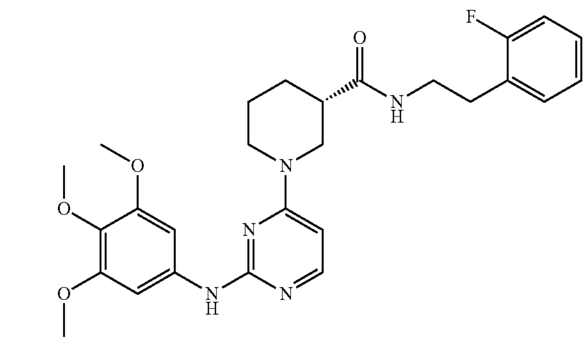 [SMILES: COc1cc(Nc2nccc(N3CCC[C@H](C(=O)NCCc4ccccc4F)C3)n2)cc(OC)c1OC] | (S)-N-(2-(2-fluorophenyl)ethyl)-1-(2-((3,4,5-trimethoxyphenyl)amino)-4-pyrimidinyl)-3-piperidinecarboxamide | 509.58 | 510.25074 |
| 103 | 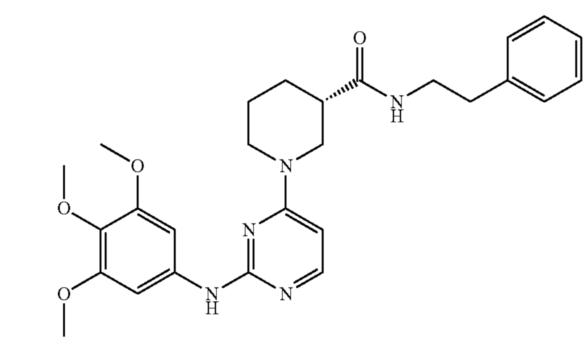 [SMILES: COc1cc(Nc2nccc(N3CCC[C@H](C(=O)NCCc4ccccc4)C3)n2)cc(OC)c1OC] | (S)-N-(2-phenylethyl)-1-(2-((3,4,5-trimethoxyphenyl)amino)-4-pyrimidinyl)-3-piperidinecarboxamide | 491.25 | 492.2 |
| 104 | 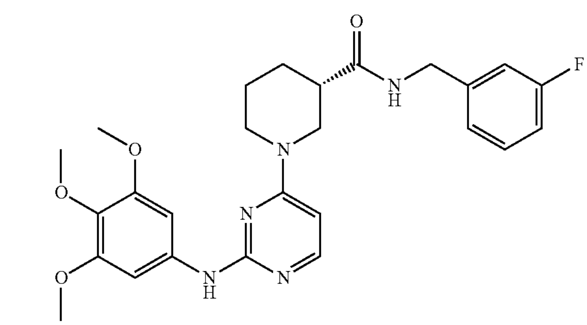 [SMILES: COc1cc(Nc2nccc(N3CCC[C@H](C(=O)NCc4cccc(F)c4)C3)n2)cc(OC)c1OC] | (S)-N-(3-fluorobenzyl)-1-(2-((3,4,5-trimethoxyphenyl)amino)-4-pyrimidinyl)-3-piperidinecarboxamide | 495.55 | 496.23474 |
| 105 | 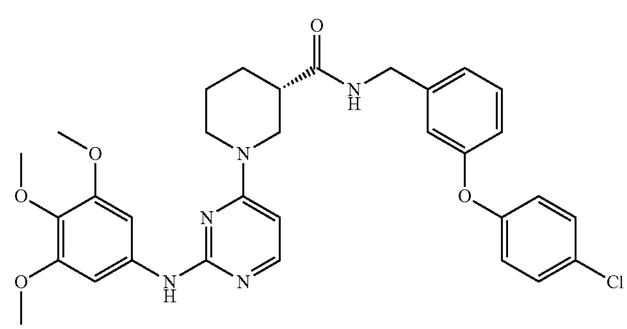 [SMILES: COc1cc(Nc2nccc(N3CCC[C@H](C(=O)NCc4cccc(Oc5ccc(Cl)cc5)c4)C3)n2)cc(OC)c1OC] | (S)-N-(3-(4-chlorophenoxy)benzyl)-1-(2-((3,4,5-trimethoxyphenyl)amino)-4-pyrimidinyl)-3-piperidinecarboxamide | 603.22 | 604.23182 |

TABLE 1-continued

Examples 14-124.
All the example compounds in the following Table were synthesized using either intermediate M2 or M3 following the method exemplified in 13.

| Example | Structure | Final Compound Name | MS (calc'd) | M + H (observed) |
|---|---|---|---|---|
| 106 | 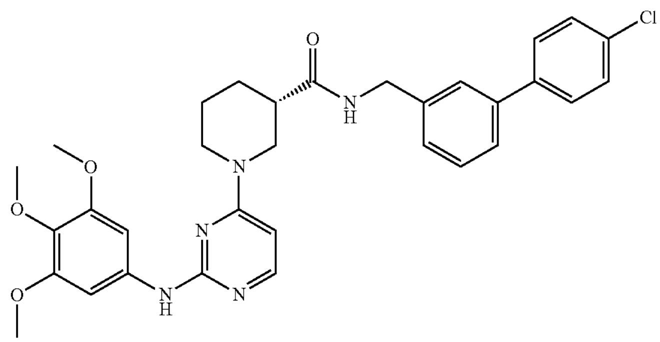 [SMILES: COc1cc(Nc2nccc(N3CCC[C@H](C(=O)NCc4cccc(-c5ccc(Cl)cc5)c4)C3)n2)cc(OC)c1OC] | (S)-N-((4'-chloro-3-biphenylyl)methyl)-1-(2-((3,4,5-trimethoxyphenyl)amino)-4-pyrimidinyl)-3-piperidinecarboxamide | 587.23 | 588.23703 |
| 107 | 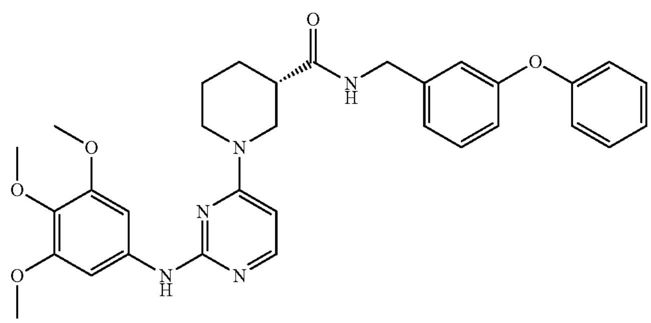 [SMILES: COc1cc(Nc2nccc(N3CCC[C@H](C(=O)NCc4cccc(Oc5ccccc5)c4)C3)n2)cc(OC)c1OC] | (S)-N-(3-phenoxybenzyl)-1-(2-((3,4,5-trimethoxyphenyl)amino)-4-pyrimidinyl)-3-piperidinecarboxamide | 569.66 | 570.27077 |
| 108 | 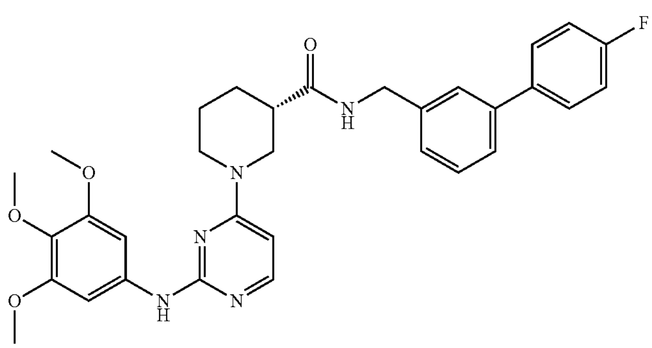 [SMILES: COc1cc(Nc2nccc(N3CCC[C@H](C(=O)NCc4cccc(-c5ccc(F)cc5)c4)C3)n2)cc(OC)c1OC] | (S)-N-((4'-fluoro-3-biphenylyl)methyl)-1-(2-((3,4,5-trimethoxyphenyl)amino)-4-pyrimidinyl)-3-piperidinecarboxamide | 571.65 | 572.26598 |
| 109 | 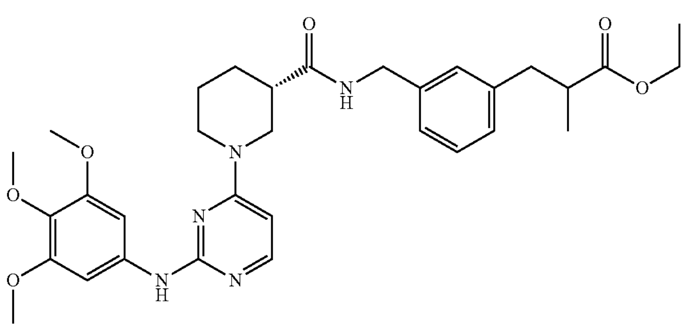 [SMILES: CCOC(=O)C(C)Cc1cccc(CNC(=O)[C@H]2CCCN(c3ccnc(Nc4cc(OC)c(OC)c(OC)c4)n3)C2)c1] | ethyl 2-methyl-3-(3-(((((S)-1-(2-((3,4,5-trimethoxyphenyl)amino)-4-pyrimidinyl)-3-piperidinyl)carbonyl)amino)methyl)phenyl)propanoate | 591.70 | 592.31226 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 110 | 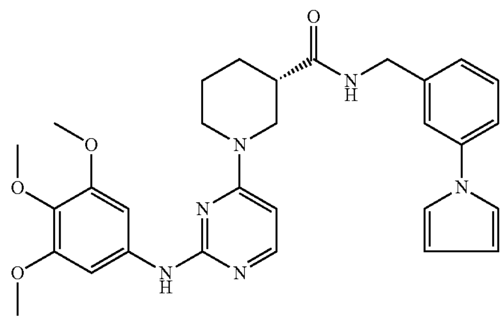 [SMILES: COc1cc(Nc2nccc(N3CCC[C@H](C(=O)NCc4cccc(-n5cccc5)c4)C3)n2)cc(OC)c1OC] | (S)-N-(3-(1H-pyrrol-1-yl)benzyl)-1-(2-((3,4,5-trimethoxyphenyl)amino)-4-pyrimidinyl)-3-piperidinecarboxamide | 542.64 | 543.27068 |
| 111 | 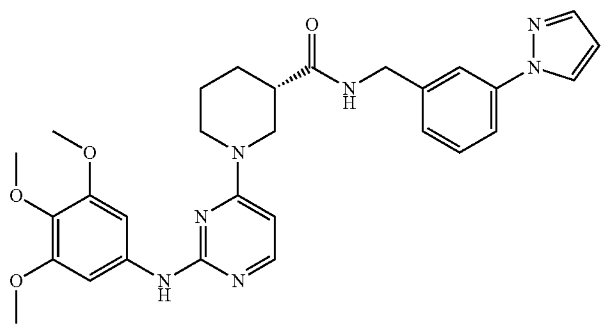 [SMILES: COc1cc(Nc2nccc(N3CCC[C@H](C(=O)NCc4cccc(-n5cccn5)c4)C3)n2)cc(OC)c1OC] | (S)-N-(3-(1H-pyrazol-1-yl)benzyl)-1-(2-((3,4,5-trimethoxyphenyl)amino)-4-pyrimidinyl)-3-piperidinecarboxamide | 543.62 | 544.26644 |
| 112 | 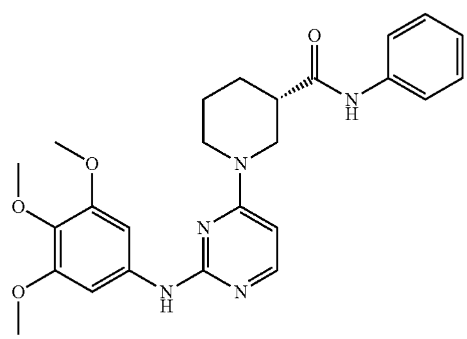 [SMILES: COc1cc(Nc2nccc(N3CCC[C@H](C(=O)Nc4ccccc4)C3)n2)cc(OC)c1OC] | (S)-N-phenyl-1-(2-((3,4,5-trimethoxyphenyl)amino)-4-pyrimidinyl)-3-piperidinecarboxamide | 463.54 | 464.22892 |
| 113 | 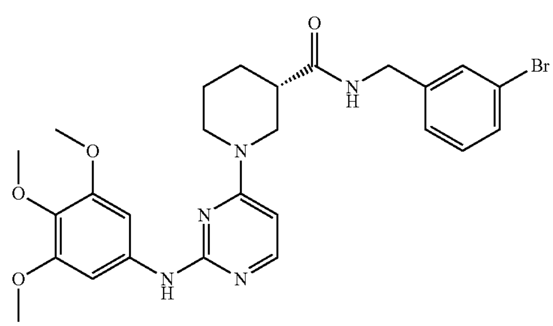 [SMILES: COc1cc(Nc2nccc(N3CCC[C@H](C(=O)NCc4cccc(Br)c4)C3)n2)cc(OC)c1OC] | (S)-N-(3-bromobenzyl)-1-(2-((3,4,5-trimethoxyphenyl)amino)-4-pyrimidinyl)-3-piperidinecarboxamide | 556.46 | 556.15536 |

TABLE 1-continued

Examples 14-124.
All the example compounds in the following Table were synthesized using either intermediate M2 or M3 following the method exemplified in 13.

| Example | Structure | Final Compound Name | MS (calc'd) | M + H (observed) |
|---|---|---|---|---|
| 114 | 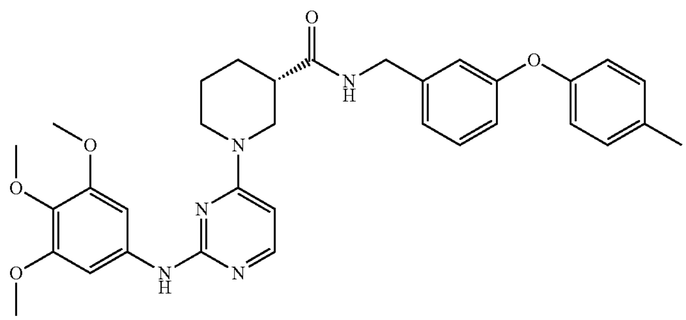 [SMILES: COc1cc(Nc2nccc(N3CCC[C@H](C(=O)NCc4cccc(Oc5ccc(C)cc5)c4)C3)n2)cc(OC)c1OC] | (S)-N-(3-(4-methylphenoxy)benzyl)-1-(2-((3,4,5-trimethoxyphenyl)amino)-4-pyrimidinyl)-3-piperidinecarboxamide | 583.69 | 584.28588 |
| 115 | 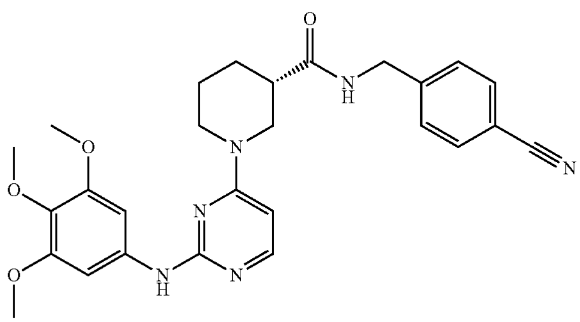 [SMILES: COc1cc(Nc2nccc(N3CCC[C@H](C(=O)NCc4ccc(C#N)cc4)C3)n2)cc(OC)c1OC] | (S)-N-(4-cyanobenzyl)-1-(2-((3,4,5-trimethoxyphenyl)amino)-4-pyrimidinyl)-3-piperidinecarboxamide | 502.57 | 503.23983 |
| 116 | 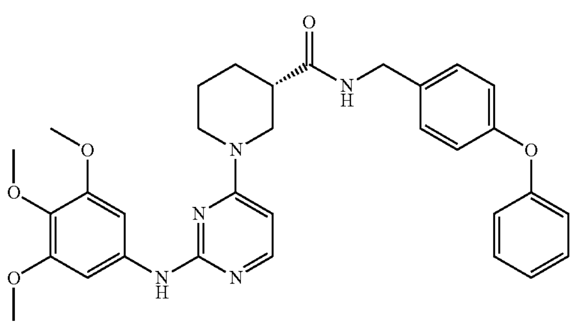 [SMILES: COc1cc(Nc2nccc(N3CCC[C@H](C(=O)NCc4ccc(Oc5ccccc5)cc4)C3)n2)cc(OC)c1OC] | (S)-N-(4-phenoxybenzyl)-1-(2-((3,4,5-trimethoxyphenyl)amino)-4-pyrimidinyl)-3-piperidinecarboxamide | 569.66 | 570.27068 |
| 117 | 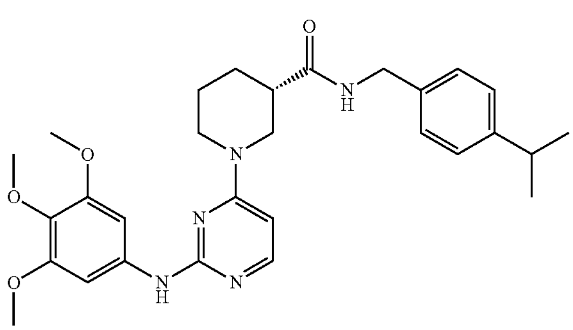 [SMILES: COc1cc(Nc2nccc(N3CCC[C@H](C(=O)NCc4ccc(C(C)C)cc4)C3)n2)cc(OC)c1OC] | (S)-N-(4-(1-methylethyl)benzyl)-1-(2-((3,4,5-trimethoxyphenyl)amino)-4-pyrimidinyl)-3-piperidinecarboxamide | 519.64 | 520.29131 |

TABLE 1-continued

Examples 14-124.
All the example compounds in the following Table were synthesized using either intermediate M2 or M3 following the method exemplified in 13.

| Example | Structure | Final Compound Name | MS (calc'd) | M + H (observed) |
|---|---|---|---|---|
| 118 | 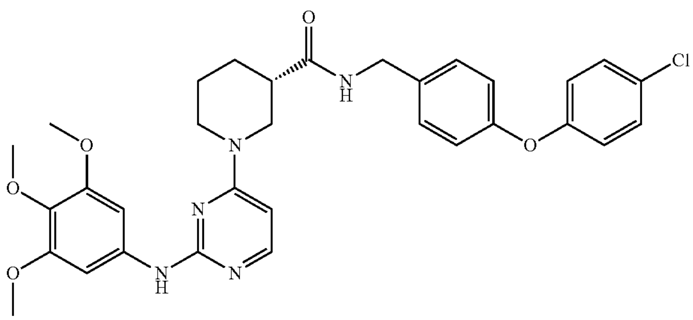 [SMILES: COc1cc(Nc2nccc(N3CCC[C@H](C(=O)NCc4ccc(Oc5ccc(Cl)cc5)cc4)C3)n2)cc(OC)c1OC] | (S)-N-(4-(4-chlorophenoxy)benzyl)-1-(2-((3,4,5-trimethoxyphenyl)amino)-4-pyrimidinyl)-3-piperidinecarboxamide | 603.22 | 604.23154 |
| 119 | 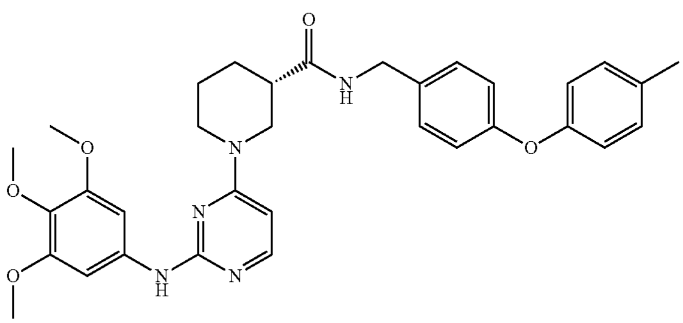 [SMILES: COc1cc(Nc2nccc(N3CCC[C@H](C(=O)NCc4ccc(Oc5ccc(C)cc5)cc4)C3)n2)cc(OC)c1OC] | (S)-N-(4-(4-methylphenoxy)benzyl)-1-(2-((3,4,5-trimethoxyphenyl)amino)-4-pyrimidinyl)-3-piperidinecarboxamide | 583.69 | 584.28628 |
| 120 | 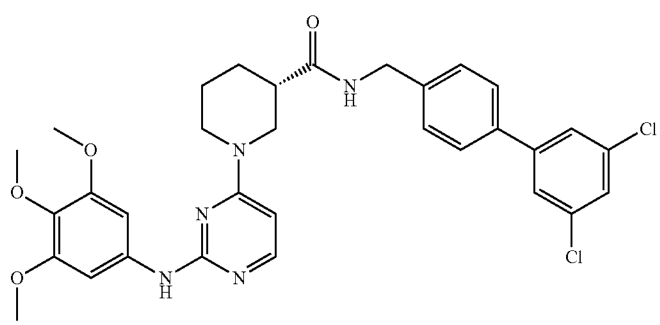 [SMILES: COc1cc(Nc2nccc(N3CCC[C@H](C(=O)NCc4ccc(-c5cc(Cl)cc(Cl)c5)cc4)C3)n2)cc(OC)c1OC] | (S)-N-((3',5'-dichloro-4-biphenylyl)methyl)-1-(2-((3,4,5-trimethoxyphenyl)amino)-4-pyrimidinyl)-3-piperidinecarboxamide | 622.55 | 622.19795 |
| 121 | 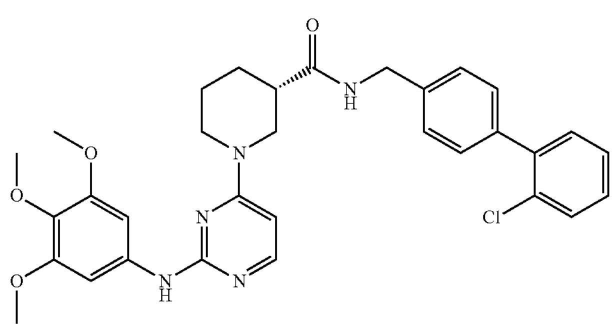 [SMILES: COc1cc(Nc2nccc(N3CCC[C@H](C(=O)NCc4ccc(-c5ccccc5Cl)cc4)C3)n2)cc(OC)c1OC] | (S)-N-((2'-chloro-4-biphenylyl)methyl)-1-(2-((3,4,5-trimethoxyphenyl)amino)-4-pyrimidinyl)-3-piperidinecarboxamide | 587.23 | 588.237158 |

TABLE 1-continued

Examples 14-124.
All the example compounds in the following Table were synthesized
using either intermediate M2 or M3 following the method exemplified in 13.

| Example | Structure | Final Compound Name | MS (calc'd) | M + H (observed) |
|---|---|---|---|---|
| 122 | 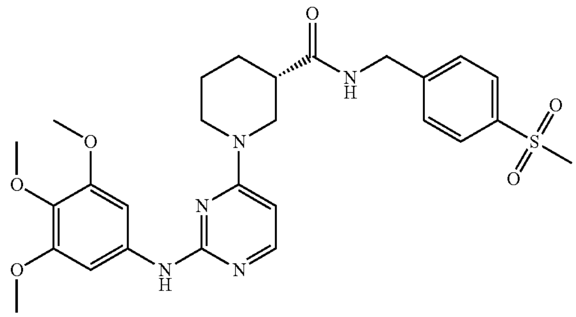 [SMILES: COc1cc(Nc2nccc(N3CCC[C@H](C(=O)NCc4ccc(S(C)(=O)=O)cc4)C3)n2)cc(OC)c1OC] | (S)-N-(4-(methylsulfonyl)benzyl)-1-(2-((3,4,5-trimethoxyphenyl)amino)-4-pyrimidinyl)-3-piperidinecarboxamide | 555.65 | 556.22170 |
| 123 | 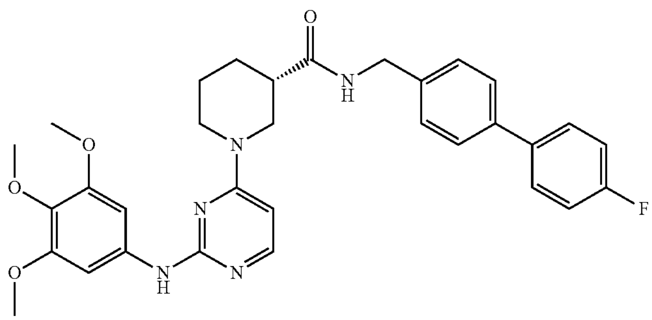 [SMILES: COc1cc(Nc2nccc(N3CCC[C@H](C(=O)NCc4ccc(-c5ccc(F)cc5)cc4)C3)n2)cc(OC)c1OC] | (S)-N-((4'-fluoro-4-biphenylyl)methyl)-1-(2-((3,4,5-trimethoxyphenyl)amino)-4-pyrimidinyl)-3-piperidinecarboxamide | 571.65 | 572.26649 |
| 124 | 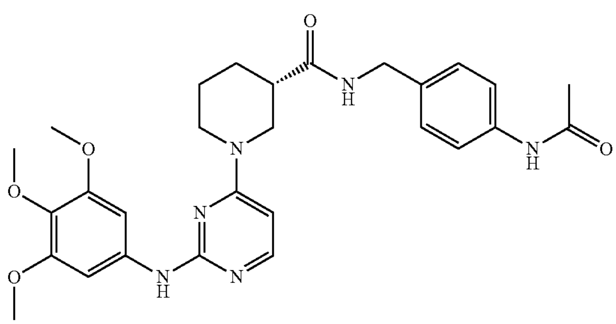 [SMILES: COc1cc(Nc2nccc(N3CCC[C@H](C(=O)NCc4ccc(NC(C)=O)cc4)C3)n2)cc(OC)c1OC] | (S)-N-(4-(acetylamino)benzyl)-1-(2-((3,4,5-trimethoxyphenyl)amino)-4-pyrimidinyl)-3-piperidinecarboxamide | 534.61 | 535.26570 |

TABLE 1a

Starting Materials for Examples 14-124.

| Ex. | Starting Material | Source |
|---|---|---|
| 14 | | Acros |
| 15 | | ASDI |
| 16, 17 | | Alfa Aesar |
| 18 | | Sigma-Aldrich |
| 19 | | Acros |

TABLE 1a-continued

Starting Materials for Examples 14-124.

| Ex. | Starting Material | Source |
|---|---|---|
| 20 | 3-chlorobenzylamine | Sigma-Aldrich |
| 21 | 3-(trifluoromethoxy)benzylamine | Lancaster |
| 22 | benzylamine | Sigma-Aldrich |
| 23 | 3-chlorobenzylamine | Sigma-Aldrich |
| 24 | 3-(trifluoromethoxy)benzylamine | Lancaster |
| 25 | (S)-1-phenylethylamine | Sigma-Aldrich |
| 26 | 1-(4-bromophenyl)ethylamine | ASDI |
| 27 | (R)-1-(4-bromophenyl)ethylamine | ASDI |
| 28 | 5-chloro-2-methylbenzylamine | ASDI |
| 29 | 4-chloro-2-fluorobenzylamine | ASDI |
| 30 | 2,2,2-trifluoro-1-phenylethylamine | J & W Pharmlab |
| 31 | 1-naphthylmethylamine | ASDI |
| 32 | 2-methoxybenzylamine | ASDI |
| 33 | 4-(trifluoromethoxy)benzylamine | ASDI |
| 34 | 4-(trifluoromethyl)benzylamine | ASDI |
| 35 | 2-methylbenzylamine | ASDI |
| 36 | 2-chlorobenzylamine | ASDI |
| 37 | 2-(trifluoromethyl)benzylamine | ASDI |
| 38 | 3-methoxybenzylamine | ASDI |

TABLE 1a-continued

Starting Materials for Examples 14-124.

| Ex. | Starting Material | Source |
|---|---|---|
| 39 | 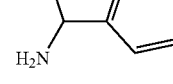 | ASDI |
| 40 | 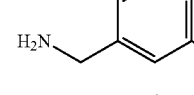 | ASDI |
| 41 | 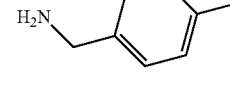 | ASDI |
| 42 | 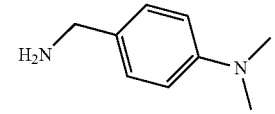 | ASDI |
| 43 | 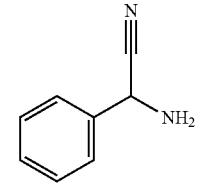 | ASDI |
| 44 | 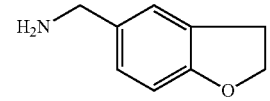 | ASDI |
| 45 | 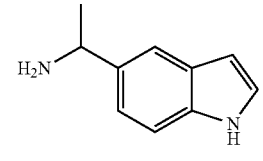 | ASDI |
| 46 | 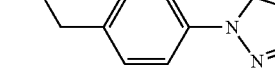 | ASDI |
| 47 | 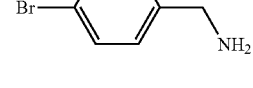 | ASDI |
| 48 | 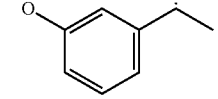 | ASDI |
| 49 | 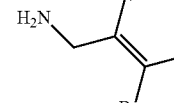 | ASDI |
| 50 | H₂N-CH(CH₃)-phenyl | Sigma-Aldrich |
| 51 | H₂N-CH(CH₃)-(4-F-phenyl) | Sigma-Aldrich |
| 52 | (S)-H₂N-CH(CH₃)-phenyl | Fluka |
| 53 | H₂N-CH(CH₃)-(4-OH-phenyl) | Frinton Laboratories |
| 54 | H₂N-C(CH₃)₂-phenyl | TCI America |
| 55 | H₂N-CH(CH₃)-(4-methylphenyl) | Sigma-Aldrich |
| 56 | H₂N-CH₂-(2-F-4-Br-phenyl) | ASDI |
| 57 | H₂N-CH₂-(2,4-diF-phenyl) | ASDI |
| 58 | H₂N-CH₂-(2-F-5-Br-phenyl) | ASDI |

TABLE 1a-continued

Starting Materials for Examples 14-124.

| Ex. | Starting Material | Source |
|---|---|---|
| 59 | 2-(aminomethyl)-4-methylthiazole | ASDI |
| 60 | 4-bromophenethylamine | ASDI |
| 61 | 2-(imidazo[1,2-a]pyridin-2-yl)ethanamine | ASDI |
| 62 | 2-phenoxyethanamine | ASDI |
| 63 | 2-amino-1-phenylethanone | ASDI |
| 64 | benzo[b]thiophen-6-ylmethanamine | PCT Int Appl 2005082859 |
| 65 | (3,4-dichlorophenyl)methanamine | ASDI |
| 66 | (3,4-dimethoxyphenyl)methanamine | ASDI |
| 67 | (3,4-difluorophenyl)methanamine | ASDI |
| 68 | (3-chloro-4-fluorophenyl)methanamine | ASDI |
| 69 | biphenyl-3-ylmethanamine | ASDI |
| 70 | (4-tert-butylphenyl)methanamine | ASDI |
| 71 | (4-nitrophenyl)methanamine | ASDI |
| 72 | (4-(4-fluorophenoxy)phenyl)methanamine | ASDI |
| 73 | (1-methyl-1,2,3,4-tetrahydroquinolin-6-yl)methanamine | ASDI |
| 74 | (3-chloro-4-methylphenyl)methanamine | ASDI |
| 75 | (4-(difluoromethoxy)phenyl)methanamine | ASDI |
| 76 | (2-methyl-1H-indol-5-yl)methanamine | ASDI |
| 77 | (2,3-dihydrobenzo[b][1,4]dioxin-6-yl)methanamine | ASDI |

TABLE 1a-continued

Starting Materials for Examples 14-124.

| Ex. | Starting Material | Source |
|---|---|---|
| 78 | 4-morpholinobenzylamine | ASDI |
| 79 | 3-(difluoromethoxy)benzylamine | ASDI |
| 80 | 3-nitrobenzylamine | ASDI |
| 81 | 3,5-dimethylbenzylamine | ASDI |
| 82 | methyl 4-(aminomethyl)benzoate | ASDI |
| 83 | 3,4-dimethylbenzylamine | Oakwood Products |
| 84 | N-(3-(aminomethyl)phenyl)methanesulfonamide | J & W PharmLab |
| 85 | 3-morpholinobenzylamine | Maybridge |
| 86 | 3-fluoro-4-(trifluoromethyl)benzylamine | Apollo |
| 87 | 3-isopropoxybenzylamine | Matrix Scientific |
| 88 | 4-isopropoxybenzylamine | Matrix Scientific |
| 89 | 2-(m-tolyl)ethanamine | Trans World Chemicals, Inc. |
| 90 | 2-(4-phenoxyphenyl)ethanamine | Trans World Chemicals, Inc. |
| 91 | 2-(4-(trifluoromethyl)phenyl)ethanamine | J & W PharmLab |
| 92 | 2-(p-tolyl)ethanamine | Sigma-Aldrich |
| 93 | 2-(4-methoxyphenyl)ethanamine | TCI America |
| 94 | 2-(3-bromophenyl)ethanamine | Sigma-Aldrich |
| 95 | 2-(3-fluorophenyl)ethanamine | Sigma-Aldrich |
| 96 | 2-(3-(trifluoromethyl)phenyl)ethanamine | Trans World Chemicals, Inc. |
| 97 | 2-(3,4-dimethylphenyl)ethanamine | Oakwood Products |

TABLE 1a-continued

Starting Materials for Examples 14-124.

| Ex. | Starting Material | Source |
|---|---|---|
| 98 | (S)-2-phenylpropan-1-amine | Aldrich Chemical company |
| 99 | 2-(2-chlorophenyl)ethan-1-amine | Aaron Chemistry |
| 100 | 2-(4-fluorophenyl)ethan-1-amine | Sigma-Aldrich |
| 101 | (R)-2-phenylpropan-1-amine | Aldrich Chemical company |
| 102 | 2-(2-fluorophenyl)ethan-1-amine | Sigma-Aldrich |
| 103 | 2-phenylethan-1-amine | Sigma-Aldrich |
| 104 | (3-fluorophenyl)methanamine | Sigma-Aldrich |
| 105 | (3-(4-chlorophenoxy)phenyl)methanamine | ASDI |
| 106 | (4'-chloro-[1,1'-biphenyl]-3-yl)methanamine | ASDI |
| 107 | (3-phenoxyphenyl)methanamine | ASDI |
| 108 | (4'-fluoro-[1,1'-biphenyl]-3-yl)methanamine | ASDI |
| 109 | ethyl 3-(3-(aminomethyl)phenyl)-2-methylpropanoate | ASDI |
| 110 | (3-(1H-pyrrol-1-yl)phenyl)methanamine | ASDI |
| 111 | (3-(1H-pyrazol-1-yl)phenyl)methanamine | ASDI |
| 112 | aniline | Fluka |
| 113 | (3-bromophenyl)methanamine | Alfa-Aesar |
| 114 | (3-(p-tolyloxy)phenyl)methanamine | Array BioPharma |
| 115 | 4-(aminomethyl)benzonitrile | Sigma-Aldrich |

TABLE 1a-continued

Starting Materials for Examples 14-124.

| Ex. | Starting Material | Source |
|---|---|---|
| 116 | 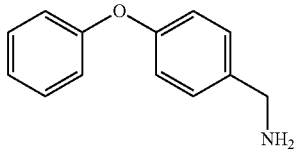 [SMILES: NCc1ccc(Oc2ccccc2)cc1] | Array BioPharma |
| 117 | 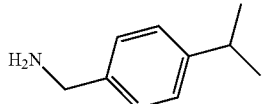 | Trans World Chemicals, Inc. |
| 118 | 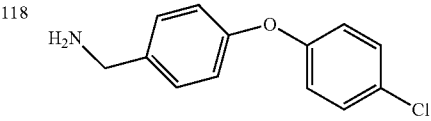 | ASDI |
| 119 | 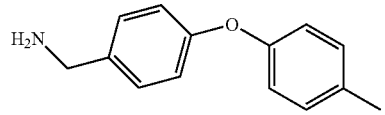 [SMILES: Cc1ccc(Oc2ccc(CN)cc2)cc1] | ASDI |
| 120 | 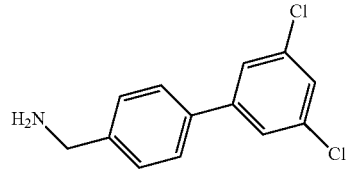 [SMILES: NCc1ccc(-c2cc(Cl)cc(Cl)c2)cc1] | ASDI |
| 121 | 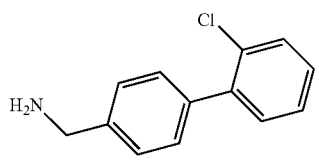 [SMILES: NCc1ccc(-c2ccccc2Cl)cc1] | ASDI |
| 122 | 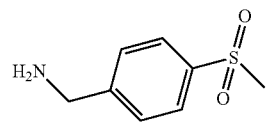 | ASDI |
| 123 | 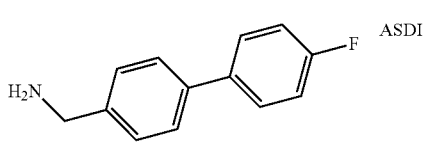 | ASDI |
| 124 | 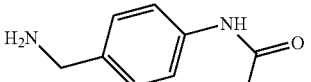 | ASDI |

Example 125

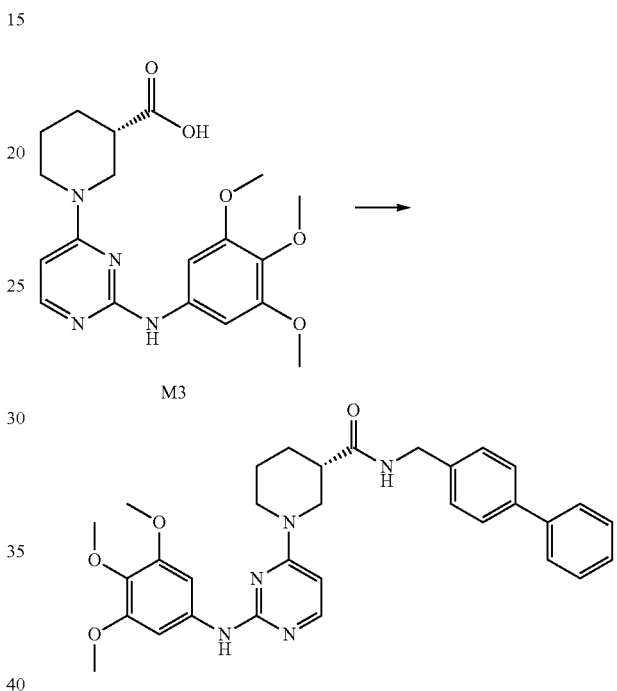

(S)—N-(Biphenyl-4-Ylmethyl)-1-(2-(3,4,5-Tri-methoxyphenylamino)Pyrimidin-4-Yl)Piperidine-3-Carboxamide (125)

To a solution of M3 (50 mg, 0.129 mmol) in DCM (3218 µL) was added 4-dimethylaminopyridine (3.93 mg, 0.032 mmol) and N,N'-dicyclohexylcarbodiimide (26.6 mg, 0.129 mmol). The resulting mixture was stirred for 10 minutes. Biphenyl-4-ylmethanamine (Sigma-Aldrich, 35 mg, 0.193 mmol) was then added and the reaction was stirred at room temperature. After 24 hours, the reaction was filtered and concentrated. The residue was purified by preparative HPLC through a Phenomenex Gemini-NX C18 110A 5 um 21×100 column eluting between water containing 0.1% NH$_4$OH and acetonitrile w/0.1% NH$_4$OH at a flow rate of 44 mL/minute over 10 minutes to give 125 as a light purple solid. $^1$H NMR (300 MHz, CDCl$_3$) δ ppm 1.50-2.11 (m, 4H) 2.36-2.49 (m, 1H) 3.24 (ddd, J=12.35, 9.79, 2.27 Hz, 1H) 3.67-3.85 (m, 10H) 3.86-3.99 (m, 1H) 4.14 (dd, J=13.45, 2.92 Hz, 1H) 4.42 (d, J=5.41 Hz, 2H) 6.04 (d, J=6.14 Hz, 1H) 6.43 (br. s., 1H) 6.81 (s, 2H) 6.89 (br. s., 1H) 7.23 (s, 2H) 7.29-7.57 (m, 7H) 7.95 (d, J=6.14 Hz, 1H); M+H 554.27512.

TABLE 2

Examples 126 and 127.

| Example | Final Compound (Structure) | Final Compound Name | MS (calc'd) | M + H (observed) |
|---|---|---|---|---|
| 126 | | (S)-N-(3-phenylpropyl)-1-(2-((3,4,5-trimethoxyphenyl)amino)-4-pyrimidinyl)-3-piperidinecarboxamide | 505.62 | 506.27559 |
| 127 | | (S)-N-(cyano(4-(trifluoromethoxy)phenyl)methyl)-1-(2-(3,4,5-trimethoxyphenylamino)pyrimidin-4-yl)piperidine-3-carboxamide | 586.56 | 587.22158 |

TABLE 2a

Method and Starting Materials for Examples 126 and 127.

| Ex. | Starting Material | Source | Intermediate | Method |
|---|---|---|---|---|
| 126 | | Alfa Aesar | M3 | Example 122 |
| 127 | | UkrOrgSynthesis | M3 | Example 122 |

Example 128

(S)-1-(2-(2,3-Dihydrobenzo[B][1,4]Dioxin-6-Ylamino)Pyrimidin-4-Yl)-N-(4-Methylbenzyl)Piperidine-3-Carboxamide (128)

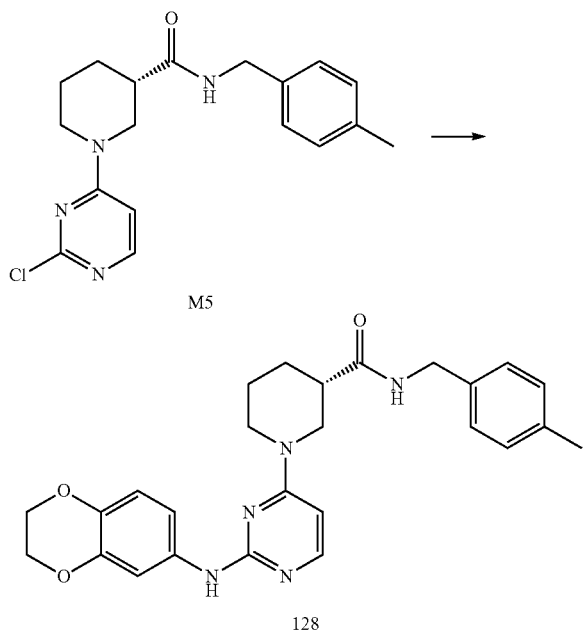

A mixture of 1,4-benzodioxan-6-amine (Sigma-Aldrich, 65.8 mg, 0.435 mmol) and (S)-1-(2-chloropyrimidin-4-yl)-N-(4-methylbenzyl)piperidine-3-carboxamide (M5, 100 mg, 0.290 mmol) in DMSO (0.6 mL) was heated at 90° C. for 16 hours. The mixture was then cooled to room temperature, filtered and was purified with reversed-phase HPLC (Phenomenex Gemini-NX 10 μL 110 Å, AXIA packed column, 100×50 mm, 60 mL/min, 10-95% ACN/H$_2$O, 0.1% TFA, 10 min gradient). After concentration of the fractions by vacuum distillation, the product was diluted with saturated aqueous NaHCO$_3$ and extracted with DCM (3×). The combined organic layers were dried over Na$_2$SO$_4$, filtered and concentrated to provide the desired product in 18% yield. $^1$H NMR (300 MHz, CDCl$_3$) δ ppm 1.66-1.79 (m, 2H), 1.85-2.00 (m, 1H), 2.04-2.19 (m, 1H), 2.30 (s, 3H), 2.45 (br. s., 1H), 3.24 (t, J=9.9 Hz, 1H), 3.69 (dd, J=13.7, 8.0 Hz, 1H), 3.83 (d, J=12.6 Hz, 1H), 4.12 (d, J=12.1 Hz, 1H), 4.19 (s, 4H), 4.34 (d, J=5.4 Hz, 2H), 6.00 (d, J=6.1 Hz, 1H), 6.39 (br. s., 1H), 6.76 (d, J=8.6 Hz, 1H), 6.85 (dd, J=10.7, 9.1 Hz, 1H), 6.79-6.92 (m, 1H), 7.07 (s, 4H), 7.17-7.22 (m, 1H), 7.89 (d, J=6.3 Hz, 1H); M+H 460.23367.

TABLE 3

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 129 | | (3S)-N-(4-methylbenzyl)-1-(2-(phenylamino)-4-pyrimidinyl)-3-piperidinecarboxamide | 401.51 | 402.22850 |
| 130 | | (3S)-N-(4-methylbenzyl)-1-(2-(3-quinolinylamino)-4-pyrimidinyl)-3-piperidinecarboxamide | 452.56 | 453.23956 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 131 | | (3S)-1-(2-(1H-indol-5-ylamino)-4-pyrimidinyl)-N-(4-methylbenzyl)-3-piperidinecarboxamide | 440.55 | 441.23938 |
| 132 | | (3S)-1-(2-((3-chlorophenyl)amino)-4-pyrimidinyl)-N-(4-methylbenzyl)-3-piperidinecarboxamide | 435.96 | 436.18952 |
| 133 | | (3S)-1-(2-((2-methoxyphenyl)amino)-4-pyrimidinyl)-N-(4-methylbenzyl)-3-piperidinecarboxamide | 431.54 | 432.23975 |
| 134 | | (3S)-1-(2-((4-methoxyphenyl)amino)-4-pyrimidinyl)-N-(4-methylbenzyl)-3-piperidinecarboxamide | 431.54 | 432.23946 |
| 135 | | (3S)-1-(2-((3-methoxyphenyl)amino)-4-pyrimidinyl)-N-(4-methylbenzyl)-3-piperidinecarboxamide | 431.54 | 432.23922 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 136 | | (3S)-1-(2-((3,5-dimethoxyphenyl)amino)-4-pyrimidinyl)-N-(4-methylbenzyl)-3-piperidinecarboxamide | 461.56 | 462.25005 |
| 137 | | (3S)-N-(4-methylbenzyl)-1-(2-((3-(trifluoromethyl)phenyl)amino)-4-pyrimidinyl)-3-piperidinecarboxamide | 469.51 | 470.21601 |
| 138 | | (3S)-1-(2-((5-(acetylamino)-2-methoxyphenyl)amino)-4-pyrimidinyl)-N-(4-methylbenzyl)-3-piperidinecarboxamide | 488.59 | 489.26085 |
| 139 | | (3S)-N-(4-methylbenzyl)-1-(2-((4-(4-morpholinyl)phenyl)amino)-4-pyrimidinyl)-3-piperidinecarboxamide | 486.62 | 487.28130 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 140 | | (3S)-1-(2-((3,4-dimethoxyphenyl)amino)-4-pyrimidinyl)-N-(4-methylbenzyl)-3-piperidinecarboxamide | 461.56 | 462.24982 |
| 141 | | (3S)-N-(4-methylbenzyl)-1-(2-((1-oxo-2,3-dihydro-1H-isoindol-4-yl)amino)-4-pyrimidinyl)-3-piperidinecarboxamide | 456.55 | 457.23453 |
| 142 | | (3S)-1-(2-((1-acetyl-3,3-dimethyl-2,3-dihydro-1H-indol-6-yl)amino)-4-pyrimidinyl)-N-(4-methylbenzyl)-3-piperidinecarboxamide | 512.65 | 513.29698 |
| 143 | | (3S)-N-(4-methylbenzyl)-1-(2-((3-(2H-1,2,3-triazol-2-ylmethyl)phenyl)amino)-4-pyrimidinyl)-3-piperidinecarboxamide | 482.59 | 483.26135 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 144 | | tert-butyl 4-(3-((4-((3S)-3-((4-methylbenzyl)carbamoyl)-1-piperidinyl)-2-pyrimidinyl)amino)-1H-pyrazol-5-yl)-1-piperidinecarboxylate | 574.73 | 575.34527 |
| 145 | | (3S)-N-(4-methylbenzyl)-1-(2-((5-(4-methylphenyl)-1H-pyrazol-3-yl)amino)-4-pyrimidinyl)-3-piperidinecarboxamide | 481.60 | 482.26611 |
| 146 | | (3S)-1-(2-((8-methoxy-2,3-dihydro-1,4-benzodioxin-6-yl)amino)-4-pyrimidinyl)-N-(4-methylbenzyl)-3-piperidinecarboxamide | 489.57 | 490.24428 |
| 147 | | (3S)-N-(4-methylbenzyl)-1-(2-((1-methyl-6-oxo-1,6-dihydro-3-pyridinyl)amino)-4-pyrimidinyl)-3-piperidinecarboxamide | 432.53 | 433.23483 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 148 | | (3S)-1-(2-((3-ethoxyphenyl)amino)-4-pyrimidinyl)-N-(4-methylbenzyl)-3-piperidinecarboxamide | 445.56 | 446.25426 |
| 149 | | (3S)-N-(4-methylbenzyl)-1-(2-((3-phenoxyphenyl)amino)-4-pyrimidinyl)-3-piperidinecarboxamide | 493.61 | 494.25446 |
| 150 | | (3S)-N-(4-methylbenzyl)-1-(2-((3-(phenylcarbonyl)phenyl)amino)-4-pyrimidinyl)-3-piperidinecarboxamide | 505.62 | 506.25438 |
| 151 | | (3S)-N-(4-methylbenzyl)-1-(2-((3-sulfamoylphenyl)amino)-4-pyrimidinyl)-3-piperidinecarboxamide | 480.59 | 481.20125 |
| 152 | | (3S)-1-(2-((3-benzylphenyl)amino)-4-pyrimidinyl)-N-(4-methylbenzyl)-3-piperidinecarboxamide | 491.64 | 492.27538 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 153 | | (3S)-1-(2-((3,5-di-tert-butylphenyl)amino)-4-pyrimidinyl)-N-(4-methylbenzyl)-3-piperidinecarboxamide | 513.73 | 514.35308 |
| 154 | | (3S)-1-(2-((4-(dimethylcarbamoyl)phenyl)amino)-4-pyrimidinyl)-N-(4-methylbenzyl)-3-piperidinecarboxamide | 472.59 | 473.26567 |
| 155 | | (3S)-1-(2-((3,5-dimethylphenyl)amino)-4-pyrimidinyl)-N-(4-methylbenzyl)-3-piperidinecarboxamide | 429.56 | 430.25984 |
| 156 | | (3S)-1-(2-((4-ethylphenyl)amino)-4-pyrimidinyl)-N-(4-methylbenzyl)-3-piperidinecarboxamide | 429.56 | 430.25979 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 157 | | (3S)-N-(4-methylbenzyl)-1-(2-((3-(methylsulfanyl)phenyl)amino)-4-pyrimidinyl)-3-piperidinecarboxamide | 447.6041 | 448.21637 |
| 158 | | (3S)-N-(4-methylbenzyl)-1-(2-((3-methylphenyl)amino)-4-pyrimidinyl)-3-piperidinecarboxamide | 415.5381 | 416.24424 |
| 159 | | (3S)-1-(2-((3,5-difluorophenyl)amino)-4-pyrimidinyl)-N-(4-methylbenzyl)-3-piperidinecarboxamide | 437.4915 | 438.20975 |
| 160 | | (3S)-N-(4-methylbenzyl)-1-(2-((3-(1-methylethoxy)phenyl)amino)-4-pyrimidinyl)-3-piperidinecarboxamide | 459.5907 | 460.27055 |
| 161 | | (3S)-N-(4-methylbenzyl)-1-(2-((4-(4-methyl-1-piperazinyl)phenyl)amino)-4-pyrimidinyl)-3-piperidinecarboxamide | 499.6593 | 500.31259 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 162 | | (3S)-1-(2-((3-ethylphenyl)amino)-4-pyrimidinyl)-N-(4-methylbenzyl)-3-piperidinecarboxamide | 429.5649 | 430.25594 |
| 163 | | (3S)-1-(2-((3,5-bis(trifluoromethyl)phenyl)amino)-4-pyrimidinyl)-N-(4-methylbenzyl)-3-piperidinecarboxamide | 537.5055 | 538.20320 |
| 164 | | (3S)-N-(4-methylbenzyl)-1-(2-((3-(trifluoromethoxy)phenyl)amino)-4-pyrimidinyl)-3-piperidinecarboxamide | 485.5074 | 486.21078 |
| 165 | | (3S)-1-(2-((4-(acetylamino)phenyl)amino)-4-pyrimidinyl)-N-(4-methylbenzyl)-3-piperidinecarboxamide | 458.563 | 459.25001 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 166 | | (3S)-1-(2-((4-cyanophenyl)amino)-4-pyrimidinyl)-N-(4-methylbenzyl)-3-piperidinecarboxamide | 426.5214 | 427.22380 |
| 167 | | (3S)-1-(2-((3-(1-hydroxyethyl)phenyl)amino)-4-pyrimidinyl)-N-(4-methylbenzyl)-3-piperidinecarboxamide | 445.5639 | 446.25489 |
| 168 | | (3S)-N-(4-methylbenzyl)-1-(2-((3-(methylcarbamoyl)phenyl)amino)-4-pyrimidinyl)-3-piperidinecarboxamide | 458.563 | 459.25017 |
| 169 | | (3S)-1-(2-((3-fluoro-5-methoxyphenyl)amino)-4-pyrimidinyl)-N-(4-methylbenzyl)-3-piperidinecarboxamide | 449.5272 | 450.22971 |
| 170 | | (3S)-1-(2-((3-methoxy-5-(trifluoromethyl)phenyl)amino)-4-pyrimidinyl)-N-(4-methylbenzyl)-3-piperidinecarboxamide | 499.5342 | 500.22652 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 171 | | (3S)-N-(4-methylbenzyl)-1-(2-((3-(1-methylethyl)phenyl)amino)-4-pyrimidinyl)-3-piperidinecarboxamide | 443.5917 | 444.27548 |
| 172 | | (3S)-N-(4-methylbenzyl)-1-(2-((4-(1-methylethyl)phenyl)amino)-4-pyrimidinyl)-3-piperidinecarboxamide | 443.5917 | 444.27555 |
| 173 | | (3S)-1-(2-((4-carbamoylphenyl)amino)-4-pyrimidinyl)-N-(4-methylbenzyl)-3-piperidinecarboxamide | 444.5362 | 445.23447 |
| 174 | | (3S)-1-(2-((3,5-dichlorophenyl)amino)-4-pyrimidinyl)-N-(4-methylbenzyl)-3-piperidinecarboxamide | 469.14 | 470.15074 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 175 | | (3S)-1-(2-((3-(benzyloxy)phenyl)amino)-4-pyrimidinyl)-N-(4-methylbenzyl)-3-piperidinecarboxamide | 507.6347 | 508.27044 |
| 176 | | (3S)-N-(4-methylbenzyl)-1-(2-((3-(1H-tetrazol-5-yl)phenyl)amino)-4-pyrimidinyl)-3-piperidinecarboxamide | 469.5503 | 470.24082 |
| 177 | | (3S)-N-(4-methylbenzyl)-1-(2-((3-(1,3-oxazol-5-yl)phenyl)amino)-4-pyrimidinyl)-3-piperidinecarboxamide | 468.5582 | 469.23442 |
| 178 | | (3S)-1-(2-((3-(acetylamino)phenyl)amino)-4-pyrimidinyl)-N-(4-methylbenzyl)-3-piperidinecarboxamide | 458.563 | 459.24998 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 179 | | (3S)-1-(2-((4-fluorophenyl)amino)-4-pyrimidinyl)-N-(4-methylbenzyl)-3-piperidinecarboxamide | 419.5014 | 420.21920 |
| 180 | | (3S)-N-(4-methylbenzyl)-1-(2-((4-methylphenyl)amino)-4-pyrimidinyl)-3-piperidinecarboxamide | 415.5381 | 416.24435 |
| 181 | | (3S)-1-(2-((3-tert-butylphenyl)amino)-4-pyrimidinyl)-N-(4-methylbenzyl)-3-piperidinecarboxamide | 457.6185 | 458.29131 |
| 182 | | (3S)-1-(2-(3-biphenylylamino)-4-pyrimidinyl)-N-(4-methylbenzyl)-3-piperidinecarboxamide | 477.6089 | 478.25999 |
| 183 | | (3S)-1-(2-((3-((acetylamino)methyl)phenyl)amino)-4-pyrimidinyl)-N-(4-methylbenzyl)-3-piperidinecarboxamide | 472.5898 | 473.26595 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 184 | | (3S)-1-(2-((3-(2-amino-2-oxoethyl)phenyl)amino)-4-pyrimidinyl)-N-(4-methylbenzyl)-3-piperidinecarboxamide | 458.563 | 459.24999 |
| 185 | | (3S)-1-(2-((3-fluorophenyl)amino)-4-pyrimidinyl)-N-(4-methylbenzyl)-3-piperidinecarboxamide | 419.5014 | 420.21912 |
| 186 | | (S)-1-(2-(4-benzoylphenylamino)pyrimidin-4-yl)-N-(4-methylbenzyl)piperidine-3-carboxamide | 505.61 | 506.25434 |
| 187 | | (S)-1-(2-(4-(2-(diethylamino)ethylcarbamoyl)phenylamino)pyrimidin-4-yl)-N-(4-methylbenzyl)piperidine-3-carboxamide | 543.70 | 544.33912 |
| 188 | | (S)-N-(4-methylbenzyl)-1-(2-(4-sulfamoylphenylamino)pyrimidin-4-yl)piperidine-3-carboxamide | 480.58 | 481.20089 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 189 | | (S)-N-(4-methylbenzyl)-1-(2-(4-(oxazol-5-yl)phenylamino)pyrimidin-4-yl)piperidine-3-carboxamide | 468.55 | 469.23385 |
| 190 | | (S)-N-(4-methylbenzyl)-1-(2-(3-(((R)-1-methylpyrrolidin-2-yl)methoxy)-5-(trifluoromethyl)phenylamino)pyrimidin-4-yl)piperidine-3-carboxamide | 582.66 | 583.29970 |
| 191 | | (S)-1-(2-(4-(1H-1,2,4-triazol-1-yl)phenylamino)pyrimidin-4-yl)-N-(4-methylbenzyl)piperidine-3-carboxamide | 468.55 | 469.24523 |
| 192 | | (S)-1-(2-(4-ethoxyphenylamino)pyrimidin-4-yl)-N-(4-methylbenzyl)piperidine-3-carboxamide | 445.56 | 446.25455 |

TABLE 3-continued

Examples 129 through 193.
All the example compounds in the following Table were synthesized using intermediate M5 following the method exemplified in 128.

| Example | Final Compound Structure | Final Compound Name | MS (calc'd) | M + H (observed) |
|---|---|---|---|---|
| 193 | | (S)-N-(4-methylbenzyl)-1-(2-(6-(3-oxopiperazin-1-yl)pyridin-3-ylamino)pyrimidin-4-yl)piperidine-3-carboxamide | 500.60 | 501.27191 |

TABLE 3a

Starting Materials and Sources for Examples 129-193.

| Ex. | Starting Material | Source |
|---|---|---|
| 129 | aniline | ASDI |
| 130 | 3-aminoquinoline | Sigma-Aldrich |
| 131 | 5-amino-1H-indole | Sigma-Aldrich |
| 132 | 3-chloroaniline | Sigma-Aldrich |
| 133 | 2-methoxyaniline | Sigma-Aldrich |
| 134 | 4-methoxyaniline | ASDI |
| 135 | 3-methoxyaniline | ASDI |
| 136 | 3,5-dimethoxyaniline | ASDI |
| 137 | 3-(trifluoromethyl)aniline | ASDI |
| 138 | N-(3-amino-4-methoxyphenyl)acetamide | ASDI |
| 139 | 4-morpholinoaniline | ASDI |
| 140 | 3,4-dimethoxyaniline | ASDI |
| 141 | 4-amino-2,3-dihydro-1H-isoindol-1-one | Matrix Scientific |
| 142 | 1-(6-amino-3,3-dimethyl-2,3-dihydro-1H-indol-1-yl)ethanone | AstaTech, Inc |

TABLE 3a-continued
Starting Materials and Sources for Examples 129-193.
| Ex. | Starting Material | Source |
|---|---|---|
| 143 | 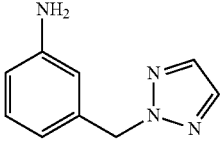 [SMILES: Nc1cccc(Cn2nccn2)c1] | DE 4303657 |
| 144 | 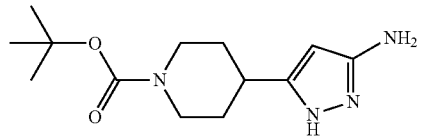 [SMILES: CC(C)(C)OC(=O)N1CCC(c2cc(N)n[nH]2)CC1] | WO 2009111279 A1 |
| 145 | 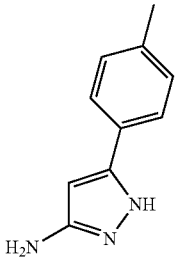 | Ryan Scientific |
| 146 | 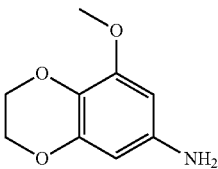 | SU 639886 A1 |
| 147 | 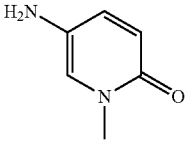 | Milestone PharmTech LLC |
| 148 | 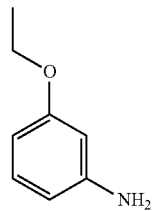 | ASDI |
| 149 | 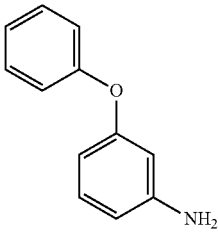 [SMILES: Nc1cccc(Oc2ccccc2)c1] | ASDI |
| 150 | 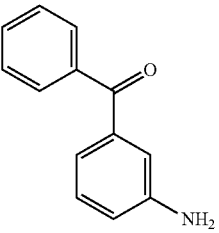 [SMILES: Nc1cccc(C(=O)c2ccccc2)c1] | ASDI |
| 151 | 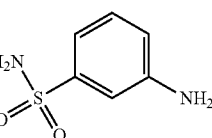 | ASDI |
| 152 | 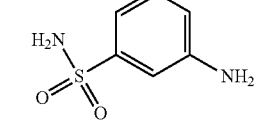 | ASDI |
| 153 | 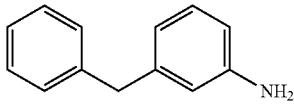 [SMILES: Nc1cccc(Cc2ccccc2)c1] | ASDI |
| 154 | 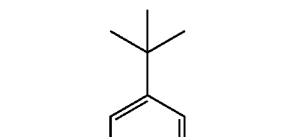 | ASDI |
| 155 | 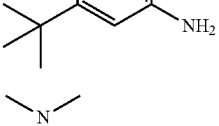 | TCI America |
| 156 | 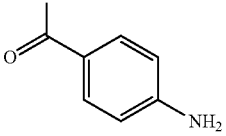 | Sigma-Aldrich |
| 157 | 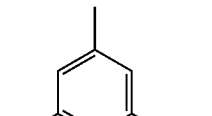 | Sigma-Aldrich |
| 158 |  | TCI America |

TABLE 3a-continued

Starting Materials and Sources for Examples 129-193.

| Ex. | Starting Material | Source |
|---|---|---|
| 159 | 3,5-difluoroaniline | Sigma-Aldrich |
| 160 | 3-isopropoxyaniline | Sigma-Aldrich |
| 161 | 4-(4-methylpiperazin-1-yl)aniline | Key Organics Limited/Bionet Research |
| 162 | 3-ethylaniline | Aldrich Chemical Company |
| 163 | 3,5-bis(trifluoromethyl)aniline | Oakwood Products, Inc. |
| 164 | 3-(trifluoromethoxy)aniline | Avocado Research |
| 165 | 4-acetamidoaniline | Alfa Aesar |
| 166 | 4-aminobenzonitrile | Sigma-Aldrich |
| 167 | 1-(3-aminophenyl)ethanol | Sigma-Aldrich |
| 168 | 3-amino-N-methylbenzamide | TCI Tokyo Kasei Kogyo Co., Ltd. |
| 169 | 3-fluoro-5-methoxyaniline | Apollo Scientific Ltd. |
| 170 | 3-methoxy-5-(trifluoromethyl)aniline | Aldrich Chemical Company |
| 171 | 3-isopropylaniline | TCI EUROPE N.V. |
| 172 | 4-isopropylaniline | Sigma-Aldrich |
| 173 | 4-aminobenzamide | Sigma-Aldrich |
| 174 | 3,5-dichloroaniline | Sigma-Aldrich |

TABLE 3a-continued

Starting Materials and Sources for Examples 129-193.

| Ex. | Starting Material | Source |
|---|---|---|
| 175 | 3-(benzyloxy)aniline | Aldrich Chemical Company |
| 176 | 3-(1H-tetrazol-5-yl)aniline | Avocado Research |
| 177 | 3-(oxazol-5-yl)aniline | Maybridge |
| 178 | N-(3-aminophenyl)acetamide | Sigma-Aldrich |
| 179 | 4-fluoroaniline | Sigma-Aldrich |
| 180 | p-toluidine | Alfa Aesar |
| 181 | 3-tert-butylaniline | Maybridge |
| 182 | 3-phenylaniline (biphenyl-3-amine) | TCI |
| 183 | N-(3-aminobenzyl)acetamide | ASDI |
| 184 | 2-(3-aminophenyl)acetamide | ChemBridge Corporation |
| 185 | 3-fluoroaniline | ASDI |
| 186 | (4-aminophenyl)(phenyl)methanone | Sigma-Aldrich |
| 187 | 4-amino-N-(2-(diethylamino)ethyl)benzamide | ASDI |
| 188 | 4-aminobenzenesulfonamide | ASDI |
| 189 | 4-(oxazol-5-yl)aniline | ASDI |

TABLE 3a-continued

Starting Materials and Sources for Examples 129-193.

| Ex. | Starting Material | Source |
|---|---|---|
| 190 | 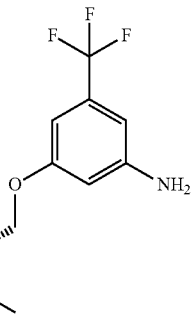 | U.S. Pat. No. 7,531,553B2 |
| 191 | 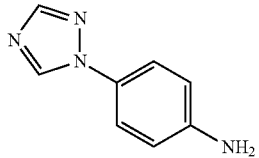 [SMILES: Nc1ccc(-n2cncn2)cc1] | ASDI |
| 192 | 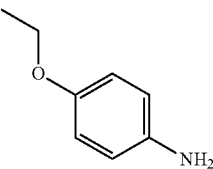 | Sigma-Aldrich |
| 193 | 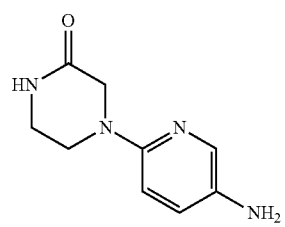 [SMILES: Nc1ccc(N2CCNC(=O)C2)nc1] | Enamine, UkrOrgSynthesis Ltd. |

Example 194

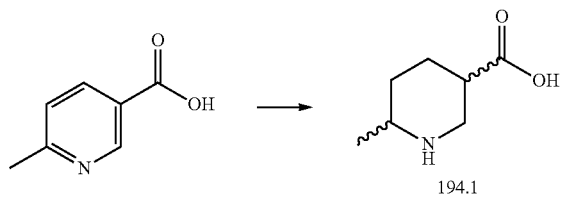

6-Methylpiperidine-3-Carboxylic Acid (194.1)

194.1 was prepared in a method analogous to 193.1 using 6-methylnicotinic acid (Alfa Aesar) in place of methyl 5-methylnicotinate to provide the desired material. ESI-MS M+H 144.0.

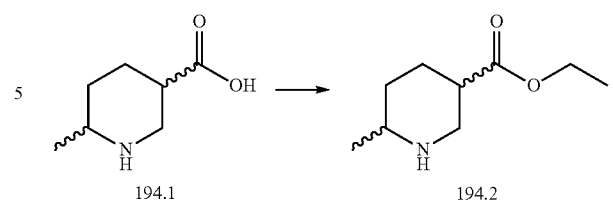

Ethyl 6-Methylpiperidine-3-Carboxylate (194.2)

To 194.1 (1044 mg, 7.29 mmol) in EtOH (5207 μL) was added concentrated hydrochloric acid (405 μL, 7.29 mmol). The resulting solution was heated at reflux for 18 hours. The reaction mixture was then cooled to room temperature and poured onto water. The reaction was brought to pH 10 with 1N sodium hydroxide in water and was then extracted with EtOAc. The organic phase was then dried over anhydrous $Na_2SO_4$ and filtered to provide ethyl 6-methylpiperidine-3-carboxylate. ESI-MS M+H 172.2.

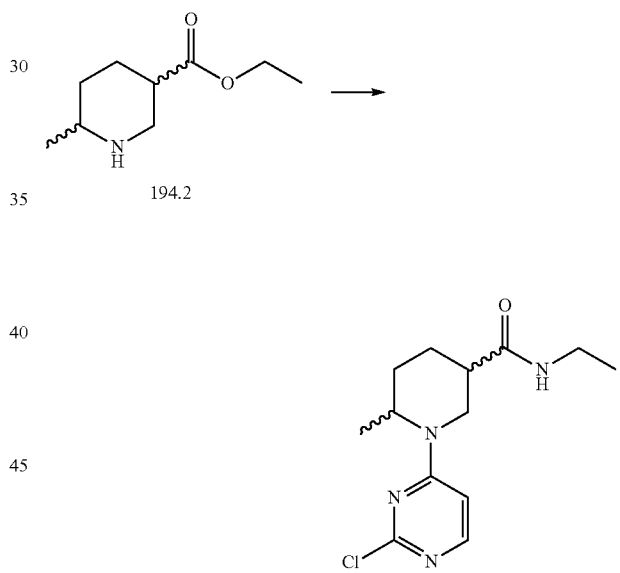

Ethyl 1-(2-Chloropyrimidin-4-Yl)-6-Methyl-Piperidine-3-Carboxylate (194.3)

194.3 was prepared in a method analogous to M1.1 using 194.2 in place of ethyl piperidine-3-carboxylate to provide the desired material as a light purple solid. $^1$H NMR (400 MHz, $CDCl_3$) δ ppm 1.17-1.25 (m, 6H) 1.48-1.55 (m, 1H) 1.84-2.03 (m, 2H) 2.07-2.16 (m, 1H) 2.74 (br. s., 1H) 3.22 (dd, J=13.89, 4.11 Hz, 1H) 4.06-4.16 (m, 2H) 4.61 (d, J=13.89 Hz, 1H) 4.66-4.77 (m, 1H) 6.47 (d, J=6.26 Hz, 1H) 8.00 (d, J=6.26 Hz, 1H) ESI-MS M+H 284.0.

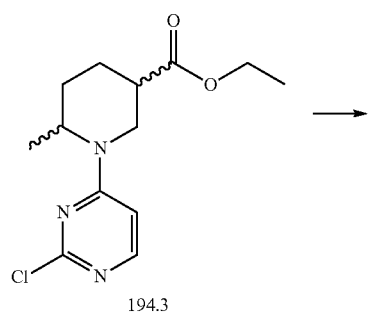

194.3

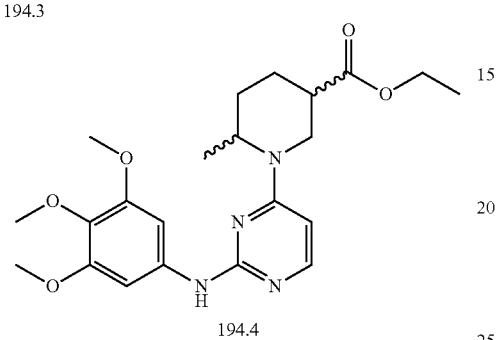

194.4

Ethyl 6-Methyl-1-(2-(3,4,5-Trimethoxyphenyl-Amino)Pyrimidin-4-Yl)Piperidine-3-Carboxylate (194.4)

194.4 was prepared in a method analogous to M1.2 using 194.3 in place of M1.1 to provide the desired material as a light purple solid. ESI-MS M+H 431.1.

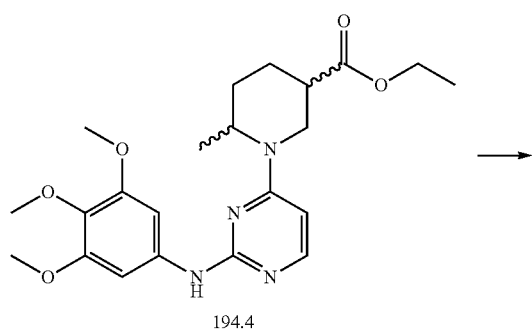

194.4

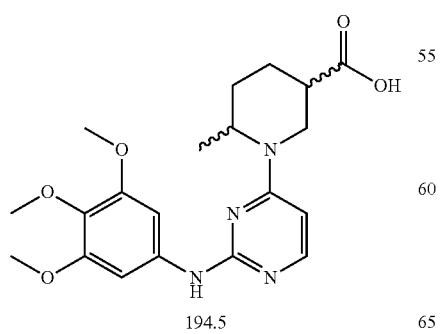

194.5

6-Methyl-1-(2-(3,4,5-Trimethoxyphenyl-Amino)Pyrimidin-4-Yl)Piperidine-3-Carboxylic Acid (194.5)

194.5 was prepared in a method analogous to example 2.3 using 194.4 in place of 2.2 to provide 6-methyl-1-(2-(3,4,5-trimethoxyphenylamino)-pyrimidin-4-yl)piperidine-3-carboxylic acid. ESI-MS M+H 403.1.

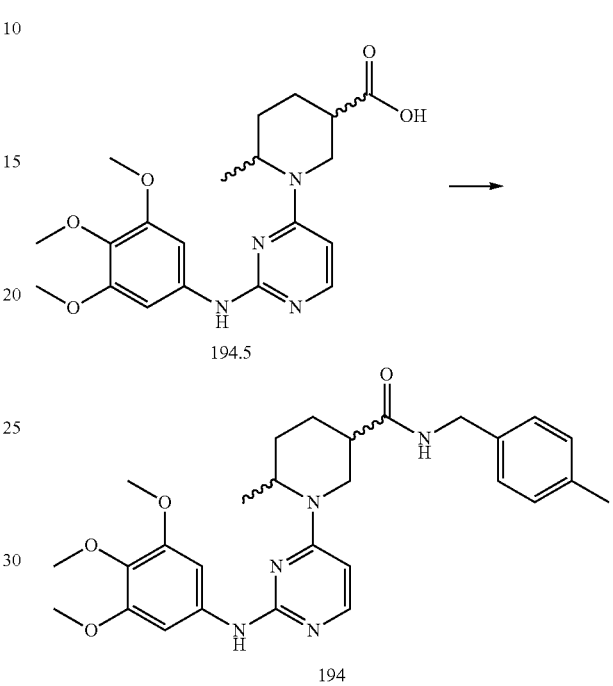

194.5

194

6-Methyl-N-(4-Methylbenzyl)-1-(2-(3,4,5-Trimethoxyphenylamino)Pyrimidin-4-Yl)Piperidine-3-Carboxamide (194)

194 was prepared in a method analogous to M5.1 using 194.5 in place of (S)-1-(tert-butoxycarbonyl)piperidine-3-carboxylic acid to provide 6-methyl-N-(4-methylbenzyl)-1-(2-(3,4,5-trimethoxyphenylamino)-pyrimidin-4-yl)piperidine-3-carboxamide. $^1$H NMR (400 MHz, CDCl$_3$) δ ppm 1.23 (d, J=6.85 Hz, 3H) 1.64-1.73 (m, 2H) 1.79 (dd, J=13.11, 2.54 Hz, 1H) 1.93-2.06 (m, 1H) 2.16-2.28 (m, 1H) 2.32 (s, 3H) 3.17 (t, J=12.62 Hz, 1H) 3.75-3.84 (m, 9H) 4.28 (dd, J=14.48, 5.09 Hz, 1H) 4.47 (dd, J=14.48, 5.87 Hz, 2H) 4.59 (br. s., 1H) 6.01 (d, J=6.26 Hz, 1H) 6.06 (t, J=5.18 Hz, 1H) 6.85 (s, 2H) 7.09-7.18 (m, 4H) 7.41 (br. s., 1H) 7.94 (d, J=6.26 Hz, 1H); M+H 506.27545.

Example 195

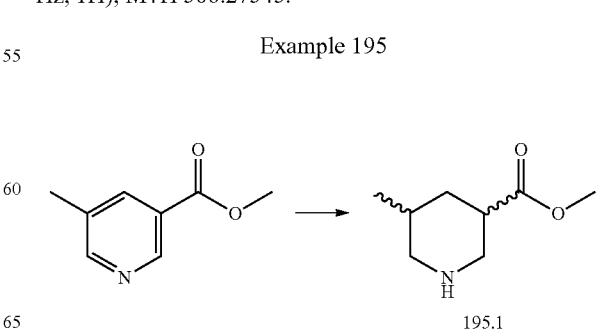

195.1

Methyl 5-Methylpiperidine-3-Carboxylate (195.1)

To a reaction vessel containing methyl 5-methylnicotinate (Alfa Aesar, 1 g, 6.62 mmol) in EtOH (12.03 mL) was added AcOH (1.203 mL). The reaction vessel was purged with nitrogen gas (3×) and 10 weight percent palladium on carbon (0.5 g, 4.70 mmol) was added. The reaction vessel was then purged with hydrogen (balloon, 1 atm) (3×) and maintained under hydrogen while stirring. After 48 hours, the reaction was filtered over Celite® brand filter aid and concentrated under reduced pressure to give methyl 5-methylpiperidine-3-carboxylate. ESI-MS M+H 158.0.

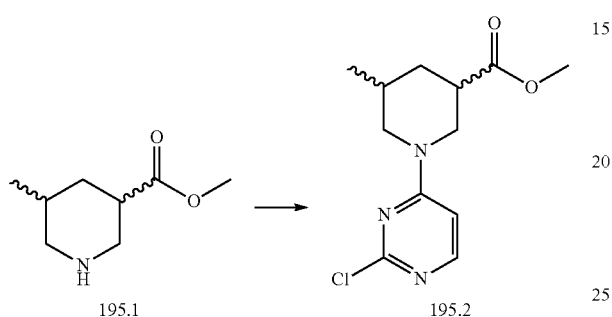

195.1    195.2

Methyl 1-(2-Chloropyrimidin-4-Yl)-5-Methyl-Piperidine-3-Carboxylate (195.2)

195.2 was prepared in a method analogous to M1.1 using 195.1 in place of ethyl piperidine-3-carboxylate to provide the desired material as a light purple solid. $^1$H NMR (400 MHz, CDCl$_3$) δ ppm 0.98 (d, J=6.65 Hz, 3H) 1.52 (ddd, J=13.64, 9.44, 4.69 Hz, 1H) 1.91 (br. s., 1H) 2.21 (d, J=13.50 Hz, 1H) 2.75-2.90 (m, 2H) 3.48 (br. s., 1H) 3.66 (s, 3H) 4.22 (dd, J=13.50, 3.72 Hz, 2H) 6.50 (d, J=6.26 Hz, 1H) 8.00 (d, J=6.26 Hz, 1H) ESI-MS M+H 270.0.

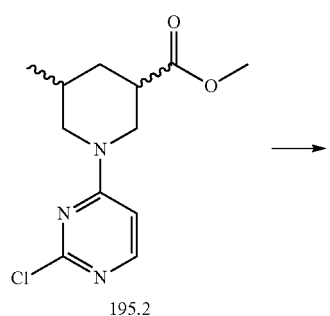

195.2

Methyl 5-Methyl-1-(2-(3,4,5-Trimethoxy-Phenylamino)Pyrimidin-4-Yl)Piperidine-3-Carboxylate (195.3)

195.3 was prepared in a method analogous to M1.2 using 195.2 in place of M1.1 to provide the desired material as a light purple solid. ESI-MS M+H 417.2.

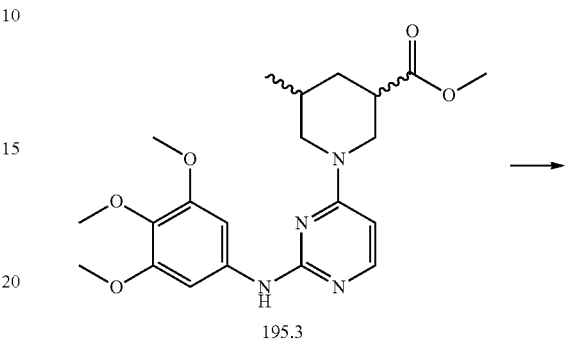

195.3

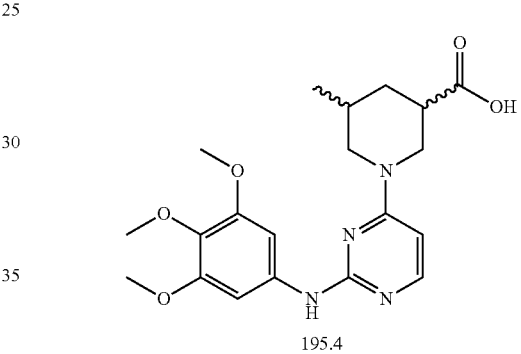

195.4

5-Methyl-1-(2-(3,4,5-Trimethoxyphenyl-Amino)Pyrimidin-4-Yl)Piperidine-3-Carboxylic Acid (195.4)

1953.4 was prepared in a method analogous to example 2.3 using 195.3 in place of 2.2 to provide 5-methyl-1-(2-(3,4,5-trimethoxyphenylamino)-pyrimidin-4-yl)piperidine-3-carboxylic acid. ESI-MS M+H 403.1.

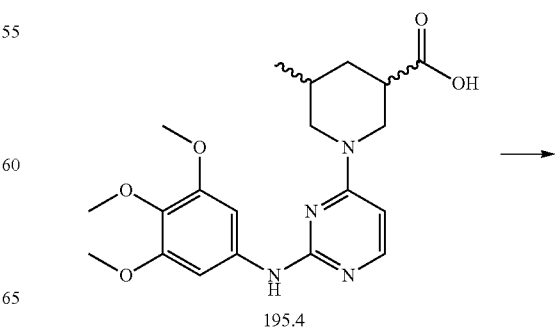

195.4

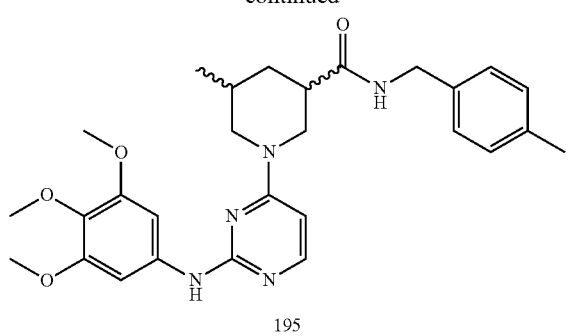

195

5-Methyl-N-(4-Methylbenzyl)-1-(2-(3,4,5-Trimethoxyphenyl Amino)Pyrimidin-4-Yl)Piperidine-3-Carboxamide (195)

195 was prepared in a method analogous to M5.1 using 195.4 in place of (S)-1-(tert-butoxycarbonyl)piperidine-3-carboxylic acid to provide 5-methyl-N-(4-methylbenzyl)-1-(2-(3,4,5-trimethoxyphenylamino)pyrimidin-4-yl)piperidine-3-carboxamide. $^1$H NMR (300 MHz, CDCl$_3$) δ ppm 0.95 (d, J=6.58 Hz, 3H) 1.41-1.55 (m, 1H) 1.79 (br. s., 1H) 2.24 (s, 3H) 2.40 (d, J=13.15 Hz, 1H) 2.57-2.69 (m, 1H) 2.86-2.99 (m, 2H) 3.40 (dd, J=14.18, 3.22 Hz, 1H) 3.77-3.91 (m, 9H) 4.01-4.14 (m, 1H) 4.26-4.38 (m, 1H) 4.53-4.68 (m, 1H) 6.03 (d, J=6.43 Hz, 1H) 6.77 (s, 2H) 6.85-7.06 (m, 5H) 7.78 (d, J=6.43 Hz, 1H) 8.26 (br. s., 1H); M+H 506.27601.

Example 196

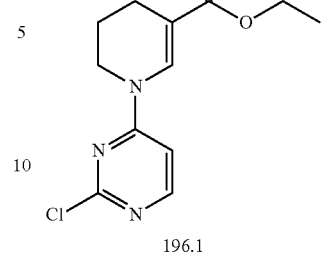

196.1

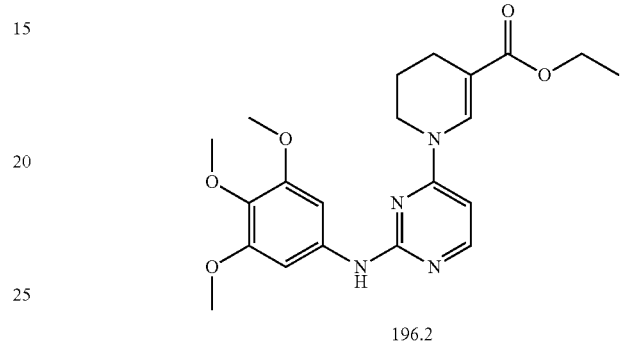

196.2

Ethyl 1-(2-(3,4,5-Trimethoxyphenylamino)Pyrimidin-4-Yl)-1,4,5,6-Tetrahydropyridine-3-Carboxylate (196.2)

Example 196.2 is synthesized in a method analogous to M1.2 using 196.1 in place of M1.1.

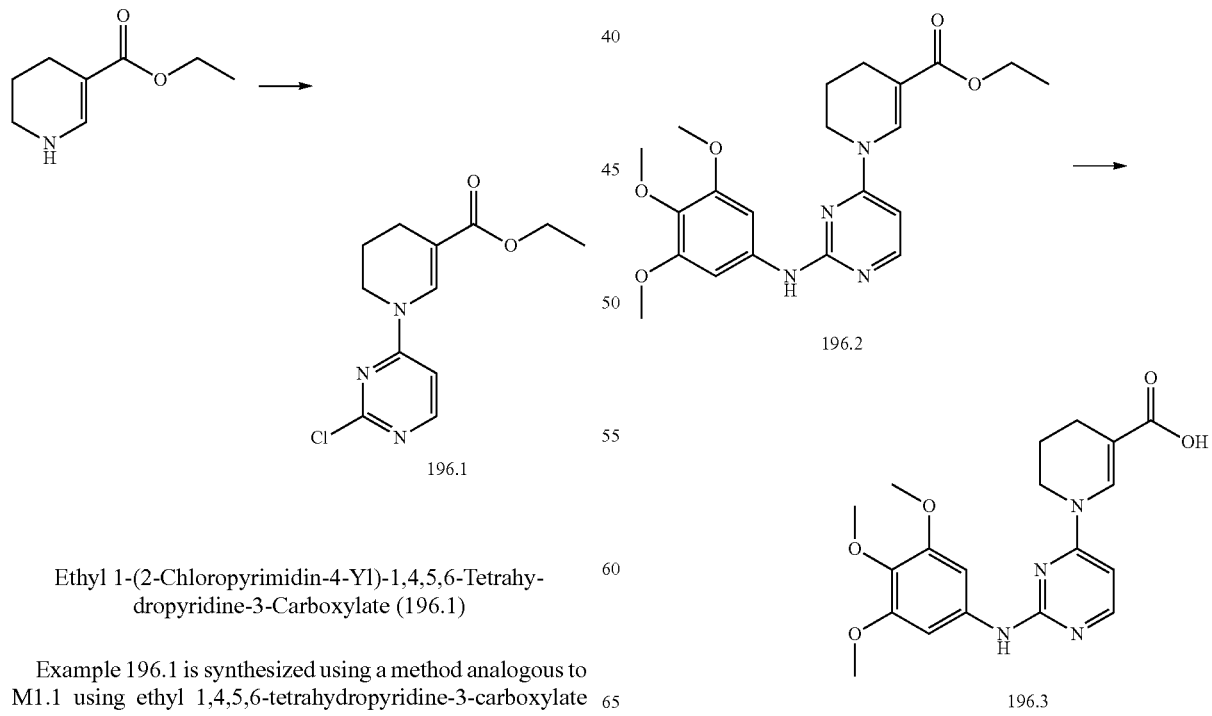

Ethyl 1-(2-Chloropyrimidin-4-Yl)-1,4,5,6-Tetrahydropyridine-3-Carboxylate (196.1)

Example 196.1 is synthesized using a method analogous to M1.1 using ethyl 1,4,5,6-tetrahydropyridine-3-carboxylate (European Journal of Organic Chemistry (2006), (19), 4343-4347) in place of ethyl piperidine-3-carboxylate.

1-(2-(3,4,5-Trimethoxyphenylamino)Pyrimidin-4-Yl)-1,4,5,6-Tetrahydropyridine-3-Carboxylic Acid (196.3)

Example 196.3 is synthesized in a method analogous to M1.3 using 196.2 in place of M1.2.

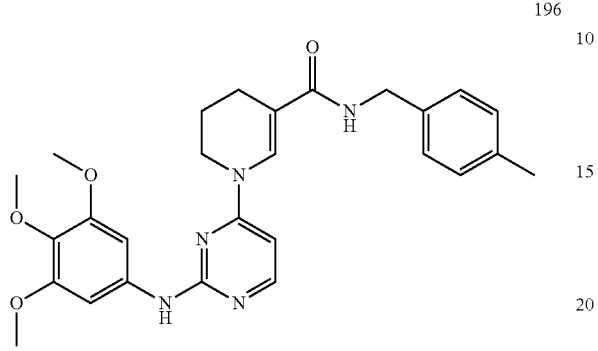

196

N-(4-Methylbenzyl)-1-(2-(3,4,5 Trimethoxyphenylamino)Pyrimidin-4-Yl)-1,4,5,6-Tetrahydropyridine-3-Carboxamide (196)

Example 196 is synthesized in a method analogous to M5.1 using 196.3 in place of (S)-1-(tert-butoxycarbonyl)piperidine-3-carboxylic acid.

ALK Inhibition in Enzyme Assay

The cytoplasmic domain (amino acids 1058-1620) of wild-type human ALK was expressed in SF9 cells as an N-terminal GST fusion protein. Kinase activity of the purified protein was assessed using a Lance® TR-FRET assay. The kinase reaction was performed in a 384-well microtiter plate using 2 nM enzyme in 20 mM HEPES (pH 7.5), 0.05% BSA, 2 mM DTT, 10 mM $MgCl_2$, 1 µM peptide substrate (Biotin-Ahx-EQEDEPEGIYGVLF-OH) (SEQ ID NO: 1), and ATP at 40 µM (the Km apparent). The reaction was allowed to proceed for 90 minutes at room temperature and was then terminated with 20 mM EDTA in 50 mM Tris (pH 7.5), 100 mM NaCl, 0.05% BSA, and 0.1% Tween-20. Phosphorylation of the peptide substrate was detected using the Lance® detection reagents streptavidin-allophycocyanin (SA-APC) and Eu-W1024 anti-phosphotyrosine antibody (PT66) from Perkin Elmer Life Sciences (Waltham, Mass.). The plates were read on a RUBY star plate reader (BMG LABTECH, Cary, N.C.) with an excitation wavelength of 320 nm. Emission was monitored at 615 nm and 665 nm, with increased emission at 665 nm indicative of peptide phosphorylation. Compound $IC_{50}$ values were calculated from the magnitude of signal in the 655 nm emission channel and were expressed as the mean of three replicates.

The following table includes ALK $IC_{50}$ values obtained using the procedure set forth above for the Example compounds described herein.

| Table of ALK $IC_{50}$ values of Example Compounds | |
|---|---|
| Example | ALK $IC_{50}$ (µM)[a] |
| 1 | ++++ |
| 2 | +++ |
| 3 | ++++ |
| 4 | +++ |
| 5 | +++ |
| 6 | ++++++ |
| 7 | +++ |
| 8 | +++ |
| 9 | ++++ |
| 10 | ++++ |
| 11 | ++ |
| 12 | + |
| 13 | +++ |
| 14 | ++++ |
| 15 | ++++ |
| 16 | ++++ |
| 17 | ++++ |
| 18 | ++ |
| 19 | +++ |
| 20 | +++ |
| 21 | ++++ |
| 22 | ++++ |
| 23 | ++++ |
| 24 | ++++++ |
| 25 | +++ |
| 26 | ++++ |
| 27 | ++++ |
| 28 | +++++ |
| 29 | +++++ |
| 30 | +++ |
| 31 | +++ |
| 32 | ++ |
| 33 | ++++++ |
| 34 | +++++ |
| 35 | ++++ |
| 36 | ++++ |
| 37 | ++ |
| 38 | ++++ |
| 39 | +++ |
| 40 | +++++ |
| 41 | +++++ |
| 42 | +++ |
| 43 | ++++ |
| 44 | ++++ |
| 45 | ++++ |
| 46 | +++ |
| 47 | +++++ |
| 48 | +++ |
| 49 | +++ |
| 50 | +++ |
| 51 | ++++ |
| 52 | +++ |
| 53 | ++ |
| 54 | +++ |
| 55 | ++++ |
| 56 | ++++++ |
| 57 | +++++ |
| 58 | ++++++ |
| 59 | +++ |
| 60 | +++++ |
| 61 | ++ |
| 62 | ++++ |
| 63 | +++ |
| 64 | ++++ |
| 65 | ++++ |
| 66 | +++ |
| 67 | ++++ |
| 68 | ++++ |
| 69 | ++++++ |
| 70 | ++++++ |
| 71 | +++ |
| 72 | ++++ |
| 73 | +++ |
| 74 | ++++ |
| 75 | ++++++ |
| 76 | +++++ |
| 77 | +++ |
| 78 | +++ |
| 79 | ++++++ |
| 80 | +++++ |
| 81 | ++ |
| 82 | +++ |
| 83 | ++++ |

-continued

| | |
|---|---|
| 84 | +++ |
| 85 | ++++++ |
| 86 | ++++ |
| 87 | ++++ |
| 88 | +++++ |
| 89 | +++++ |
| 90 | ++++ |
| 91 | +++++ |
| 92 | ++++ |
| 93 | ++++ |
| 94 | ++++++ |
| 95 | ++++ |
| 96 | ++++++ |
| 97 | +++ |
| 98 | ++++ |
| 99 | +++ |
| 100 | ++++ |
| 101 | +++ |
| 102 | ++++ |
| 103 | ++++ |
| 104 | ++++ |
| 105 | +++ |
| 106 | ++++++ |
| 107 | ++++ |
| 108 | ++++++ |
| 109 | ++++ |
| 110 | ++++++ |
| 111 | ++++ |
| 112 | ++++ |
| 113 | ++++++ |
| 114 | +++ |
| 115 | ++++ |
| 116 | +++++ |
| 117 | ++++++ |
| 118 | ++++ |
| 119 | ++++ |
| 120 | +++ |
| 121 | ++++ |
| 122 | +++ |
| 123 | ++++ |
| 124 | +++ |
| 125 | ++++ |
| 126 | ++ |
| 127 | ++++++ |
| 128 | +++ |
| 129 | +++ |
| 130 | +++ |
| 131 | +++ |
| 132 | +++ |
| 133 | +++ |
| 134 | ++++ |
| 135 | +++ |
| 136 | ++++ |
| 137 | +++ |
| 138 | +++ |
| 139 | +++ |
| 140 | ++++ |
| 141 | ++++ |
| 142 | +++ |
| 143 | ++++ |
| 144 | +++ |
| 145 | ++ |
| 146 | ++++ |
| 147 | ++ |
| 148 | ++++ |
| 149 | ++++ |
| 150 | ++++ |
| 151 | ++++ |
| 152 | ++++ |
| 153 | +++ |
| 154 | +++ |
| 155 | +++ |
| 156 | +++ |
| 157 | ++++ |
| 158 | ++++ |
| 159 | +++ |
| 160 | ++++ |
| 161 | ++++ |
| 162 | ++++ |
| 163 | ++++ |
| 164 | +++ |
| 165 | +++ |
| 166 | +++ |
| 167 | ++++ |
| 168 | +++ |
| 169 | ++++ |
| 170 | ++++ |
| 171 | ++++ |
| 172 | +++ |
| 173 | +++ |
| 174 | +++ |
| 175 | +++ |
| 176 | ++ |
| 177 | ++++ |
| 178 | ++++ |
| 179 | +++ |
| 180 | +++ |
| 181 | ++++ |
| 182 | ++++ |
| 183 | ++++ |
| 184 | ++++ |
| 185 | +++ |
| 186 | ++ |
| 187 | ++++ |
| 188 | ++++ |
| 189 | +++ |
| 190 | +++++ |
| 191 | +++ |
| 192 | +++ |
| 193 | +++ |
| 194 | ++++ |
| 195 | +++ |
| 196 | ND[b] |

[a]$IC_{50}$ Ranges:
+     $IC_{50} > 10\ \mu M$
++    $5\ \mu M \leq EC_{50} \leq 10\ \mu M$
+++   $1\ \mu M \leq EC_{50} < 5\ \mu M$
++++   $0.1\ \mu M \leq EC_{50} < 1\ \mu M$
+++++   $0.05\ \mu M \leq EC_{50} < 0.1\ \mu M$
++++++   $EC_{50} < 0.05\ \mu M$

[b]ND means not determined

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING

In accordance with 37 CFR 1.52(e)(5), a Sequence Listing in the form of a text file (entitled "Sequence_Listing_ST25", 1 kilobyte in size) is incorporated herein by reference in its entirety.

What is claimed:

1. A compound of Formula I:

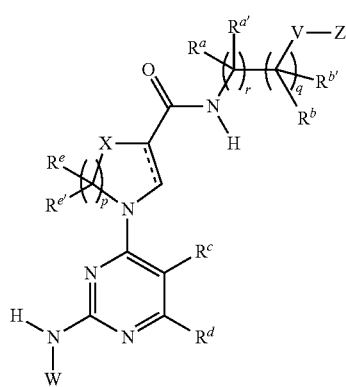

or a pharmaceutically acceptable salt thereof, a stereoisomer thereof, a pharmaceutically acceptable salt of the stereoisomer, or a mixture thereof,
wherein:
X is selected from —$CH_2$—, —N(H)—, —O—, or —S—;
V is absent or is selected from —$CH_2$—, —O—, —S—, or —NH—; wherein if V is —O—, —S—, or —NH—, then r is 1 and q is 1;
the subscript p is selected from 0, 1, 2, or 3, wherein X is $CH_2$ if p is 0;
the subscript q is selected from 0 or 1;
the subscript r is selected from 0 or 1:
the ----- symbol indicates that the bond can be a single or double bond;
Z is a $C_6$-$C_{10}$ aryl or a 5-10 membered heteroaryl comprising 1, 2, 3, or 4 heteroatoms independently selected from O, S, or N, wherein the $C_6$-$C_{10}$ aryl or the 5-10 membered heteroaryl are unsubstituted or are optionally substituted with 1, 2, 3, or 4 substituents independently selected from —Z', —O—Z', —S—Z', —NH—Z', —$CH_2$Z', —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —C(=O)NH—Z', —$SO_2NH_2$, —$SO_2$NH(($C_1$-$C_4$)alkyl), —$SO_2$N(($C_1$-$C_4$)alkyl)$_2$, —$SO_2$NH—Z', —$NHSO_2$—($C_1$-$C_4$)alkyl, —$NHSO_2$—Z', —NHC(=O)—($C_1$-$C_4$)alkyl, —NHC(=O)—Z', —$SO_2$—($C_1$-$C_4$)alkyl, —$SO_2$—Z', —SO—($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—Z', —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)alkyl, —($C_1$-$C_4$)alkylene-C(=O)—O—($C_1$-$C_4$)alkyl, —($C_1$-$C_4$)alkylene-C(=O)—OH, —OH, —O—($C_1$-$C_6$)alkyl, —SH, —S—($C_1$-$C_6$)alkyl, —$OCF_3$, or —$OCHF_2$; and two adjacent substituents on the $C_6$-$C_{10}$ aryl or the 5-10 membered heteroaryl may join to form a 5 or 6 membered ring comprising 0, 1, or 2 heteroatoms selected from O, N, or S; and further wherein the $C_6$-$C_{10}$ aryl and the 5-10 membered heteroaryl may be monocyclic or bicyclic and further wherein both rings of a bicyclic $C_6$-$C_{10}$ aryl or a bicyclic 5-10 membered heteroaryl may be aromatic or one of the rings may be partially saturated and the other ring may be aromatic and either the partially saturated ring or the aromatic ring may be bonded to V, if present, or to the C atom bearing $R^b$ and $R^{b'}$ if V is not present, or to the C atom bearing $R^a$ and $R^{a'}$ if V is not present and q is 0, or to the N atom bonded to the C(=O) if V is not present, q is 0, and r is 0; and further wherein, the partially saturated ring of a bicyclic $C_6$-$C_{10}$ aryl or a bicyclic 5-10 membered heteroaryl may include a —C(=O)— ring member;
Z' is a $C_6$-$C_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the $C_6$-$C_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —$NO_2$, —($C_1$-$C_6$)alkyl, —($C_2$-$C_6$)alkenyl, —($C_2$-$C_6$)alkynyl, —($C_1$-$C_4$)alkylene-OH, —$NH_2$, —NH(($C_1$-$C_4$)alkyl), —N(($C_1$-$C_4$)alkyl)$_2$, —C(=O)$NH_2$, —C(=O)NH(($C_1$-$C_4$)alkyl), —C(=O)N(($C_1$-$C_4$)alkyl)$_2$, —$SO_2NH_2$, —$SO_2$NH(($C_1$-$C_4$)alkyl), —$SO_2$N(($C_1$-$C_4$)alkyl)$_2$, —$NHSO_2$—($C_1$-$C_4$)alkyl, —NHC(=O)—($C_1$-$C_4$)alkyl, —$SO_2$—($C_1$-$C_4$)alkyl, —SO($C_1$-$C_4$)alkyl, —($C_1$-$C_4$)alkylene-NH—C(=O)—($C_1$-$C_4$)alkyl, —$CF_3$, —C(=O)—($C_1$-$C_4$)alkyl, —$CO_2$H, —C(=O)—O—($C_1$-$C_4$)alkyl, —C(=O)NH—($C_1$-$C_4$)alkylene-$NH_2$, —C(=O)NH—($C_1$-$C_4$)alkylene-NH(($C_1$-$C_4$)alkyl), —C(=O)NH—($C_1$-$C_4$)alkylene-N(($C_1$-$C_4$)alkyl)$_2$, —($C_1$-$C_4$)alkylene-C(=O)—($C_1$-$C_4$)

alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$;

R$^a$ and R$^{a'}$ are absent if r is 0 or are independently selected from —H, —(C$_1$-C$_6$)alkyl, —C≡N, —OH, or —CF$_3$; or R$^a$ and R$^{a'}$ may together represent a =O; or R$^a$ and R$^{a'}$ may join together with the carbon atom to which they are attached to form a cycloalkyl ring having from 3 to 6 members;

R$^b$ and R$^{b'}$ are absent if q is 0 or are independently selected from —H, —(C$_1$-C$_6$)alkyl, —C≡N, —OH, or —CF$_3$; or R$^b$ and R$^{b'}$ may together represent a =O; or R$^b$ and R$^{b'}$ may join together with the carbon atom to which they are attached to form a cycloalkyl ring having from 3 to 6 members;

R$^c$ is selected from —H, —(C$_1$-C$_6$)alkyl, —CF$_3$, —F, —Cl, —Br, or —I;

R$^d$ is selected from —H, —(C$_1$-C$_6$)alkyl, —CF$_3$, —F, —Cl, —Br, or —I;

R$^e$ and R$^{e'}$ are independently selected from —H or —(C$_1$-C$_6$)alkyl;

W is a C$_6$-C$_{10}$ aryl, a 5-10 membered heteroaryl comprising 1, 2, 3 or 4 heteroatoms independently selected from O, S, or N, or a 5-7 membered heterocyclyl comprising 1, 2, or 3 heteroatoms selected from O, S, or N, wherein the C$_6$-C$_{10}$ aryl, the 5-10 membered heteroaryl, or the 5-7 membered heterocyclyl are unsubstituted or are optionally substituted with 1, 2, 3, or 4 substituents independently selected from —W', —O—W', —S—W', —CH$_2$—W', —N(H)—W', —O—CH$_2$—W', —C(=O)—W', —C(=O)NH—W', —SO$_2$NH—W', —NHSO$_2$—W', —NHC(=O)—W', —SO$_2$—W', —F, —Cl, —Br, —I, —C≡N, —NO$_2$, (C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH$_4$C$_1$-C$_4$)alkylene-NH$_2$, —C(=O)NH—(C$_1$-C$_4$)alkylene-NH((C$_1$-C$_4$)alkyl), —C(=O)NH$_4$C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$; and two adjacent substituents on the C$_6$-C$_{10}$ aryl or the 5-10 membered heteroaryl may join to form a 5 or 6 membered ring comprising 0, 1, or 2 heteroatoms selected from O, N, or S; and further wherein the C$_6$-C$_{10}$ aryl and the 5-10 membered heteroaryl may be monocyclic or bicyclic and further wherein both rings of a bicyclic C$_6$-C$_{10}$ aryl or a bicyclic 5-10 membered heteroaryl may be aromatic or one of the rings may be partially saturated and the other ring may be aromatic and either the partially saturated ring or the aromatic ring may be bonded to the N atom to which W is attached; and further wherein, the partially saturated ring of a bicyclic C$_6$-C$_{10}$ aryl or a bicyclic 5-10 membered heteroaryl may include a —C(=O)— ring member and the 5-7 membered heterocyclyl group may include a —C(=O)— ring member; and W' is a C$_6$-C$_{10}$ aryl, a 5-10 membered heteroaryl comprising 1, 2, 3, or 4 heteroatoms independently selected from O, S, or N, or a 5-7 membered heterocyclyl comprising 1, 2, or 3 heteroatoms selected from O, S, or N, wherein the C$_6$-C$_{10}$ aryl, the 5-10 membered heteroaryl, or the 5-7 membered heterocyclyl are unsubstituted or are optionally substituted with 1 or 2 substituents independently selected from —F, —Cl, —Br, —I, —C≡N, —NO$_2$, —(C$_1$-C$_6$)alkyl, —(C$_2$-C$_6$)alkenyl, —(C$_2$-C$_6$)alkynyl, —(C$_1$-C$_4$)alkylene-OH, —NH$_2$, —NH((C$_1$-C$_4$)alkyl), —N((C$_1$-C$_4$)alkyl)$_2$, —C(=O)NH$_2$, —C(=O)NH((C$_1$-C$_4$)alkyl), —C(=O)N((C$_1$-C$_4$)alkyl)$_2$, —SO$_2$NH$_2$, —SO$_2$NH((C$_1$-C$_4$)alkyl), —SO$_2$N((C$_1$-C$_4$)alkyl)$_2$, —NHSO$_2$—(C$_1$-C$_4$)alkyl, —NHC(=O)—(C$_1$-C$_4$)alkyl, —SO$_2$—(C$_1$-C$_4$)alkyl, —SO—(C$_1$-C$_4$)alkyl, —(C$_1$-C$_4$)alkylene-NH—C(=O)—(C$_1$-C$_4$)alkyl, —CF$_3$, —C(=O)—(C$_1$-C$_4$)alkyl, —CO$_2$H, —C(=O)—O—(C$_1$-C$_4$)alkyl, —C(=O)NH—(C$_1$-C$_4$)alkylene-NH$_2$, —C(=O)NH—(C$_1$-C$_4$)alkylene-NH((C$_1$-C$_4$)alkyl), —C(=O)NH—(C$_1$-C$_4$)alkylene-N((C$_1$-C$_4$)alkyl)$_2$, —(C$_1$-C$_4$)alkylene-C(=O)—(C$_1$-C$_4$)alkyl, —(C$_1$-C$_4$)alkylene-C(=O)—O—(C$_1$-C$_4$)alkyl, —(C$_1$-C$_4$)alkylene-C(=O)—OH, —OH, —O—(C$_1$-C$_6$)alkyl, —SH, —S—(C$_1$-C$_6$)alkyl, —OCF$_3$, or —OCHF$_2$.

2. The compound of claim 1, wherein p is 2.
3. The compound of claim 1, wherein r is 1.
4. The compound of claim 1, wherein V is absent.
5. The compound of claim 1, wherein V is —O—.
6. The compound of claim 1, wherein V is —CH$_2$—.
7. The compound of claim 1, wherein X is —CH$_2$—.
8. The compound of claim 1, wherein X is —O—.
9. The compound of claim 1, wherein X is —S—.
10. The compound of claim 1, wherein X is —N(H)—.
11. The compound of claim 1, wherein q is 0.
12. The compound of claim 1, wherein q is 1 and R$^b$ and R$^{b'}$ are independently selected from —H, —CH$_3$, or R$^b$ and R$^{b'}$, when taken together, represent a =O.
13. The compound of claim 1, wherein the compound of Formula I is a compound of Formula II:

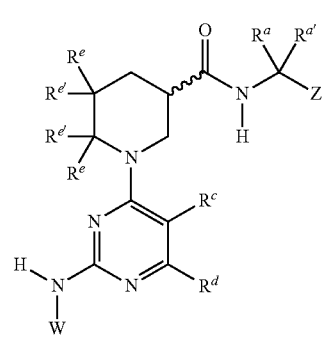

II or a pharmaceutically acceptable salt thereof, a stereoisomer thereof, a pharmaceutically acceptable salt of the stereoisomer, or a mixture thereof, wherein the symbol ⌇ indicates that the chiral carbon atom to which the ⌇ is attached may have the R stereochemistry, the S stereochemistry, or may be a mixture of compounds with the R and S stereochemistry wherein the mixture may be racemic, or the mixture may include a greater amount of compounds with the R stereochemistry compared to the amount of compounds with the S stereochemistry, or the mixture may include a greater amount of compounds with the S stereochemistry compared to the amount of compounds with the R stereochemistry.

14. The compound of claim 13, wherein the compound of Formula II is a compound of Formula IIA:

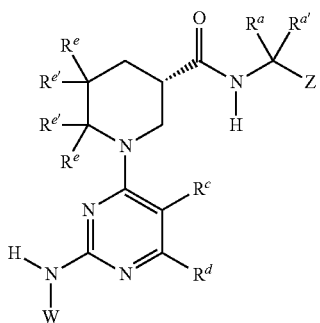

IIA or a pharmaceutically acceptable salt thereof.

15. The compound of claim 13, wherein the compound of Formula II is a compound of Formula IIB:

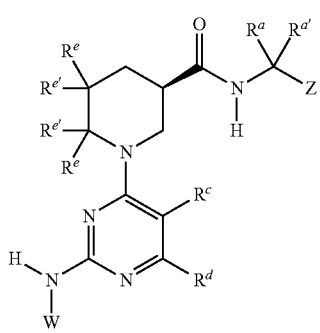

IIB or a pharmaceutically acceptable salt thereof.

16. The compound of claim 13, wherein $R^e$ and $R^{e'}$ are independently selected from —H or —CH$_3$.

17. The compound of claim 16, wherein $R^e$ and $R^{e'}$ are both —H.

18. The compound of claim 13, wherein $R^a$ and $R^{a'}$ are independently selected from —H or —CH$_3$.

19. The compound of claim 18, wherein $R^a$ and $R^{a'}$ are both —H.

20. The compound of claim 13, wherein $R^c$ is selected from —H or —CH$_3$.

21. The compound of claim 20, wherein $R^c$ is —H.

22. The compound of claim 13, wherein $R^d$ is selected from —H or —CH$_3$.

23. The compound of claim 22, wherein $R^d$ is —H.

24. The compound of claim 1, wherein r is 0.

25. The compound of claim 24, wherein q is 0.

26. The compound of claim 1, wherein Z is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, quinolinyl, isoquinolinyl, 1,2,3,4,4a,8a-hexahydroquinolinyl, 2,3-dihydrobenzo[b][1,4]dioxinyl, pyridazinyl, pyrazinyl, indazolyl, isothiazolyl, or oxazolyl.

27. The compound of claim 1, wherein Z is an unsubstituted or substituted phenyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, quinolinyl, isoquinolinyl, 1,2,3,4,4a,8a-hexahydroquinolinyl, or 2,3-dihydrobenzo[b][1,4]dioxinyl.

28. The compound of claim 1, wherein Z is an unsubstituted or substituted phenyl.

29. The compound of claim 28, wherein Z is selected from

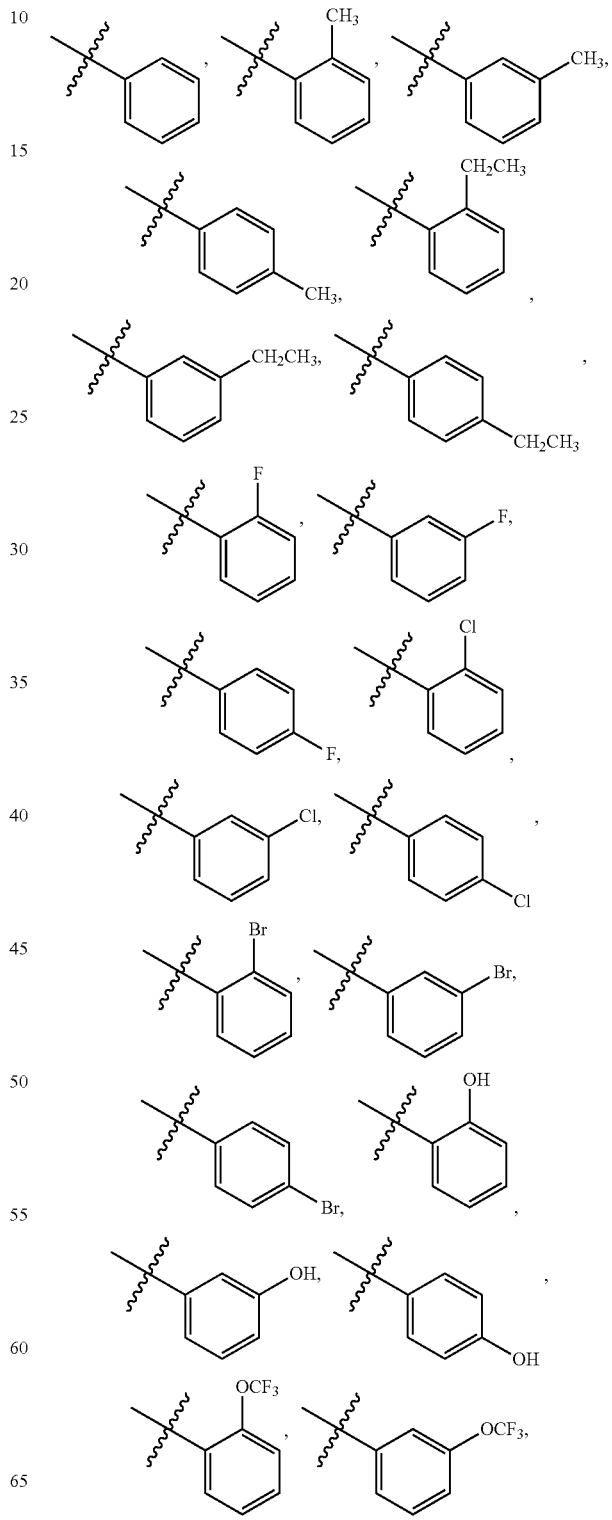

227
-continued
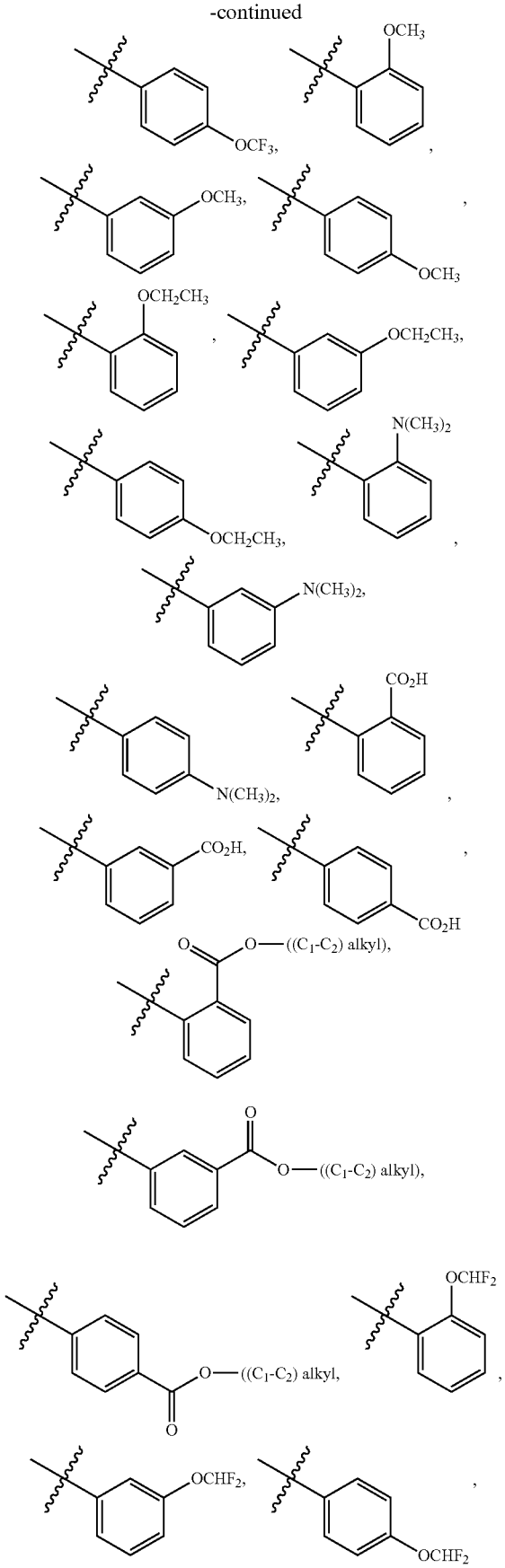
228
-continued
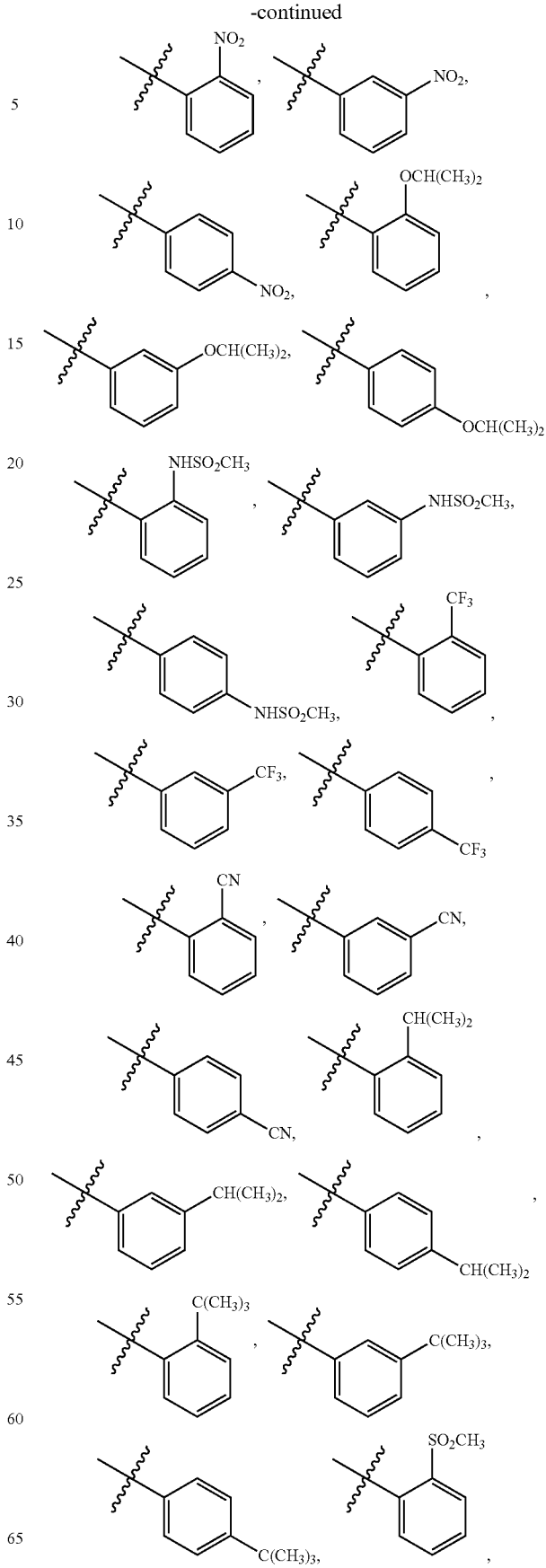

-continued

-continued

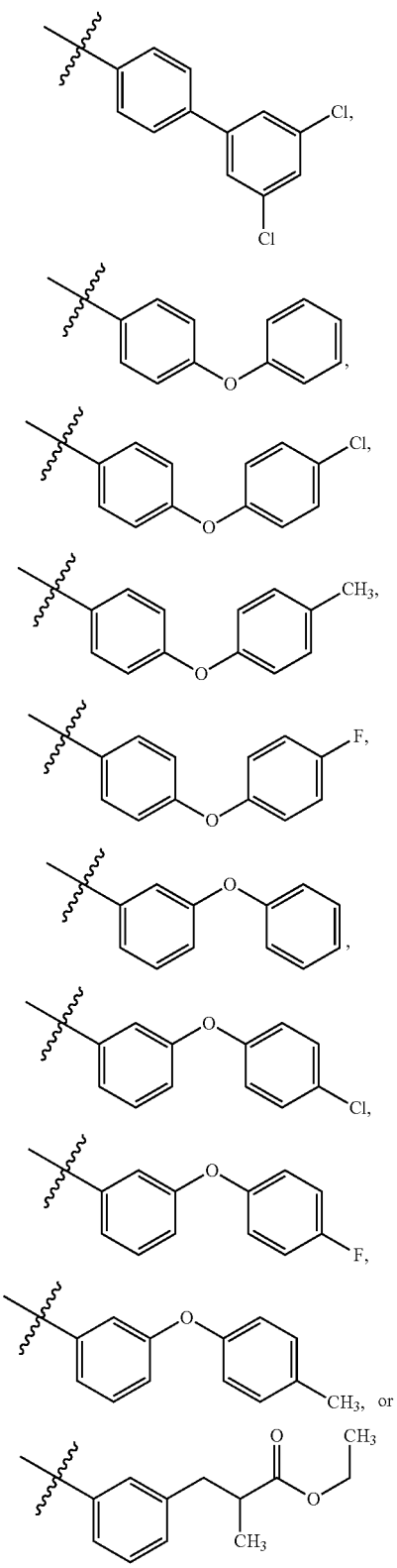

wherein the symbol ∿ when drawn through a bond indicates the point of attachment to the rest of the molecule.

30. The compound of claim 26, wherein Z is selected from

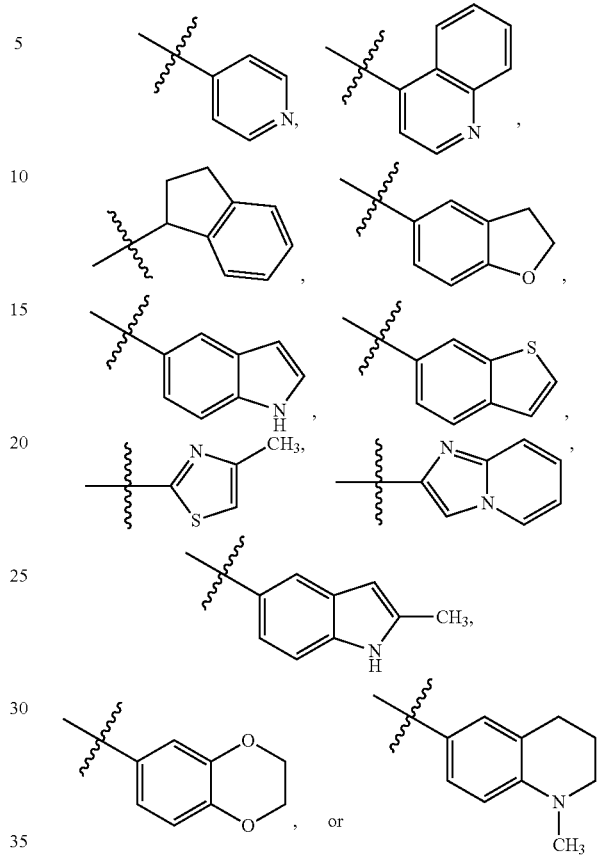

wherein the symbol ∿ when drawn through a bond indicates the point of attachment to the rest of the molecule.

31. The compound of claim 1, wherein Z is substituted with at least one substituent selected from —Z' or —OZ'.

32. The compound of claim 31, wherein Z is phenyl and Z' is an optionally substituted phenyl.

33. The compound of claim 1, wherein W is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, isoindolin-1-onyl, indolinyl, pyrazolyl, pyridinonyl, quinolinyl, isoquinolinyl, 1,2,3,4,4a,8a-hexahydroquinolinyl, 2,3-dihydrobenzo[b][1,4]dioxinyl, pyridazinyl, pyrazinyl, indazolyl, isothiazolyl, or oxazolyl.

34. The compound of claim 1, wherein W is an unsubstituted or substituted phenyl, pyridyl, pyrimidinyl, naphthyl, indanyl, 2,3-dihydrobenzofuranyl, benzofuranyl, benzothiophenyl, indolyl, thiazolyl, imidazolyl, imidazo[1,2-a]pyridyl, isoindolin-1-onyl, indolinyl, pyrazolyl, pyridinonyl, quinolinyl, isoquinolinyl, 1,2,3,4,4a,8a-hexahydroquinolinyl, or 2,3-dihydrobenzo[b][1,4]dioxinyl.

35. The compound of claim 1, wherein W is an unsubstituted or substituted phenyl, pyridyl, indolyl, isoindolin-1-onyl, indolinyl, pyrazolyl, pyridinonyl, quinolinyl, isoquinolinyl, or 2,3-dihydrobenzo[b][1,4]dioxinyl.

36. The compound claim 1, wherein W is an unsubstituted or substituted phenyl.

37. The compound of claim 1, wherein W is selected from
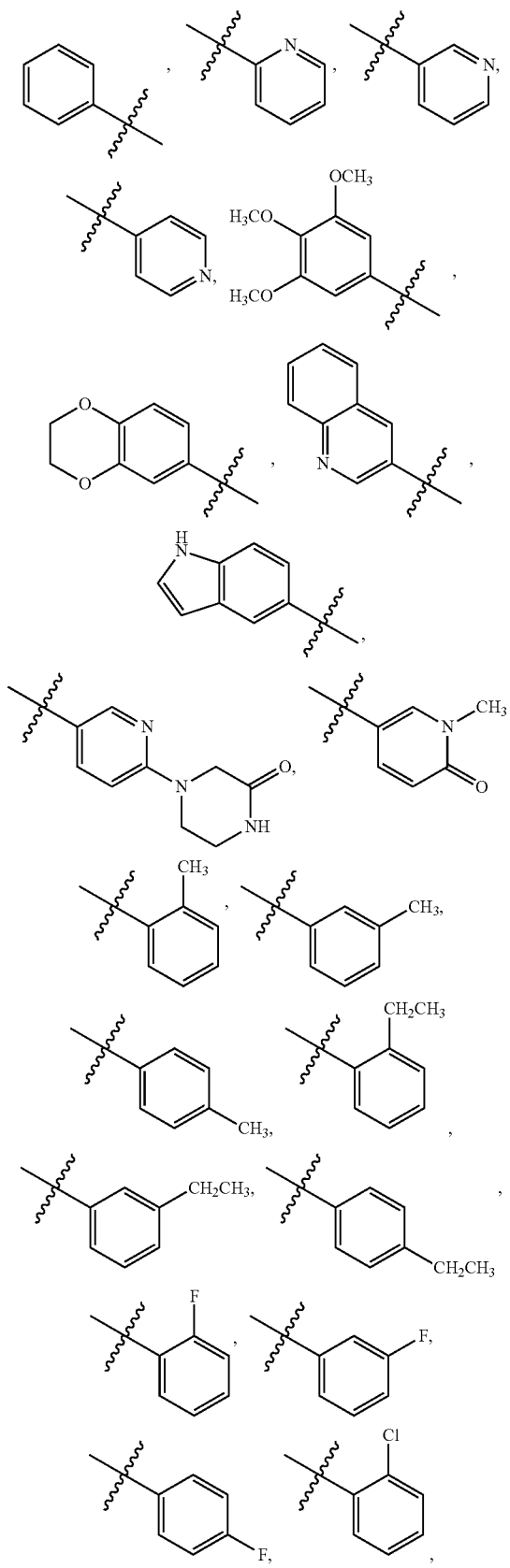
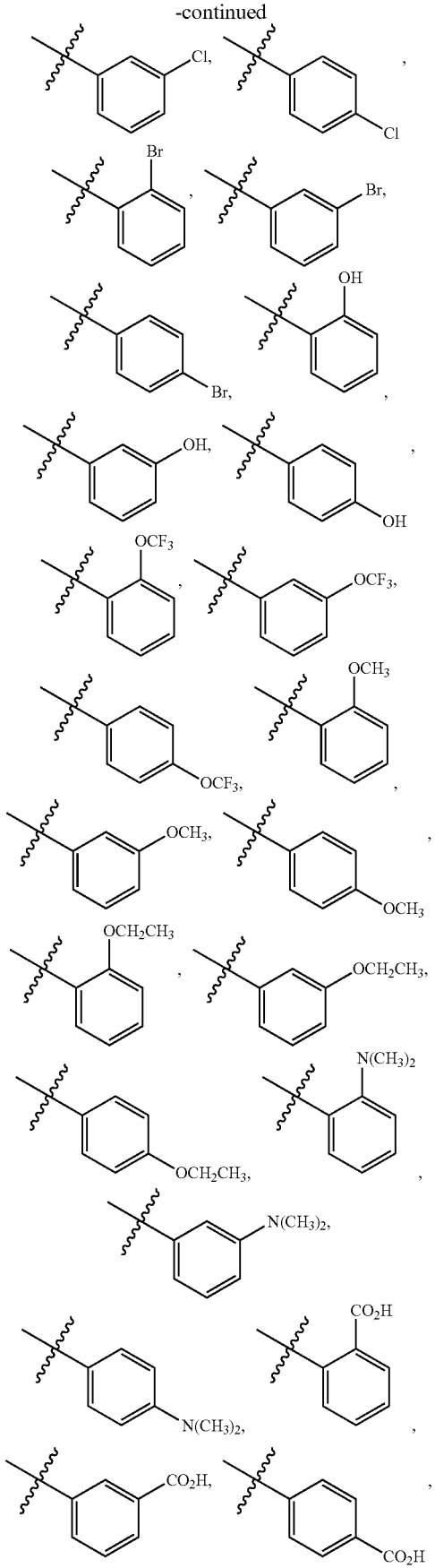

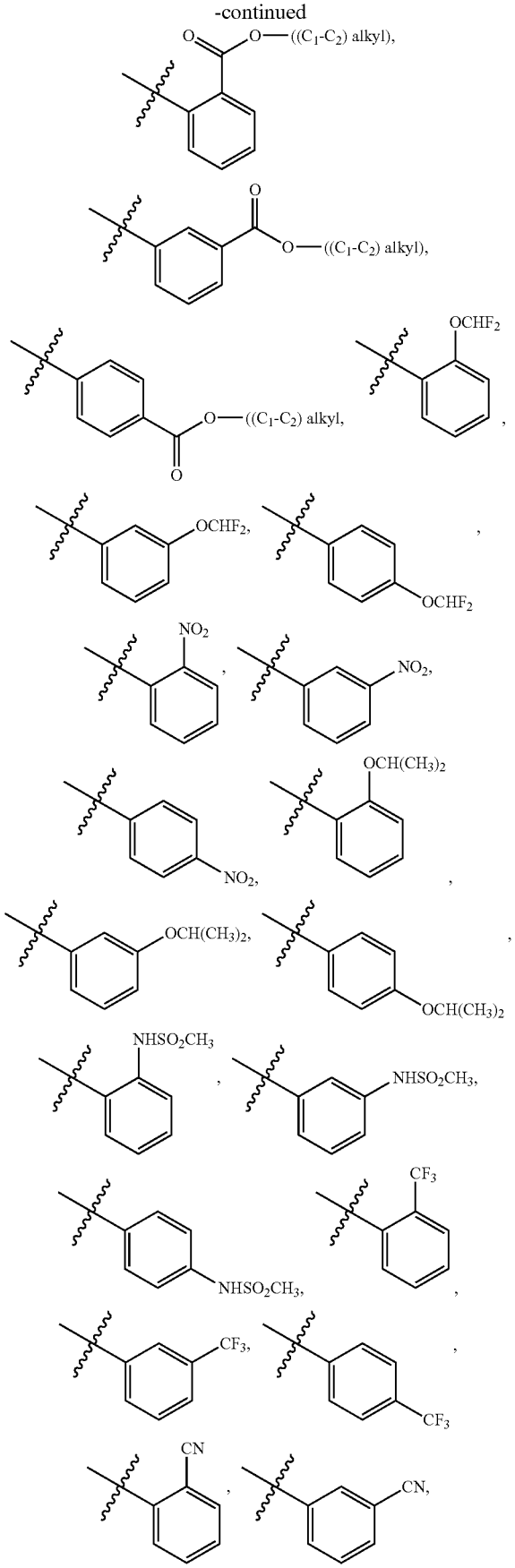
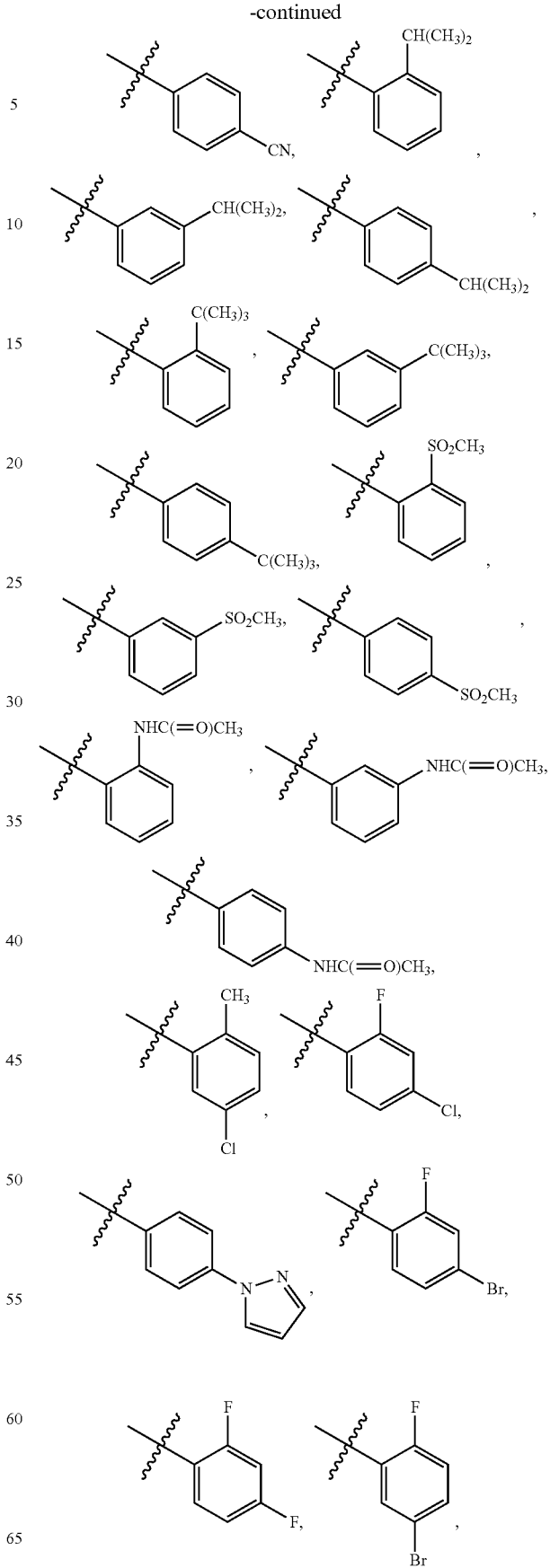

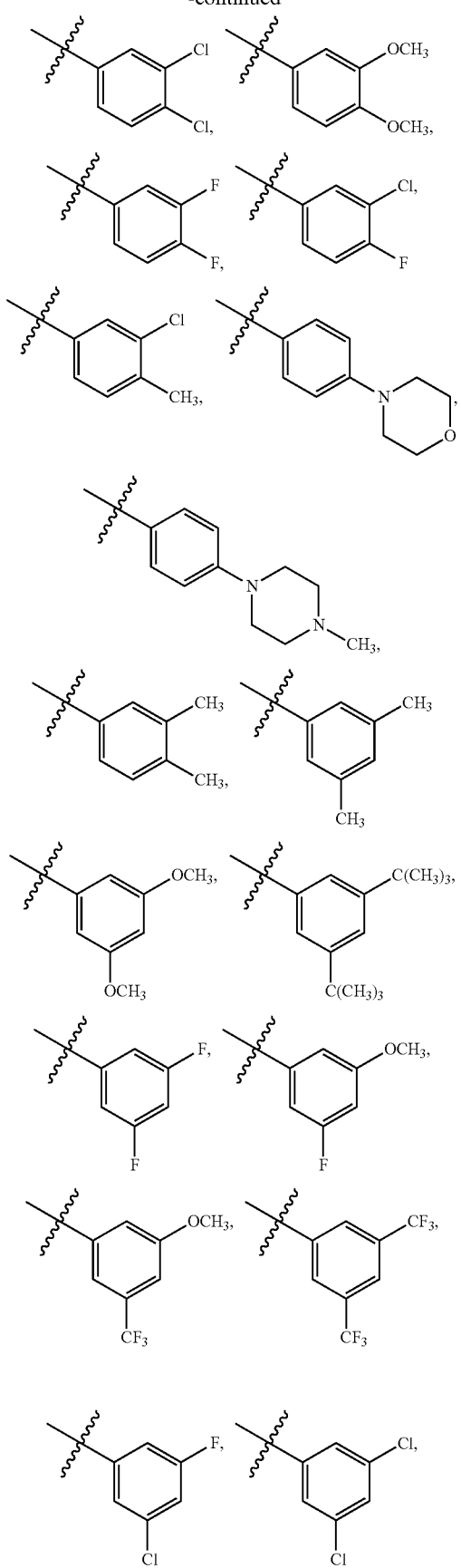
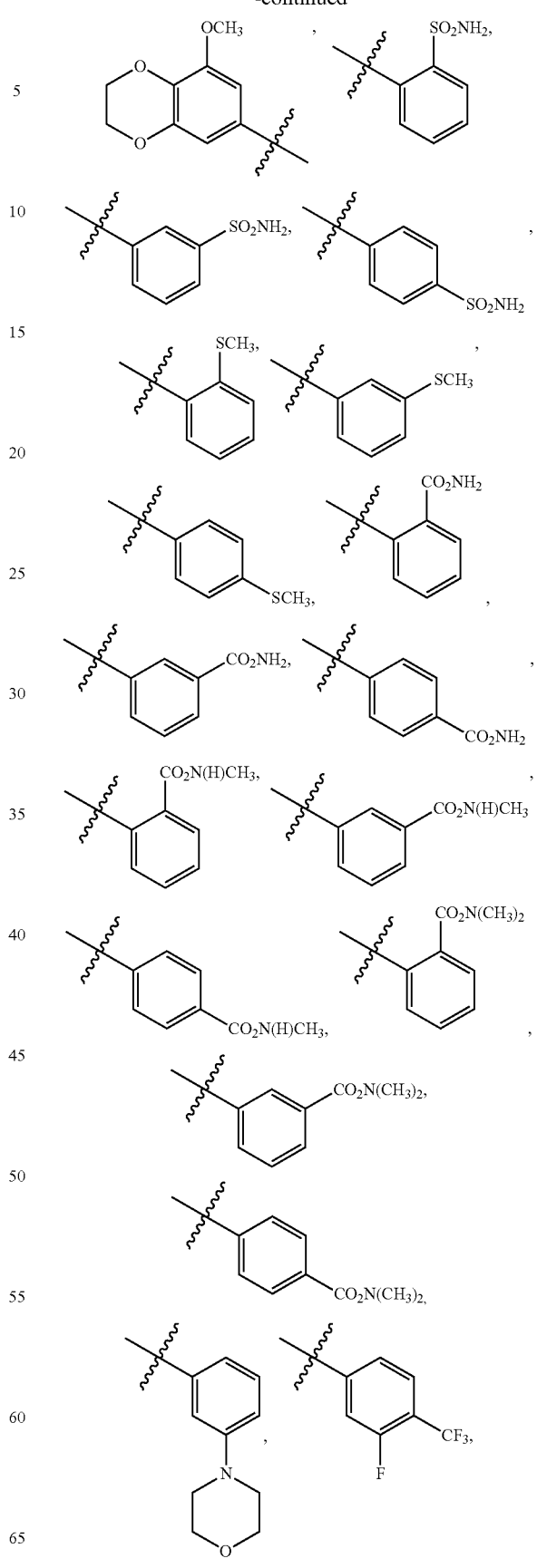

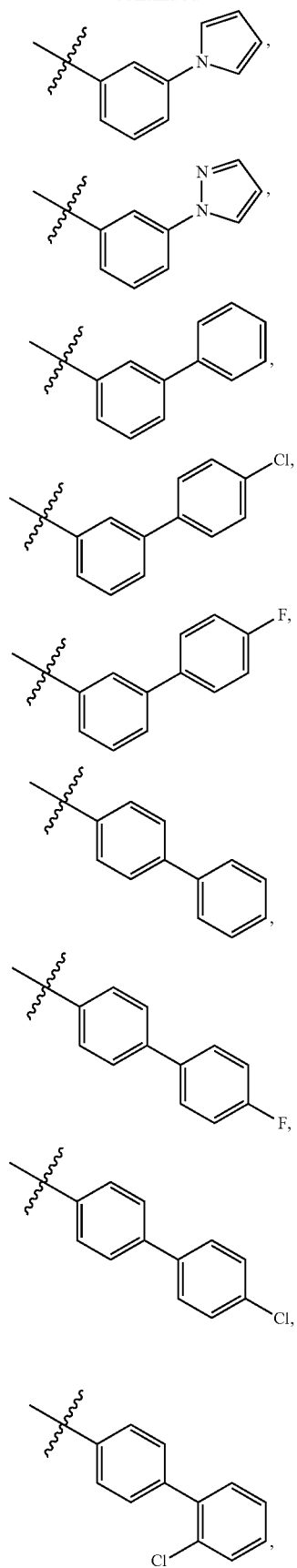
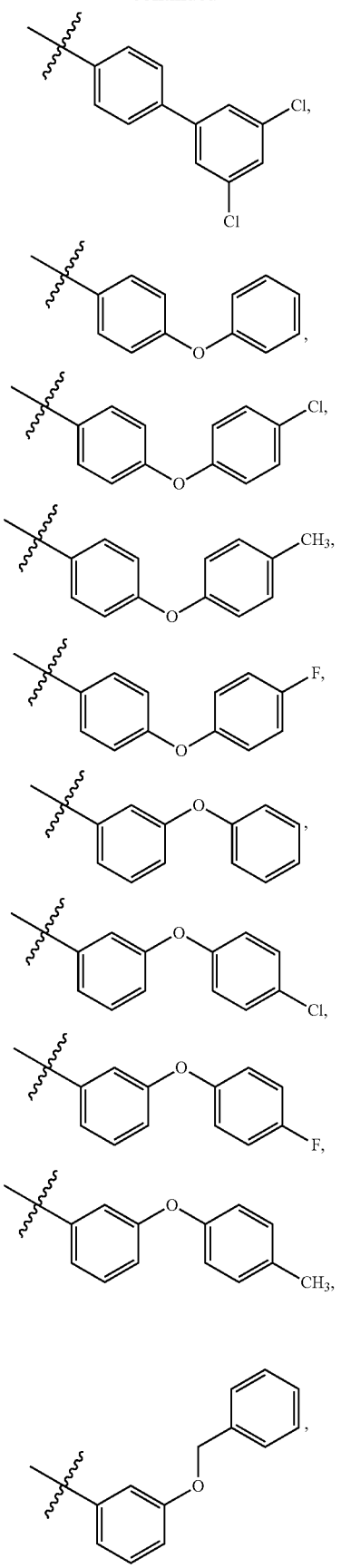

241
-continued

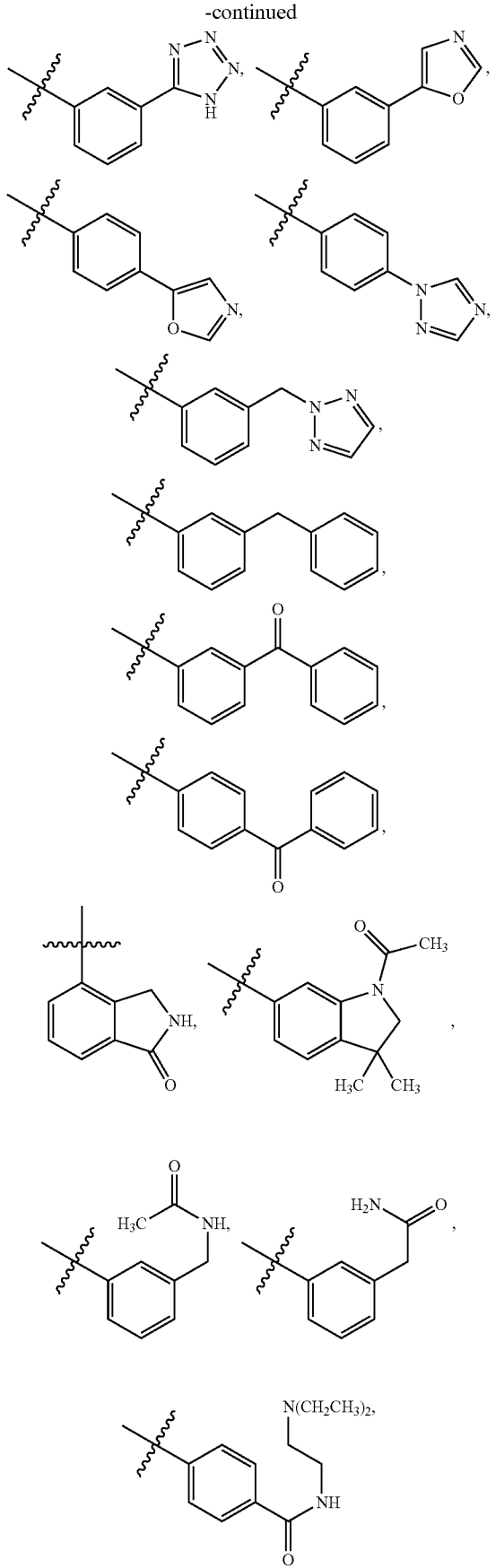

242
-continued

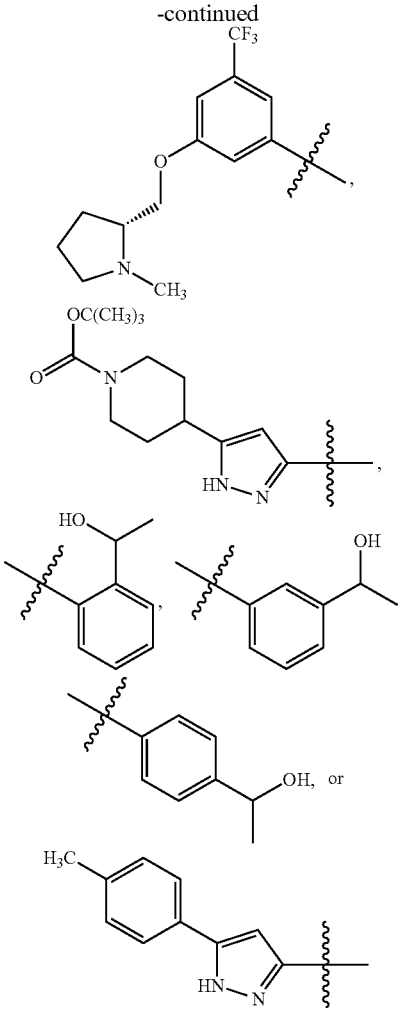

wherein the symbol ⁓ when drawn through a bond indicates the point of attachment to the rest of the molecule.

38. The compound of claim 1, wherein W is substituted with at least one substituent selected from —W', —O—W', —CH₂—W', N(H)—W', —O—CH₂—W', or —C(=O)—W'.

39. The compound of claim 1, wherein W is a phenyl substituted with at least one —O—($C_1$-$C_6$)alkyl group.

40. The compound of claim 1, wherein the compound is selected from

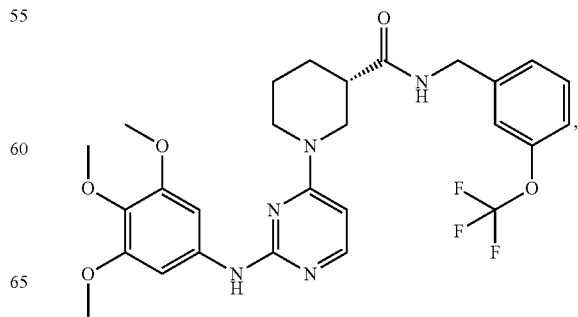

243
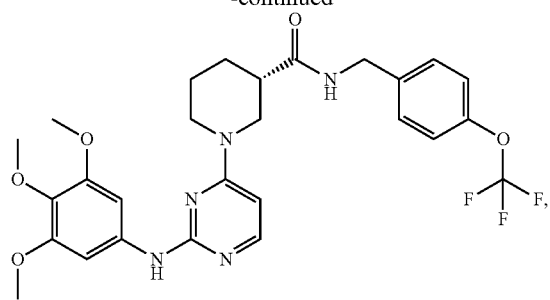
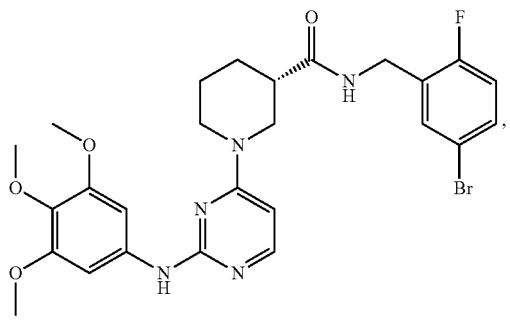
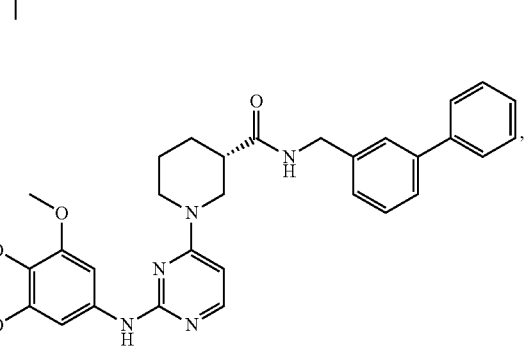
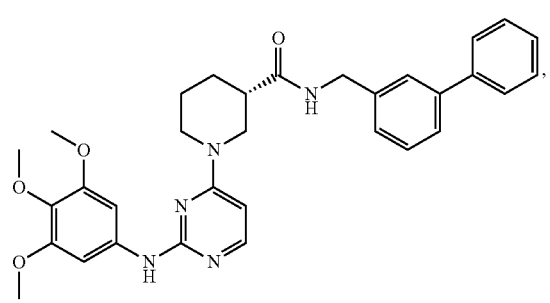
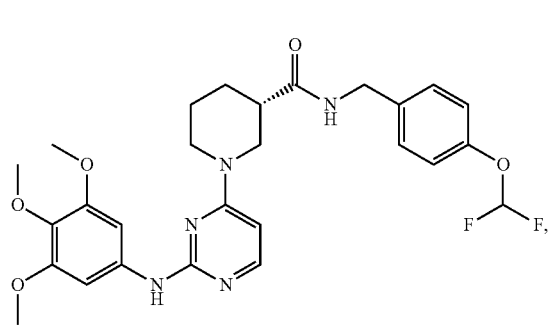
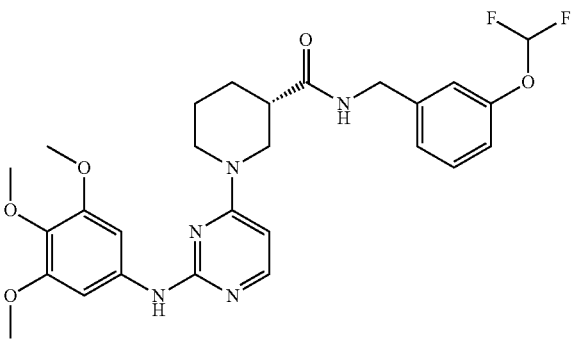
244
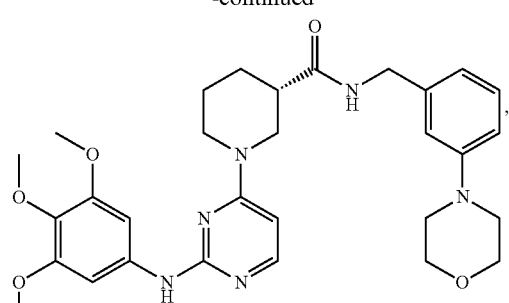
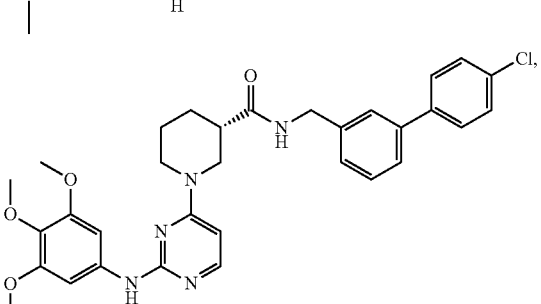
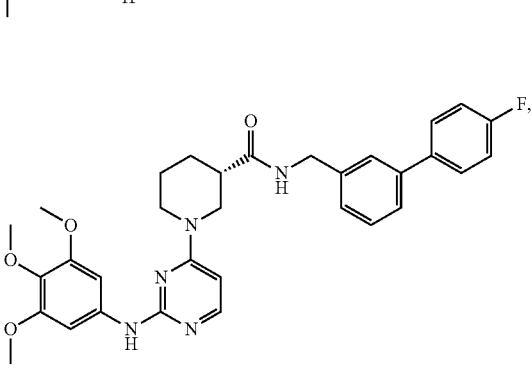
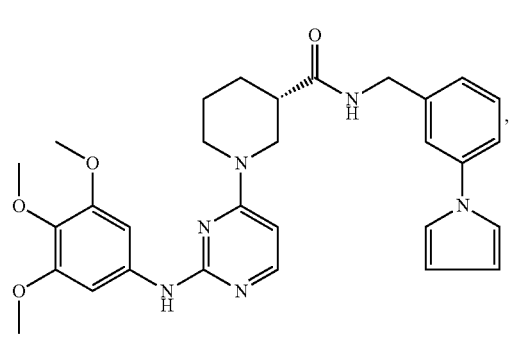
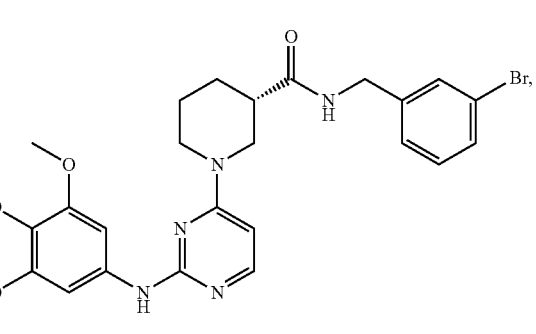

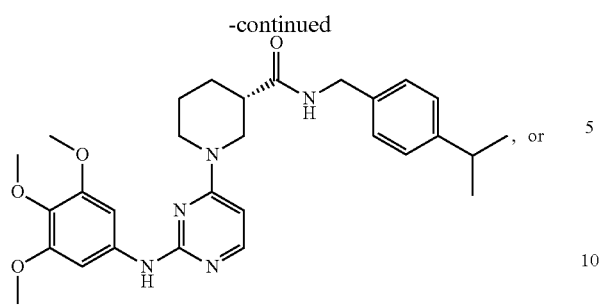, or
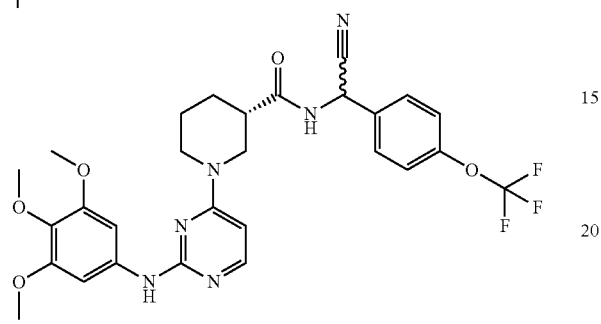
or a pharmaceutically acceptable salt thereof.
41. A pharmaceutical composition comprising a therapeutically effective amount of the compound according to claim 1 and at least one pharmaceutically acceptable excipient, carrier, or diluent.
* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Homo sapiens
<220> FEATURE:
<221> NAME/KEY: Biotin-Ahx
<222> LOCATION: (1)..(1)

<400> SEQUENCE: 1

Glu Gln Glu Asp Glu Pro Glu Gly Ile Tyr Gly Val Leu Phe
1               5                   10